US007175988B2

(12) United States Patent
Roschke et al.

(10) Patent No.: US 7,175,988 B2
(45) Date of Patent: Feb. 13, 2007

(54) HUMAN G-PROTEIN CHEMOKINE RECEPTOR (CCR5) HDGNR10

(75) Inventors: Viktor Roschke, Rockville, MD (US); Craig A. Rosen, Laytonsville, MD (US); Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 538 days.

(21) Appl. No.: 10/067,800

(22) Filed: Feb. 8, 2002

(65) Prior Publication Data

US 2003/0100058 A1 May 29, 2003

Related U.S. Application Data

(63) Continuation-in-part of application No. PCT/US01/04153, filed on Feb. 9, 2001, and a continuation-in-part of application No. 09/779,880, filed on Feb. 9, 2001, now abandoned.

(60) Provisional application No. 60/341,725, filed on Dec. 21, 2001, provisional application No. 60/328,447, filed on Oct. 12, 2001, provisional application No. 60/310,458, filed on Aug. 8, 2001, provisional application No. 60/297,257, filed on Jun. 12, 2001.

(51) Int. Cl.

| | |
|---|---|
| ***G01N 33/53*** | (2006.01) |
| ***C07K 16/00*** | (2006.01) |
| ***A61K 39/395*** | (2006.01) |

(52) U.S. Cl. .................. 435/7.1; 530/387.1; 424/130.1

(58) Field of Classification Search ................ 530/300, 530/380, 387.1

See application file for complete search history.

(56) References Cited

U.S. PATENT DOCUMENTS

| | | | |
|---|---|---|---|
| 5,314,992 | A | 5/1994 | Guyre et al. |
| 5,440,021 | A | 8/1995 | Chuntharapai et al. |
| 5,652,133 | A | 7/1997 | Murphy |
| 5,707,815 | A | 1/1998 | Charo et al. |
| 5,776,729 | A | 7/1998 | Soppet et al. |
| 5,798,206 | A | 8/1998 | Neurath et al. |
| 5,817,310 | A | 10/1998 | Ramakrishnan et al. |
| 5,912,176 | A | 6/1999 | Wang |
| 5,919,776 | A | 7/1999 | Hagmann et al. |
| 5,928,881 | A | 7/1999 | Barnette et al. |
| 5,939,320 | A | 8/1999 | Littman et al. |
| 5,939,538 | A | 8/1999 | Leavitt et al. |
| 5,961,976 | A | 10/1999 | Wang |
| 5,962,462 | A | 10/1999 | Mills et al. |
| 5,994,515 | A | 11/1999 | Hoxie |
| 6,013,644 | A | 1/2000 | Mills et al. |
| 6,025,154 | A | 2/2000 | Li et al. |
| 6,057,102 | A | 5/2000 | Landau et al. |
| 6,075,181 | A | 6/2000 | Kucherlapati et al. |
| 6,107,019 | A | 8/2000 | Allaway et al. |
| 6,132,987 | A | 10/2000 | Charo et al. |
| 6,153,431 | A | 11/2000 | Beretta et al. |
| 6,258,527 | B1 | 7/2001 | Littman et al. |
| 6,265,184 | B1 | 7/2001 | Gray et al. |
| 6,268,477 | B1 | 7/2001 | Gray et al. |
| 6,287,805 | B1 | 9/2001 | Graham et al. |
| 6,344,545 | B1 | 2/2002 | Allaway et al. |
| 6,448,375 | B1 | 9/2002 | Samson et al. |
| 6,511,826 | B2 | 1/2003 | Li et al. |
| 6,528,625 | B1 | 3/2003 | Wu et al. |
| 6,692,938 | B2 | 2/2004 | Samson et al. |
| 6,743,594 | B1 | 6/2004 | Li et al. |
| 6,759,519 | B2 | 7/2004 | Li et al. |
| 6,797,811 | B1 | 9/2004 | Gray et al. |
| 6,800,447 | B2 | 10/2004 | Samson et al. |
| 6,800,729 | B2 | 10/2004 | Li et al. |
| 2001/0000241 | A1 | 4/2001 | Li et al. |
| 2002/0048786 | A1 | 4/2002 | Rosen et al. |
| 2002/0061834 | A1 | 5/2002 | Rosen et al. |
| 2002/0076745 | A1 | 6/2002 | Li et al. |
| 2002/0099176 | A1 | 7/2002 | Li et al. |
| 2003/0023044 | A1 | 1/2003 | Li et al. |
| 2003/0166024 | A1 | 9/2003 | Rosen et al. |

(Continued)

FOREIGN PATENT DOCUMENTS

| | | |
|---|---|---|
| CA | 2146328 | 5/1994 |

(Continued)

OTHER PUBLICATIONS

Benjamini and Leskowitz, Immunology: A short course, Wiley-Liss Inc., 1991, pp. 51-58.*

(Continued)

*Primary Examiner*—Sharon Turner
(74) *Attorney, Agent, or Firm*—Sterne, Kessler, Goldstein & Fox P.L.L.C.

(57) ABSTRACT

The present invention relates to a novel human protein called Human G-protein Chemokine Receptor (CCR5) HDGNR10, and isolated polynucleotides encoding this protein. The invention is also directed to human antibodies that bind Human G-protein Chemokine Receptor (CCR5) HDGNR10 and to polynucleotides encoding those antibodies. Also provided are vectors, host cells, antibodies, and recombinant methods for producing Human G-protein Chemokine Receptor (CCR5) HDGNR10 and human anti-Human G-protein Chemokine Receptor (CCR5) HDGNR10 antibodies. The invention further relates to diagnostic and therapeutic methods useful for diagnosing and treating diseases, disorders, and/or conditions related to this novel human protein and these novel human antibodies.

24 Claims, 7 Drawing Sheets

U.S. PATENT DOCUMENTS

2004/0151719 A1 8/2004 Li et al.

FOREIGN PATENT DOCUMENTS

| | | |
|---|---|---|
| CA | 2128208 | 6/1994 |
| EP | 0 671 391 | 9/1995 |
| EP | 0 612 723 | 8/1997 |
| EP | 0 834 564 | 5/1998 |
| EP | 0 945 4640 | 9/1999 |
| EP | 0 979 655 | 2/2000 |
| FR | 2 771 423 | 5/1999 |
| JP | 10-179180 | 7/1998 |
| JP | 11-243960 | 9/1999 |
| JP | 11-292795 | 10/1999 |
| RU | 2126048 | 2/1999 |
| WO | WO 92/01810 A1 | 2/1992 |
| WO | WO 94/11504 | 5/1994 |
| WO | WO 95/19436 | 7/1995 |
| WO | WO 96/22371 | 7/1996 |
| WO | WO 96/23068 | 8/1996 |
| WO | WO 96/38559 | 12/1996 |
| WO | WO 96/39437 | 12/1996 |
| WO | WO 97/00960 | 1/1997 |
| WO | WO 97/19696 | 6/1997 |
| WO | WO 97/21812 | 6/1997 |
| WO | WO 97/22698 | 6/1997 |
| WO | WO 97/25340 | 7/1997 |
| WO | WO 97/28258 | 8/1997 |
| WO | WO 97/32019 | 9/1997 |
| WO | WO 97/35881 | 10/1997 |
| WO | WO 97/37005 | 10/1997 |
| WO | WO 97/41225 | 11/1997 |
| WO | WO 97/41230 | 11/1997 |
| WO | WO 97/44055 | 11/1997 |
| WO | WO 97/45543 | 12/1997 |
| WO | WO 97/46697 | 12/1997 |
| WO | WO 97/47318 | 12/1997 |
| WO | WO 97/47319 | 12/1997 |
| WO | WO 97/49424 | 12/1997 |
| WO | WO 98/00535 | 1/1998 |
| WO | WO 98/02151 A2 | 1/1998 |
| WO | WO 98/05798 | 2/1998 |
| WO | WO 98/11218 A1 | 3/1998 |
| WO | WO 98/14480 | 4/1998 |
| WO | WO 98/15569 | 4/1998 |
| WO | WO 98/17308 | 4/1998 |
| WO | WO 98/18826 | 5/1998 |
| WO | WO 98/20166 | 5/1998 |
| WO | WO 98/25604 | 6/1998 |
| WO | WO 98/25605 | 6/1998 |
| WO | WO 98/25617 | 6/1998 |
| WO | WO 98/27815 | 7/1998 |
| WO | WO 98/30218 | 7/1998 |
| WO | WO 98/31364 | 7/1998 |
| WO | WO 98/34945 | 8/1998 |
| WO | WO 98/38212 | 9/1998 |
| WO | WO 98/42354 | 10/1998 |
| WO | WO 98/44158 | 10/1998 |
| WO | WO 98/51705 | 11/1998 |
| WO | WO 98/54317 | 12/1998 |
| WO | WO 98/55873 | 12/1998 |
| WO | WO 98/56421 | 12/1998 |
| WO | WO 98/58536 | 12/1998 |
| WO | WO 98/58966 | 12/1998 |
| WO | WO 99/01127 | 1/1999 |
| WO | WO 99/04794 | 2/1999 |
| WO | WO 99/06561 | 2/1999 |
| WO | WO 99/08703 | 2/1999 |
| WO | WO 99/09984 | 3/1999 |
| WO | WO 99/12416 | 3/1999 |
| WO | WO 99/13112 | 3/1999 |
| WO | WO 99/14378 | 3/1999 |
| WO | WO 99/17773 | 4/1999 |
| WO | WO 99/23107 | 5/1999 |
| WO | WO 99/23253 | 5/1999 |
| WO | WO 99/24065 | 5/1999 |
| WO | WO 99/24553 | 5/1999 |
| WO | WO 99/27122 | 6/1999 |
| WO | WO 99/27939 | 6/1999 |
| WO | WO 99/28474 | 6/1999 |
| WO | WO 99/32100 | 7/1999 |
| WO | WO 99/32138 | 7/1999 |
| WO | WO 99/33989 | 7/1999 |
| WO | WO 99/36518 | 7/1999 |
| WO | WO 99/38514 | 8/1999 |
| WO | WO 99/43711 | 9/1999 |
| WO | WO 99/46372 | 9/1999 |
| WO | WO 99/51751 | 10/1999 |
| WO | WO 99/53033 | 10/1999 |
| WO | WO 99/62535 | 12/1999 |
| WO | WO 99/66944 | 12/1999 |
| WO | WO 99/67429 | 12/1999 |
| WO | WO 00/02045 | 1/2000 |
| WO | WO 00/05265 | 2/2000 |
| WO | WO 00/06085 | 2/2000 |
| WO | WO 00/06146 | 2/2000 |
| WO | WO 00/06153 | 2/2000 |
| WO | WO 00/08043 | 2/2000 |
| WO | WO 00/09525 | 2/2000 |
| WO | WO 00/10965 | 3/2000 |
| WO | WO 00/14220 | 3/2000 |
| WO | WO 00/15663 | 3/2000 |
| WO | WO 00/15785 | 3/2000 |
| WO | WO 01/058915 A3 | 8/2001 |
| WO | WO 01/58916 A2 | 8/2001 |
| WO | WO 01/96388 | 12/2001 |
| WO | WO 02/064612 A2 | 8/2002 |

OTHER PUBLICATIONS

Database EMBL Online, Accession No. AF031237, from Mummidi, S., et al. (first available Jan. 1998).

Mummidi, S. et al., "The Human CC Chemokine Receptor 5 (CCR5) Gene," *J. Biol. Chem. 272*:30662-30671, American Society for Biochemistry and Molecular Biology (Dec. 1997).

European Search Report for European Patent Application No. EP01912713, European Patent Office, Netherlands, mailed on May 25, 2004.

Alkhatib, G., et al., "CC CKR5: A RANTES, MIP-1α, MIP-1β Receptor as a Fusion Cofactor for Macrophage -Tropic HIV-1," *Science 272*:1955-1958, American Association for the Advancement of Science (Jun. 1996).

Balter, M., "Elusive HIV-Suppressor Factors Found," *Science 270*:1560-1561, American Association for the Advancement of Science (Dec. 1995).

Balter, M., "A Second Coreceptor for HIV In Early Stages of Infection," *Science 272*:1740, American Association for the Advancement of Science (Jun. 1996).

Choe, H., et al., "The β-Chemokine Receptors CCR3 and CCRS Facilitate Infection by Primary HIV-1 Isolates," *Cell 85*:1135-1148, Cell Press (Jun. 1996).

Cocchi, F., et al., "Identification of RANTES, MIP-α, and MIP-1β as the Major HIV-Suppressive Factors Produced by CD8+ T Cells," *Science 270*:1811-1815, American Association for the Advancement of Science (Dec. 1995).

Cohen, J., "Likely HIV Cofactor Found," *Science 272*:809-810, American Association for the Advancement of Science (May 1996).

Combadiere, C., et al., "Cloning and functional expression of a human eosinophil CC chemokine receptor," *J. Biol. Chem. 270*:16491-16494, American Society for Biochemistry and Molecular Biology (Jul. 1995).

Combadiere, C., et al., "Monocyte Chemoattractant Protein-3 Is a Functional Ligand for CC Chemokine Receptors 1 and 2," *J. Biol. Chem. 270*:29671-29675, American Society for Biochemistry and Molecular Biology (Dec. 1995).

Combadiere, C., et al., "Additions and Corrections to: Cloning and functional expression of a human eosinophil CC chemokine receptor," *J. Biol. Chem. 270*:30235, The American Society for Biochemistry and Molecular Biology (Dec. 1995).

Combadiere, C., et al., "Cloning and functional expression of CC CKR5, a human monocyte CC chemokine receptor selective for MIP-1α, MIP-1β, and RANTES," *J. Leukocyte Biol. 60*:147-152, The Society for Leukocyte Biology (Jul. 1996).

Deng, H., et al., "Identification of a major co-receptor for primary isolates of HIV-1," *Nature 381*:661-666, Macmillan Publishing Group (Jun. 1996).

Dimitrov, D.S., "Fusin—a place for HIV-1 and T4 cells to meet," *Nature Med. 2*:640-641, Nature Publishing Group (Jun. 1996).

Doranz, B.J., et al., "A Dual-Tropic Primary HIV-1 Isolate That Uses Fusin and the β-Chemkine Receptors CKR-5, CKR-3, and CKR-2b as Fusion Cofactors," *Cell 85*:1149-1158, Cell Press (Jun. 1996).

Dragic, T., et al., "HIV-1 entry into CD4+ cells is mediated by the chemokine receptor CC-CKR-5," *Nature 381*:667-673, Macmillan Publishing Group (Jun. 1996).

Feng, Y., et al., "HIV-1 Entry Cofactor: Functional cDNA Cloning of a Seven-Transmembrane, G Protein-Coupled Receptor," *Science 272*:872-877, America Association for the Advancement of Science (May 1996).

Gura, T., "Chemokines Take Center Stage in Inflammatory Ills," *Science 272*:954-956, American Association for the Advancement of Science (May 1996).

Marshall, E., "HIV Experts vs. Sequencers in Patent Race," *Science 275*:1263, American Association for the Advancement of Science (Feb. 1997).

Murphy, P.M., "The Molecular Biology of Leukocyte Chemoattractant Receptors," *Annu. Rev. Immunol. 12*:593-633, Annual Reviews, Inc. (1994).

Raport, C.J., et al., "Molecular Cloning and Functional Characterization of a Novel Human CC Chemokine Receptor (CCR5) for RANTES, MIP-1β, and MIP-1α," *J. Biol. Chem. 271*:17161-17166, American Society for Biochemistry and Molecular Bilogy (Jul. 1996).

Samson, M., et al., "Molecular Cloning and Functional Expression of a New Human CC-Chemokine Receptor Gene," *Chem. Abstracts 124*:993, Abstract No. 258056e, The American Chemical Society (May 1996).

Samson, M., et al., "Molecular Cloning and Functional Expression of a New Human CC-Chemokine Receptor Gene," *Biochemistry 35*:3362-3367, American Chemical Society (Mar. 1996).

Travis, J., "Multiple doors for HIV to enter cells," *Science News 149*:390, Science Service (Jun. 1996).

Weiss, R.A., and Clapham, P.R., "Hot fusion of HIV," *Nature 381*:647-648, Macmillan Publishing Group (Jun. 1996).

English language abstract of EP 0 612 723 A1, Derwent World Patents Index (Dialog File 351), WPI Accession No. 1994-265874/199433.

English language abstract of EP 0 671 391 A1, Derwent World Patents Index (Dialog File 351), WPI Accession No. 1995-312725/199541.

English language abstract of EP 0 979 655, Derwent World Patents Index (Dialog File 351), WPI Accession No. 2000-197082/200018.

English language abstract of FR 2 771 423 A1, Derwent World Patents Index (Dialog File 351), WPI Accession No. 12523594.

English language abstract of JP 11-243960 A, Derwent World Patents Index (Dialog File 351), WPI Accession No. 12797479.

English language abstract of JP 11-292795 A, Derwent World Patents Index (Dialog Fi 351), WPI Accession No. 1999-620207/199953.

English language abstract of RU 2 126 048, Derwent World Patents Index (Dialog File 351), WPI Accession No. 13109249.

Brühl, H., et al., "Depletion of CCR5-Expressing Cells with Bispecific Antibodies and Chemokine Toxins: A New Strategy in the Treatment of Chronic Inflammatory Diseases and HIV," *J. Immunol. 166*:2420-2426, The American Association of Immunologists (Feb. 2001).

Gomez-Reino, J.J., et al., "Association of Rheumatoid Arthritis with a Functional Chemokine Receptor, CCR5," *Arthritis Rheum. 42*:989-992, American College of Rheumatology (May 1999).

Jobling, M.G., and Holmes, R.K., "Analysis of structure and function of the B subunit of cholera toxin by the use of site-directed mutagenesis," *Mol. Microbiol. 5*:1755-1767, Blackwell Science (1991).

Lerner, R.A., "Tapping the immunological repertoire to produce antibodies of predetermined specificity," *Nature 299*:592-596, Macmillan Journals Ltd (1982).

Mack, M., et al., "Predominance of Mononuclear Cells Expressing the Chemokine Receptor CCR5 in Synovial Effusions of Patients with Different Forms of Arthritis," *Arthritis Rheum. 42*:981-988, American College of Rheumatology (May 1999).

Murdoch, C., and Finn, A., "Chemokine receptors and their role in inflammation and infectious diseases," *Blood 95*:3032-3043, The American Society of Hematology (May 2000).

Skolnick, J., and Fetrow, J.S., "From genes to protein structure and function: novel applications of computational approaches in the genomic era," *TIBTECH 18*:34-39, Elsevier Science Ltd (Jan. 2000).

Suzuki, N., et al., "Selective accumulation of CCR5$^+$ T lymphocytes into inflamed joints of rheumatoid arthritis," *Intl. Immunol. 11*:553-559, The Japanese Society for Immunology and Oxford University Press (Apr. 1999).

Zang, Y.C.Q., et al., "Aberrant T cell migration toward RANTES and MIP-1α in patients with multiple sclerosis: Overexpression of chemokine receptor CCR5," *Brain 123*:1874-1882, Oxford Universiy Press (Sep. 2000).

"Myocardial Infarction," in The Merck Manual of Diagnosis and Therapy, Seventeenth Edition, Centennial Edition, Section 16,Chapter 202, Beers, M.H., and Berkow, R., eds., Merck & Co., Inc. (1999) <http://www.merck.com/pubs/Manual/section16/chapter202/202d.htm> (visited Aug. 2001).

"CCR-5 Antibodies-Human Chemokine Receptor Antibodies," Aves Labs, Inc., <http://www.aveslab.com/ccr5.html>, (visited Aug. 2001).

"Euroscreen Available Products: Mammalian recombinant cell lines," Euroscreen s.a. (1999), <http://www.euroscreen.be/products/cell_lines.html>, (visited Aug. 2001).

"Specification Sheet H-1001," Aves Labs, Inc., <http://www.aveslab.com/specs/h1001.html>, (visited Aug. 2001).

"CCR-5 (CCR5) Chemokine Receptor antibodies available through Research Diagnostics Inc.," Research Diagnostics Inc., <http://www.researchd.com/cytokines/ccr5ab.htm>, (visited Aug. 2001).

GenBank Report, Accession No. AF019772, submitted by Doranz, B.J. et al. (Sep. 1997).

English language abstract of WO 97/41230, Derwent World Patents Index (Dialog File 351), WPI Accession No. 11573252.

English language abstract of WO 98/55873, Derwent World Patents Index (Dialog File 351), WPI Accession No. 12336308.

English language abstract of WO 00/15785, Derwent World Patents Index (Dialog File 351), WPI Accession No. 13099553.

Burbach, J.P.H., and Meijer, O.C., "The structure of neuropeptide receptors," *Eur. J. Pharmacol. 227*:1-18, Elsevier Science Publishers B.V. (1992).

Greenwood, M.T., et al., "Ligand Binding Pocket of the Human Somatostatin Receptor 5: Mutational Analysis of the Extracellular Domains," *Mol. Pharmacol. 52*:807-814, The American Society for Pharmacology and Experimental Therapeutics (1997).

Larhammar, D., et al., "The Receptor Revolution—Multiplicity of G-Protein-Coupled Receptors," *Drug Design and Discovery 9*:179-188, Harwood Academic Publishers GmbH (1993).

GenBank ref file $NP_{13}000570.1$ (chemokine receptor 5 [*Homo sapiens*]) BLAST Homology Search Alignment.

U.S. Appl. No. 10/127,764, Li, et al., filed Apr. 23, 2002 (Not Published).

U.S. Appl. No. 10/791,905, Li, et al., filed Mar. 4, 2004 (Not Published).

Promega, "3. Nucleic Acids: Primers and Linkers," in *1993/94 Catalog*, Promega Corporation (1993).

Baba, M., et al., "A small-molecule, nonpeptide CCR5 antagonist with highly potent and selective anti-HIV activity," *Proc. Natl. Acad. Sci. U.S.A. 96*:5698-5703, National Academy of Sciences (1999).

BD Pharmingen™ Technical Data Sheet, "R-Phycoerythrin (R-PE)-Conjugated Mouse Anti-human Monoclonal Antibody," Revision 002, BD Biosciences Pharmingen (Aug. 2004).

Björndal, A., et al., "Coreceptor usage of primary human immunodeficiency virus type 1 isolates varies according to biological phenotype," *J. Virol. 71*(10):7478-7487, American Society for Microbiology (1997).

Blanpain, C., et al., "Multiple charged and aromatic residues in CCR5 amino-terminal domain are involved in high affinity binding of both chemokines and HIV-1 Env protein," *J. Biol. Chem. 274*(49):34719-34727, American Society for Biochemistry and Molecular Biology (1999).

Blanpain, C., et al., "Extracellular cysteines of CCR5 are required for chemokine binding, but dispensable for HIV-1 coreceptor activity", *J. Biol. Chem. 274*(27):18902-18908, American Society for Biochemistry and Molecular Biology (1999).

Bleul, C.C., et al., "The HIV coreceptors CXCR4 and CCR5 are differentially expressed and regulated on human T lymphocytes", *Proc. Natl. Acad. Sci. U.S.A. 94*:1925-1930, National Academy of Sciences (1997).

Chackerian, B., et al., "Induction of autoantibodies to mouse CCR5 with recombinant papillomavirus particles," *Proc. Natl. Acad. Sci. U.S.A. 96*:2373-2378, National Academy of Sciences (1999).

Davies, B. and Morris, T., "Physiological parameters in laboratory animals and humans," *Pharmaceut. Res. 10*:1093-1095, Plenum Publishing Corp. (1993).

Dejucq, N., et al., "Expanded tropism of primary human immunodeficiency virus type 1 R5 strains to CD4+ T-cell lines determined by the capacity to exploit low concentrations of CCR5," *J. Virol. 73*(9):7842-7847, American Society for Microbiology (1999).

Doranz, B.J., et al., "A small-molecule inhibitor directed against the chemokine receptor CXCR4 prevents its use as an HIV-1 coreceptor," *J. Exp. Med. 186*(8):1395-1400, The Rockefeller University Press (1997).

Dragic, T., et al., "A binding pocket for a small molecule inhibitor of HIV-1 entry within the transmembrane helices of CCR5," *Proc. Natl. Acad. Sci. U.S.A. 97*(10):5639-5644, National Academy of Sciences (May 2000).

Dürig, J., et al., "Differential expression of chemokine receptors in B cell malignancies," *Leukemia 15*(5):752-756, Nature Publishing Group (May 2001).

Dybul, M., et al., "Guidelines for using antiretroviral agents among HIV-infected adults and adolescents. The panel on clinical practices for treatment of HIV," *Annals of Int. Med.*, 137(5):381-433, American College of Physicians (Sep. 2002).

Farzan, M., et al., "A Tyrosine-rich region in the N terminus of CCR5 is important for human immunodeficiency virus type 1 entry and mediates an association between gp120 and CCR5," *J. Virol. 72*(2):1160-1164, American Society for Microbiology (1998).

Fleuridor, R., et al., "CD1d-restricted natural killer T cells are potent targets for human immunodeficiency virus infection," *Immunology 108*(1):3-9, Blackwell Publishing Ltd. (Jan. 2003).

Genoud, S., et al., "CCR5-Mediated human immunodeficiency virus entry depends on an amino-terminal gp120-binding site and on the conformational integrity of all four extracellular domains," *J. Virol. 73*(2):1645-1648, American Society for Microbiology (1999).

He, J., et al., "Human immunodeficiency virus type 1 viral protein R (Vpr) arrests cells in the $G_2$ phase of the cell cycle by inhibiting $p34^{cdc2}$ activity," *J. Virol. 69*(11):6705-6711, American Society for Microbiology (1995).

Holland, A.U., et al., "α-complementation assay for HIV envelope glycoprotein-mediated fusion," *J. Virol. 319*:343-352, Elsevier Inc. (Feb. 2004).

Hong, Y-L., et al., "New reporter cell lines to study macrophage-tropic HIV envelope protein- mediated cell-cell fusion," *AIDS Res. Hum. Retroviruses 15*(18):1667-1672, Mary Ann Liebert, Inc. (1999).

Howell, D.N., et al., "Natural killing target antigens as inducers of interferon: studies with an immunoselected, natural killing-resistant human T-lymphoblastoid cell line," *J. Immunol. 134*:971-976, The American Association of Immunologists (1985).

Kedzierska, K., et al., "The Influence of cytokines, chemokines and their receptors on HIV-1 replication in monocytes and macrophages," *Rev. Med. Virol. 13*:39-56, John Wiley and Sons, Ltd. (Jan.-Feb. 2003).

Kilby, J.M. and Eron, J.J. "Novel therapies based on mechanisms of HIV-1 cell entry," *N. Engl. J. Med. 384*:2228-2238, Massachusetts Medical Society (May 2003).

Königs, C., et al., "Monoclonal antibody screening of a phage-displayed random peptide library reveals mimotopes of chemokine receptor CCR5: Implications for the tertiary structure of the receptor and for and N-terminal binding site for HIV-1 gp120," *Eur. J. Immunol. 30*:1162-1171, Wiley-VCH Verlag GmbH (Apr. 2000).

Kottilil, S., et al., "Expression of chemokine and inhibitory receptors on natural killer cells: effect of immune activation and HIV viremia," *J. Infect. Dis. 189*:1193-1198, National Institute of Allergy and Infectious Diseases (Apr. 2004).

Lachgar, A., et al., "Binding of HIV-1 to RBCs involves the Duffy antigen receptors for chemokines (DARC)," *Biomed. & Pharmacother. 52*:436-439, Elsevier (1998).

Lalezari, J.P., et al., "Enfuvirtide, an HIV-1 fusion inhibitor, for drug-resistant HIV infection in North and South America," *N. Engl. J. Med. 348*(22):2175-2185, Massachusetts Medical Society (May 2003); correction attached, *N. Engl. J. Med. 349*(11):1100 (Sep. 2003).

Lin, Y-L., et al., Cell surface CCR5 density determines the postentry efficiency of R5 HIV-1 infection. *Proc. Natl. Acad. Sci. U.S.A. 99*(24):15590-15595, The National Academy of Sciences (Nov. 2002).

Lin, P-F., et al., "A small molecule HIV-1 inhibitor that targets the HIV-1 envelope and inhibits CD4 receptor binding," *Proc. Natl. Acad. Sci. U.S.A. 100*(19):11013-11018, The National Academy of Sciences (Sep. 2003).

Liu, R., et al., "Homozygous defect in HIV-1 coreceptor accounts for resistance of some multiply-exposed individuals to HIV-1 infection," *Cell 86*:367-377, Cell Press (1996).

Lopalco, L., et al., "CCR5-Reactive antibodies in seronegative partners of HIV-seropositive individuals down-modulate surface CCR5 in vivo and neutralize the infectivity of R5 strains of HIV-1 in vitro," *J. Immunol. 164*:3426-3433, The American Association of Immunologists (Mar. 2000).

Lusso, P., et al., "Growth of macrophage-tropic and primary human immunodeficiency virus type 1 (HIV-1) isolates in a unique CD4+ T-cell clone (PM1): Failure to downregulate CD4 and to interfere with cell-line-tropic HIV-1," *J. Virol. 69*:3712-3720, American Society for Microbiology (1995).

Lyerly, H.K., et al., "Anti-gp 120 antibodies from HIV seropositive individuals mediate broadly reactive anti-HIV ADCC," *AIDS Res. Hum. Retroviruses 3*:409-422, Mary Ann Liebert, Inc. (1987).

Martin, J.C. and Bandrés, J.C., "Cells of the monocyte-macrophage lineage and pathogenesis of HIV-1 infection," *J. Acquir. Immune Defic. Syndr. 22*(5):413-440, Lippincott Williams and Wilkins, Inc. (1999).

Mirzabekov, T., et al., "Enhanced Expression, Native Purification, and Characterization of CCR5, a Principal HIV-1 Coreceptor," *J. Biol. Chem. 274*(40):28746-28750, The American Society for Biochemistry and Molecular Biology, Inc. (1999).

Moore, J.P., et al., "The CCR5 and CXCR4 coreceptors—central to understanding the transmission and pathogenesis of human immunodeficiency virus type 1 infection," *AIDS Res. Hum. Retroviruses 20*(1):111-126, Mary Ann Liebert, Inc. (Jan. 2004).

Moosmann, P. and Rusconi, S., "Alpha complementation of LacZ in mammalian cells," *Nucleic Acids Res. 24*(6):1171-1172, Oxford University Press (1996).

Mueller, A., et al., "Pharmacological characterization of the chemokine receptor, CCR5," *Br. J. Pharmacology 135*(4):1033-1043, Nature Publishing Group (Feb. 2002).

Münch, J., et al., "Hemofiltrate CC chemokine 1[9-74] causes effective internalization of CCR5 and is a potent inhibitor of R5-tropic human immunodeficiency virus type 1 strains in primary T cells and macrophages," *Antimicrob. Agents Chemother. 46*:982-990, The American Society for Microbiology (Apr. 2002).

Nansen, A., et al., "The role of CC chemokine receptor 5 in antiviral immunity," *Blood 99*(4):1237-1245, The American Society of Hematology (Feb. 2002).

Nieto, M., et al., "Roles of chemokines and receptor polarization in NK-target cell interactions," *J. Immunol. 161*:3330-3339, The American Association of Immunologists (1998).

Perera, L.P., et al., "IL-15 induces the expression of chemokines and their receptors in T lymphocytes," *J. Immuno. 162*:2606-2612, The American Association of Immunologists (1999).

Pozniak, A.L., et al., "Effect of short-term monotherapy with UK-427,857 on viral load in HIV-infected patients," *Program and abstracts from the 43rd Annual Interscience Conference on Antimicrobial Agents and Chemotherapy* (43rd ICAAC), pp. 14-17, Coe-Truman Technologies, Inc. (Sep. 2003).

Rabut, G.E.E., et al., "Alanine substitutions of polar and nonpolar residues in the amino-terminal domain of CCR5 differently impair entry of macrophage- and dualtropic isolates of human immunodeficiency virus type 1," *J. Virol. 72*(4):3464-3468, American Society for Microbiology (1998).

Reeves, J.D., et al., "Sensitivity of HIV-1 to entry inhibitors correlates with envelope/coreceptor affinity, receptor density, and fusion kinetics," *Proc. Natl. Acad. Sci. U.S.A. 99*(25):16249-16254, The National Academy of Sciences (Dec. 2002).

Reynes, J., et al., "CD4+ T cell surface CCR5 density as a determining factor of virus load in persons infected with human immunodeficiency virus type1," *J. Infect. Dis. 181*:927-932, The infectious Diseases Society of America (Mar. 2000).

Richman, D.D., et al., "Rapid evolution of the neutralizing antibody responsive to HIV type 1 infection," *Proc. Natl. Acad. Sci. U.S.A. 100*(7):4144-4149, The National Academy of Sciences (Apr. 2003).

Roederer, M., et al., "HIV does not replicate in naive CD4 T cells stimulated with CD3/CD28," *J. Clin. Invest. 99*(7):1555-1564, The American Society for Clinical Investigation, Inc. (1997).

Rottman, J.B., et al., "Cellular localization of the chemokine receptor CCR5: correlation to cellular targets of HIV-1 infection," *Amer. J. Path. 151*(5):1341-1351, American Society for Investigative Pathology (1997).

Rucker, J., et al., "Regions in β-chemokine receptors CCR5 and CCR2b that determine HIV-1 cofactor specificity," *Cell 87*:437-446, Cell Press (1996).

Samson, M., et al., "The second extracellular loop of CCR5 is the major determinant of ligand specificity," *J. Biol. Chem. 272*(40):24934-24941, American Society for Biochemistry and Molecular Biology, Inc. (1997).

Samson, M., et al., "Resistance to HIV-1 infection in Caucasian Individuals bearing mutant alleles of the CCR-5 chemokine receptor gene," *Nature 382*(22):722-725, Nature Publishing Group (1996).

Schecter, A.D., et al., "Human vascular smooth muscle cells possess functional CCR5," *J. Biol. Chem,.* 275(8):5466-5471, American Society for Biochemistry and Molecular Biology, Inc. (Oct. 2000).

Siciliano, S.J., et al., "A critical site in the core of the CCR5 chemokine receptor required for binding and infectivity of human immunodeficiency virus type 1," *J. Biol. Chem. 274*(4):1905-1913, American Society for Biochemistry and Molecular Biology, Inc. (1999).

Spina, C.A., et al., "Preferential replication of HIV-1 in the CD45RO memory cell subset of primary CD4 lymphocytes in vitro," *J. Clin. Invest. 99*(7):1774-1785, The American Society for Clinical Investigation, Inc. (1997).

Spira, S., et al., "Impact of clade diversity on HIV-1 virulence, antiretroviral drug sensitivity and drug resistance," *J. Antimicrob. Chemother. 51*:229-240, The British Society for Antimicrobial Chemotherapy (Jan. 2003).

Starr-Spires, L.D. and Collman, R.G. "HIV-1 entry and entry inhibitors as therapeutic agents," *Clin. Lab. Med. 22*:681-701, Elsevier Science (USA) (Sep. 2002).

Steinberger, P., et al., "Functional deletion of the CCR5 receptor by intracellular immunization produces cells that are refractory to CCR5-dependent HIV-1 infection and cell fusion," *Proc. Natl. Acad. Sci. U.S.A. 97*(2):805-810, The National Academy of Sciences (Jan. 2000).

Strizki, J.M., et al, "SCH-C (SCH 351125), an orally bioavailable, small molecule antagonist of the chemokine receptor CCR5, is a potent inhibitor of HIV-1 infection *in vitro* and *in vivo," Proc. Natl. Acad. Sci. U.S.A. 98*(22):12718-12723, The National Academy of Sciences (Oct. 2001).

Thormeyer, D., et al., "Characterization of lacZ complementation deletions using membrane receptor dimerization," *BioTechniques 34*:346-355, Eaton Publishing (Feb. 2003).

Trkola, A., et al., "HIV-1 escape from a small molecule, CCR5-specific entry inhibitor does not involve CXCR4 use," *Proc. Natl. Acad. Sci. U.S.A. 99*(1):395-400, The National Academy of Sciences (Jan. 2002).

Trkola, A., et al., "A cell line-based neutralization assay for primary human immunodeficiency virus type 1 isolates that use either the CCR5 or the CXCR4 coreceptor," *J. Virol. 73*(11):6966-8974, American Society for Microbiology (1999).

Trkola, A., et al., "Potent, broad-spectrum inhibition of human immunodeficiency virus type 1 by the CCR5 monoclonal antibody PRO 140," *J. Virol. 75*(2):579-588, American Society for Microbiology (Jan. 2001).

Tuttle, D.L., et al., "Expression of CCR5 increases during monocyte differentiation and directly mediates macrophage susceptibility to infection by human immunodeficiency virus type 1," *J. Virol. 72*(6): 4962-4969, American Society for Microbiology (1998).

Unutmaz, D. and Littman, D.R. "Expression pattern of HIV-1 coreceptors on T cells: Implications for viral transmission and lymphocyte homing," *Proc. Natl. Acad. Sci. U.S.A. 94*:1615-1618, The National Academy of Sciences (1997).

Van Rij, R.P., et al., "Differential coreceptor expression allows for independent evolution of non-syncytium-inducing and syncytium-inducing HIV-1," *J. Clin. Invest. 106*(8):1039-1052, The American Society for Clinical Investigation, Inc. (Oct. 2000).

Wahl, S.M., et al., "Permissive factors for HIV-1 infection of macrophages," *J. Leukoc. Biol. 68*(3):303-310, The Society of Leukocyte Biology (Sep. 2000).

Wahl, S.M., et al., "Viral and host cofactors facilitate HIV-1 replication in macrophages," *J. Leukoc. Biol. 74*(5):726-735, The Society of Leukocyte Biology (Nov. 2003).

Wang, Z., et al., "CCR5 HIV-1 coreceptor activity. Role of cooperativity between residues in N-terminal extracellular and intracellular domains," *J. Biol. Chem. 274*(40):28413-28419, American Society for Biochemistry and Molecular Biology, Inc. (1999).

Weinhold, K.J., et al., "Measurement of direct and indirect forms of anti-HIV-1 ADCC: Implications for other retroviral disease," *Dev. Biol.* Standard 72:343-348, 21st Congress of the IABS on Progress in Animal Retroviruses, S. Karger (1990).

Welply, J.K., et al., "β-Galactosidase α-complementation," *J. Biol. Chem. 256*(13):6804-6810, American Society for Biochemistry and Molecular Biology, Inc. (1981).

Woods, T.C., et al., "Loss of inducible virus in CD45RA naive cells after human immunodeficiency virus-1 entry accounts for preferential viral replication in CD45RO memory cells," *Blood 89*(5):1635-1641, American Society of Hematology (1997).

Wu, L., et al., "CCR5 levels and expression pattern correlate with infectability by macrophage-tropic HIV-1, in vitro," *J. Exp. Med. 185*(9):1681-1691, The Rockefeller University Press (1997).

U.S. Appl. No. 10/994,679, Roschke et al., filed Nov. 23, 2004 (Not Published).

Olson, W.C., et al., "Differential Inhibition of Human Immunodeficiency Virus Type 1 Fusion, gp120 Binding, and CC-Chemokine Activity by Monoclonal Antibodies to CCR5," *J. Virol. 73*:4145-4155, American Society for Microbiology (May 1999).

Osbourn, J.K., et al., "Directed selection of MIP-1α neutralizing CCR5 antibodies from a phage display human antibody library," *Nat. Biotechnol. 16*:778-781, Nature Pub. Co (Aug. 1998).
Supplementary Partial European Search Report for European Patent Application No. EP 02 71 8923, completed Nov. 29, 2004.
Database UniProt, Accession No. AAW90287, Berchtold, P., and Escher, R.F.A., Sep. 7, 1999.
Database UniProt, Accession No. AX355922, Devaux, B., et al., Feb. 6, 2002.
Database UniProt, Accession No. P18135, Kipps, T.J., et al., Nov. 1, 1990.
Database UniProt, Accession No. AAR38672, Marasco, W.A., et al., Nov. 1, 1993.
Database EMBL, Accession No. Z75404, Tonnelle, C., et al., Apr. 30, 1997.
Database EMBL, Accession No. Z14196, Cuisinier, A.M., et al., Jan. 20, 1993.
Database EMBL, Accession No. Z27170, Bensimon, C., et al., Nov. 12, 1993.
Database EMBL, Accession No. S66101, Bhat, N.M., et al., Dec. 6, 1993.
Database EMBL, Accession No. AJ388647, Capello, D., et al., Jul. 22, 1999.
Database EMBL, Accession No. Z46310, Chapman, C.J., et al., Dec. 12, 1994.
Charo, I.F., et al., "Molecular cloning and functional expression of two monocyte chemoattractant protein 1 receptors reveals alternative splicing of the carboxyl-terminal tails," *Proc. Natl. Acad. Sci. USA 91*:2752-2756, National Academy of Science (Mar. 1994).
Eva, C., et al., "Molecular cloning of a novel G protein-coupled receptor that may belong to the neuropeptide receptor family," *FEBS Letters 271*:81-84, Elsevier Science B.V. (1990).
Gao, J.-L., et al., "Structure and Functional Expression of the Human Macrophage Inflammatory Protein 1α/RANTES Receptor," *J. Exp. Med. 117*:1421-1427, Rockefeller University Press (1993).
George, D.G., et al., "Chapter 12. Current Methods in Sequence Comparison and Analysis," in *Macromolecular Sequencing and Synthesis. Selected Methods and Applications*, Schlesinger, D.H., ed., Alan R. Liss, Inc., New York, NY, pp. 127-149 (1988).
Hla, T., and Maciag, T., "An abundant transcript induced in differentiating human endothelial cells encodes a polypeptide with structural similarities to G-protein-coupled receptors," *J. Biol. Chem. 265*:9308-9313, American Society for Biochemistry and Molecular Biology, Inc. (1990).
Libert, F., et al., "Selective amplification and cloning of four new members of the G protein-coupled receptor family," *Science 244*:569-572, American Association for the Advancement of Science (1989).
Meyerhof, W., et al., "Molecular cloning of a novel putative G-protein coupled receptor expressed during rat spermiogenesis," *FEBS Letters 284*:155-160, Elsevier Science B.V. (1991).
Neote, K., et al., "Molecular Cloning, Functional Expression, and Signaling Characteristics of a C-C Chemokine Receptor," *Cell 72*:415-425, Cell Press (1993).
Nomura, H., et al., "Molecular cloning of cDNAs encoding a LD78 receptor and putative leukocyte chemotactic peptide receptors," *Int. Immunol. 5*:1239-1249, Oxford University Press (1993).
Ross, P.C., et al., "RTA, a candidate G protein-coupled receptor: cloning, sequencing, and tissue distribution," *Proc. Natl. Acad. Sci. USA 87*:3052-3056, National Academy of Science (1990).
Yamagami, S., et al., "cDNA Cloning and Functional Expression of a Human Monocyte Chemoattractant Protein 1 Receptor," *Biochem. Biophys. Res. Commun. 202*:1156-1162, Academic Press, Inc. (Jul. 1994).
NCBI Entres, Genbank Report, Accession No. M74240, Beckman, M.P., et al. (1991).
NCBI Entrez, Genbank Report, Accession No. L10918, Gao, J.-L., et al. (1993).
NCBI Entrez, Genbank Report, Accession No. U03882, Charo, I.F., et al. (Jun. 1994).
NCBI Entrez, Genbank Report, Accession No. D10925, Nomura, H., et al. (Sep. 1994).
NCBI Entrez, Genbank Report, Accession No. L09230, Neote, K., et al. (Dec. 1994).
NCBI Entrez, Genbank Report, Accession No. L24445, Prado, G.N., et al. (May 1994).
NCBI Entrez, Genbank Report, Accession No. U29677, Post, T.W., et al. (Jan. 1996).
NCBI Entrez, Genbank Report, Accession No. U28406, Gao, J.L., and Murphy, P.M. (Feb. 1996).
NCBI Entrez, Genbank Report, Accession No. D29984, Yamagami, S., et al. (Aug. 1994).
NCBI Entrez, Genbank Report, Accession No. U47036, Boring, L., et al. (Mar. 1996).
NCBI Entrez, Genbank Report, Accession No. U47035, Boring, L., et al. (Mar. 1996).
NCBI Entrez, Genbank Report, Accession No. U28694, Combadiere, C., et al. (Jun. 1995).
NCBI Entrez, Genbank Report, Accession No. U51717, Kurihara, T., and Bravo, R. (May 1996).
NCBI Entrez, Genbank Report, Accession No. X94151, Meyer, A., et al. (Jul. 1996).
NCBI Entrez, Genbank Report, Accession No. U54994, Report, C.J., et al. (Jul. 1996).
NCBI Entrez, Genbank Report, Accession No. X99393, Samson, M., et al. (Sep. 1996).
NCBI Entrez, Genbank Report, Accession No. U56819, Heesen, M., et al. (Sep. 1996).
NCBI Entrez, Genbank Report, Accession No. U49727, Ponath, P.D., et al. (Aug. 1996).
NCBI Entrez, Genbank Report, Accession No. X91492, Samson, M., et al. (Apr. 1996).
NCBI Entrez, Genbank Report, Accession No. U51241, Daugherty, B.L. (Aug. 1996).
NCBI Entrez, Genbank Report, Accession No. U57840, Combadiere, C., et al. (Jun. 1996).
NCBI Entrez, Genbank Report, Accession No. U68565, Kuziel, W.A., and Maeda, N. (Dec. 1996).
NCBI Entrez, Genbank Report, Accession No. U70988, Dunstan, C.A.N., et al. (Oct. 1996).
Lee, N., and Kerlavage, A.R., "Molecular Biology of G-Protein-Coupled Receptors," *Drug News and Perspectives 6*:488-497, J.R. Prous S.A. (1993).
Oliveira, L., et al., "A common motif in G-protein-coupled seven transmembrane helix receptors," *J. Comput. Aided Mol. Des. 7*:649-658, Escom Science Publishers (1993).
Probst, W.C., et al., "Sequence Alignment of the G-Protein Coupled Receptor Superfamily," *DNA Cell Biol. 11*:1-20, May Ann Liebert, Inc. (1992).
Database UniProt, Accession No. P01608, Hilschmann, N. (first available 1986).
Database UniProt, Accession No. P01594, Schiechl, H. and Hilschmann, N. (first available 1986).
Database UniProt, Accession No. P01607, Palm, W. and Hilschmann, N. (first available 1986).
Database UniProt, Accession No. P01593, Titani, K., et al. (first available 1986).
Database UniProt, Accession No. P80362, Huang, D.-B., et al. (first available 1995).
Database EMBL, Accession No. Z31395, Hawkins, R.E., et al. (first available 1994).
Database EMBL, Accession No. Z34909, David, D. (first available 1995).
Database EMBL, Accession No. AB021535, Hakoda, M. (first available 1999).
Database EMBL, Accession No. U80090, Glas, A.M., et al. (first available 1997).
Database EMBL, Accession No. AY043104, Ghiotto, F., et al., (first available Jan. 2002).
Bendig, M.M., "Humanization of Rodent Monoclonal Antibodies by CDR Grafting," *Methods 8*:83-93, Academic Press, Inc. (Oct. 1995).
Cunningham, M.W., et al., "Cytotoxic and Viral Neutralizing Antibodies Crossreact With Streptococcal M Protein, Enteroviruses, and Human Cardiac Myosin," *Proc. Natl. Acad. Sci. USA 89*:1320-1324, National Academy of Sciences (Feb. 1992).
Horuk, R., "Molecular Properties of the Chemokine Receptor Family," *Trends in Pharmacol. Sci. 15*:159-165, Elsevier Science (May 1994).
Lee, B., et al., "Epitope Mapping of CCR5 Reveals Multiple Conformational States and Distinct but Overlapping Structures Involved in Chemokine and Coreceptor Function," *J. Biol. Chem. 274*:9617-9626, American Society for Biochemistry and Molecular Biology (Apr. 1999).
Olson, W., et al., "Differential Inhibition of Human Immunodeficiency Virus Type 1 Fusion, gp120 Binding, and CC-Chemokine Activity by Monoclonal Antibodies to CCR5," *J. Virol. 73*:4145-4155, American Society for Microbiology (May 1999).
Osbourn, J.K., et al., "Directed Selection of MIP-1α Neutralizing CCR5 Antibodies from a Phage Display Human Antibody Library," *Nature Biotechnol. 16*:778-781, Nature Publishing Group (Aug. 1998).
Schall, T.J., "Biology of the RANTES/SIS Cytokine Family," *Cytokine 3*:165-183, Academic Press, Inc. (May 1991).
Wu, L., et al., "Interaction of Chemokine Receptor CCR5 with its Ligands:Multiple Domains for HIV-1 gp 120 Binding and a Single Domain for Chemokine Binding," *J. Exp. Med. 186*:1373-1381. The Rockefeller University Press (Oct. 1997).
Leong, S.R., et al., "Complete Mutagenesis of the Extracellular Domain of Interleukin-8 (IL-8) Type A Receptor Identifies Charged Residues Mediating IL-8 Binding and Signal Transduction," *J. Biol. Chem. 269*:19343-19348, American Society for Biochemistry and Molecular Biology (1994).
Bowie, J.U., et al. "Deciphering the Message in Protein Sequences: Tolerance to Amino Acid Substitutions," *Science 247*:1306-1310, American Association for the Advancement of Science (1990).
Vila-Coro, A.J., et al., "HIV-1 infection through the CCR5 receptor is blocked by receptor dimerization," *Proc. Natl. Acad. Sci. USA* 97:3388-3393, The National Academy of Sciences, (Mar. 2000).
Baba, M., et al. "A small-molecule, nonpeptide CCR5 antagonist with highly potent and selective anti-HIV activity," *Proc. Natl. Acad. Sci. U.S.A.* 96:5698-5703, National Academy of Sciences (1999).
BD Pharmingen™ Technical Data Sheet, "R-Phycoerythrin (R-PE)-Conjugated Mouse Anti-human Monoclonal Antibody," Revision 002, BD Biosciences Pharmingen (Aug. 2004).

* cited by examiner

```
          10                            30                            50
GTGAGATGGTGCTTTCATGAATTCCCCCAACAAGAGCCAAGCTCTCCATCTAGTGGACAG
          70                            90                           110
GGAAGCTAGCAGCAAACCTTCCCTTCACTACGAAACTTCATTGCTTGGCCCAAAAGAGAG
         130                           150                           170
TTAATTCAATGTAGACATCTATGTAGGCAATTAAAAACCTATTGATGTATAAAACAGTTT
         190                           210                           230
GCATTCATGGAGGGCAACTAAATACATTCTAGGACTTTATAAAAGATCACTTTTTATTTA
         250                           270                           290
TGCACAGGGTGGAACAAGATGGATTATCAAGTGTCAAGTCCAATCTATGACATCAATTAT
                        M  D  Y  Q  V  S  S  P  I  Y  D  I  N  Y
         310                           330                           350
TATACATCGGAGCCCTGCCCAAAAATCAATGTGAAGCAAATCGCAGCCCGCCTCCTGCCT
Y  T  S  E  P  C  P  K  I  N  V  K  Q  I  A  A  R  L  L  P
         370                           390                           410
CCGCTCTACTCACTGGTGTTCATCTTTGGTTTTGTGGGCAACATGCTGGTCATCCTCATC
P  L  Y  S  L  V  F  I  F  G  F  V  G  N  M  L  V  I  L  I
         430                           450                           470
CTGATAAACTGCCAAAGGCTGGAGAGCATGACTGACATCTACCTGCTCAACCTGGCCATC
L  I  N  C  Q  R  L  E  S  M  T  D  I  Y  L  L  N  L  A  I
         490                           510                           530
TCTGACCTGTTTTTCCTTCTTACTGTCCCCTTCTGGGCTCACTATGCTGCCGCCCAGTGG
S  D  L  F  F  L  L  T  V  P  F  W  A  H  Y  A  A  A  Q  W
         550                           570                           590
GACTTTGGAAATACAATGTGTCAACTCTTGACAGGGCTCTATTTTATAGGCTTCTTCTCT
D  F  G  N  T  M  C  Q  L  L  T  G  L  Y  F  I  G  F  F  S
         610                           630                           650
GGAATCTTCTTCATCATCCTCCTGACAATCGATAGGTACCTGGCTATCGTCCATGCTGTG
G  I  F  F  I  I  L  L  T  I  D  R  Y  L  A  I  V  H  A  V
         670                           690                           710
TTTGCTTTAAAAGCCAGGACGGTCACCTTTGGGGTGGTGACAAGTGTGATCACTTGGGTG
F  A  L  K  A  R  T  V  T  F  G  V  V  T  S  V  I  T  W  V
         730                           750                           770
GTGGCTGTGTTTGCGTCTCTCCCAGGAATCATCTTTACCAGATCTCAAAAAGAAGGTCTT
V  A  V  F  A  S  L  P  G  I  I  F  T  R  S  Q  K  E  G  L
         790                           810                           830
CATTACACCTGCAGCTCTCATTTTCCATACAGTCAGTATCAATTCTGGAAGAATTTCCAG
H  Y  T  C  S  S  H  F  P  Y  S  Q  Y  Q  F  W  K  N  F  Q
         850                           870                           890
ACATTAAAGATAGTCATCTTGGGGCTGGTCCTGCCGCTGCTTGTCATGGTCATCTGCTAC
T  L  K  I  V  I  L  G  L  V  L  P  L  L  V  M  V  I  C  Y
         910                           930                           950
TCGGGAATCCTAAAAACTCTGCTTCGGTGTCGAAATGAGAAGAAGAGGCACAGGGCTGTG
S  G  I  L  K  T  L  L  R  C  R  N  E  K  K  R  H  R  A  V
```

FIG.1A

```
        970                 990                1010
AGGCTTATCTTCACCATCATGATTGTTTATTTTCTCTTCTGGGCTCCCTACAACATTGTC
R  L  I  F  T  I  M  I  V  Y  F  L  F  W  A  P  Y  N  I  V
        1030                1050               1070
CTTCTCCTGAACACCTTCCAGGAATTCTTTGGCCTGAATAATTGCAGTAGCTCTAACAGG
L  L  L  N  T  F  Q  E  F  F  G  L  N  N  C  S  S  S  N  R
        1090                1110               1130
TTGGACCAAGCTATGCAGGTGACAGAGACTCTTGGGATGACGCACTGCTGCATCAACCCC
L  D  Q  A  M  Q  V  T  E  T  L  G  M  T  H  C  C  I  N  P
        1150                1170               1190
ATCATCTATGCCTTTGTCGGGGAGAAGTTCAGAAACTACCTCTTAGTCTTCTTCCAAAAG
I  I  Y  A  F  V  G  E  K  F  R  N  Y  L  L  V  F  F  Q  K
        1210                1230               1250
CACATTGCCAAACGCTTCTGCAAATGCTGTTCTATTTTCCAGCAAGAGGCTCCCGAGCGA
H  I  A  K  R  F  C  K  C  C  S  I  F  Q  Q  E  A  P  E  R
        1270                1290               1310
GCAAGCTCAGTTTACACCCGATCCACTGGGGAGCAGGAAATATCTGTGGGCTTGTGACAC
A  S  S  V  Y  T  R  S  T  G  E  Q  E  I  S  V  G  L  *
        1330                1350               1370
GGACTCAAGTGGGCTGGTGACCCAGTCAGAGTTGTGCACATGGCTTAGTTTTCATACACA
        1390                1410
GCCTGGGCTGGGGGTGGGGTGGAAGAGGTCTTTT
```

FIG.1B

```
               .         .         .         .         .
   4  QVSSPIYDINYYTSEPCPKINVKQIAARLLPPLYSLVFIFGFVGNMLVIL  53
      :  ..::|.:|  :.||.|::||||:|.||||||||||||||||||||:|
  18  EEVTTFFDYDY..GAPCHKFDVKQIGAQLLPPLYSLVFIFGFVGNMLVVL  65

               .         .         .         .         .
  54  ILINCQRLESMTDIYLLNLAISDLFFLLTVPFWAHYAAAQWDFGNTMCQL  103
      |||||.:|.::|||||||||||||:||:|:|:||| ||.:| |||.||.|
  66  ILINCKKLKCLTDIYLLNLAISDLLFLITLPLWAHSAANEWVFGNAMCKL  115

               .         .         .         .         .
 104  LTGLYFIGFFSGIFFIILLTIDRYLAIVHAVFALKARTVTFGVVTSVITW  153
      :|||| ||:|:|||||||||||||||||||||||||||||||||||||||
 116  FTGLYHIGYFGGIFFIILLTIDRYLAIVHAVFALKARTVTFGVVTSVITW  165

               .         .         .         .         .
 154  VVAVFASLPGIIFTRSQKEGLHYTCSSHFPYSQYQFWKNFQTLKIVILGL  203
      :||||||:||||||::|||:  |.|:..|| :    |.||:|:.  ||||
 166  LVAVFASVPGIIFTKCQKEDSVYVCGPYFPRG....WNNFHTIMRNILGL  211

               .         .         .         .         .
 204  VLPLLVMVICYSGILKTLLRCRNEKKRHRAVRLIFTIMIVYFLFWAPYNI  253
      |||||:||||||||||||||||||||||||||:||||||||||||.||||
 212  VLPLLIMVICYSGILKTLLRCRNEKKRHRAVRVIFTIMIVYFLFWTPYNI  261

               .         .         .         .         .
 254  VLLLNTFQEFFGLNNCSSSNRLDQAMQVTETLGMTHCCINPIIYAFVGEK  303
      |:|||||||||||.||.|...|||| ||||||||||||||||||||||||
 262  VILLNTFQEFFGLSNCESTSQLDQATQVTETLGMTHCCINPIIYAFVGEK  311

               .         .         .         .         .
 304  FRNYLLVFFQKHIAKRFCKCCSIFQQEAPERASSVYTRS...TGEQEISV  350
      ||..: : :. :|| .: |..:  ..  |::. .| |.:   . :.: |:
 312  FRSLFHIALGCRIA.PLQKPVCGGPGVRPGKNVKVTTQGLLDGRGKGKSI  360

 351  G 351
      |
 361  G 361
```

Anti-CCR5 1D8 VH Sequence

1 CAG GTG CAG CTG CAG GAG TCG GGC CCA GGA CTG GTG AAG CCT TCG GAG ACC CTG TCC CTC
1 Q V Q L Q E S G P G L V K P S E T L S L

CDR1

61 ACC TGC ACT GTC TCT GGT GGC TCC ATC AGT AGT TTC TAC TGG AGC TGG ATC CGG CAG CCC
21 T C T V S G G S I S S F Y W S W I R Q P

CDR2

121 GCC GGG AAG GGA CTG GAC TGG ATT GGG CGT ATC TAT ACC AGC GGG AAC ACC AAC TAC AAC
41 A G K G L D W I G R I Y T S G N T N Y N

181 CCC TCC CTC AAG AGT CGA GTC ACC ATG TCA GTA GAC ACG TCC AAG AAC CGG TTC TCC CTG
61 P S L K S R V T M S V D T S K N R F S L

241 AAA CTG AGC TCT GTG ACC GCC GCG GAC ACG GCC GTG TAT TAC TGT GCG AGA GAT CGG GGC
81 K L S S V T A A D T A V Y Y C A R D R G

CDR3

301 AGC AGC TGG TAC CCC GAT GCT TTT GAT ATC TGG GGC CAA GGG ACA ATG GTC ACC GTC TCC
101 S S W Y P D A F D I W G Q G T M V T V S

361 TCA
121 S

Anti-CCR5 1D8 VK Sequence

1 GAT ATT GTG TTG ACG CAT TCT CCA GGC ACC CTG TCT TTG TCT CCA GGG GAA AGA GCC ACC
1 D I V L T H S P G T L S L S P G E R A T

CDR1

61 CTC TCC TGC AGG GCC AGT CAG CGT GTT ACC AGC AGC TGC TTA GCC TGG TAC CAG CAG AAA
21 L S C R A S Q R V T S S C L A W Y Q Q K

CDR2

121 CCT GGC CAG GCT CCC AGG CTC CTC ATC TAT GGT ACA TCC AGC AGG GCC ACT GGC ATC CCA
41 P G Q A P R L L I Y G T S S R A T G I P

181 GAC AGG TTC AGT GGC AGT GGG TCT GGG ACA GAC TTC ACT CTC ACC ATC AGC AGA CTG GAG
61 D R F S G S G S G T D F T L T I S R L E

CDR3

241 CCT GAA GAT TTT GCA GTG TAT TAC TGT CAG CAG TAT GTT AGC TCA CCT CTC ACC TTC GGC
81 P E D F A V Y Y C Q Q Y V S S P L T F G

301 CAA GGG ACA CGA CTC GAG ATC AAA CGT
101 Q G T R L E I K R

FIG.4

Anti-CCR5 3C9 VH

1 GAG GTG CAG CTG GTG GAG TCT GGG GGA GGC TTG GTA AAG TCT GGG GGG TCC CTT AGA CTC 60
1 E V Q L V E S G G G L V K S G G S L R L 20

CDR1

61 TCC TGT GCA GCC TCC GGA TTC ACT TTC AGT AAC GCC TGG ATG ACC TGG GTC CGC CAG GCT 120
21 S C A A S G F T F S N A W M T W V R Q A 40

CDR2

121 CCA GGG AAG AGG CTG GAG TGG GTT GGC CGT ATT AAA AGC AAT GCT GAT GGT GGG TCA ACA 180
41 P G K R L E W V G R I K S N A D G G S T 60

181 GAC TAC GCT GCA CCC GTG AAA GGC AGA TTC ACC ATC TCA AGA GAT GAT TCA AAA AAC ACG 240
61 D Y A A P V K G R F T I S R D D S K N T 80

241 CTG TAT CTG CAA ATG AAC AGC CTG AAA ACC GAG GAC ACA GCC GTG TAT TAC TGT AAC ACA 300
81 L Y L Q M N S L K T E D T A V Y Y C N T 100

CDR3

301 GAT AAG GGT GGG AGC TAC CCC TAC TAC TAC TAC GGT ATG GAC GTC TGG GGC CAA GGG ACC 360
101 D K G G S Y P Y Y Y Y G M D V W G Q G T 120

361 ACG GTC ACC GTC TCC TCA G 379
121 T V T V S S 127

Anti-CCR5 3C9 VK

1 GAC ATC CAG ATG ACC CAG TCT CCA TCC TCC CTG TCT GCA TCT GTA GGA GAC AGA GTC ACC 60
1 D I Q M T Q S P S S L S A S V G D R V T 20

CDR1

61 ATC ACT TGC CGG GCA AGT CAG GGC ATT AGA AAT GAT TTA GGC TGG TAT CAG CAG AAA CCA 120
21 I T C R A S Q G I R N D L G W Y Q Q K P 40

CDR2

121 GGG AAA GCC CCT AAG CGC CTG ATC TAT GAT GCA TCC AGT TTG CAA AGT GGG GTC CCA TCA 180
41 G K A P K R L I Y D A S S L Q S G V P S 60

181 AGG TTC AGC GGC AGT GGA TCT GGG ACA GAA TTC ACT CTC ACA ATC AGC AGC CTG CAG CCT 240
61 R F S G S G S G T E F T L T I S S L Q P 80

CDR3

241 GAA GAT TTT GCA ACT TAT TAC TGT CTA CAG CAT AAT AGT TAC CCA TTC ACT TTC GGC CCT 300
81 E D F A T Y Y C L Q H N S Y P F T F G P 100

301 GGG ACC AAA GTG GAT ATC AAA CGA 324
101 G T K V D I K R 108

FIG.5

Anti-CCR5 9E6 VH

```
  1 GAG GTG CAG CTG GTG GAG TCT GGC CCA GGA CTG GTG AAG CCT TCG GAG ACC CTG TCC CTC  60
  1  E   V   Q   L   V   E   S   G   P   G   L   V   K   P   S   E   T   L   S   L   20
                                            CDR1
 61 ACC TGC ACT GTC TCT GGT GGC TCC ATC AGT AGT TAC TAC TGG AGC TGG ATC CGG CAG CCC 120
 21  T   C   T   V   S   G   G   S   I   S   S   Y   Y   W   S   W   I   R   Q   P   40
                                                         CDR2
121 CCA GGG AAG GGA CTG GAG TGG ATT GGG TAT ATC TAT TAC AGT GGG AGC ACC AAC TAC AAC 180
 41  P   G   K   G   L   E   W   I   G   Y   I   Y   Y   S   G   S   T   N   Y   N   60

181 CCC TCC CTC AAG AGT CGA GTC ACC ATA TCA GTA GAC ACG TCC AAG AAC CAG TTC TCC CTG 240
 61  P   S   L   K   S   R   V   T   I   S   V   D   T   S   K   N   Q   F   S   L   80

241 AAG CTG AGC TCT GTG ACC GCT GCG GAC ACG GCC GTG TAT TAC TGT GCG AGA GAT GTC ATG 300
 81  K   L   S   S   V   T   A   A   D   T   A   V   Y   Y   C   A   R   D   V   M  100
                                CDR3
301 CAG CAG CCG GTA CGG GGT TAC TAC TAC TAC TAC GGT ATG GAC GTC TGG GGC CAA GGA ACC 360
101  Q   Q   P   V   R   G   Y   Y   Y   Y   Y   G   M   D   V   W   G   Q   G   T  120

361 CTG GTC ACC GTC TCC TCA 378
121  L   V   T   V   S   S  126
```

Anti-CCR5 9E6 VK

```
  1 GAA ATT GTG TTG ACG CAG TCT CCA GGC ACC CTG TCT TTG TCT CCA GGG GAA AGA GTC ACC  60
  1  E   I   V   L   T   Q   S   P   G   T   L   S   L   S   P   G   E   R   V   T   20
                                  CDR1
 61 CTC TCC TGC AGG GCC AGT CAG AGA GTT AGC AAC AGC TAC TTA GCC TGG TAC CAG CAG AAA 120
 21  L   S   C   R   A   S   Q   R   V   S   N   S   Y   L   A   W   Y   Q   Q   K   40
                                                       CDR2
121 CCT GGC CAG GCT CCC AGG TTC CTC ATC TAT GGT GTA TCC AGC AGG GCC ACT GGC ATC CCA 180
 41  P   G   Q   A   P   R   F   L   I   Y   G   V   S   S   R   A   T   G   I   P   60

181 GAC AGG TTC AGT GGC AGT GGG TCT GGG ACA GAC TTC ACT CTC ACC ATC AGC AGA CTG GAG 240
 61  D   R   F   S   G   S   G   S   G   T   D   F   T   L   T   I   S   R   L   E   80
                                                          CDR3
241 CCT GAA GAT TTT GCA GTG TAT TAC TGT CAG CAG TAT GGT AGT TCA CCG TGG ACG TTC GGC 300
 81  P   E   D   F   A   V   Y   Y   C   Q   Q   Y   G   S   S   P   W   T   F   G  100

301 CAA GGG ACC AAG GTG GAA ATC AAA CGA 327
101  Q   G   T   K   V   E   I   K   R  109
```

FIG.6

SEQUENCE LISTING

```
<160> NUMBER OF SEQ ID NOS: 70

<210> SEQ ID NO 1
<211> LENGTH: 1414
<212> TYPE: DNA
<213> ORGANISM: Homo sapiens
<220> FEATURE:
<221> NAME/KEY: CDS
<222> LOCATION: (259)..(1314)

<400> SEQUENCE: 1

gtgagatggt gctttcatga attcccccaa caagagccaa gctctccatc tagtggacag      60

ggaagctagc agcaaacctt cccttcacta cgaaacttca ttgcttggcc caaaagagag     120

ttaattcaat gtagacatct atgtaggcaa ttaaaaacct attgatgtat aaaacagttt     180

gcattcatgg agggcaacta aatacattct aggactttat aaaagatcac tttttattta     240

tgcacagggt ggaacaag atg gat tat caa gtg tca agt cca atc tat gac       291
                    Met Asp Tyr Gln Val Ser Ser Pro Ile Tyr Asp
                    1               5                   10

atc aat tat tat aca tcg gag ccc tgc cca aaa atc aat gtg aag caa       339
Ile Asn Tyr Tyr Thr Ser Glu Pro Cys Pro Lys Ile Asn Val Lys Gln
            15                  20                  25

atc gca gcc cgc ctc ctg cct ccg ctc tac tca ctg gtg ttc atc ttt       387
Ile Ala Ala Arg Leu Leu Pro Pro Leu Tyr Ser Leu Val Phe Ile Phe
        30                  35                  40

ggt ttt gtg ggc aac atg ctg gtc atc ctc atc ctg ata aac tgc caa       435
Gly Phe Val Gly Asn Met Leu Val Ile Leu Ile Leu Ile Asn Cys Gln
    45                  50                  55

agg ctg gag agc atg act gac atc tac ctg ctc aac ctg gcc atc tct       483
Arg Leu Glu Ser Met Thr Asp Ile Tyr Leu Leu Asn Leu Ala Ile Ser
60                  65                  70                  75

gac ctg ttt ttc ctt ctt act gtc ccc ttc tgg gct cac tat gct gcc       531
Asp Leu Phe Phe Leu Leu Thr Val Pro Phe Trp Ala His Tyr Ala Ala
                80                  85                  90

gcc cag tgg gac ttt gga aat aca atg tgt caa ctc ttg aca ggg ctc       579
Ala Gln Trp Asp Phe Gly Asn Thr Met Cys Gln Leu Leu Thr Gly Leu
            95                  100                 105

tat ttt ata ggc ttc ttc tct gga atc ttc ttc atc atc ctc ctg aca       627
Tyr Phe Ile Gly Phe Phe Ser Gly Ile Phe Phe Ile Ile Leu Leu Thr
        110                 115                 120

atc gat agg tac ctg gct atc gtc cat gct gtg ttt gct tta aaa gcc       675
Ile Asp Arg Tyr Leu Ala Ile Val His Ala Val Phe Ala Leu Lys Ala
    125                 130                 135

agg acg gtc acc ttt ggg gtg gtg aca agt gtg atc act tgg gtg gtg       723
```

-continued

```
Arg Thr Val Thr Phe Gly Val Val Thr Ser Val Ile Thr Trp Val Val
140                 145                 150                 155

gct gtg ttt gcg tct ctc cca gga atc atc ttt acc aga tct caa aaa      771
Ala Val Phe Ala Ser Leu Pro Gly Ile Ile Phe Thr Arg Ser Gln Lys
                160                 165                 170

gaa ggt ctt cat tac acc tgc agc tct cat ttt cca tac agt cag tat      819
Glu Gly Leu His Tyr Thr Cys Ser Ser His Phe Pro Tyr Ser Gln Tyr
            175                 180                 185

caa ttc tgg aag aat ttc cag aca tta aag ata gtc atc ttg ggg ctg      867
Gln Phe Trp Lys Asn Phe Gln Thr Leu Lys Ile Val Ile Leu Gly Leu
        190                 195                 200

gtc ctg ccg ctg ctt gtc atg gtc atc tgc tac tcg gga atc cta aaa      915
Val Leu Pro Leu Leu Val Met Val Ile Cys Tyr Ser Gly Ile Leu Lys
    205                 210                 215

act ctg ctt cgg tgt cga aat gag aag aag agg cac agg gct gtg agg      963
Thr Leu Leu Arg Cys Arg Asn Glu Lys Lys Arg His Arg Ala Val Arg
220                 225                 230                 235

ctt atc ttc acc atc atg att gtt tat ttt ctc ttc tgg gct ccc tac     1011
Leu Ile Phe Thr Ile Met Ile Val Tyr Phe Leu Phe Trp Ala Pro Tyr
                240                 245                 250

aac att gtc ctt ctc ctg aac acc ttc cag gaa ttc ttt ggc ctg aat     1059
Asn Ile Val Leu Leu Leu Asn Thr Phe Gln Glu Phe Phe Gly Leu Asn
            255                 260                 265

aat tgc agt agc tct aac agg ttg gac caa gct atg cag gtg aca gag     1107
Asn Cys Ser Ser Ser Asn Arg Leu Asp Gln Ala Met Gln Val Thr Glu
        270                 275                 280

act ctt ggg atg acg cac tgc tgc atc aac ccc atc atc tat gcc ttt     1155
Thr Leu Gly Met Thr His Cys Cys Ile Asn Pro Ile Ile Tyr Ala Phe
    285                 290                 295

gtc ggg gag aag ttc aga aac tac ctc tta gtc ttc ttc caa aag cac     1203
Val Gly Glu Lys Phe Arg Asn Tyr Leu Leu Val Phe Phe Gln Lys His
300                 305                 310                 315

att gcc aaa cgc ttc tgc aaa tgc tgt tct att ttc cag caa gag gct     1251
Ile Ala Lys Arg Phe Cys Lys Cys Cys Ser Ile Phe Gln Gln Glu Ala
                320                 325                 330

ccc gag cga gca agc tca gtt tac acc cga tcc act ggg gag cag gaa     1299
Pro Glu Arg Ala Ser Ser Val Tyr Thr Arg Ser Thr Gly Glu Gln Glu
            335                 340                 345

ata tct gtg ggc ttg tgacacggac tcaagtgggc tggtgaccca gtcagagttg     1354
Ile Ser Val Gly Leu
        350

tgcacatggc ttagttttca tacacagcct gggctggggg tggggtggaa gaggtctttt   1414


<210> SEQ ID NO 2
<211> LENGTH: 352
<212> TYPE: PRT
<213> ORGANISM: Homo sapiens

<400> SEQUENCE: 2

Met Asp Tyr Gln Val Ser Ser Pro Ile Tyr Asp Ile Asn Tyr Tyr Thr
1               5                   10                  15

Ser Glu Pro Cys Pro Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Gln Arg Leu Glu Ser Met
    50                  55                  60

Thr Asp Ile Tyr Leu Leu Asn Leu Ala Ile Ser Asp Leu Phe Phe Leu
65                  70                  75                  80
```

-continued

```
Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Ile Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350
```

<210> SEQ ID NO 3
<211> LENGTH: 30
<212> TYPE: DNA
<213> ORGANISM: Artificial Sequence
<220> FEATURE:
<223> OTHER INFORMATION: 5' Oligonucleotide primer for HDGNR10

<400> SEQUENCE: 3
cggaattcct ccatggatta tcaagtgtca 30

<210> SEQ ID NO 4
<211> LENGTH: 29
<212> TYPE: DNA
<213> ORGANISM: Artificial Sequence
<220> FEATURE:
<223> OTHER INFORMATION: 3' Oligonucleotide primer for HDGNR10

<400> SEQUENCE: 4
cggaagcttc gtcacaagcc cacagatat 29

<210> SEQ ID NO 5
<211> LENGTH: 34

-continued

<212> TYPE: DNA
<213> ORGANISM: Artificial Sequence
<220> FEATURE:
<223> OTHER INFORMATION: 5' Oligonucleotide primer for HDGNR10

<400> SEQUENCE: 5
gtccaagctt gccaccatgg attatcaagt gtca 34

<210> SEQ ID NO 6
<211> LENGTH: 61
<212> TYPE: DNA
<213> ORGANISM: Artificial Sequence
<220> FEATURE:
<223> OTHER INFORMATION: 3' Oligonucleotide primer for HDGNR10

<400> SEQUENCE: 6
ctagctcgag tcaagcgtag tctgggacgt cgtatgggta gcacaagccc acagatattt 60
c 61

<210> SEQ ID NO 7
<211> LENGTH: 30
<212> TYPE: DNA
<213> ORGANISM: Artificial Sequence
<220> FEATURE:
<223> OTHER INFORMATION: 5' Oligonucleotide primer for HDGNR10

<400> SEQUENCE: 7
cgggatccct ccatggatta tcaagtgtca 30

<210> SEQ ID NO 8
<211> LENGTH: 29
<212> TYPE: DNA
<213> ORGANISM: Artificial Sequence
<220> FEATURE:
<223> OTHER INFORMATION: 3' Oligonucleotide primer for HDGNR10

<400> SEQUENCE: 8
cgggatcccg ctcacaagcc cacagatat 29

<210> SEQ ID NO 9
<211> LENGTH: 344
<212> TYPE: PRT
<213> ORGANISM: Homo sapiens

<400> SEQUENCE: 9

Glu Glu Val Thr Thr Phe Phe Asp Tyr Asp Tyr Gly Ala Pro Cys His
1 5 10 15

Lys Phe Asp Val Lys Gln Ile Gly Ala Gln Leu Leu Pro Pro Leu Tyr
20 25 30

Ser Leu Val Phe Ile Phe Gly Phe Val Gly Asn Met Leu Val Val Leu
35 40 45

Ile Leu Ile Asn Cys Lys Lys Leu Lys Cys Leu Thr Asp Ile Tyr Leu
50 55 60

Leu Asn Leu Ala Ile Ser Asp Leu Leu Phe Leu Ile Thr Leu Pro Leu
65 70 75 80

Trp Ala His Ser Ala Ala Asn Glu Trp Val Phe Gly Asn Ala Met Cys
85 90 95

Lys Leu Phe Thr Gly Leu Tyr His Ile Gly Tyr Phe Gly Gly Ile Phe
100 105 110

Phe Ile Ile Leu Leu Thr Ile Asp Arg Tyr Leu Ala Ile Val His Ala
115 120 125

-continued

Val Phe Ala Leu Lys Ala Arg Thr Val Thr Phe Gly Val Val Thr Ser
130 135 140

Val Ile Thr Trp Leu Val Ala Val Phe Ala Ser Val Pro Gly Ile Ile
145 150 155 160

Phe Thr Lys Cys Gln Lys Glu Asp Ser Val Tyr Val Cys Gly Pro Tyr
165 170 175

Phe Pro Arg Gly Trp Asn Asn Phe His Thr Ile Met Arg Asn Ile Leu
180 185 190

Gly Leu Val Leu Pro Leu Leu Ile Met Val Ile Cys Tyr Ser Gly Ile
195 200 205

Leu Lys Thr Leu Leu Arg Cys Arg Asn Glu Lys Lys Arg His Arg Ala
210 215 220

Val Arg Val Ile Phe Thr Ile Met Ile Val Tyr Phe Leu Phe Trp Thr
225 230 235 240

Pro Tyr Asn Ile Val Ile Leu Leu Asn Thr Phe Gln Glu Phe Phe Gly
245 250 255

Leu Ser Asn Cys Glu Ser Thr Ser Gln Leu Asp Gln Ala Thr Gln Val
260 265 270

Thr Glu Thr Leu Gly Met Thr His Cys Cys Ile Asn Pro Ile Ile Tyr
275 280 285

Ala Phe Val Gly Glu Lys Phe Arg Ser Leu Phe His Ile Ala Leu Gly
290 295 300

Cys Arg Ile Ala Pro Leu Gln Lys Pro Val Cys Gly Gly Pro Gly Val
305 310 315 320

Arg Pro Gly Lys Asn Val Lys Val Thr Thr Gln Gly Leu Leu Asp Gly
325 330 335

Arg Gly Lys Gly Lys Ser Ile Gly
340

<210> SEQ ID NO 10
<211> LENGTH: 733
<212> TYPE: DNA
<213> ORGANISM: Homo sapiens

<400> SEQUENCE: 10
gggatccgga gcccaaatct tctgacaaaa ctcacacatg cccaccgtgc ccagcacctg 60
aattcgaggg tgcaccgtca gtcttcctct tccccccaaa acccaaggac accctcatga 120
tctcccggac tcctgaggtc acatgcgtgg tggtggacgt aagccacgaa gaccctgagg 180
tcaagttcaa ctggtacgtg gacggcgtgg aggtgcataa tgccaagaca aagccgcggg 240
aggagcagta caacagcacg taccgtgtgg tcagcgtcct caccgtcctg caccaggact 300
ggctgaatgg caaggagtac aagtgcaagg tctccaacaa agccctccca acccccatcg 360
agaaaaccat ctccaaagcc aaagggcagc cccgagaacc acaggtgtac accctgcccc 420
catcccggga tgagctgacc aagaaccagg tcagcctgac ctgcctggtc aaaggcttct 480
atccaagcga catcgccgtg gagtgggaga gcaatgggca gccggagaac aactacaaga 540
ccacgcctcc cgtgctggac tccgacggct ccttcttcct ctacagcaag ctcaccgtgg 600
acaagagcag gtggcagcag gggaacgtct tctcatgctc cgtgatgcat gaggctctgc 660
acaaccacta cacgcagaag agcctctccc tgtctccggg taaatgagtg cgacggccgc 720
gactctagag gat 733

<210> SEQ ID NO 11
<211> LENGTH: 5

-continued

<212> TYPE: PRT
<213> ORGANISM: Membrane proximal region motif
<220> FEATURE:
<221> NAME/KEY: Variant
<222> LOCATION: (3)
<223> OTHER INFORMATION: May be any amino acid

<400> SEQUENCE: 11

Trp Ser Xaa Trp Ser
1 5

<210> SEQ ID NO 12
<211> LENGTH: 86
<212> TYPE: DNA
<213> ORGANISM: Artificial Sequence
<220> FEATURE:
<223> OTHER INFORMATION: 5' Primer for Gamma Activation Site-SV40 Early Promoter Construct

<400> SEQUENCE: 12
gcgcctcgag atttccccga aatctagatt tccccgaaat gatttccccg aaatgatttc 60
cccgaaatat ctgccatctc aattag 86

<210> SEQ ID NO 13
<211> LENGTH: 27
<212> TYPE: DNA
<213> ORGANISM: Artificial Sequence
<220> FEATURE:
<223> OTHER INFORMATION: 3' Oligonucleotide primer for SV40 Early Promoter

<400> SEQUENCE: 13
gcggcaagct ttttgcaaag cctaggc 27

<210> SEQ ID NO 14
<211> LENGTH: 271
<212> TYPE: DNA
<213> ORGANISM: Artificial Sequence
<220> FEATURE:
<223> OTHER INFORMATION: Gamma Activation Site-SV40 Early Promoter Construct

<400> SEQUENCE: 14
ctcgagattt ccccgaaatc tagatttccc cgaaatgatt tccccgaaat gatttccccg 60
aaatatctgc catctcaatt agtcagcaac catagtcccg cccctaactc cgcccatccc 120
gcccctaact ccgcccagtt ccgcccattc tccgccccat ggctgactaa ttttttttat 180
ttatgcagag gccgaggccg cctcggcctc tgagctattc cagaagtagt gaggaggctt 240
ttttggaggc ctaggctttt gcaaaaagct t 271

<210> SEQ ID NO 15
<211> LENGTH: 32
<212> TYPE: DNA
<213> ORGANISM: Artificial Sequence
<220> FEATURE:
<223> OTHER INFORMATION: 5' Oligonucleotide primer for EGR-1 Promoter Sequence

<400> SEQUENCE: 15
gcgctcgagg gatgacagcg atagaacccc gg 32

<210> SEQ ID NO 16
<211> LENGTH: 31
<212> TYPE: DNA
<213> ORGANISM: Artificial Sequence
<220> FEATURE:

-continued

<223> OTHER INFORMATION: 3' Oligonucleotide primer for EGR-1 Promoter Sequence

<400> SEQUENCE: 16
gcgaagcttc gcgactcccc ggatccgcct c 31

<210> SEQ ID NO 17
<211> LENGTH: 12
<212> TYPE: DNA
<213> ORGANISM: Homo Sapiens

<400> SEQUENCE: 17
ggggactttc cc 12

<210> SEQ ID NO 18
<211> LENGTH: 73
<212> TYPE: DNA
<213> ORGANISM: Artificial Sequence
<220> FEATURE:
<223> OTHER INFORMATION: 5' Oligonucleotide primer for NF-KB-SV40 Early Promoter Construct

<400> SEQUENCE: 18
gcggcctcga ggggactttc ccggggactt tccggggact ttccgggact ttccatcctg 60
ccatctcaat tag 73

<210> SEQ ID NO 19
<211> LENGTH: 27
<212> TYPE: DNA
<213> ORGANISM: Artificial Sequence
<220> FEATURE:
<223> OTHER INFORMATION: 3' Oligonucleotide primer for SV40 Early Promoter

<400> SEQUENCE: 19
gcggcaagct ttttgcaaag cctaggc 27

<210> SEQ ID NO 20
<211> LENGTH: 256
<212> TYPE: DNA
<213> ORGANISM: Artificial Sequence
<220> FEATURE:
<223> OTHER INFORMATION: NF-KB-SV40 Early Promoter Construct

<400> SEQUENCE: 20
ctcgagggga ctttcccggg gactttccgg ggactttccg ggactttcca tctgccatct 60
caattagtca gcaaccatag tcccgcccct aactccgccc atcccgcccc taactccgcc 120
cagttccgcc cattctccgc cccatggctg actaattttt tttatttatg cagaggccga 180
ggccgcctcg gcctctgagc tattccagaa gtagtgagga ggcttttttg gaggcctagg 240
cttttgcaaa aagctt 256

<210> SEQ ID NO 21
<211> LENGTH: 1056
<212> TYPE: DNA
<213> ORGANISM: Homo sapiens
<220> FEATURE:
<221> NAME/KEY: CDS
<222> LOCATION: (1)..(1056)

<400> SEQUENCE: 21

```
atg gat tat caa gtg tca agt cca atc tat gac atc aat tat tat aca       48
Met Asp Tyr Gln Val Ser Ser Pro Ile Tyr Asp Ile Asn Tyr Tyr Thr
1               5                   10                  15
```

-continued

```
tcg gag ccc tgc caa aaa atc aat gtg aag caa atc gca gcc cgc ctc        96
Ser Glu Pro Cys Gln Lys Ile Asn Val Lys Gln Ile Ala Ala Arg Leu
            20                  25                  30

ctg cct ccg ctc tac tca ctg gtg ttc atc ttt ggt ttt gtg ggc aac       144
Leu Pro Pro Leu Tyr Ser Leu Val Phe Ile Phe Gly Phe Val Gly Asn
        35                  40                  45

atg ctg gtc atc ctc atc ctg ata aac tgc aaa agg ctg aag agc atg       192
Met Leu Val Ile Leu Ile Leu Ile Asn Cys Lys Arg Leu Lys Ser Met
    50                  55                  60

act gac atc tac ctg ctc aac ctg gcc atc tct gac ctg ttt ttc ctt       240
Thr Asp Ile Tyr Leu Leu Asn Leu Ala Ile Ser Asp Leu Phe Phe Leu
65                  70                  75                  80

ctt act gtc ccc ttc tgg gct cac tat gct gcc gcc cag tgg gac ttt       288
Leu Thr Val Pro Phe Trp Ala His Tyr Ala Ala Ala Gln Trp Asp Phe
                85                  90                  95

gga aat aca atg tgt caa ctc ttg aca ggg ctc tat ttt ata ggc ttc       336
Gly Asn Thr Met Cys Gln Leu Leu Thr Gly Leu Tyr Phe Ile Gly Phe
            100                 105                 110

ttc tct gga atc ttc ttc atc atc ctc ctg aca atc gat agg tac ctg       384
Phe Ser Gly Ile Phe Phe Ile Ile Leu Leu Thr Ile Asp Arg Tyr Leu
        115                 120                 125

gct gtc gtc cat gct gtg ttt gct tta aaa gcc agg acg gtc acc ttt       432
Ala Val Val His Ala Val Phe Ala Leu Lys Ala Arg Thr Val Thr Phe
    130                 135                 140

ggg gtg gtg aca agt gtg atc act tgg gtg gtg gct gtg ttt gcg tct       480
Gly Val Val Thr Ser Val Ile Thr Trp Val Val Ala Val Phe Ala Ser
145                 150                 155                 160

ctc cca gga atc atc ttt acc aga tct caa aaa gaa ggt ctt cat tac       528
Leu Pro Gly Ile Ile Phe Thr Arg Ser Gln Lys Glu Gly Leu His Tyr
                165                 170                 175

acc tgc agc tct cat ttt cca tac agt cag tat caa ttc tgg aag aat       576
Thr Cys Ser Ser His Phe Pro Tyr Ser Gln Tyr Gln Phe Trp Lys Asn
            180                 185                 190

ttc cag aca tta aag ata gtc atc ttg ggg ctg gtc ctg ccg ctg ctt       624
Phe Gln Thr Leu Lys Ile Val Ile Leu Gly Leu Val Leu Pro Leu Leu
        195                 200                 205

gtc atg gtc atc tgc tac tcg gga atc cta aaa act ctg ctt cgg tgt       672
Val Met Val Ile Cys Tyr Ser Gly Ile Leu Lys Thr Leu Leu Arg Cys
    210                 215                 220

cga aat gag aag aag agg cac agg gct gtg agg ctt atc ttc acc atc       720
Arg Asn Glu Lys Lys Arg His Arg Ala Val Arg Leu Ile Phe Thr Ile
225                 230                 235                 240

atg att gtt tat ttt ctc ttc tgg gct ccc tac aac att gtc ctt ctc       768
Met Ile Val Tyr Phe Leu Phe Trp Ala Pro Tyr Asn Ile Val Leu Leu
                245                 250                 255

ctg aac acc ttc cag gaa ttc ttt ggc ctg aat aat tgc agt agc tct       816
Leu Asn Thr Phe Gln Glu Phe Phe Gly Leu Asn Asn Cys Ser Ser Ser
            260                 265                 270

aac agg ttg gac caa gct atg cag gtg aca gag act ctt ggg atg acg       864
Asn Arg Leu Asp Gln Ala Met Gln Val Thr Glu Thr Leu Gly Met Thr
        275                 280                 285

cac tgc tgc atc aac ccc atc atc tat gcc ttt gtc ggg gag aag ttc       912
His Cys Cys Ile Asn Pro Ile Ile Tyr Ala Phe Val Gly Glu Lys Phe
    290                 295                 300

aga aac tac ctc tta gtc ttc ttc caa aag cac att gcc aaa cgc ttc       960
Arg Asn Tyr Leu Leu Val Phe Phe Gln Lys His Ile Ala Lys Arg Phe
305                 310                 315                 320

tgc aaa tgc tgt tct att ttc cag caa gag gct ccc gag cga gca agc      1008
Cys Lys Cys Cys Ser Ile Phe Gln Gln Glu Ala Pro Glu Arg Ala Ser
                325                 330                 335
```

```
tca gtt tac acc cga tcc act gag gag cag gaa ata tct gtg ggc ttg      1056
Ser Val Tyr Thr Arg Ser Thr Glu Glu Gln Glu Ile Ser Val Gly Leu
            340                 345                 350


<210> SEQ ID NO 22
<211> LENGTH: 352
<212> TYPE: PRT
<213> ORGANISM: Homo sapiens

<400> SEQUENCE: 22

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Glu Glu Gln Glu Ile Ser Val Gly Leu
            340                 345                 350
```

-continued

<210> SEQ ID NO 23
<211> LENGTH: 23
<212> TYPE: DNA
<213> ORGANISM: Artificial Sequence
<220> FEATURE:
<223> OTHER INFORMATION: 5' Oligonucleotide primer for VH Domain

<400> SEQUENCE: 23
caggtgcagc tggtgcagtc tgg 23

<210> SEQ ID NO 24
<211> LENGTH: 23
<212> TYPE: DNA
<213> ORGANISM: Artificial Sequence
<220> FEATURE:
<223> OTHER INFORMATION: 5' Oligonucleotide primer for VH Domain

<400> SEQUENCE: 24
caggtcaact taagggagtc tgg 23

<210> SEQ ID NO 25
<211> LENGTH: 23
<212> TYPE: DNA
<213> ORGANISM: Artificial Sequence
<220> FEATURE:
<223> OTHER INFORMATION: 5' Oligonucleotide primer for VH Domain

<400> SEQUENCE: 25
gaggtgcagc tggtggagtc tgg 23

<210> SEQ ID NO 26
<211> LENGTH: 23
<212> TYPE: DNA
<213> ORGANISM: Artificial Sequence
<220> FEATURE:
<223> OTHER INFORMATION: 5' Oligonucleotide primer for VH Domain

<400> SEQUENCE: 26
caggtgcagc tgcaggagtc ggg 23

<210> SEQ ID NO 27
<211> LENGTH: 23
<212> TYPE: DNA
<213> ORGANISM: Artificial Sequence
<220> FEATURE:
<223> OTHER INFORMATION: 5' Oligonucleotide primer for VH Domain

<400> SEQUENCE: 27
gaggtgcagc tgttgcagtc tgc 23

<210> SEQ ID NO 28
<211> LENGTH: 23
<212> TYPE: DNA
<213> ORGANISM: Artificial Sequence
<220> FEATURE:
<223> OTHER INFORMATION: 5' Oligonucleotide primer for VH Domain

<400> SEQUENCE: 28
caggtacagc tgcagcagtc agg 23

<210> SEQ ID NO 29
<211> LENGTH: 24
<212> TYPE: DNA
<213> ORGANISM: Artificial Sequence
<220> FEATURE:
<223> OTHER INFORMATION: 5' Oligonucleotide primer for VH Domain -continued

<400> SEQUENCE: 29
tgaggagacg gtgaccaggg tgcc 24

<210> SEQ ID NO 30
<211> LENGTH: 24
<212> TYPE: DNA
<213> ORGANISM: Artificial Sequence
<220> FEATURE:
<223> OTHER INFORMATION: 5' Oligonucleotide primer for VH Domain

<400> SEQUENCE: 30
tgaagagacg gtgaccattg tccc 24

<210> SEQ ID NO 31
<211> LENGTH: 24
<212> TYPE: DNA
<213> ORGANISM: Artificial Sequence
<220> FEATURE:
<223> OTHER INFORMATION: 5' Oligonucleotide primer for VH Domain

<400> SEQUENCE: 31
tgaggagacg gtgaccaggg ttcc 24

<210> SEQ ID NO 32
<211> LENGTH: 24
<212> TYPE: DNA
<213> ORGANISM: Artificial Sequence
<220> FEATURE:
<223> OTHER INFORMATION: 5' Oligonucleotide primer for VH Domain

<400> SEQUENCE: 32
tgaggagacg gtgaccgtgg tccc 24

<210> SEQ ID NO 33
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 33
gacatccaga tgacccagtc tcc 23

<210> SEQ ID NO 34
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 34
gatgttgtga tgactcagtc tcc 23

<210> SEQ ID NO 35
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 35
gatattgtga tgactcagtc tcc 23

<210> SEQ ID NO 36

-continued

<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 36
gaaattgtgt tgacgcagtc tcc 23

<210> SEQ ID NO 37
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 37
gacatcgtga tgacccagtc tcc 23

<210> SEQ ID NO 38
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 38
gaaacgacac tcacgcagtc tcc 23

<210> SEQ ID NO 39
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 39
gaaattgtgc tgactcagtc tcc 23

<210> SEQ ID NO 40
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 40
cagtctgtgt tgacgcagcc gcc 23

<210> SEQ ID NO 41
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 41
cagtctgccc tgactcagcc tgc 23

<210> SEQ ID NO 42
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 42

-continued tcctatgtgc tgactcagcc acc 23

<210> SEQ ID NO 43
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 43
tcttctgagc tgactcagga ccc 23

<210> SEQ ID NO 44
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 44
cacgttatac tgactcaacc gcc 23

<210> SEQ ID NO 45
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 45
caggctgtgc tcactcagcc gtc 23

<210> SEQ ID NO 46
<211> LENGTH: 23
<212> TYPE: DNA
<213> ORGANISM: Artificial Sequence
<220> FEATURE:
<223> OTHER INFORMATION: 5' Oligonucleotide primer for VL Domain

<400> SEQUENCE: 46
aattttatgc tgactcagcc cca 23

<210> SEQ ID NO 47
<211> LENGTH: 24
<212> TYPE: DNA
<213> ORGANISM: Artificial Sequence
<220> FEATURE:
<223> OTHER INFORMATION: 3' Oligonucleotide primer for VL Domain

<400> SEQUENCE: 47
acgtttgatt tccaccttgg tccc 24

<210> SEQ ID NO 48
<211> LENGTH: 24
<212> TYPE: DNA
<213> ORGANISM: Artificial Sequence
<220> FEATURE:
<223> OTHER INFORMATION: 3' Oligonucleotide primer for VL Domain

<400> SEQUENCE: 48
acgtttgatc tccagcttgg tccc 24

<210> SEQ ID NO 49
<211> LENGTH: 24
<212> TYPE: DNA

-continued

```
<213> ORGANISM: Artificial Sequence
<220> FEATURE:
<223> OTHER INFORMATION: 3' Oligonucleotide primer for VL Domain

<400> SEQUENCE: 49

acgtttgata tccactttgg tccc                                             24


<210> SEQ ID NO 50
<211> LENGTH: 24
<212> TYPE: DNA
<213> ORGANISM: Artificial Sequence
<220> FEATURE:
<223> OTHER INFORMATION: 3' Oligonucleotide primer for VL Domain

<400> SEQUENCE: 50

acgtttgatc tccaccttgg tccc                                             24


<210> SEQ ID NO 51
<211> LENGTH: 24
<212> TYPE: DNA
<213> ORGANISM: Artificial Sequence
<220> FEATURE:
<223> OTHER INFORMATION: 3' Oligonucleotide primer for VL Domain

<400> SEQUENCE: 51

acgtttaatc tccagtcgtg tccc                                             24


<210> SEQ ID NO 52
<211> LENGTH: 23
<212> TYPE: DNA
<213> ORGANISM: Artificial Sequence
<220> FEATURE:
<223> OTHER INFORMATION: 3' Oligonucleotide primer for VL Domain

<400> SEQUENCE: 52

cagtctgtgt tgacgcagcc gcc                                              23


<210> SEQ ID NO 53
<211> LENGTH: 23
<212> TYPE: DNA
<213> ORGANISM: Artificial Sequence
<220> FEATURE:
<223> OTHER INFORMATION: 3' Oligonucleotide primer for VL Domain

<400> SEQUENCE: 53

cagtctgccc tgactcagcc tgc                                              23


<210> SEQ ID NO 54
<211> LENGTH: 23
<212> TYPE: DNA
<213> ORGANISM: Artificial Sequence
<220> FEATURE:
<223> OTHER INFORMATION: 3' Oligonucleotide primer for VL Domain

<400> SEQUENCE: 54

tcctatgtgc tgactcagcc acc                                              23


<210> SEQ ID NO 55
<211> LENGTH: 23
<212> TYPE: DNA
<213> ORGANISM: Artificial Sequence
<220> FEATURE:
<223> OTHER INFORMATION: 3' Oligonucleotide primer for VL Domain

<400> SEQUENCE: 55

tcttctgagc tgactcagga ccc                                              23
```

-continued

<210> SEQ ID NO 56
<211> LENGTH: 23
<212> TYPE: DNA
<213> ORGANISM: Artificial Sequence
<220> FEATURE:
<223> OTHER INFORMATION: 3' Oligonucleotide primer for VL Domain

<400> SEQUENCE: 56

```
cacgttatac tgactcaacc gcc                                          23
```

<210> SEQ ID NO 57
<211> LENGTH: 23
<212> TYPE: DNA
<213> ORGANISM: Artificial Sequence
<220> FEATURE:
<223> OTHER INFORMATION: 3' Oligonucleotide primer for VL Domain

<400> SEQUENCE: 57

```
caggctgtgc tcactcagcc gtc                                          23
```

<210> SEQ ID NO 58
<211> LENGTH: 23
<212> TYPE: DNA
<213> ORGANISM: Artificial Sequence
<220> FEATURE:
<223> OTHER INFORMATION: 3' Oligonucleotide primer for VL Domain

<400> SEQUENCE: 58

```
aattttatgc tgactcagcc cca                                          23
```

<210> SEQ ID NO 59
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION:

<400> SEQUENCE: 59

```
cag gtg cag ctg cag gag tcg ggc cca gga ctg gtg aag cct tcg gag       48
Gln Val Gln Leu Gln Glu Ser Gly Pro Gly Leu Val Lys Pro Ser Glu
1               5                   10                  15

acc ctg tcc ctc acc tgc act gtc tct ggt ggc tcc atc agt agt ttc       96
Thr Leu Ser Leu Thr Cys Thr Val Ser Gly Gly Ser Ile Ser Ser Phe
            20                  25                  30

tac tgg agc tgg atc cgg cag ccc gcc ggg aag gga ctg gac tgg att      144
Tyr Trp Ser Trp Ile Arg Gln Pro Ala Gly Lys Gly Leu Asp Trp Ile
        35                  40                  45

ggg cgt atc tat acc agc ggg aac acc aac tac aac ccc tcc ctc aag      192
Gly Arg Ile Tyr Thr Ser Gly Asn Thr Asn Tyr Asn Pro Ser Leu Lys
    50                  55                  60

agt cga gtc acc atg tca gta gac acg tcc aag aac cgg ttc tcc ctg      240
Ser Arg Val Thr Met Ser Val Asp Thr Ser Lys Asn Arg Phe Ser Leu
65                  70                  75                  80

aaa ctg agc tct gtg acc gcc gcg gac acg gcc gtg tat tac tgt gcg      288
Lys Leu Ser Ser Val Thr Ala Ala Asp Thr Ala Val Tyr Tyr Cys Ala
                85                  90                  95

aga gat cgg ggc agc agc tgg tac ccc gat gct ttt gat atc tgg ggc      336
Arg Asp Arg Gly Ser Ser Trp Tyr Pro Asp Ala Phe Asp Ile Trp Gly
            100                 105                 110

caa ggg aca atg gtc acc gtc tcc tca                                  363
Gln Gly Thr Met Val Thr Val Ser Ser
```

-continued

```
        115                 120


<210> SEQ ID NO 60
<211> LENGTH: 121
<212> TYPE: PRT
<213> ORGANISM: Homo sapiens

<400> SEQUENCE: 60

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Phe
            20                  25                  30

Tyr Trp Ser Trp Ile Arg Gln Pro Ala Gly Lys Gly Leu Asp Trp Ile
        35                  40                  45

Gly Arg Ile Tyr Thr Ser Gly Asn Thr Asn Tyr Asn Pro Ser Leu Lys
    50                  55                  60

Ser Arg Val Thr Met Ser Val Asp Thr Ser Lys Asn Arg Phe Ser Leu
65                  70                  75                  80

Lys Leu Ser Ser Val Thr Ala Ala Asp Thr Ala Val Tyr Tyr Cys Ala
                85                  90                  95

Arg Asp Arg Gly Ser Ser Trp Tyr Pro Asp Ala Phe Asp Ile Trp Gly
            100                 105                 110

Gln Gly Thr Met Val Thr Val Ser Ser
        115                 120


<210> SEQ ID NO 61
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION:

<400> SEQUENCE: 61

gat att gtg ttg acg cat tct cca ggc acc ctg tct ttg tct cca ggg       48
Asp Ile Val Leu Thr His Ser Pro Gly Thr Leu Ser Leu Ser Pro Gly
1               5                   10                  15

gaa aga gcc acc ctc tcc tgc agg gcc agt cag cgt gtt acc agc agc       96
Glu Arg Ala Thr Leu Ser Cys Arg Ala Ser Gln Arg Val Thr Ser Ser
            20                  25                  30

tgc tta gcc tgg tac cag cag aaa cct ggc cag gct ccc agg ctc ctc      144
Cys Leu Ala Trp Tyr Gln Gln Lys Pro Gly Gln Ala Pro Arg Leu Leu
        35                  40                  45

atc tat ggt aca tcc agc agg gcc act ggc atc cca gac agg ttc agt      192
Ile Tyr Gly Thr Ser Ser Arg Ala Thr Gly Ile Pro Asp Arg Phe Ser
    50                  55                  60

ggc agt ggg tct ggg aca gac ttc act ctc acc atc agc aga ctg gag      240
Gly Ser Gly Ser Gly Thr Asp Phe Thr Leu Thr Ile Ser Arg Leu Glu
65                  70                  75                  80

cct gaa gat ttt gca gtg tat tac tgt cag cag tat gtt agc tca cct      288
Pro Glu Asp Phe Ala Val Tyr Tyr Cys Gln Gln Tyr Val Ser Ser Pro
                85                  90                  95

ctc acc ttc ggc caa ggg aca cga ctc gag atc aaa cgt                  327
Leu Thr Phe Gly Gln Gly Thr Arg Leu Glu Ile Lys Arg
            100                 105


<210> SEQ ID NO 62
<211> LENGTH: 109
<212> TYPE: PRT
<213> ORGANISM: Homo sapiens
```

<400> SEQUENCE: 62

Asp Ile Val Leu Thr His Ser Pro Gly Thr Leu Ser Leu Ser Pro Gly
1 5 10 15

Glu Arg Ala Thr Leu Ser Cys Arg Ala Ser Gln Arg Val Thr Ser Ser
20 25 30

Cys Leu Ala Trp Tyr Gln Gln Lys Pro Gly Gln Ala Pro Arg Leu Leu
35 40 45

Ile Tyr Gly Thr Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Val Ser Ser Pro
85 90 95

Leu Thr Phe Gly Gln Gly Thr Arg Leu Glu Ile Lys Arg
100 105

<210> SEQ ID NO 63
<211> LENGTH: 379
<212> TYPE: DNA
<213> ORGANISM: Homo sapiens
<220> FEATURE:
<221> NAME/KEY: CDS
<222> LOCATION: (1)..(378)
<223> OTHER INFORMATION:

<400> SEQUENCE: 63 gag gtg cag ctg gtg gag tct ggg gga ggc ttg gta aag tct ggg ggg 48
Glu Val Gln Leu Val Glu Ser Gly Gly Gly Leu Val Lys Ser Gly Gly
1 5 10 15 tcc ctt aga ctc tcc tgt gca gcc tcc gga ttc act ttc agt aac gcc 96
Ser Leu Arg Leu Ser Cys Ala Ala Ser Gly Phe Thr Phe Ser Asn Ala
20 25 30 tgg atg acc tgg gtc cgc cag gct cca ggg aag agg ctg gag tgg gtt 144
Trp Met Thr Trp Val Arg Gln Ala Pro Gly Lys Arg Leu Glu Trp Val
35 40 45 ggc cgt att aaa agc aat gct gat ggt ggg tca aca gac tac gct gca 192
Gly Arg Ile Lys Ser Asn Ala Asp Gly Gly Ser Thr Asp Tyr Ala Ala
50 55 60 ccc gtg aaa ggc aga ttc acc atc tca aga gat gat tca aaa aac acg 240
Pro Val Lys Gly Arg Phe Thr Ile Ser Arg Asp Asp Ser Lys Asn Thr
65 70 75 80 ctg tat ctg caa atg aac agc ctg aaa acc gag gac aca gcc gtg tat 288
Leu Tyr Leu Gln Met Asn Ser Leu Lys Thr Glu Asp Thr Ala Val Tyr
85 90 95 tac tgt aac aca gat aag ggt ggg agc tac ccc tac tac tac tac ggt 336
Tyr Cys Asn Thr Asp Lys Gly Gly Ser Tyr Pro Tyr Tyr Tyr Tyr Gly
100 105 110 atg gac gtc tgg ggc caa ggg acc acg gtc acc gtc tcc tca g 379
Met Asp Val Trp Gly Gln Gly Thr Thr Val Thr Val Ser Ser
115 120 125

<210> SEQ ID NO 64
<211> LENGTH: 126
<212> TYPE: PRT
<213> ORGANISM: Homo sapiens

<400> SEQUENCE: 64

Glu Val Gln Leu Val Glu Ser Gly Gly Gly Leu Val Lys Ser Gly Gly
1 5 10 15

-continued

```
Ser Leu Arg Leu Ser Cys Ala Ala Ser Gly Phe Thr Phe Ser Asn Ala
            20                  25                  30

Trp Met Thr Trp Val Arg Gln Ala Pro Gly Lys Arg Leu Glu Trp Val
        35                  40                  45

Gly Arg Ile Lys Ser Asn Ala Asp Gly Gly Ser Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Asn Thr Asp Lys Gly Gly Ser Tyr Pro Tyr Tyr Tyr Tyr Gly
            100                 105                 110

Met Asp Val Trp Gly Gln Gly Thr Thr Val Thr Val Ser Ser
        115                 120                 125


<210> SEQ ID NO 65
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION:

<400> SEQUENCE: 65

gac atc cag atg acc cag tct cca tcc tcc ctg tct gca tct gta gga       48
Asp Ile Gln Met Thr Gln Ser Pro Ser Ser Leu Ser Ala Ser Val Gly
1               5                   10                  15

gac aga gtc acc atc act tgc cgg gca agt cag ggc att aga aat gat       96
Asp Arg Val Thr Ile Thr Cys Arg Ala Ser Gln Gly Ile Arg Asn Asp
            20                  25                  30

tta ggc tgg tat cag cag aaa cca ggg aaa gcc cct aag cgc ctg atc      144
Leu Gly Trp Tyr Gln Gln Lys Pro Gly Lys Ala Pro Lys Arg Leu Ile
        35                  40                  45

tat gat gca tcc agt ttg caa agt ggg gtc cca tca agg ttc agc ggc      192
Tyr Asp Ala Ser Ser Leu Gln Ser Gly Val Pro Ser Arg Phe Ser Gly
    50                  55                  60

agt gga tct ggg aca gaa ttc act ctc aca atc agc agc ctg cag cct      240
Ser Gly Ser Gly Thr Glu Phe Thr Leu Thr Ile Ser Ser Leu Gln Pro
65                  70                  75                  80

gaa gat ttt gca act tat tac tgt cta cag cat aat agt tac cca ttc      288
Glu Asp Phe Ala Thr Tyr Tyr Cys Leu Gln His Asn Ser Tyr Pro Phe
                85                  90                  95

act ttc ggc cct ggg acc aaa gtg gat atc aaa cga                      324
Thr Phe Gly Pro Gly Thr Lys Val Asp Ile Lys Arg
            100                 105


<210> SEQ ID NO 66
<211> LENGTH: 108
<212> TYPE: PRT
<213> ORGANISM: Homo sapiens

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Asp Ala Ser Ser Leu Gln Ser Gly Val Pro Ser Arg Phe Ser Gly
```

-continued

```
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Lys Arg
            100                 105


<210> SEQ ID NO 67
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION:

<400> SEQUENCE: 67

gag gtg cag ctg gtg gag tct ggc cca gga ctg gtg aag cct tcg gag       48
Glu Val Gln Leu Val Glu Ser Gly Pro Gly Leu Val Lys Pro Ser Glu
1               5                   10                  15

acc ctg tcc ctc acc tgc act gtc tct ggt ggc tcc atc agt agt tac       96
Thr Leu Ser Leu Thr Cys Thr Val Ser Gly Gly Ser Ile Ser Ser Tyr
            20                  25                  30

tac tgg agc tgg atc cgg cag ccc cca ggg aag gga ctg gag tgg att      144
Tyr Trp Ser Trp Ile Arg Gln Pro Pro Gly Lys Gly Leu Glu Trp Ile
        35                  40                  45

ggg tat atc tat tac agt ggg agc acc aac tac aac ccc tcc ctc aag      192
Gly Tyr Ile Tyr Tyr Ser Gly Ser Thr Asn Tyr Asn Pro Ser Leu Lys
    50                  55                  60

agt cga gtc acc ata tca gta gac acg tcc aag aac cag ttc tcc ctg      240
Ser Arg Val Thr Ile Ser Val Asp Thr Ser Lys Asn Gln Phe Ser Leu
65                  70                  75                  80

aag ctg agc tct gtg acc gct gcg gac acg gcc gtg tat tac tgt gcg      288
Lys Leu Ser Ser Val Thr Ala Ala Asp Thr Ala Val Tyr Tyr Cys Ala
                85                  90                  95

aga gat gtc atg cag cag ccg gta cgg ggt tac tac tac tac tac ggt      336
Arg Asp Val Met Gln Gln Pro Val Arg Gly Tyr Tyr Tyr Tyr Tyr Gly
            100                 105                 110

atg gac gtc tgg ggc caa gga acc ctg gtc acc gtc tcc tca              378
Met Asp Val Trp Gly Gln Gly Thr Leu Val Thr Val Ser Ser
        115                 120                 125


<210> SEQ ID NO 68
<211> LENGTH: 126
<212> TYPE: PRT
<213> ORGANISM: Homo sapiens

<400> SEQUENCE: 68

Glu Val Gln Leu Val Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

-continued

```
                85                  90                  95

Arg Asp Val Met Gln Gln Pro Val Arg Gly Tyr Tyr Tyr Tyr Tyr Gly
            100                 105                 110

Met Asp Val Trp Gly Gln Gly Thr Leu Val Thr Val Ser Ser
        115                 120                 125


<210> SEQ ID NO 69
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION:

<400> SEQUENCE: 69

gaa att gtg ttg acg cag tct cca ggc acc ctg tct ttg tct cca ggg       48
Glu Ile Val Leu Thr Gln Ser Pro Gly Thr Leu Ser Leu Ser Pro Gly
1               5                   10                  15

gaa aga gtc acc ctc tcc tgc agg gcc agt cag aga gtt agc aac agc       96
Glu Arg Val Thr Leu Ser Cys Arg Ala Ser Gln Arg Val Ser Asn Ser
            20                  25                  30

tac tta gcc tgg tac cag cag aaa cct ggc cag gct ccc agg ttc ctc      144
Tyr Leu Ala Trp Tyr Gln Gln Lys Pro Gly Gln Ala Pro Arg Phe Leu
        35                  40                  45

atc tat ggt gta tcc agc agg gcc act ggc atc cca gac agg ttc agt      192
Ile Tyr Gly Val Ser Ser Arg Ala Thr Gly Ile Pro Asp Arg Phe Ser
    50                  55                  60

ggc agt ggg tct ggg aca gac ttc act ctc acc atc agc aga ctg gag      240
Gly Ser Gly Ser Gly Thr Asp Phe Thr Leu Thr Ile Ser Arg Leu Glu
65                  70                  75                  80

cct gaa gat ttt gca gtg tat tac tgt cag cag tat ggt agt tca ccg      288
Pro Glu Asp Phe Ala Val Tyr Tyr Cys Gln Gln Tyr Gly Ser Ser Pro
                85                  90                  95

tgg acg ttc ggc caa ggg acc aag gtg gaa atc aaa cga                  327
Trp Thr Phe Gly Gln Gly Thr Lys Val Glu Ile Lys Arg
            100                 105


<210> SEQ ID NO 70
<211> LENGTH: 109
<212> TYPE: PRT
<213> ORGANISM: Homo sapiens

<400> SEQUENCE: 70

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Arg Val Ser Asn Ser
            20                  25                  30

Tyr Leu Ala Trp Tyr Gln Gln Lys Pro Gly Gln Ala Pro Arg Phe Leu
        35                  40                  45

Ile Tyr Gly Val Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg
            100                 105
```

HUMAN G-PROTEIN CHEMOKINE RECEPTOR (CCR5) HDGNR10

CROSS-REFERENCE TO RELATED APPLICATIONS

This application is a continuation-in-part of International Application No. PCT/US01/04153, filed Feb. 9, 2001, and which published in English under PCT Article 21(2); and is a continuation-in-part of U.S. application Ser. No. 09/779, 880, filed 9 Feb. 2001 now abandoned; and claims the benefit of U.S. Provisional Application No. 60/297,257, filed 12 Jun. 2001; and claims the benefit of U.S. Provisional Application No. 60/310,458, filed 8 Aug. 2001; and claims the benefit of U.S. Provisional Application No. 60/328,447, filed 12 Oct. 2001; and claims the benefit of U.S. Provisional Application No. 60/341,725, filed 21 Dec. 2001; each of said applications is hereby incorporated herein by reference.

FIELD OF THE INVENTION

The present invention relates to a novel human gene encoding a polypeptide which is a member of the G-protein Chemokine Receptor (CCR5) family. More specifically, the present invention relates to a polynucleotide encoding a novel human polypeptide named Human G-protein Chemokine Receptor (CCR5) HDGNR10, referred to herein as “G-protein Chemokine Receptor” or “HDGNR10.” This invention also relates to G-protein Chemokine Receptor (CCR5) polypeptides, as well as vectors, host cells, antibodies directed to G-protein Chemokine Receptor (CCR5) polypeptides, and the recombinant methods for producing the same. Also provided are diagnostic methods for detecting diseases, disorders, and/or conditions related to the immune system and HIV infection, and therapeutic methods for treating, preventing, and/or diagnosing such diseases, disorders, and/or conditions. The invention further relates to screening methods for identifying agonists and antagonists of G-protein Chemokine Receptor (CCR5) activity. The G-protein Chemokine Receptor (CCR5) is also known as CCR5.

BACKGROUND OF THE INVENTION

It is well established that many medically significant biological processes are mediated by proteins participating in signal transduction pathways that involve G-proteins and/or second messengers, e.g., cAMP (Lefkowitz, *Nature,* 351:353–354 (1991)). Herein these proteins are referred to as proteins participating in pathways with G-proteins or PPG-proteins. Some examples of these proteins include the GPC receptors, such as those for adrenergic agents and dopamine (Kobilka, B. K., et al., *PNAS,* 84:46–50 (1987); Kobilka, B. K., et al., *Science,* 238:650–656 (1987); Bunzow, J. R., et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., *Science,* 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins, endothelial differentiation gene-1 receptor and rhodopsins, odorant, cytomegalovirus receptors, etc.

G-protein coupled receptors can be intracellularly coupled by heterotrimeric G-proteins to various intracellular enzymes, ion channels and transporters (see, Johnson et al., *Endoc., Rev.,* 10:317–331 (1989)). Different G-protein α-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Chemokines, also referred to as intercrine cytokines, are a subfamily nof structurally and functionally related cytokines. These molecules are 8–10 kd in size. In general, chemokines exhibit 20% to 75% homology at the amino acid level and are characterized by four conserved cysteine residues that form two disulfide bonds. Based on the arrangement of the first two cysteine residues, chemokines have been classified into two subfamilies, alpha and beta. In the alpha subfamily, the first two cysteines are separated by one amino acid and hence are referred to as the “C-X-C” subfamily. In the beta subfamily, the two cysteines are in an adjacent position and are, therefore, referred to as the “C—C” subfamily. Thus far, at least nine different members of this family have been identified in humans.

The intercrine cytokines exhibit a wide variety of functions. A hallmark feature is their ability to elicit chemotactic migration of distinct cell types, including monocytes, neutrophils, T lymphocytes, basophils and fibroblasts. Many chemokines have proinflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. In addition to their involvement in inflammation, certain chemokines have been shown to exhibit other activities. For example, macrophage inflammatory protein 1 (MIP-1) is able to suppress hematopoietic stem cell proliferation, platelet factor-4 (PF-4) is a potent inhibitor of endothelial cell growth, Interleukin-8 (IL-8) promotes proliferation of keratinocytes, and GRO is an autocrine growth factor for melanoma cells.

In light of the diverse biological activities, it is not surprising that chemokines have been implicated in a number of physiological and disease conditions, including lymphocyte trafficking, wound healing, hematopoietic regulation and immunological disorders such as allergy, asthma and arthritis.

Thus, there is a need for polypeptides that modulate immune system regulation, since disturbances of such regulation may be involved in diseases, disorders, and/or conditions relating to the immune system. Therefore, there is a need for identification and characterization of such human polypeptides which can play a role in detecting, preventing, ameliorating or correcting such diseases, disorders, and/or conditions.

The G-protein Chemokine Receptor (CCR5) is a seven-pass transmembrane G-protein coupled receptor that is expressed in cells of the immune system such as, for example, macrophages, including immature dendritic cells such as Langerhans cells, and T cells, including Th0 and Th1 effector cells. G-protein Chemokine Receptor (CCR5) has also been detected in microglia, astrocytes, neurons, and vascular endothelial cells of the central nervous system (CNS). G-protein Chemokine Receptor (CCR5) is also expressed in monocyes and T cells in the synovial fluid of rheumatoid arthritis patients, and has also been implicated in other forms of arthritis.

Ligands of G-protein Chemokine Receptor (CCR5) include MIP-1α, MIP-1β, MCP-1, MCP-2, MCP-3, MCP-4, RANTES, and Eotaxin. CCR5 is also a major co-receptor for HIV, and may be also be recognized by other infectious agents, such as other viruses, to allow entry into the cell. It was recently discovered that certain individuals harboring a mutation of the CCR5 gene, were resistant to HIV infection despite multiple exposure to the virus. This mutation abrogated expression of CCR5 at the cell surface (Liu et al., Cell 86:1 (1996)).

HIV is currently the leading lethal infectious disease in the world, causing 2.6 million deaths in 1999. The number of deaths resulting from HIV infection will continue to increase; In 1999, there were 5.6 million new cases of HIV infection and 33.6 million infected people living in the world. Although there are currently 14 approved drugs to treat HIV, as many as one half of pateints fail to be succesfully (with success being defined as no detectable HIV RNA in serum (which in effect is equal to fewer than 50 copies/ml of HIV-1 RNA) treated after a one year drug regimen. The reasons for the inability of these drug regimens to effectively treat HIV are several fold: use of certain drugs results in the development of drug resistant HIV strains; some individuals are intolerant to certain drugs or the drugs have bad side effects; patients have difficulty complying with complex dosing regimens; and the drugs may not be able to access reservoirs of HIV in the body. Thus, there remains a need in the art to develop immproved HIV vaccines and therapies.

SUMMARY OF THE INVENTION

The present invention relates to novel polynucleotides and the encoded polypeptides of G-protein Chemokine Receptor (CCR5). Moreover, the present invention relates to vectors, host cells, antibodies, and recombinant and synthetic methods for producing the polypeptides and polynucleotides. Also provided are diagnostic methods for detecting diseases, disorders, and/or conditions related to the polypeptides and polynucleotides, and therapeutic methods for treating, preventing, and/or diagnosing such diseases, disorders, and/or conditions. The invention further relates to screening methods for identifying binding partners of G-protein Chemokine Receptor (CCR5).

In accordance with one aspect of the present invention, there are provided novel mature receptor polypeptides as well as biologically active and diagnostically or therapeutically useful fragments, analogs and derivatives thereof. The G-protein Chemokine Receptor (CCR5) polypeptides of the present invention are of human origin.

In accordance with another aspect of the present invention, there are provided isolated nucleic acid molecules encoding the G-protein Chemokine Receptor (CCR5) polypeptides of the present invention, including mRNAs, DNAs, cDNAs, genomic DNA as well as antisense analogs thereof and biologically active and diagnostically or therapeutically useful fragments thereof.

In accordance with a further aspect of the present invention, there are provided processes for producing the G-protein Chemokine Receptor (CCR5) polypeptides by recombinant techniques comprising culturing recombinant prokaryotic and/or eukaryotic host cells, containing nucleic acid sequences encoding the receptor polypeptides of the present invention, under conditions promoting expression of said polypeptides and subsequent recovery of said polypeptides.

In accordance with yet a further aspect of the present invention, there are provided antibodies that bind the G-protein Chemokine Receptor (CCR5) polypeptides. The present invention encompasses antibodies (including molecules comprising, or alternatively consisting of, antibody fragments or variants thereof) that immunospecifically bind to a G-protein Chemokine Receptor (CCR5) polypeptide or polypeptide fragment or variant of a G-protein Chemokine Receptor (CCR5). In particular, the invention encompasses antibodies (including molecules comprising, or alternatively consisting of, antibody fragments or variants thereof) that immunospecifically bind to a polypeptide or polypeptide fragment or variant of human G-protein Chemokine Receptor (CCR5) such as those of SEQ ID NO:2 or of the polypeptide encoded by the deposited clone.

The present invention relates to methods and compositions for preventing, treating or ameliorating a disease or disorder comprising administering to an animal, preferably a human, an effective amount of one or more antibodies or fragments or variants thereof, or related molecules, that immunospecifically bind to a G-protein Chemokine Receptor (CCR5) or a fragment or variant thereof. In specific embodiments, the present invention relates to methods and compositions for preventing, treating or ameliorating a disease or disorder associated with G-protein Chemokine Receptor (CCR5) function or G-protein Chemokine Receptor (CCR5) ligand function or aberrant G-protein Chemokine Receptor (CCR5) or G-protein Chemokine Receptor (CCR5) ligand expression, comprising administering to an animal, preferably a human, an effective amount of one or more antibodies or fragments or variants thereof, or related molecules, that immunospecifically bind to a G-protein Chemokine Receptor (CCR5) or a fragment or variant thereof. In highly preferred embodiments, the present invention relates to antibody-based methods and compositions for preventing, treating or ameliorating HIV infection and/or conditions associated with HIV infection. Other diseases and disorders which can be treated, prevented or ameliorated with the antibodies of the invention include, but are not limited to, immune disorders (e.g., autoimmune disorders such as multiple sclerosis, Grave's disease, and rheumatoid arthritis), neurodegenerative disorders (e.g., Alzheimer's disease) inflammatory disorders (e.g., asthma, allergic disorders, or inflammatory kidney diseases such as glomerulonephritis), infectious diseases (e.g., Hepatitis infections, herpes viral infections, and other viral infections) and proliferative disorders.

The present invention also encompasses methods and compositions for detecting, diagnosing, or prognosing diseases or disorders comprising administering to an animal, preferably a human, an effective amount of one or more antibodies or fragments or variants thereof, or related molecules, that immunospecifically bind to G-protein Chemokine Receptor (CCR5) or a fragment or variant thereof. In specific embodiments, the present invention also encompasses methods and compositions for detecting, diagnosing, or prognosing diseases or disorders associated with G-protein Chemokine Receptor (CCR5) function or G-protein Chemokine Receptor (CCR5) ligand function or aberrant G-protein Chemokine Receptor (CCR5) or G-protein Chemokine Receptor (CCR5) ligand expression, comprising administering to an animal, preferably a human, an effective amount of one or more antibodies or fragments or variants thereof, or related molecules, that immunospecifically bind to G-protein Chemokine Receptor (CCR5) or a fragment or variant thereof. In highly preferred embodiments, the present invention relates to antibody-based methods and compositions for detecting, diagnosing, or prognosing HIV infection and/or conditions associated with HIV infection. Other diseases and disorders which can be detected, diagnosed, or prognosed with the antibodies of the invention include, but are not limited to, immune disorders (e.g., autoimmune disorders such as multiple sclerosis, Grave's disease, and rheumatoid arthritis), neurodegenerative disorders (e.g., Alzheimer's disease) inflammatory (e.g., asthma, allergic disorders, or inflammatory kidney diseases such as glomerulonephritis), infectious diseases (e.g., Hepatitis infections, herpes viral infections, and other viral infections) and proliferative disorders.

Another embodiment of the present invention includes the use of the antibodies of the invention as a diagnostic tool to monitor the expression of G-protein Chemokine Receptor (CCR5) expression on cells.

The present invention also encompasses cell lines that express antibodies that immunospecifically bind one or more G-protein Chemokine Receptor (CCR5) polypeptides (e.g., SEQ ID NO:2, or the polypeptide encoded by the deposited clone).

Further, the present invention encompasses the polynucleotides encoding the antibodies expressed by such cell lines, as well as the amino acid sequences encoding the antibodies expressed by these cell lines. Molecules comprising, or alternatively consisting of, fragments or variants of these antibodies (e.g., heavy chains, VH domains, VH CDRs, light chains, VL domains, or VL CDRs having an amino acid sequence of any one of those expressed by an antibody-expressing cell line of the invention, that immunospecifically bind to one or more G-protein Chemokine Receptor (CCR5) or fragments or variants thereof are also encompassed by the invention, as are nucleic acid molecules that encode these antibodies and/or molecules. In highly preferred embodiments, the present invention encompasses antibodies, or fragments or variants thereof, that bind to the extracellular regions/domains of one or more G-protein Chemokine Receptor (CCR5) or fragments and variants thereof.

The present inventors have generated hybridoma cell lines that express antibodies that immunospecifically bind one or more G-protein Chemokine Receptor (CCR5) polypeptides (e.g., SEQ ID NO:2 or the polypeptide encoded by the deposited clone). Thus, the invention encompasses these cell lines, listed in Table 2 below which were deposited with the American Type Culture Collection ("ATCC") on the dates listed in Table 2 and given the ATCC Deposit Numbers identified in Table 2 The ATCC is located at 10801 University Boulevard, Manassas, Va. 20110–2209, USA. The ATCC deposit was made pursuant to the terms of the Budapest Treaty on the international recognition of the deposit of microorganisms for purposes of patent procedure.

Further, the present invention encompasses the polynucleotides encoding the antibodies expressed by these cell lines, as well as the amino acid sequences encoding the antibodies expressed by these cell lines. Molecules comprising, or alternatively consisting of, fragments or variants of these antibodies (e.g., heavy chains, VH domains, VH CDRs, light chains, VL domains, or VL CDRs having an amino acid sequence of any one of those expressed by one or more cell lines referred to in Table 2), that immunospecifically bind to one or more G-protein Chemokine Receptor (CCR5) or fragments or variants thereof are also encompassed by the invention, as are nucleic acid molecules that encode these antibodies and/or molecules. In highly preferred embodiments, the present invention encompasses antibodies, or fragments or variants thereof, that bind to the extracellular regions/domains of one or more G-protein Chemokine Receptor (CCR5) or fragments and variants thereof.

The present invention also provides antibodies that bind one or more G-protein Chemokine Receptor (CCR5) polypeptides which are coupled to a detectable label, such as an enzyme, a fluorescent label, a luminescent label, or a bioluminescent label. The present invention also provides antibodies that bind one or more G-protein Chemokine Receptor (CCR5) polypeptides which are coupled to a therapeutic or cytotoxic agent. The present invention also provides antibodies that bind one or more G-protein Chemokine Receptor (CCR5) polypeptides which are coupled to a radioactive material.

The present invention further provides antibodies that inhibit or abolish the ability of HIV to bind to, enter into/fuse with (infect), and/or replicate in G-protein Chemokine Receptor (CCR5) expressing cells. In highly preferred embodiments of the present invention, anti-G-protein Chemokine Receptor (CCR5) antibodies of the present invention are used to treat, prevent or ameliorate HIV infection and/or conditions associated with HIV infection. In other highly preferred embodiments, anti-G-protein Chemokine Receptor (CCR5) antibodies of the present invention are administered to an individual alone or in combination with other therapeutic compounds, especially anti-retroviral agents, to treat, prevent or ameliorate HIV infection and/or conditions associated with HIV infection.

The present invention also provides antibodies that bind one or more G-protein Chemokine Receptor (CCR5) polypeptides that act as either G-protein Chemokine Receptor (CCR5) agonists or G-protein Chemokine Receptor (CCR5) antagonists. In specific embodiments, the antibodies of the invention stimulate chemotaxis of G-protein Chemokine Receptor (CCR5) expressing cells. In other specific embodiments, the antibodies of the invention inhibit G-protein Chemokine Receptor (CCR5) ligand binding to a G-protein Chemokine Receptor (CCR5). In other specific embodiments, the antibodies of the invention upregulate G-protein Chemokine Receptor (CCR5) expression.

The present invention also provides antibodies that downregulate G-protein Chemokine Receptor (CCR5) expression. In still other specific embodiments, the anti-G-protein Chemokine Receptor (CCR5) antibodies of the invention downregulate G-protein Chemokine Receptor (CCR5) expression by promoting G-protein Chemokine Receptor (CCR5) internalization.

The present invention further provides antibodies that inhibit or abolish the binding of a G-protein Chemokine Receptor (CCR5) ligand, (e.g., MIP1-beta MIP-1alpha, MCP-1, MCP-2, MCP-3, MCP-4, RANTES, and Eotaxin), to G-protein Chemokine Receptor (CCR5) expressing cells.

The present invention also provides for a nucleic acid molecule(s), generally isolated, encoding an antibody (including molecules, such as scFvs, VH domains, or VL domains, that comprise, or alternatively consist of, an antibody fragment or variant thereof) of the invention. The present invention also provides a host cell transformed with a nucleic acid molecule encoding an antibody (including molecules, such as scFvs, VH domains, or VL domains, that comprise, or alternatively consist of, an antibody fragment or variant thereof) of the invention and progeny thereof. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail below.

In another embodiment, the present invention provides vaccines comprising, or alternatively consisting of, G-protein Chemokine Receptor (CCR5) polynucleotides or polypeptides or fragments, variants or derivatives thereof.

In accordance with another aspect of the present invention there are provided methods of screening for compounds which bind to and activate or inhibit activation of the G-protein Chemokine Receptor (CCR5) polypeptides of the present invention.

In accordance with still another embodiment of the present invention there are provided processes of administering compounds to a host which bind to and activate the receptor polypeptide of the present invention which are useful in stimulating haematopoiesis, wound healing, coagulation, angiogenesis, to treat solid tumors, chronic infections, leukemia, T-cell mediated auto-immune diseases, parasitic infections, psoriasis, and to stimulate growth factor activity.

In accordance with another aspect of the present invention there is provided a method of administering the receptor polypeptides of the present invention via gene therapy to treat conditions related to underexpression of the polypeptides or underexpression of a ligand for the G-protein Chemokine Receptor (CCR5) polypeptide.

In accordance with still another embodiment of the present invention there are provided processes of administering compounds to a host which bind to and inhibit activation of the receptor polypeptides of the present invention which are useful in the prevention and/or treatment of allergy, atherogenesis, anaphylaxis, malignancy, chronic and acute inflammation, histamine and IgE-mediated allergic reactions, prostaglandin-independent fever, bone marrow failure, silicosis, sarcoidosis, rheumatoid arthritis, shock and hyper-eosinophilic syndrome.

In accordance with yet another aspect of the present invention, there are provided nucleic acid probes comprising nucleic acid molecules of sufficient length to specifically hybridize to the polynucleotide sequences of the present invention.

In accordance with still another aspect of the present invention, there are provided diagnostic assays for detecting diseases related to mutations in the nucleic acid sequences encoding such polypeptides and for detecting an altered level of the soluble form of the receptor polypeptides.

In accordance with yet a further aspect of the present invention, there are provided processes for utilizing such receptor polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 shows the DNA sequence and the corresponding deduced amino acid sequence of the G-protein coupled receptor of the present invention. The standard one-letter abbreviation for amino acids is used. Sequencing was performed using a 373 Automated DNA sequencer (Applied Biosystems, Inc.).

FIG. 2 illustrates an amino acid alignment of the G-protein Chemokine Receptor (CCR5) of the present invention and the human MCP-1 receptor (SEQ ID NO:9). This figure shows the regions of identity between the amino acid sequence of the G-protein Chemokine Receptor (CCR5) protein and the translation product of the human MCP-1 receptor A (MCP-1 RA) (SEQ ID NO:9), determined by BLAST analysis. Identical amino acids between the two polypeptides are indicated by lines, while highly conservative amino acid are indicated by colons and conservative amino acids are indicated by periods. By examining the regions of identical, highly conserved and conserved amino acids, the skilled artisan can readily identify conserved domains between the two polypeptides. These conserved domains are preferred embodiments of the present invention.

Figure 3:
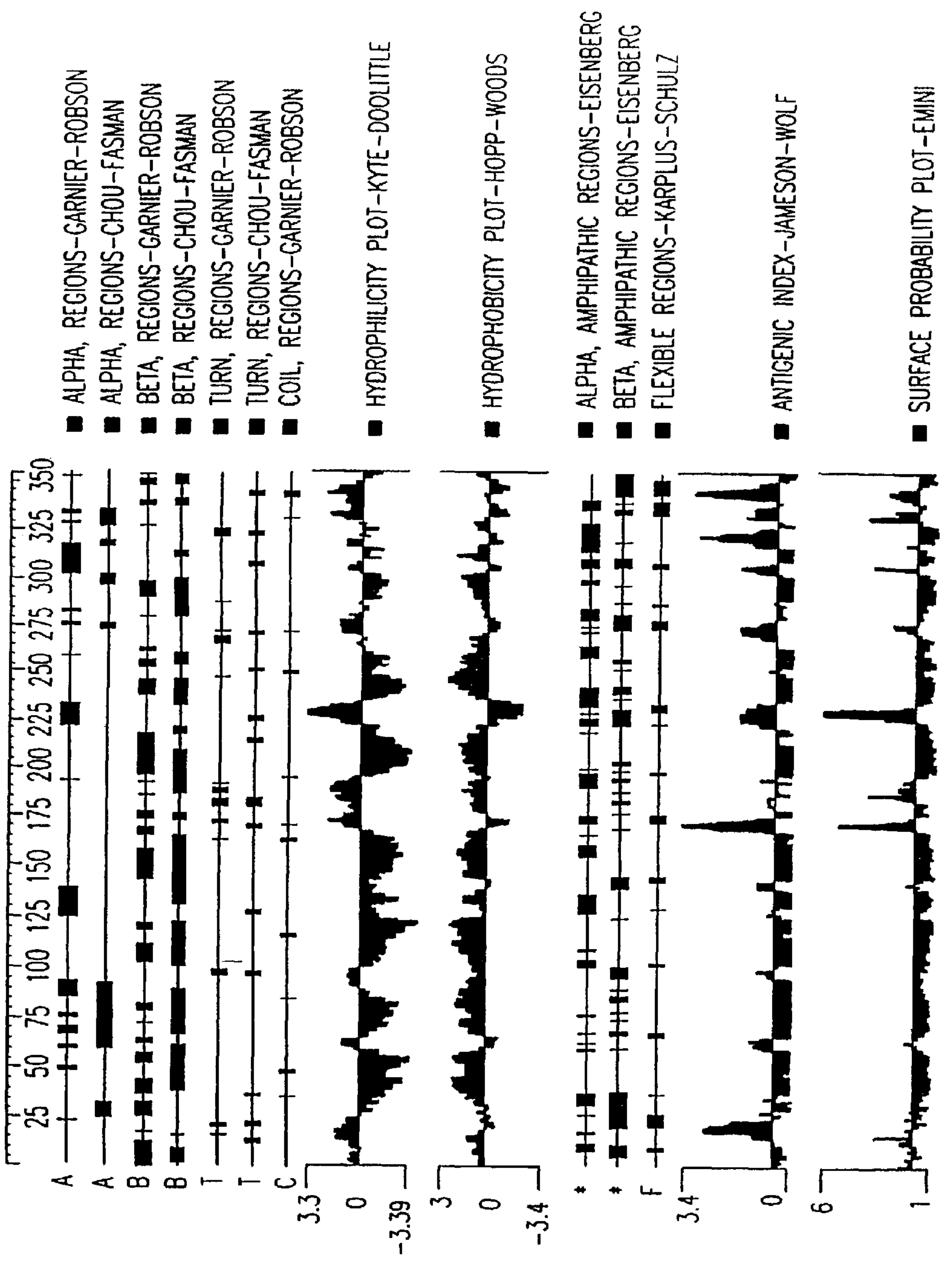
FIG. 3 shows an analysis of the G-protein Chemokine Receptor (CCR5) amino acid sequence. Alpha, beta, turn and coil regions; hydrophilicity and hydrophobicity; amphipathic regions; flexible regions; antigenic index and surface probability are shown, and all were generated using the default settings. In the "Antigenic Index or Jameson-Wolf" graph, the positive peaks indicate locations of the highly antigenic regions of the G-protein Chemokine Receptor (CCR5) protein, i.e., regions from which epitope-bearing peptides of the invention can be obtained. The domains defined by these graphs are contemplated by the present invention.

The data presented in FIG. 3 are also represented in tabular form in Table 1. The columns are labeled with the headings "Res", "Position", and Roman Numerals I–XIV. The column headings refer to the following features of the amino acid sequence presented in FIG. 3, and Table 1: "Res": amino acid residue of SEQ ID NO:2 and FIG. 1; "Position": position of the corresponding residue within SEQ ID NO:2 and FIG. 1; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VI: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

FIG. 4 shows the polynucleotide and amino acid sequence of the VH (SEQ ID NOs:59–60) and VL (SEQ ID NOs: 61–62) domains of anti-CCR5 antibody XF11.1D8. Each CDR is indicated by a line above the nucleotide sequence. See also, Table 6.

FIG. 5 shows the polynucleotide and amino acid sequence of the VH (SEQ ID NOs:63–64) and VL (SEQ ID NOs: 65–66) domains of anti-CCR5 antibody XF22.3C9 (i.e., XF22.3C9.6). Each CDR is indicated by a line above the nucleotide sequence. See also, Table 6.

FIG. 6 shows the polynucleotide and amino acid sequence of the VH (SEQ ID NOs:67–68) and VL (SEQ ID NOs: 69–70) domains of anti-CCR5 antibody XF22.9E6. Each CDR is indicated by a line above the nucleotide sequence. See also, Table 6.

DETAILED DESCRIPTION

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the clone deposited as ATCC Deposit No. 97183 on Jun. 1, 1995. A sample of the deposited clone, which contains the open reading frame of the G-protein Chemokine Receptor (CCR5), has been obtained from the ATCC and has been resequenced. The sequence data from the resequenced clone is shown in SEQ ID NO:21 and 22. SEQ ID NO:21 differs from SEQ ID NO:1 at 5 positions (nucleotides 320, 433, 442, 646, and 1289 of SEQ ID NO:1) SEQ ID NO:22 differs from SEQ ID NO:2 at 5 positions (amino acid residues 21, 59, 62, 130, and 344).

The polynucleotide of this invention was discovered in a genomic library derived from human monocytes. It is structurally related to the G-protein-coupled receptor family. It contains an open reading frame encoding a protein of 352 amino acid residues. The protein exhibits the highest degree of homology to a human MCP-1 receptor (SEQ ID NO:9) with 70.1% identity and 82.9% similarity over a 347 amino acid stretch.

Polynucleotides of the invention include, but are not limited to, the nucleotide sequence of SEQ ID NO:1, the nucleotide sequence of the HDGNR10 deposited clone (ATCC Deposit Number 97183), the nucleotide sequence of SEQ ID NO:21), and/or fragments, variants or derivatives thereof.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited clone.

The polynucleotide which encodes for the mature polypeptide of FIG. 1 or for the mature polypeptide encoded by the deposited clone may include: only the coding sequence for the mature polypeptide; the coding sequence for the mature polypeptide and additional coding sequence such as a transmembrane (TM) or intra-cellular domain; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 or the polypeptide encoded by the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the deposited clone as well as variants of such polynucleotides which variants encode for a fragment, derivative or analog of the polypeptide of FIG. 1 (SEQ ID NO:2) or the polypeptide encoded by the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides may also encode for a soluble form of the G-protein Chemokine Receptor (CCR5) polypeptide which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., *Cell,* 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the DNAs of FIG. 1 (SEQ ID NO:1) or the deposited clone.

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ iID NO:1 or of the deposited clone, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 or that encoded by the deposited clone as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, or sell the deposited materials, and no such license is hereby granted.

The present invention further relates to a G-protein Chemokine Receptor (CCR5) polypeptide which has the deduced amino acid sequence of FIG. 1 (SEQ ID NO:2) or which has the amino acid sequence encoded by the deposited clone (SEQ ID NO:22), as well as fragments, analogs and derivatives of such polypeptide.

The terms "fragment," "derivative" and "analog" when referring to the polypeptide of FIG. 1 or that encoded by the deposited clone, means a polypeptide which either retains substantially the same biological function or activity as such polypeptide, i.e. functions as a G-protein Chemokine Receptor (CCR5), or retains the ability to bind the ligand or the receptor even though the polypeptide does not function as a G-protein Chemokine Receptor (CCR5), for example, a soluble form of the receptor. An analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO: 2) or that encoded by the deposited clone may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) or that encoded by the deposited clone as well as polypeptides which have at least 70% similarity (preferably a 70% identity) to the polypeptide of SEQ ID NO:2) or to that encoded by the deposited clone and more preferably a 90% similarity (more preferably a 90% identity) to the polypeptide of SEQ ID NO:2) or to that encoded by the deposited clone and still more preferably a 95% similarity (still more preferably a 90% identity) to the polypeptide of SEQ ID NO:2 and to portions of such polypeptide with such portion of the polypeptide generally containing at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

Fragments or portions of the polypeptides of the present invention may be employed for producing the corresponding full-length polypeptide by peptide synthesis, therefore, the fragments may be employed as intermediates for producing the full-length polypeptides. Fragments or portions of the polynucleotides of the present invention may be used to synthesize full-length polynucleotides of the present invention.

The term "gene" means the segment of DNA involved in producing a polypeptide chain; it includes regions preceding and following the coding region "leader and trailer" as well as intervening sequences (introns) between individual coding segments (exons).

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2) or to that encoded by the deposited clone (in particular the mature polypeptide) as well as polypeptides which have at least 70% similarity (preferably at least 70% identity) and more preferably at least 90% similarity (more preferably at least 90% identity) and still more preferably at least 95% similarity (still more preferably at least 95% identity) to the polypeptide of SEQ ID NO:2) or to that encoded by the deposited clone and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*, lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila* and *Spodoptera* Sf9; animal cells such as CHO, COS or Bowes melanoma; adenovirus; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., et al., *Basic Methods in Molecular Biology*, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning: A Laboratory Manual, Second Edition*, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces,* and *Staphylococcus,* although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein Chemokine Receptor (CCR5) polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics to human disease.

The G-protein Chemokine Receptor (CCR5) of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, drosophila or *E. coli*. In particular, a polynucleotide encoding the receptor of the present invention is employed to transfect cells to thereby express the G-protein Chemokine Receptor (CCR5). The expressed receptor is then contacted with a test compound to observe binding, stimulation or inhibition of a functional response.

One such screening procedure involves the use of melanophores which are transfected to express the G-protein Chemokine Receptor (CCR5) of the present invention. Such a screening technique is described in PCT WO 92/01810 published Feb. 6, 1992.

Thus, for example, such assay may be employed for screening for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining a compound which activates the receptor by contacting such cells with compounds to be screened and determining whether such compound generates a signal, i.e., activates the receptor.

Other screening techniques include the use of cells which express the G-protein Chemokine Receptor (CCR5) (for example, transfected CHO cells) in a system which measures extracellular pH changes caused by receptor activation, for example, as described in *Science* 246:181–296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the G-protein Chemokine Receptor (CCR5) into *Xenopus* oocytes to transiently express the receptor. The receptor oocytes, may then be contacted with the receptor ligand and a compound to be screened, followed by detection of inhibition or activation of a calcium signal in the case of screening for compounds which are thought to inhibit activation of the receptor.

Another screening technique involves expressing the G-protein Chemokine Receptor (CCR5) in which the receptor is linked to a phospholipase C or D. As representative examples of such cells, there may be mentioned endothelial cells, smooth muscle cells, embryonic kidney cells, etc. The screening may be accomplished as hereinabove described by detecting activation of the receptor or inhibition of activation of the receptor from the phospholipase second signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the G-protein Chemokine Receptor (CCR5) such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

An antibody, or in some cases an oligopeptide, may activate a G-protein Chemokine Receptor (CCR5) of the present invention, by binding to the G-protein Chemokine Receptor (CCR5) and initiating second messenger response. Antibodies include anti-idiotypic antibodies which recognize unique determinants generally associated with the antigen-binding site of an antibody. Potential agonist compounds also include proteins which are closely related to the ligand of the G-protein Chemokine Receptor (CCR5), e.g., a fragment of the ligand.

An antibody, or in some cases an oligopeptide, may antagonize a G-protein Chemokine Receptor (CCR5) of the present invention, by binding to the G-protein Chemokine Receptor (CCR5) but failing to elicit a second messenger response such that the activity of the G-protein Chemokine Receptor (CCR5) is prevented. Antibodies include anti-idiotypic antibodies which recognize unique determinants generally associated with the antigen-binding site of an antibody. Potential antagonist compounds also include proteins which are closely related to the ligand of the G-protein Chemokine Receptor (CCR5), e.g., a fragment of the ligand that has lost biological function and elicits no response when binding to the G-protein Chemokine Receptor (CCR5).

An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix; see Lee et al., *Nucl. Acids Res.* 6:3073 (1979); Cooney et al, *Science* 241:456 (1988); and Dervan et al., *Science* 251:1360 (1991)), thereby preventing transcription and the production of G-protein Chemokine Receptor (CCR5). The antisense RNA oligonucleotide hybridizes to the mRNA in vivo and blocks translation of mRNA molecules into G-protein coupled receptor (antisense—Okano, *J. Neurochem.* 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein Chemokine Receptor (CCR5).

A small molecule which binds to the G-protein Chemokine Receptor (CCR5), making it inaccessible to ligands such that normal biological activity is prevented, for example small peptides or peptide-like molecules, may also be used to inhibit activation of the receptor polypeptide of the present invention.

A soluble form of the G-protein Chemokine Receptor (CCR5), e.g. a fragment of the receptors, may be used to inhibit activation of the receptor by binding to the ligand to a polypeptide of the present invention and preventing the ligand from interacting with membrane bound G-protein Chemokine Receptor (CCR5).

The compounds which bind to and activate the G-protein Chemokine Receptor (CCR5) of the present invention may be employed to stimulate haematopoiesis, wound healing, coagulation, angiogenesis, to treat solid tumors, chronic infections, leukemia, T-cell mediated auto-immune diseases, parasitic infections, psoriasis, and to stimulate growth factor activity.

The compounds which bind to and inhibit the G-protein Chemokine Receptor (CCR5) of the present invention may be employed to treat allergy, atherogenesis, anaphylaxis, malignancy, chronic and acute inflammation, histamine and IgE-mediated allergic reactions, prostaglandin-independent fever, bone marrow failure, silicosis, sarcoidosis, rheumatoid arthritis, shock and hyper-eosinophilic syndrome.

The compounds may be employed in combination with a suitable pharmaceutical carrier. Such compositions comprise a therapeutically effective amount of the compound and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the compounds of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The G-protein Chemokine Receptor (CCR5) polypeptides and antagonists or agonists which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques* 7:980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described).; the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAM12, and DAN cell lines as described in Miller, *Human Gene Therapy* 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein Chemokine Receptor (CCR5) can bind to such receptor which comprises contacting a mammalian cell which expresses a G-protein Chemokine Receptor (CCR5) with the ligand under conditions permitting binding of ligands to the G-protein Chemokine Receptor (CCR5), detecting the presence of a ligand which binds to the receptor and thereby determining whether the ligand binds to the G-protein Chemokine Receptor (CCR5). The systems hereinabove described for determining agonists and/or antagonists may also be employed for determining ligands which bind to the receptor.

This invention also provides a method of detecting expression of a G-protein Chemokine Receptor (CCR5) polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to a G-protein Chemokine Receptor (CCR5) polypeptide of the present invention, by low stringency cross hybridization, or by identifying receptors that interact with related natural or synthetic ligands and or elicit similar behaviors after genetic or pharmacological blockade of the chemokine receptor polypeptides of the present invention.

Fragments of the genes may be used as a hybridization probe for a cDNA library to isolate other genes which have a high sequence similarity to the genes of the present invention, or which have similar biological activity. Probes of this type are at least 20 bases, preferably at least 30 bases and most preferably at least 50 bases or more. The probe may also be used to identify a cDNA clone corresponding to a full length transcript and a genomic clone or clones that contain the complete gene of the present invention including regulatory and promoter regions, exons and introns. An example of a screen of this type comprises isolating the coding region of the gene by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

The present invention also contemplates the use of the genes of the present invention as a diagnostic, for example, some diseases result from inherited defective genes. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., colorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., *Nature* 324:163–166 (1986)) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radiolabeled RNA of the invention or alternatively, radiolabeled antisense DNA sequences of the invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radiolabeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA* 85:4397–4401(1985)).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the G-protein Chemokine Receptor (CCR5) polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the G-protein Chemokine Receptor (CCR5) polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any G-protein Chemokine Receptor (CCR5) proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to G-protein Chemokine Receptor (CCR5) proteins. Unattached reporter antibody is then washed out. Peroxidase substrates are then added to the dish and the amount of color developed in a given time period is a measurement of the amount of G-protein Chemokine Receptor (CCR5) proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the clone. Computer analysis of the DNA of the deposited clone is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-DNA libraries.

Fluorescence in situ hybridization (FISH) of a DNA clone to a metaphase chromosomal spread can be used to provide a precise chromosomal location in one step. This technique can be used with DNA as short as 50 or 60 bases. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, *Nature* 256:495–497 (1975)), the trioma technique, the human B-cell hybridoma technique (Kozbor et al., *Immunology Today* 4:72 (1983)), and the EBV-hybridoma technique to produce human monoclonal antibodies (Cole, et al., in *Monoclonal Antibodies and Cancer Therapy*, Alan R. Liss, Inc. (1985), pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., *Nucleic Acids Res.* 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., *Virology* 52:456–457 (1973).

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In the present invention, a "secreted" or "soluble" G-protein Chemokine Receptor (CCR5) protein refers to a protein capable of being directed to the ER, secretory vesicles, or the extracellular space as a result of a signal sequence, as well as a G-protein Chemokine Receptor (CCR5) protein released into the extracellular space without necessarily containing a signal sequence. If the G-protein Chemokine Receptor (CCR5) secreted protein is released into the extracellular space, the G-protein Chemokine Receptor (CCR5) secreted protein can undergo extracellular processing to produce a "mature" G-protein Chemokine Receptor (CCR5) protein. Release into the extracellular space can occur by many mechanisms, including exocytosis and proteolytic cleavage. Examples of secreted or soluble G-protein Chemokine Receptor (CCR5) protein include fragments comprising, or alternatively consisting of, portions of the G-protein Chemokine Receptor (CCR5) described herein. Preferred secreted or soluble fragments comprise an extracellular loop, an intracellular loop, the N-terminal extracellular domain, or the C-terminal intracellular domain, or fragments therof. Additional preferred secreted or soluble fragments comprise an epitope of the the G-protein Chemokine Receptor (CCR5), such as described herein.

As used herein, a G-protein Chemokine Receptor (CCR5) "polynucleotide" refers to a molecule having a nucleic acid sequence contained in SEQ ID NO:1 or the G-protein Chemokine Receptor DNA contained within the clone deposited with the ATCC. For example, the G-protein Chemokine Receptor (CCR5) polynucleotide can contain the nucleotide sequence of the full length genomic sequence, including the 5' and 3' untranslated sequences, the coding region, with or without the signal sequence, the secreted protein coding region, as well as fragments, epitopes, domains, and variants of the nucleic acid sequence. Moreover, as used herein, a G-protein Chemokine Receptor (CCR5) "polypeptide" refers to a molecule having the translated amino acid sequence generated from the polynucleotide as broadly defined.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the G-protein Chemokine Receptor (CCR5) gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

A representative clone containing the open reading frame of the sequence for SEQ ID NO:1 was deposited with the American Type Culture Collection ("ATCC") on Jun. 1, 1995, and was given the ATCC Deposit Number 97183. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A G-protein Chemokine Receptor (CCR5) "polynucleotide" also includes those polynucleotides capable of hybridizing, under stringent hybridization conditions, to sequences contained in SEQ ID NO:1, the complement thereof, or the DNA within the deposited clone. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the G-protein Chemokine Receptor (CCR5) polynucleotides under lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a DNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The G-protein Chemokine Receptor (CCR5) polynucleotide can be composed of any polyribonucleotide or polydeoxribonucleotide, which may be unmodified RNA or DNA or modified RNA or DNA. For example, G-protein Chemokine Receptor (CCR5) polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the G-protein Chemokine Receptor (CCR5) polynucleotides can be composed of triple-stranded regions comprising RNA or DNA or both RNA and DNA. G-protein Chemokine Receptor (CCR5) polynucleotides may also contain one or more modified bases or DNA or RNA backbones modified for stability or for other reasons. “Modified” bases include, for example, tritylated bases and unusual bases such as inosine. A variety of modifications can be made to DNA and RNA; thus, “polynucleotide” embraces chemically, enzymatically, or metabolically modified forms.

G-protein Chemokine Receptor (CCR5) polypeptides can be composed of amino acids joined to each other by peptide bonds or modified peptide bonds, i.e., peptide isosteres, and may contain amino acids other than the 20 gene-encoded amino acids. The G-protein Chemokine Receptor (CCR5) polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in the G-protein Chemokine Receptor (CCR5) polypeptide, including the peptide backbone, the amino acid side-chains and the amino or carboxyl termini. It will be appreciated that the same type of modification may be present in the same or varying degrees at several sites in a given G-protein Chemokine Receptor (CCR5) polypeptide. Also, a given G-protein Chemokine Receptor (CCR5) polypeptide may contain many types of modifications. G-protein Chemokine Receptor (CCR5) polypeptides may be branched, for example, as a result of ubiquitination, and they may be cyclic, with or without branching. Cyclic, branched, and branched cyclic G-protein Chemokine Receptor (CCR5) polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

“SEQ ID NO:1” refers to a G-protein Chemokine Receptor (CCR5) polynucleotide sequence while “SEQ ID NO:2” refers to a G-protein Chemokine Receptor (CCR5) polypeptide sequence.

A G-protein Chemokine Receptor (CCR5) polypeptide “having biological activity” refers to polypeptides exhibiting activity similar, but not necessarily identical to, an activity of a G-protein Chemokine Receptor (CCR5) polypeptide, including mature forms, as measured in a particular biological assay, with or without dose dependency. In the case where dose dependency does exist, it need not be identical to that of the G-protein Chemokine Receptor (CCR5) polypeptide, but rather substantially similar to the dose-dependence in a given activity as compared to the G-protein Chemokine Receptor (CCR5) polypeptide (i.e., the candidate polypeptide will exhibit greater activity or not more than about 25-fold less and, preferably, not more than about tenfold less activity, and most preferably, not more than about three-fold less activity relative to the G-protein Chemokine Receptor (CCR5) polypeptide.)

G-Protein Chemokine Receptor (CCR5) Polynucleotides and Polypeptides

Clone HDGNR10 was isolated from a human monocyte genomic DNA library. This clone contains the entire coding region identified as SEQ ID NO:2. The deposited clone contains a DNA insert having a total of 1414 nucleotides, which encodes a predicted open reading frame of 352 amino acid residues. (See FIG. 1.) The open reading frame begins at a N-terminal methionine located at nucleotide position 259, and ends at the last triplet coding for an amino acid at nucleotide position 1314. The stop codon is at positions 1315–1317.

Subsequent expression analysis also showed G-protein Chemokine Receptor (CCR5) expression in macrophages, including immature dendritic cells such as Langerhans cells, and T cells, including Th0 and Th1 effector cells, a pattern consistent with immune system-specific expression. G-protein Chemokine Receptor (CCR5) has also been detected in microglia, astrocytes, neurons, and vascular endothelial cells of the central nervous system (CNS). G-protein Chemokine Receptor (CCR5) is also expressed in monocyes and T cells in the synovial fluid of rheumatoid arthritis patients, and has also been implicated in other forms of arthritis.

G-Protein Coupled Chemokine Receptors. Using BLAST analysis, SEQ ID NO:2 was found to be homologous to members of the G-Protein COUPLED Chemokine Receptor family. Particularly, SEQ ID NO:2 contains domains homologous to the translation product of the MonoMac 6 mRNA for human MCP-1 receptor (MCP-1R) A (FIG. 2) (GenBank Accession No. U03882; SEQ ID NO:9), including the conserved transmembrane domain containing seven transmembrane segments characteristic of the G-protein coupled receptor family, which begins with amino acid 37 of SEQ ID NO:2 or the polypeptide encoded by the deposited clone. G-protein Chemokine Receptor (CCR5) also includes the DRY motif, which is known to be required for signal transduction, found in many G-protein coupled receptors immediately following the third transmembrane segment. Because MCP-1R is thought to be important in the immune system, the homology between MCP-1R and G-protein Chemokine Receptor (CCR5) suggests that G-protein Chemokine Receptor (CCR5) may also be involved in the immune system.

A second MCP-1R sequence has also been isolated which is identical to the MCP-1RA sequence from the 5' untranslated region through the putative seventh transmembrane domain but which contains a different cytoplasmic tail. This second sequence, termed MCP-1RB, appears to be an alternatively spliced version of MCP-1RA. It is described further in U.S. Pat. No. 5,707,815.

Domains. Using BLAST analysis, SEQ ID NO:2 was found to be homologous to members of the G-protein Chemokine Receptor (CCR5) family. Particularly, SEQ ID NO:2 contains domains homologous to the translation product of the MonoMac 6 mRNA for human MCP-1 receptor (MCP-1R) A (FIG. 2) (GenBank Accession No. U03882; SEQ ID NO:9), including the following conserved domains: (a) a predicted N-terminal extracellular domain located at about amino acids 1 to 36; (b) a predicted transmembrane domain located at about amino acids 37 to 305; and (c) a predicted C-terminal intracellular domain located at about amino acids 306 to 352. The predicted transmembrane domain includes: seven transmembrane segments at about amino acids 37 to 58 (segment 1), 68 to 88 (segment 2), 103 to 124 (segment 3), 142 to 166 (segment 4), 196 to 223 (segment 5), 236 to 260 (segment 6), and 287 to 305 (segment 7); three intracellular loops at about amino acids 59 to 67 (intracellular loop 1), 125 to 141 (intracellular loop 2), and 224 to 235 (intracellular loop 3); and three extracellular loops at about amino acids 89 to 102 (extracellular loop 1), 167 to 195 (extracellular loop 2), and 261 to 274 (extracellular loop 3). These polypeptide fragments of G-protein Chemokine Receptor (CCR5) as defined above or as encoded by the deposited clone (SEQ ID NO:22) are specifically contemplated in the present invention, as are combinations of these and other regions disclosed herein. Also contemplated are polypeptides which exclude one or more of these domains, segments, and loops. The "loops" are also referred to as "regions," "domains," and "portions" herein and in the art, e.g., extracellular "regions", intracellular "regions", extracellular "domains", and intracellular "domains", extracellular "portions", and intracellular "portions".

SEQ ID NO:1 and the translated SEQ ID NO:2 are sufficiently accurate and otherwise suitable for a variety of uses well known in the art and described further below. For instance, SEQ ID NO:1 is useful for designing nucleic acid hybridization probes that will detect nucleic acid sequences contained in SEQ ID NO:1 or the DNA contained in the deposited clone. These probes will also hybridize to nucleic acid molecules in biological samples, thereby enabling a variety of forensic and diagnostic methods of the invention. Similarly, polypeptides identified from SEQ ID NO:2 may be used, for example, to generate antibodies which bind specifically to proteins G-protein Chemokine Receptor.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1 and the predicted translated amino acid sequence identified as SEQ ID NO:2, but also a sample of plasmid DNA containing a human DNA of G-protein Chemokine Receptor (CCR5) deposited with the ATCC. The nucleotide sequence of the deposited G-protein Chemokine Receptor (CCR5) clone can readily be determined by sequencing the deposited clone in accordance with known methods. The predicted G-protein Chemokine Receptor (CCR5) amino acid sequence can then be verified from such deposits. Moreover, the amino acid sequence of the protein encoded by the deposited clone can also be directly determined by peptide sequencing or by expressing the protein in a suitable host cell containing the deposited human G-protein Chemokine Receptor (CCR5) DNA, collecting the protein, and determining its sequence. A sample of the deposited clone, which contains the open reading frame of the G-protein Chemokine Receptor (CCR5), has been obtained from the ATCC and has been resequenced. The sequence data from the resequenced clone is shown in SEQ ID NO:21 and 22. SEQ ID NO:21 differs from SEQ ID NO:1 at 5 positions (nucleotides 320, 433, 442, 646, and 1289 of SEQ ID NO:1) SEQ ID NO:22 differs from SEQ ID NO:2 at 5 positions (amino acid residues 21, 59, 62, 130, and 344).

The present invention also relates to the G-protein Chemokine Receptor (CCR5) gene corresponding to SEQ ID NO:1, SEQ ID NO:2, or the deposited clone. The G-protein Chemokine Receptor (CCR5) gene can be isolated in accordance with known methods using the sequence information disclosed herein. Such methods include preparing probes or primers from the disclosed sequence and identifying or amplifying the G-protein Chemokine Receptor (CCR5) gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:1, SEQ ID NO:2, or a the deposited clone, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

The G-protein Chemokine Receptor (CCR5) polypeptides can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The G-protein Chemokine Receptor (CCR5) polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

G-protein Chemokine Receptor (CCR5) polypeptides are preferably provided in an isolated form, and preferably are substantially purified. A recombinantly produced version of a G-protein Chemokine Receptor (CCR5) polypeptide, including the secreted polypeptide, can be substantially purified using techniques described herein or otherwise known in the art, such as, for example, by the one-step method described in Smith and Johnson, Gene 67:31–40 (1988). G-protein Chemokine Receptor (CCR5) polypeptides also can be purified from natural, synthetic or recombinant sources using techniques described herein or otherwise known in the art, such as, for example, antibodies of the invention raised against the G-protein Chemokine Receptor (CCR5) protein.

The present invention provides a polynucleotide comprising, or alternatively consisting of, the nucleic acid sequence of SEQ ID NO:1, and/or a clone contained in ATCC deposit 97183. The present invention also provides a polypeptide comprising, or alternatively, consisting of, the polypeptide sequence of SEQ ID NO:2 and/or a polypeptide encoded by the clone contained in ATCC deposit 97183. Polynucleotides encoding a polypeptide comprising, or alternatively consisting of the polypeptide sequence of SEQ ID NO:2 and/or a polypeptide sequence encoded by the clone contained in ATCC deposit 97183 are also encompassed by the invention.

Signal Sequences

As described herein, the present invention also encompasses fusions of a signal sequence with the polypeptide of SEQ ID NO:2, and fragments thereof, and/or the polypeptide encoded by the deposited clone, and fragments thereof, to direct secretion of the polypeptide or fragment. Polynucleotides encoding such fusions are also encompassed by the invention.

The present invention also encompasses mature forms of the polypeptide having the sequence of SEQ ID NO:2, and fragments thereof, and/or the polypeptide sequence encoded by the deposited clone, and fragments thereof. Polynucleotides encoding the mature forms (such as, for example, the polynucleotide sequence in SEQ ID NO:1, and fragments thereof, and/or the polynucleotide sequence contained in the deposited clone, and fragments thereof) are also encompassed by the invention.

According to the signal hypothesis, proteins secreted by mammalian cells have a signal or secretary leader sequence which is cleaved from the mature protein once export of the growing chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

The deduced amino acid sequence of a secreted polypeptide can be analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinje are incorporated.

As one of ordinary skill would appreciate, however, cleavage sites sometimes vary from organism to organism and cannot be predicted with absolute certainty. Cleavage of a heterologous signal sequence in a fusion protein may occur at the junction of the polypeptide sequences or cleavage may occur at a position on either side of the junction. Accordingly, the present invention provides secreted polypeptides having a sequence shown in SEQ ID NO:2, and fragments thereof, which have an N-terminus beginning within 5 residues (i.e., +or −5 residues) of the predicted cleavage point. Similarly, it is also recognized that in some cases, cleavage of the signal sequence from a secreted protein is not entirely uniform, resulting in more than one secreted species. These polypeptides and fragments, and the polynucleotides encoding such polypeptides and fragments, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein or fragment produced by expression of the polynucleotide sequence of SEQ ID NO:1 or a fragment thereof and/or the polynucleotide sequence contained in the deposited clone or a fragment thereof, in a mammalian cell (e.g., COS cells, as described below). These polypeptides, and the polynucleotides encoding such polypeptides, are contemplated by the present invention.

Polynucleotide and Polypeptide Variants

The present invention is directed to variants of the polynucleotide sequence disclosed in SEQ ID NO:1, the complementary strand thereto, and/or the sequence contained in a deposited clone.

The present invention also encompasses variants of the polypeptide sequence disclosed in SEQ ID NO:2 and/or encoded by a deposited clone.

"Variant" refers to a polynucleotide or polypeptide differing from the G-protein Chemokine Receptor (CCR5) polynucleotide or polypeptide, but retaining essential properties thereof. Generally, variants are overall closely similar, and, in many regions, identical to the G-protein Chemokine Receptor (CCR5) polynucleotide or polypeptide.

The present invention is also directed to nucleic acid molecules which comprise, or alternatively consist of, a nucleotide sequence which is at least 80%, 85%, 90%, 95%, 96%, 97%, 98% or 99% identical to, for example, the nucleotide coding sequence in SEQ ID NO:1 or the complementary strand thereto, the nucleotide coding sequence contained in a deposited clone or the complementary strand thereto, a nucleotide sequence encoding the polypeptide of SEQ ID NO:2, a nucleotide sequence encoding the polypeptide encoded by the HDGNR10 deposited clone, and/or polynucleotide fragments of any of these nucleic acid molecules (e.g., those fragments described herein). Polynucleotides which hybridize to these nucleic acid molecules under stringent hybridization conditions or lower stringency conditions are also encompassed by the invention, as are polypeptides encoded by these polynucleotides.

The present invention is also directed to polypeptides which comprise, or alternatively consist of, an amino acid sequence which is at least 80%, 85%, 90%, 95%, 96%, 97%, 98%, 99% identical to, for example, the polypeptide sequence shown in SEQ ID NO:2, the polypeptide sequence encoded by the deposited clone, and/or polypeptide fragments of any of these polypeptides (e.g., those fragments described herein).

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the G-protein Chemokine Receptor (CCR5) polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of SEQ ID NO:1, the ORF (open reading frame) of the HDGNR10 DNA in the deposited clone, or any fragment specified as described herein.

As a practical matter, whether any particular nucleic acid molecule or polypeptide is at least 80%, 85%, 90%, 95%, 96%, 97%, 98% or 99% identical to a nucleotide sequence or polypeptide of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequences of SEQ ID NO:2 or to the amino acid sequence encoded by the deposited clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237–245(1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The G-protein Chemokine Receptor (CCR5) variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. G-protein Chemokine Receptor (CCR5) polynucleotide variants can be produced for a variety of reasons, e.g., to optimize codon expression for a particular host (change codons in the human mRNA to those preferred by a bacterial host such as *E. coli*).

Naturally occurring G-protein Chemokine Receptor (CCR5) variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the G-protein Chemokine Receptor (CCR5) polypeptides. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes G-protein Chemokine Receptor (CCR5) polypeptide variants which show substantial biological activity. Such variants include deletions, insertions, inversions, repeats, and substitutions selected according to general rules known in the art so as have little effect on activity.

The present application is directed to nucleic acid molecules at least 90%, 95%, 96%, 97%, 98% or 99% identical to the nucleic acid sequences disclosed herein, (e.g., encoding a polypeptide having the amino acid sequence of an N and/or C terminal deletion disclosed below as m-n of SEQ ID NO:2) or which correspond to the polypeptide encoded by the deposited clone, irrespective of whether they encode a polypeptide having G-protein Chemokine Receptor (CCR5) functional activity. This is because even where a particular nucleic acid molecule does not encode a polypeptide having G-protein Chemokine Receptor (CCR5) functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having G-protein Chemokine Receptor (CCR5) functional activity include, inter alia, (1) isolating a G-protein Chemokine Receptor (CCR5) gene or allelic or splice variants thereof in a cDNA library; (2) in situ hybridization (e.g., "FISH") to metaphase chromosomal spreads to provide precise chromosomal location of the G-protein Chemokine Receptor (CCR5) gene, as described in Verma et al., Human Chromosomes: A Manual of Basic Techniques, Pergamon Press, New York (1988); and (3) Northern Blot analysis for detecting G-protein Chemokine Receptor (CCR5) mRNA expression in specific tissues.

Preferred, however, are nucleic acid molecules having sequences at least 90%, 95%, 96%, 97%, 98% or 99% identical to the nucleic acid sequences disclosed herein, which do, in fact, encode a polypeptide having G-protein Chemokine Receptor (CCR5) functional activity. By "a polypeptide having G-protein Chemokine Receptor (CCR5) functional activity" is intended polypeptides exhibiting activity similar, but not necessarily identical, to a functional activity of the G-protein Chemokine Receptor (CCR5) polypeptides of the present invention (e.g., complete (full-length) G-protein Chemokine Receptor (CCR5), mature G-protein Chemokine Receptor (CCR5) and soluble G-protein Chemokine Receptor (CCR5) (e.g., having sequences contained in the extracellular domain or regions of G-protein Chemokine Receptor) as measured, for example, in a particular immunoassay or biological assay. For example, a G-protein Chemokine Receptor (CCR5) functional activity can routinely be measured by determining the ability of a G-protein Chemokine Receptor (CCR5) polypeptide to bind a G-protein Chemokine Receptor (CCR5) ligand. G-protein Chemokine Receptor (CCR5) functional activity may also be measured by determining the ability of a polypeptide, such as cognate ligand which is free or expressed on a cell surface, to induce cells expressing the polypeptide.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited clone, the nucleic acid sequence shown in FIG. 1 (SEQ ID NO:1), or fragments thereof, will encode polypeptides "having G-protein Chemokine Receptor (CCR5) functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having G-protein Chemokine Receptor (CCR5) functional activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

For example, site directed changes at the amino acid level of G-protein Chemokine Receptor (CCR5) can be made by replacing a particular amino acid with a conservative amino acid. Preferred conservative mutations of G-protein Chemokine Receptor (CCR5) (SEQ ID NO:2) include: M1 replaced with A, G, I, L, S, T, or V; D2 replaced with E; Y3 replaced with F, or W; Q4 replaced with N; V5 replaced with A, G, I, L, S, T, or M; S6 replaced with A, G, I, L, T, M, or V; S7 replaced with A, G, I, L, T, M, or V; I9 replaced with A, G, L, S, T, M, or V; Y10 replaced with F, or W; D11 replaced with E; I12 replaced with A, G, L, S, T, M, or V; N13 replaced with Q; Y14 replaced with F, or W; Y15 replaced with F, or W; T16 replaced with A, G, I, L, S, M, or V; S17 replaced with A, G, I, L, T, M, or V; E18 replaced with D; K22 replaced with H, or R; I23 replaced with A, G, L, S, T, M, or V; N24 replaced with Q; V25 replaced with A, G, I, L, S, T, or M; K26 replaced with H, or R; Q27 replaced with N; I28 replaced with A, G, L, S, T, M, or V; A29 replaced with G, I, L, S, T, M, or V; A30 replaced with G, I, L, S, T, M, or V; R31 replaced with H, or K;L32 replaced with A, G, I, S, T, M, or V; L33 replaced with A, G, I, S, T, M, or V; L36 replaced with A, G, I, S, T, M, or V; Y37 replaced with F, or W;S38 replaced with A, G, I, L, T, M, or V; L39 replaced with A, G, I, S, T, M, or V; V40 replaced with A, G, I, L, S, T, or M; F41 replaced with W, or Y;I42 replaced with A, G, L, S, T, M, or V; F43 replaced with W, or Y; G44 replaced with A, I, L, S, T, M, or V; F45 replaced with W, or Y; V46 replaced with A, G, I, L, S, T, or M; G47 replaced with A, I, L, S, T, M, or V; N48 replaced with Q; M49 replaced with A, G, I, L, S, T, or V; L50 replaced with A,G, I, S, T, M, or V; V51 replaced with A, G, I, L, S, T, or M; I52 replaced with A, G, L, S, T, M, or V; L53 replaced with A, G, I, S, T, M, or V; I54replaced with A, G, L, S, T, M, or V; L55 replaced with A, G, I, S, T, M, or V; I56 replaced with A, G, L, S, T, M, or V; N57 replaced with Q; Q59 replaced with N; R60 replaced with H, or K; L61 replaced with A, G, I, S, T, M, or V; E62 replaced with D; S63 replaced with A, G, I, L, T, M, or V; M64 replaced with A, G, I, L, S, T, or V; T65 replaced with A, G, I, L, S, M, or V; D66 replaced with E; I67 replaced with A, G, L, S, T, M, or V; Y68 replaced with F, or W; L69 replaced with A, G, I, S, T, M, or V; L70 replaced with A, G, I, S, T, M, or V; N71 replaced with Q; L72 replaced with A, G, I, S, T, M, or V; A73 replaced with G, I, L, S, T, M, or V; I74 replaced with A, G, L, S, T, M, or V; S75 replaced with A, G, I, L, T, M, or V; D76 replaced with E; L77 replaced with A, G, I, S, T, M, or V; F78 replaced with W, or Y; F79 replaced with W, or Y; L80 replaced with A, G, I, S, T, M, or V; L81 replaced with A, G, I, S,T, M, or V; T82 replaced with A, G, I, L, S, M, or V; V83 replaced with A, G, I, L, S, T, or M; F85 replaced with W, or Y; W86 replaced with F, or Y; A87replaced with G, I, L, S, T, M, or V; H88 replaced with K, or R; Y89 replaced with F, or W; A90 replaced with G, I, L, S, T, M, or V; A91 replaced with G,I, L, S, T, M, or V; A92 replaced with G, I, L, S, T, M, or V; Q93 replaced with N; W94 replaced with F, or Y; D95 replaced with E; F96 replaced with W, or Y; G97 replaced with A, I, L, S, T, M, or V; N98 replaced with Q; T99 replaced with A, G, I, L, S, M, or V; M100 replaced with A, G, I, L, S, T, or V;Q102 replaced with N; L103 replaced with A, G, I, S, T, M, or V; L104 replaced with A, G, I, S, T, M, or V; T105 replaced with A, G, I, L, S, M, or V;G106 replaced with A, I, L, S, T, M, or V; L107 replaced with A, G, I, S, T, M, or V; Y108 replaced with F, or W; F109 replaced with W, or Y; I110 replaced with A, G, L, S, T, M, or V; G111 replaced with A, I, L, S, T, M, or V; F112 replaced with W, or Y; F113 replaced with W, or Y; S114 replaced with A, G, I, L, T, M, or V; G115 replaced with A, I, L, S, T, M, or V; I116 replaced with A, G, L, S, T, M, or V; F117 replaced with W, or Y; F118 replaced with W, or Y; I119 replaced with A, G, L, S, T, M, or V; I120 replaced with A, G, L, S, T, M, or V; L121 replaced with A, G, I, S, T, M, or V; L122 replaced with A, G, I, S, T, M, or V; T123 replaced with A, G, I, L, S, M, or V; I124 replaced with A, G, L, S, T, M, or V; D125 replaced with E; R126 replaced with H, or K; Y127 replaced with F, or W; L128 replaced with A, G, I, S, T, M, or V; A129 replaced with G, I, L, S, T, M, or V; I130replaced with A, G, L, S, T, M, or V; V131 replaced with A, G, I, L, S, T, or M; H132 replaced with K, or R; A133 replaced with G, I, L, S, T, M, or V;V134 replaced with A, G, I, L, S, T, or M; F135 replaced with W, or Y; A136 replaced with G, I, L, S, T, M, or V; L137 replaced with A, G, I, S, T, M, or V; K138 replaced with H, or R; A139 replaced with G, I, L, S, T, M, or V; R140 replaced with H, or K; T141 replaced with A, G, I, L, S, M, or V; V142 replaced with A, G, I, L, S, T, or M; T143 replaced with A, G, I, L, S, M, or V; F144 replaced with W, or Y; G145 replaced with A, I, L, S, T, M, or V;V146 replaced with A, G, I, L, S, T, or M; V147 replaced with A, G, I, L, S, T, or M; T148 replaced with A, G, I, L, S, M, or V; S149 replaced with A, G,I, L, T, M, or V; V150 replaced with A, G, I, L, S, T, or M; I151 replaced with A, G, L, S, T, M, or V; T152 replaced with A, G, I, L, S, M, or V; W153 replaced with F, or Y; V154 replaced with A, G, I, L, S, T, or M; V155 replaced with A, G, I, L, S, T, or M; A156 replaced with G, I, L, S, T, M, or V;V157 replaced with A, G, I, L, S, T, or M; F158 replaced with W, or Y; A159 replaced with G, I, L, S, T, M, or V; S160 replaced with A, G, I, L, T, M, or V; L161 replaced with A, G, I, S, T, M, or V; G163 replaced with A, I, L, S, T, M, or V; I164 replaced with A, G, L, S, T, M, or V; I165 replaced with A,G, L, S, T, M, or V; F166 replaced with W, or Y; T167 replaced with A, G, I, L, S, M, or V; R168 replaced with H, or K; S169 replaced with A, G, I, L, T,M, or V; Q170 replaced with N; K171 replaced with H, or R; E172 replaced with D; G173 replaced with A, I, L, S, T, M, or V; L174 replaced with A, G, I, T, M, or V; H175 replaced with K, or R; Y176 replaced with F, or W; T177 replaced with A, G, I, L, S, M, or V; S179 replaced with A, G, I, L, T, M, or V; S180 replaced with A, G, I, L, T, M, or V; H181 replaced with K, or R; F182 replaced with W, or Y; Y184 replaced with F, or W; S185 replaced with A,G, I, L, T, M, or V; Q186 replaced with N; Y187 replaced with F, or W; Q188 replaced with N; F189 replaced with W, or Y; W190 replaced with F, or Y;K191 replaced with H, or R; N192 replaced with Q; F193 replaced with W, or Y; Q194 replaced with N; T195 replaced with A, G, I, L, S, M, or V; L196 replaced with A, G, I, S, T, M, or V; K197 replaced with H, or R; I198 replaced with A, G, L, S, T, M, or V; V199 replaced with A, G, I, L, S, T, or M;I200 replaced with A, G, L, S, T, M, or V; L201 replaced with A, G, I, S, T, M, or V; G202 replaced with A, I, L, S, T, M, or V; L203 replaced with A, G,I, S, T, M, or V; V204 replaced with A, G, I, L, S, T, or M; L205 replaced with A, G, I, S, T, M, or V; L207 replaced with A, G, I, S, T, M, or V; L208replaced with A, G, I, S, T, M, or V; V209 replaced with A, G, I, L, S, T, or M; M210 replaced with A, G, I, L, S, T, or V; V211 replaced with A, G, I, L,S, T, or M; I212 replaced with A, G, L, S, T, M, or V; Y214 replaced with F, or W; S215 replaced with A, G, I, L, T, M, or V; G216 replaced with A, I, L,S, T, M, or V; I217 replaced with A, G, L, S, T, M, or V; L218 replaced with A, G, I, S, T, M, or V; K219 replaced with H, or R; T220 replaced with A, G,I, L, S, M, or V; L221 replaced with A, G, I, S, T, M, or V; L222 replaced with A, G, I, S, T, M, or V; R223 replaced with H, or K; R225 replaced with H, or K; N226 replaced with Q; E227 replaced with D; K228 replaced with H, or R; K229 replaced with H, or R; R230 replaced with H, or K; H231 replaced with K, or R; R232 replaced with H, or K; A233 replaced with G, I, L, S, T, M, or V; V234 replaced with A, G, I, L, S, T, or M; R235 replaced with H, or K; L236 replaced with A, G, I, S, T, M, or V; I237 replaced with A, G, L, S, T, M, or V; F238 replaced with W, or Y; T239 replaced with A, G, I, L, S, M, or V; I240 replaced with A, G, L, S, T, M, or V; M241 replaced with A, G, I, L, S, T, or V; I242 replaced with A, G, L, S, T, M, or V; V243 replaced with A, G, I, L, S, T, or M; Y244 replaced with F, or W; F245 replaced with W, or Y; L246 replaced with A, G, I, S, T, M, or V; F247 replaced with W, or Y;W248 replaced with F, or Y; A249 replaced with G, I, L, S, T, M, or V; Y251 replaced with F, or W; N252 replaced with Q; I253 replaced with A, G, L, S,T, M, or V; V254 replaced with A, G, I, L, S, T, or M; L255 replaced with A, G, I, S, T, M, or V; L256 replaced with A, G, I, S, T, M, or V; L257 replaced with A, G, I, S, T, M, or V; N258 replaced with Q; T259 replaced with A, G, I, L, S, M, or V; F260 replaced with W, or Y; Q261 replaced with N; E262 replaced with D; F263 replaced with W, or Y; F264 replaced with W, or Y; G265 replaced with A, I, L, S, T, M, or V; L266 replaced with A, G, I, S, T, M, or V; N267 replaced with Q; N268 replaced with Q; S270 replaced with A, G, I, L, T, M, or V; S271 replaced with A, G, I, L, T, M, or V; S272 replaced with A, G, I, L, T, M, or V; N273 replaced with Q; R274 replaced with H, or K; L275 replaced with A, G, I, S, T, M, or V; D276 replaced with E; Q277 replaced with N; A278 replaced with G, I, L, S, T, M, or V; M279 replaced with A, G, I, L, S, T, or V; Q280 replaced with N; V281 replaced with A, G, I, L, S, T, or M; T282 replaced with A, G, I, L, S, M, or V; E283 replaced with D; T284 replaced with A, G, I, L, S, M, or V; L285 replaced with A, G, I, S, T, M, or V;G286 replaced with A, I, L, S, T, M, or V; M287 replaced with A, G, I, L, S, T, or V; T288 replaced with A, G, I, L, S, M, or V; H289 replaced with K, or R; I292 replaced with A, G, L, S, T, M, or V; N293 replaced with Q; I295 replaced with A, G, L, S, T, M, or V; I296 replaced with A, G, L, S, T, M, or V; Y297 replaced with F, or W; A298 replaced with G, I, L, S, T, M, or V; F299 replaced with W, or Y; V300 replaced with A, G, I, L, S, T, or M; G301 replaced with A, I, L, S, T, M, or V; E302 replaced with D; K303 replaced with H, or R; F304 replaced with W, or Y; R305 replaced with H, or K; N306 replaced with Q; Y307 replaced with F, or W; L308 replaced with A, G, I, S, T, M, or V; L309 replaced with A, G, I, S, T, M, or V; V310 replaced with A,G, I, L, S, T, or M; F311 replaced with W, or Y; F312 replaced with W, or Y; Q313 replaced with N; K314 replaced with H, or R; H315 replaced with K, or R; I316 replaced with A, G, L, S, T, M, or V; A317 replaced with G, I, L, S, T, M, or V; K318 replaced with H, or R; R319 replaced with H, or K; F320 replaced with W, or Y; K322 replaced with H, or R; S325 replaced with A, G, I, L, T, M, or V; I326 replaced with A, G, L, S, T, M, or V; F327 replaced with W, or Y; Q328 replaced with N; Q329 replaced with N; E330 replaced with D; A331 replaced with G, I, L, S, T, M, or V; E333 replaced with D; R334 replaced with H, or K; A335 replaced with G, I, L, S, T, M, or V; S336 replaced with A, G, I, L, T, M, or V; S337 replaced with A, G, I, L, T, M, or V;V338 replaced with A, G, I, L, S, T, or M; Y339 replaced with F, or W; T340 replaced with A, G, I, L, S, M, or V; R341 replaced with H, or K; S342 replaced with A, G, I, L, T, M, or V; T343 replaced with A, G, I, L, S, M, or V; G344 replaced with A, I, L, S, T, M, or V; E345 replaced with D; Q346 replaced with N; E347 replaced with D; I348 replaced with A, G, L, S, T, M, or V; S349 replaced with A, G, I, L, T, M, or V; V350 replaced with A, G, I, L,S, T, or M; G351 replaced with A, I, L, S, T, M, or V; and/or L352 replaced with A, G, I, S, T, M, or V.

Preferred conservative mutations of G-protein Chemokine Receptor (CCR5) as encoded by the deposited HDGNR10 clone (SEQ ID NO:22) include: M1 replaced with A, G, I, L, S, T, or V; D2 replaced with E; Y3 replaced with F, or W; Q4 replaced with N; V5 replaced with A, G, I, L, S, T, or M; S6 replaced with A, G, I, L, T, M, or V; S7 replaced with A, G, I, L, T, M, or V; I9 replaced with A, G, L,S, T, M, or V; Y10 replaced with F, or W; D11 replaced with E; I12 replaced with A, G, L, S, T, M, or V; N13 replaced with Q; Y14 replaced with F, or W; Y15 replaced with F, or W; T16 replaced with A, G, I, L, S, M, or V; S17 replaced with A, G, I, L, T, M, or V; E18 replaced with D; Q21 replaced with N; K22 replaced with H, or R; I23 replaced with A, G, L, S, T, M, or V; N24 replaced with Q; V25 replaced with A, G, I, L, S, T, or M; K26 replaced with H, or R; Q27 replaced with N; I28 replaced with A, G, L, S, T, M, or V; A29 replaced with G, I, L, S, T, M, or V; A30 replaced with G, I, L, S, T, M, or V; R31 replaced with H, or K;L32 replaced with A, G, I, S, T, M, or V; L33 replaced with A, G, I, S, T, M, or V; L36 replaced with A, G, I, S, T, M, or V; Y37 replaced with F, or W;S38 replaced with A, G, I, L, T, M, or V; L39 replaced with A, G, I, S, T, M, or V; V40 replaced with A, G, I, L, S, T, or M; F41 replaced with W, or Y;I42 replaced with A, G, L, S, T, M, or V; F43 replaced with W, or Y; G44 replaced with A, G, L, S, T, M, or V; F45 replaced with W, or Y; V 46 replaced with A, G, I, L, S, T, or M; G47 replaced with A, I, L, S, T, M, or V; N48 replaced with Q; M49 replaced with A, G, I, L, S, T, or V; L50 replaced with A,G, I, S, T, M, or V; V51 replaced with A, G, I, L, S, T, or M; I52 replaced with A, G, L, S, T, M, or V; L53 replaced with A, G, I, S, T, M, or V; I54 replaced with A, G, L, S, T, M, or V; L55 replaced with A, G, I, S, T, M, or V; I56 replaced with A, G, L, S, T, M, or V; N57 replaced with Q; K59 replaced with H, or R; R60 replaced with H, or K; L61 replaced with A, G, I, S, T, M, or V; K62 replaced with H, or R; S63 replaced with A, G, I, L, T, M, or V; M64 replaced with A, G, I, L, S, T, or V; T65 replaced with A, G, I, L, S, M, or V; D66 replaced with E; I67 replaced with A, G, L, S, T, M, or V; Y68 replaced with F, or W; L69 replaced with A, G, I, S, T, M, or V; L70 replaced with A, G, I, S, T, M, or V; N71 replaced with Q; L72 replaced with A, G, I, S, T, M, or V; A73 replaced with G, I, L, S, T, M, or V; I74 replaced with A, G, L, S, T, M, or V; S75 replaced with A, G, I, L, T, M, or V; D76 replaced with E; L77 replaced with A, G, I, S, T, M, or V; F78 replaced with W, or Y; F79 replaced with W, or Y; L80 replaced with A, G, I, S, T, M, or V; L81 replaced with A, G, I, S,T, M, or V; T82 replaced with A, G, I, L, S, M, or V; V83 replaced with A, G, I, L, S, T, or M; F85 replaced with W, or Y; W86 replaced with F, or Y; A87 replaced with G, I, L, S, T, M, or V; H88 replaced with K, or R; Y89 replaced with F, or W; A90 replaced with G, I, L, S, T, M, or V; A91 replaced with G,I, L, S, T, M, or V; A92 replaced with G, I, L, S, T, M, or V; Q93 replaced with N; W94 replaced with F, or Y; D95 replaced with E; F96 replaced with W, or Y; G97 replaced with A, I, L, S, T, M, or V; N98 replaced with Q; T99 replaced with A, G, I, L, S, M, or V; M100 replaced with A, G, I, L, S, T, or V;Q102 replaced with N; L103 replaced with A, G, I, S, T, M, or V; L104 replaced with A, G, I, S, T, M, or V; T105 replaced with A, G, I, L, S, M, or V;G106 replaced with A, I, L, S, T, M, or V; L107 replaced with A, G, I, S, T, M, or V; Y108 replaced with F, or W; F109 replaced with W, or Y; I110 replaced with A, G, L, S, T, M, or V; G111 replaced with A, I, L, S, T, M, or V; F112 replaced with W, or Y; F113 replaced with W, or Y; S114 replaced with A, G, I, L, T, M, or V; G115 replaced with A, I, L, S, T, M, or V; I116 replaced with A, G, L, S, T, M, or V; F117 replaced with W, or Y; F118 replaced with W, or Y; I119 replaced with A, G, L, S, T, M, or V; I120 replaced with A, G, L, S, T, M, or V; L121 replaced with A, G, I, S, T, M, or V; L122 replaced with A, G, I, S, T, M, or V; T123 replaced with A, G, I, L, S, M, or V; I124 replaced with A, G, L, S, T, M, or V; D125 replaced with E; R126 replaced with H, or K; Y127 replaced with F, or W; L128 replaced with A, G, I, S, T, M, or V; A129 replaced with G, I, L, S, T, M, or V; V130 replaced with A, G, I, L, S, T, or M; V131 replaced with A, G, I, L, S, T, or M; H132 replaced with K, or R; A133 replaced with G, I, L, S, T, M, or V;V134 replaced with A, G, I, L, S, T, or M; F135 replaced with W, or Y; A136 replaced with G, I, L, S, T, M, or V; L137 replaced with A, G, I, S, T, M, or V; K138 replaced with H, or R; A139 replaced with G, I, L, S, T, M, or V; R140 replaced with H, or K; T141 replaced with A, G, I, L, S, M, or V; V142 replaced with A, G, I, L, S, T, or M; T143 replaced with A, G, I, L, S, M, or V; F144 replaced with W, or Y; G145 replaced with A, I, L, S, T, M, or V;V146 replaced with A, G, I, L, S, T, or M; V147 replaced with A, G, I, L, S, T, or M; T148 replaced with A, G, I, L, S, M, or V; S149 replaced with A, G,I, L, T, M, or V; V150 replaced with A, G, I, L, S, T, or M; I151 replaced with A, G, L, S, T, M, or V; T152 replaced with A, G, I, L, S, M, or V; W153 replaced with F, or Y; V154 replaced with A, G, I, L, S, T, or M; V155 replaced with A, G, I, L, S, T, or M; A156 replaced with G, I, L, S, T, M, or V;V157 replaced with A, G, I, L, S, T, or M; F158 replaced with W, or Y; A159 replaced with G, I, L, S, T, M, or V; S160 replaced with A, G, I, L, T, M, or V; L161 replaced with A, G, I, S, T, M, or V; G163 replaced with A, I, L, S, T, M, or V; I164 replaced with A, G, L, S, T, M, or V; I165 replaced with A,G, L, S, T, M, or V; F166 replaced with W, or Y; T167 replaced with A, G, I, L, S, M, or V; R168 replaced with H, or K; S169 replaced with A, G, I, L, T,M, or V; Q170 replaced with N; K171 replaced with H, or R; E172 replaced with D; G173 replaced with A, I, L, S, T, M, or V; L174 replaced with A, G, I,S, T, M, or V; H175 replaced with K, or R; Y176 replaced with F, or W; T177 replaced with A, G, I, L, S, M, or V; S179 replaced with A, G, I, L, T, M, or V; S180 replaced with A, G, I, L, T, M, or V; H181 replaced with K, or R; F182 replaced with W, or Y; Y184 replaced with F, or W; S185 replaced with A,G, A, L, T, M, or V; Q186 replaced with N; Y187 replaced with F, or W; Q188 replaced with N; F189 replaced with W, or Y; W190 replaced with F, or Y;K191 replaced with H, or R; N192 replaced with Q; F193 replaced with W, or Y; Q194 replaced with N; T I95 replaced with A, G, I, L, S, M, or V; L196 replaced with A, G, I, S, T, M, or V; K197 replaced with H, or R; I198 replaced with A, G, L, S, T, M, or V; V199 replaced with A, G, I, L, S, T, or M;I200 replaced with A, G, L, S, T, M, or V; L201 replaced with A, G, I, S, T, M, or V; G202 replaced with A, I, L, S, T, M, or V; L203 replaced with A, G,I, S, T, M, or V; V204 replaced with A, G, I, L, S, T, or M; L205 replaced with A, G, I, S, T, M, or V; L207 replaced with A, G, I, S, T, M, or V; L208replaced with A, G, I, S, T, M, or V; V209 replaced with A, G, I, L, S, T, or M; M210 replaced with A, G, I, L, S, T, or V; V211 replaced with A, G, I, L,S, T, or M; I212 replaced with A, G, L, S, T, M, or V; Y214 replaced with F, or W; S215 replaced with A, G, I, L, T, M, or V; G216 replaced with A, I, L,S, T, M, or V; I217 replaced with A, G, L, S, T, M, or V; L218 replaced with A, G, I, S, T, M, or V; K219 replaced with H, or R; T220 replaced with A, G,I, L, S, M, or V; L221 replaced with A, G, I, S, T, M, or V; L222 replaced with A, G, I, S, T, M, or V; R223 replaced with H, or K; R225 replaced with H, or K; N226 replaced with Q; E227 replaced with D; K228 replaced with H, or R; K229 replaced with H, or R; R230 replaced with H, or K; H231 replaced with K, or R; R232 replaced with H, or K; A233 replaced with G, I, L, S, T, M, or V; V234 replaced with A, G, I, L, S, T, or M; R235 replaced with H, or K; L236 replaced with A, G, I, S, T, M, or V; I237 replaced with A, G, L, S, T, M, or V; F238 replaced with W, or Y; T239 replaced with A, G, I, L, S, M, or V; I240 replaced with A, G, L, S, T, M, or V; M241 replaced with A, G, I, L, S, T, or V; I242 replaced with A, G, L, S, T, M, or V; V243 replaced with A, G, I, L, S, T, or M; Y244 replaced with F, or W; F245 replaced with W, or Y; L246 replaced with A, G, I, S, T, M, or V; F247 replaced with W, or Y;W248 replaced with F, or Y; A249 replaced with G, I, L, S, T, M, or V; Y251 replaced with F, or W; N252 replaced with Q; I253 replaced with A, G, L, S,T, M, or V; V254 replaced with A, G, I, L, S, T, or M; L255 replaced with A, G, I, S, T, M, or V; L256 replaced with A, G, I, S, T, M, or V; L257 replaced with A, G, I, S, T, M, or V; N258 replaced with Q; T259 replaced with A, G, I, L, S, M, or V; F260 replaced with W, or Y; Q261 replaced with N; E262 replaced with D; F263 replaced with W, or Y; F264 replaced with W, or Y; G265 replaced with A, I, L, S, T, M, or V; L266 replaced with A, G, I, S, T, M, or V; N267 replaced with Q; N268 replaced with Q; S270 replaced with A, G, I, L, T, M, or V; S271 replaced with A, G, I, L, T, M, or V; S272 replaced with A, G, I, L, T, M, or V; N273 replaced with Q; R274 replaced with H, or K; L275 replaced with A, G, I, S, T, M, or V; D276 replaced with E; Q277 replaced with N; A278 replaced with G, I, L, S, T, M, or V; M279 replaced with A, G, I, L, S, T, or V; Q280 replaced with N; V281 replaced with A, G, I, L, S, T, or M; T282 replaced with A, G, I, L, S, M, or V; E283 replaced with D; T284 replaced with A, G, I, L, S, M, or V; L285 replaced with A, G, I, S, T, M, or V;G286 replaced with A, I, L, S, T, M, or V; M287 replaced with A, G, I, L, S, T, or V; T288 replaced with A, G, I, L, S, M, or V; H289 replaced with K, or R; I292 replaced with A, G, L, S, T, M, or V; N293 replaced with Q; I295 replaced with A, G, L, S, T, M, or V; I296 replaced with A, G, L, S, T, M, or V; Y297 replaced with F, or W; A298 replaced with G, I, L, S, T, M, or V; F299 replaced with W, or Y; V300 replaced with A, G, I, L, S, T, or M; G301 replaced with A, I, L, S, T, M, or V; E302 replaced with D; K303 replaced with H, or R; F304 replaced with W, or Y; R305 replaced with H, or K; N306 replaced with Q; Y307 replaced with F, or W; L308 replaced with A, G, I, S, T, M, or V; L309 replaced with A, G, I, S, T, M, or V; V310 replaced with A,G, I, L, S, T, or M; F311 replaced with W, or Y; F312 replaced with W, or Y; Q313 replaced with N; K314 replaced with H, or R; H315 replaced with K, or R; I316 replaced with A, G, L, S, T, M, or V; A317 replaced with G, I, L, S, T, M, or V; K318 replaced with H, or R; R319 replaced with H, or K; F320 replaced with W, or Y; K322 replaced with H, or R; S325 replaced with A, G, I, L, T, M, or V; I326 replaced with A, G, L, S, T, M, or V; F327 replaced with W, or Y; Q328 replaced with N; Q329 replaced with N; E330 replaced with D; A331 replaced with G, I, L, S, T, M, or V; E333 replaced with D; R334 replaced with H, or K; A335 replaced with G, I, L, S, T, M, or V; S336 replaced with A, G, I, L, T, M, or V; S337 replaced with A, G, I, L, T, M, or V;V338 replaced with A, G, I, L, S, T, or M; Y339 replaced with F, or W; T340 replaced with A, G, I, L, S, M, or V; R341 replaced with H, or K; S342 replaced with A, G, I, L, T, M, or V; T343 replaced with A, G, I, L, S, M, or V; E344 replaced with D; E345 replaced with D; Q346 replaced with N; E347 replaced with D; I348 replaced with A, G, L, S, T, M, or V; S349 replaced with A, G, I, L, T, M, or V; V350 replaced with A, G, I, L,S, T, or M; G351 replaced with A, I, L, S, T, M, or V; and/or L352 replaced with A, G, I, S, T, M, or V.

The resulting constructs can be routinely screened for activities or functions described throughout the specification and known in the art. Preferably, the resulting constructs have an increased and/or a decreased G-protein Chemokine Receptor (CCR5) activity or function, while the remaining G-protein Chemokine Receptor (CCR5) activities or functions are maintained. More preferably, the resulting constructs have more than one increased and/or decreased G-protein Chemokine Receptor (CCR5) activity or function, while the remaining G-protein Chemokine Receptor (CCR5) activities or functions are maintained.

Besides conservative amino acid substitution, variants of G-protein Chemokine Receptor (CCR5) include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, G-protein Chemokine Receptor (CCR5) polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

For example, preferred non-conservative substitutions of G-protein Chemokine Receptor (CCR5) (SEQ ID NO:2) include: M1 replaced with D, E, H, K, R, N, Q, F, W, Y, P, or C; D2 replaced with H, K, R, A, G, I,L, S, T, M, V, N, Q, F, W, Y, P, or C; Y3 replaced with D, E, H, K, R, N, Q, A, G, I, L, S, T, M, V, P, or C; Q4 replaced with D, E, H, K, R, A, G, I, L, S, T, M, V, F, W, Y, P, or C; V5 replaced with D, E, H, K, R, N, Q, F, W, Y, P, or C; S6 replaced with D, E, H, K, R, N, Q, F, W, Y, P, or C; S7 replaced with D, E, H, K, R, N, Q, F, W, Y, P, or C; P8 replaced with D, E, H, K, R, A, G, I, L, S, T, M, V, N, Q, F, W, Y, or C; I9 replaced with D, E, H, K, R, N, Q, F, W, Y, P, or C; Y10 replaced with D, E, H, K, R, N, Q, A, G, I, L, S, T, M, V, P, or C; D11 replaced with H, K, R, A, G, I, L, S, T, M, V, N, Q, F, W, Y, P, or C; I12 replaced with D, E, H, K, R, N, Q, F, W, Y, P, or C; N13 replaced with D, E, H, K, R, A, G, I, L, S, T, M, V, F, W, Y, P, or C; Y14 replaced with D, E, H, K, R, N, Q, A, G, I, L, S, T, M, V, P, or C; Y15 replaced with D, E, H, K, R, N, Q, A, G, I, L, S, T, M, V, P, or C; T16 replaced with D, E, H, K, R, N, Q, F, W, Y, P, or C; S17 replaced with D, E, H, K, R, N, Q, F, W, Y, P, or C; E18 replaced with H, K, R, A, G, I, L, S,T, M, V, N, Q, F, W, Y, P, or C; P19 replaced with D, E, H, K, R, A, G, I, L, S, T, M, V, N, Q, F, W, Y, or C; C20 replaced with D, E, H, K, R, A, G, I, L, S, T, M, V, N, Q, F, W, Y, or P; P21 replaced with D, E, H, K, R, A, G, I, L, S, T, M, V, N, Q, F, W, Y, or C; K22 replaced with D, E, A, G, I, L, S, T, M, V, N, Q, F, W, Y, P, or C; I23 replaced with D, E, H, K, R, N, Q, F, W, Y, P, or C; N24 replaced with D, E, H, K, R, A, G, I, L, S, T, M, V, F, W, Y, P, or C; V25 replaced with D, E, H, K, R, N, Q, F, W, Y, P, or C; K26 replaced with D, E, A, G, I, L, S, T, M, V, N, Q, F, W, Y, P, or C; Q27 replaced with D, E, H, K, R, A, G, I, L, S, T, M, V, F, W, Y, P, or C; I28 replaced with D, E, H, K, R, N, Q, F, W, Y, P, or C; A29 replaced with D, E, H, K, R, N, Q, F, W, Y, P, or C; A30 replaced with D, E, H, K, R, N, Q, F, W, Y, P, or C; R31 replaced with D, E, A, G, I, L, S, T, M, V, N, Q, F, W, Y, P, or C; L32 replaced with D, E, H, K, R, N, Q, F, W, Y, P, or C; L33 replaced with D, E, H, K, R, N, Q, F, W, Y, P, or C; P34 replaced with D, E, H, K, R, A, G, I, L, S, T, M, V, N, Q, F, W, Y, or C; P35 replaced with D, E, H, K, R, A, G, I, L, S, T, M, V, N, Q, F, W, Y, or C; L36 replaced with D, E,H, K, R, N, Q, F, W, Y, P, or C; Y37 replaced with D, E, H, K, R, N, Q, A, G, I, L, S, T, M, V, P, or C; S38 replaced with D, E, H, K, R, N, Q, F, W, Y, P, or C; L39 replaced with D, E, H, K, R, N, Q, F, W, Y, P, or C; V40 replaced with D, E, H, K, R, N, Q, F, W, Y, P, or C; F41 replaced with D, E, H, K, R, N, Q, A, G, I, L, S, T, M, V, P, or C; I42 replaced with D, E, H, K, R, N, Q, F, W, Y, P, or C; F43 replaced with D, E, H, K, R, N, Q, A, G, I, L,S, T, M, V, P, or C; G44 replaced with D, E, H, K, R, N, Q, F, W, Y, P, or C; F45 replaced with D, E, H, K, R, N, Q, A, G, I, L, S, T, M, V, P, or C; V46 replaced with D, E, H, K, R, N, Q, F, W, Y, P, or C; G47 replaced with D, E, H, K, R, N, Q, F, W, Y, P, or C; N48 replaced with D, E, H, K, R, A, G, I, L, S, T, M, V, F, W, Y, P, or C; M49 replaced with D, E, H, K, R, N, Q, F, W, Y, P, or C; L50 replaced with D, E, H, K, R, N, Q, F, W, Y, P, or C; V51 replaced with D, E, H, K, R, N, Q, F, W, Y, P, or C; I52 replaced with D, E, H, K, R, N, Q, F, W, Y, P, or C; L53 replaced with D, E, H, K, R,N, Q, F, W, Y, P, or C; L54 replaced with D, E, H, K, R, N, Q, F, W, Y, P, or C; L55 replaced with D, E, H, K, R, N, Q, F, W, Y, P, or C; I56 replaced with D, E, H, K, R, N, Q, F, W, Y, P, or C; N57 replaced with D, E, H, K, R, A, G, I, L, S, T, M, V, F, W, Y, P, or C; C58 replaced with D, E, H, K, R, A, G, I, L, S, T, M, V, N, Q, F, W, Y, or P; Q59 replaced with D, E, H, K, R, A, G, I, L, S, T, M, V, F, W, Y, P, or C; R60 replaced with D, E, A, G, I, L, S, T, M, V, N, Q, F, W, Y, P, or C; L61 replaced with D, E, H, K, R, N, Q, F, W, Y, P, or C; E62 replaced with H, K, R, A, G, I, L, S, T, M, V, N, Q, F, W, Y, P, or C; S63 replaced with D, E, H, K, R, N, Q, F, W, Y, P, or C; M64 replaced with D, E, H, K, R, N, Q, F, W, Y, P, or C; T65 replaced with D, E, H, K, R, N, Q, F, W, Y, P, or C; D66 replaced with H, K, R, A, G, I, L, S, T, M, V, N, Q, F, W, Y, P, or C; I67 replaced with D, E, H, K, R, N, Q, F, W, Y, P, or C; Y68 replaced with D, E, H, K, R, N, Q, A, G, I, L, S, T, M, V, P, or C; L69 replaced with D, E, H, K, R, N, Q, F, W, Y, P, or C; L70 replaced with D, E, H, K, R, N, Q, F, W, Y, P, or C; N71 replaced with D, E, H, K, R, A, G, I, L, S, T, M, V, F, W, Y, P, or C; L72 replaced with D, E, H, K, R, N, Q, F, W, Y, P, or C; A73 replaced with D, E, H, K, R, N, Q, F, W, Y, P, or C; I74 replaced with D, E, H, K, R, N, Q, F, W, Y, P, or C; S75 replaced with D, E, H, K, R, N, Q, F, W, Y, P, or C; D76 replaced with H, K, R, A, G, I, L, S, T, M, V, N, Q, F, W, Y, P, or C; L77 replaced with D, E, H, K, R, N, Q, F, W, Y, P, or C; F78 replaced with D, E, H, K, R, N, Q, A, G, I, L, S, T, M, V, P, or C; F79 replaced with D, E, H, K, R, N, Q, A, G, I, L, S, T, M, V, P, or C; L80 replaced with D, E, H, K, R, N, Q, F, W, Y, P, or C; L81 replaced with D, E, H, K, R, N, Q, F, W, Y, P, or C; T82 replaced with D, E, H, K, R, N, Q, F, W, Y, P, or C; V83 replaced with D, E, H, K, R, N, Q, F, W, Y, P, or C; P84 replaced with D, E, H, K, R, A, G, I, L, S, T, M, V, N, Q, F, W, Y, or C; F85 replaced with D, E, H, K, R, N, Q, A, G, I, L, S, T, M, V, P, or C; W86 replaced with D, E, H, K, R, N, Q, A, G, I, L, S, T, M, V, P, or C; A87 replaced with D, E, H, K, R, N, Q, F, W, Y, P, or C; H88 replaced with D, E, A, G, I, L, S, T, M, V, N, Q, F, W, Y, P, or C; Y89 replaced with D, E, H, K, R, N, Q, A, G, I, L, S, T, M, V, P, or C; A90 replaced with D, E, H, K, R, N, Q, F, W, Y, P, or C; A91 replaced with D, E, H, K, R, N, Q, F, W, Y, P, or C; A92 replaced with D, E, H, K, R, N, Q, F, W, Y, P, or C; Q93 replaced with D, E, H, K, R, A, G, I, L, S, T, M, V, F, W, Y, P, or C; W94 replaced with D, E, H, K, R, N, Q, A, G, I, L, S, T, M, V, P, or C; D95 replaced with H, K, R, A, G, I, L, S, T, M, V, N, Q, F, W, Y, P, or C; F96 replaced with D, E, H, K, R, N, Q, A, G, I, L, S, T, M, V, P, or C; G97 replaced with D, E, H, K, R, N, Q, F, W, Y, P, or C; N98replaced with D, E, H, K, R, A, G, I, L, S, T, M, V, F, W, Y, P, or C; T99 replaced with D, E, H, K, R, N, Q, F, W, Y, P, or C; M100 replaced with D, E, H, K, R, N, Q, F, W, Y, P, or C; ClOl replaced with D, E, H, K, R, A, G, I, L, S, T, M, V, N, Q, F, W, Y, or P; Q102 replaced with D, E, H, K, R, A, G, I, L, S, T, M, V, F, W, Y, P, or C; L103 replaced with D, E, H, K, R, N, Q, F, W, Y, P, or C; L104 replaced with D, E, H, K, R, N, Q, F, W, Y, P, or C; T105 replaced with D, E, H, K, R, N, Q, F, W, Y, P, or C; G106 replaced with D, E, H, K, R, N, Q, F, W, Y, P, or C; L107 replaced with D, E, H, K, R, N, Q, F, W, Y, P, or C; Y108 replaced with D, E, H, K, R, N, Q, A, G, I, L, S, T, M, V, P, or C; F109 replaced with D, E, H, K, R, N, Q, A, G, I, L, S, T, M, V, P, or C; I110 replaced with D, E, H, K, R, N, Q, F, W, Y, P, or C; G111 replaced with D, E, H, K, R, N, Q, F, W, Y, P, or C; F112 replaced with D, E, H, K, R, N, Q, A, G, I, L, S, T, M, V, P, or C; F113 replaced with D, E, H, K, R, N, Q, A, G, I, L, S, T, M, V, P, or C; S114 replaced with D, E, H, K, R, N, Q, F, W, Y, P, or C; G115 replaced with D, E, H, K, R, N, Q, F, W, Y, P, or C; I116 replaced with D, E, H, K, R, N, Q, F, W, Y, P, or C; F117 replaced with D, E, H, K, R, N, Q, A, G, I, L, S, T, M, V, P, or C; F118 replaced with D, E, H, K, R, N, Q, A, G, I, L, S, T, M, V, P, or C; I119replaced with D, E, H, K, R, N, Q, F, W, Y, P, or C; I120 replaced with D, E, H, K, R, N, Q, F, W, Y, P, or C; L121 replaced with D, E, H, K, R, N, Q, F, W, Y, P, or C; L122 replaced with D, E, H, K, R, N, Q, F, W, Y, P, or C; T123 replaced with D, E, H, K, R, N, Q, F, W, Y, P, or C; I124 replaced with D, E, H, K, R, N, Q, F, W, Y, P, or C; D125 replaced with H, K, R, A, G, I, L, S, T, M, V, N, Q, F, W, Y, P, or C; R126 replaced with D, E, A, G, I, L, S, T, M, V, N, Q, F, W, Y, P, or C; Y127 replaced with D, E, H, K, R, N, Q, A, G, I, L, S, T, M, V, P, or C; L128 replaced with D, E, H, K, R, N, Q, F, W, Y, P, or C; A129 replaced with D, E, H, K, R, N, Q, F, W, Y, P, or C; I130 replaced with D, E, H, K, R, N, Q, F, W, Y, P, or C; V131 replaced with D, E, H, K, R, N, Q, F, W, Y, P, or C; H132 replaced with D, E, A, G, I, L, S, T, M, V, N, Q, F, W, Y, P, or C; A133 replaced with D, E, H, K, R, N, Q, F, W, Y, P, or C; V134 replaced with D, E, H, K, R, N, Q, F, W, Y, P, or C; F135 replaced with D, E, H, K, R, N, Q, A, G, I, L, S, T, M, V, P, or C; A136 replaced with D, E, H, K, R, N, Q, F, W, Y, P, or C; L137 replaced with D, E, H, K, R, N, Q, F, W, Y, P, or C; K138 replaced with D, E, A, G, I, L, S, T, M, V, N, Q, F, W, Y, P, or C; A139 replaced with D, E, H, K, R, N, Q, F, W, Y, P, or C; R140 replaced with D, E, A, G, I, L, S, T, M, V, N, Q, F, W, Y, P, or C; T141 replaced with D, E, H, K, R, N, Q, F, W, Y, P, or C; V142 replaced with D, E, H, K, R, N, Q, F, W, Y, P, or C; T143 replaced with D, E, H, K, R, N, Q, F, W, Y, P, or C; F144 replaced with D, E, H, K, R, N, Q, A, G, I, L, S, T, M, V, P, or C; G145 replaced with D, E, H, K, R, N, Q, F, W, Y, P, or C; V146 replaced with D, E, H, K, R, N, Q, F, W, Y, P, or C; V147 replaced with D, E, H, K, R, N, Q, F, W, Y, P, or C; T148 replaced with D, E, H, K, R, N, Q, F, W, Y, P, or C; S149 replaced with D, E, H, K, R, N, Q, F, W, Y, P, or C; V150 replaced with D, E, H, K, R, N, Q, F, W, Y, P, or C; I151 replaced with D, E, H, K, R, N, Q, F, W, Y, P, or C; T152 replaced with D, E, H, K, R, N, Q, F, W, Y, P, or C; W153 replaced with D, E, H, K, R, N, Q, A, G, I, L, S, T, M, V, P, or C; V154 replaced with D, E, H, K, R, N, Q, F, W, Y, P, or C; V155 replaced with D, E, H, K, R, N, Q, F, W, Y, P, or C; A156 replaced with D, E, H, K, R, N, Q, F, W, Y, P, or C; V157 replaced with D, E, H, K, R, N, Q, F, W, Y, P, or C; F158 replaced with D, E, H, K, R, N, Q, A, G, I, L, S, T, M, V, P, or C; A159 replaced with D, E, H, K, R, N, Q, F, W, Y, P, or C; S160 replaced with D, E, H, K, R, N, Q, F, W, Y, P, or C; L161 replaced with D, E, H, K, R, N, Q, F, W, Y, P, or C; P162 replaced with D, E, H, K, R, A, G, I, L, S, T, M, V, N, Q, F, W, Y, or C; G163 replaced with D, E, H, K, R, N, Q, F, W, Y, P, or C; I164 replaced with D, E, H, K, R, N, Q, F, W, Y, P, or C; I165 replaced with D, E, H, K, R, N, Q, F, W, Y, P, or C; F166 replaced with D, E, H, K, R, N, Q, A, G, I, L, S, T, M, V, P, or C; T167 replaced with D, E, H, K, R, N, Q, F, W, Y, P, or C; R168 replaced with D, E, A, G, I, L, S, T, M, V, N, Q, F, W, Y, P, or C; S169 replaced with D, E, H, K, R, N, Q, F, W, Y, P, or C; Q170 replaced with D, E, H, K, R, A, G, I, L, S, T, M, V, F, W, Y, P, or C; K171 replaced with D, E, A, G, I, L, S, T, M, V, N, Q, F, W, Y, P, or C; E172 replaced with H, K, R, A, G, I, L, S, T, M, V, N, Q, F, W, Y, P, or C; G173 replaced with D, E, H, K, R, N, Q, F, W, Y, P, or C; L174 replaced with D, E, H, K, R, N, Q, F, W, Y, P, or C; H175 replaced with D, E, A, G, I, L, S, T, M, V, N, Q, F, W, Y, P, or C; Y176 replaced with D, E, H, K, R, N, Q, A, G, I, L, S, T, M, V, P, or C; T177 replaced with D, E, H, K, R, N, Q, F, W, Y, P, or C; C178 replaced with D, E, H, K, R, A, G, I, L, S, T, M, V, N, Q, F, W, Y, or P; S179 replaced with D, E, H, K, R, N, Q, F, W, Y, P, or C; S180 replaced with D, E, H, K, R, N, Q, F, W, Y, P, or C; H181 replaced with D, E, A, G, I, L, S, T, M, V, N, Q, F, W, Y, P, or C; F182 replaced with D, E, H, K, R, N, Q, A, G, I, L, S, T, M, V, P, or C; P183 replaced with D, E, H, K, R, A, G, I, L, S, T, M, V, N, Q, F, W, Y, or C; Y184 replaced with D, E, H, K, R, N, Q, A, G, I, L, S, T, M, V, P, or C; S185 replaced with D, E, H, K, R, N, Q, F, W, Y, P, or C; Q186 replaced with D, E, H, K, R, A, G, I, L, S, T, M, V, F, W, Y, P, or C; Y187 replaced with D, E, H, K, R, N, Q, A, G, I, L, S, T, M, V, P, or C; Q188 replaced with D, E, H, K, R, A, G, I, L, S, T, M, V, F, W, Y, P, or C; F189 replaced with D, E, H, K, R, N, Q, A, G, I, L, S, T, M, V, P, or C; W190 replaced with D, E, H, K, R, N, Q, A, G, I, L, S, T, M, V, P, or C; K191 replaced with D, E, A, G, I, L, S, T, M, V, N, Q, F, W, Y, P, or C; N192 replaced with D, E, H, K, R, A, G, I, L, S, T, M, V, F, W, Y, P, or C; F193 replaced with D, E, H, K, R, N, Q, A, G, I, L, S, T, M, V, P, or C; Q194 replaced with D, E, H, K, R, A, G, I, L, S, T, M, V, F, W, Y, P, or C; T195 replaced with D, E, H, K, R, N, Q, F, W, Y, P, or C; L196 replaced with D, E, H, K, R, N, Q, F, W, Y, P, or C; K197 replaced with D, E, A, G, I, L, S, T, M, V, N, Q, F, W, Y, P, or C; I198 replaced with D, E, H, K, R, N, Q, F, W, Y, P, or C; V199 replaced with D, E, H, K, R, N, Q, F, W, Y, P, or C; I200 replaced with D, E, H, K, R, N, Q, F, W, Y, P, or C; L201 replaced with D, E, H, K, R, N, Q, F, W, Y, P, or C; G202 replaced with D, E, H, K, R, N, Q, F, W, Y, P, or C; L203 replaced with D, E, H, K, R, N, Q, F, W, Y, P, or C; V204 replaced with D, E, H, K, R, N, Q, F, W, Y, P, or C; L205 replaced with D, E, H, K, R, N, Q, F, W, Y, P, or C; P206 replaced with D, E, H, K, R, A, G, I, L, S, T, M, V, N, Q, F, W, Y, or C; L207 replaced with D, E, H, K, R, N, Q, F, W, Y, P, or C; L208 replaced with D, E, H, K, R, N, Q, F, W, Y, P, or C; V209 replaced with D, E, H, K, R, N, Q, F, W, Y, P, or C; M210 replaced with D, E, H, K, R, N, Q, F, W, Y, P, or C; V211 replaced with D, E, H, K, R, N, Q, F, W, Y, P, or C; I212 replaced with D, E, H, K, R, N, Q, F, W, Y, P, or C; C213 replaced with D, E, H, K, R, A, G, I, L, S, T, M, V, N, Q, F, W, Y, or P; Y214 replaced with D, E, H, K, R, N, Q, A, G, I, L, S, T, M, V, P, or C; S215 replaced with D, E, H, K, R, N, Q, F, W, Y, P, or C; G216 replaced with D, E, H, K, R, N, Q, F, W, Y, P, or C; I217 replaced with D, E, H, K, R, N, Q, F, W, Y, P, or C; L218 replaced with D, E, H, K, R, N, Q, F, W, Y, P, or C; K219 replaced with D, E, A, G, I, L, S, T, M, V, N, Q, F, W, Y, P, or C; T220 replaced with D, E, H, K, R, N, Q, F, W, Y, P, or C; L221 replaced with D, E, H, K, R, N, Q, F, W, Y, P. or C; L222 replaced with D, E, H, K, R, N, Q, F, W, Y, P, or C; R223 replaced with D, E, A, G, I, L, S, T, M, V, N, Q, F, W, Y, P, or C; C224 replaced with D, E, H, K, R, A, G, I, L, S, T, M, V, N, Q, F, W, Y, or P; R225 replaced with D, E, A, G, I, L, S, T, M, V, N, Q, F, W, Y, P, or C; N226 replaced with D, E, H, K, R, A, G, I, L, S, T, M, V, F, W, Y, P, or C; E227 replaced with H, K, R, A, G, I, L, S, T, M, V, N, Q, F, W, Y, P, or C; K228 replaced with D, E, A, G, I, L, S, T, M, V, N, Q, F, W, Y, P, or C; K229 replaced with D, E, A, G, I, L, S, T, M, V, N, Q, F, W, Y, P, or C; R230 replaced with D, E, A, G, I, L, S, T, M, V, N, Q, F, W, Y, P, or C; H231 replaced with D, E, A, G, I, L, S, T, M, V, N, Q, F, W, Y, P, or C; R232 replaced with D, E, A, G, I, L, S, T, M, V, N, Q, F, W, Y, P, or C; A233 replaced with D, E, H, K, R, N, Q, F, W, Y, P, or C; V234 replaced with D, E, H, K, R, N, Q, F, W, Y, P, or C; R235 replaced with D, E, A, G, I, L, S, T, M, V, N, Q, F, W, Y, P, or C; L236 replaced with D, E, H, K, R, N, Q, F, W, Y, P, or C; I237 replaced with D, E, H, K, R, N, Q, F, W, Y, P, or C; F238 replaced with D, E, H, K, R, N, Q, A, G, I, L, S, T, M, V, P, or C; T239 replaced with D, E, H, K, R, N, Q, F, W, Y, P, or C; I240 replaced with D, E, H, K, R, N, Q, F, W, Y, P, or C; M241 replaced with D, E, H, K, R, N, Q, F, W, Y, P, or C; I242 replaced with D, E, H, K, R, N, Q, F, W, Y, P, or C; V243 replaced with D, E, H, K, R, N, Q, F, W, Y, P, or C; Y244 replaced with D, E, H, K, R, N, Q, A, G, I, L, S, T, M, V, P, or C; F245 replaced with D, E, H, K, R, N, Q, A, G, I, L, S, T, M, V, P, or C; L246 replaced with D, E, H, K, R, N, Q, F, W, Y, P, or C; F247 replaced with D, E, H, K, R, N, Q, A, G, I, L, S, T, M, V, P, or C; W248 replaced with D, E, H, K, R, N, Q, A, G, I, L, S, T, M, V, P, or C; A249 replaced with D, E, H, K, R, N, Q, F, W, Y, P, or C; P250 replaced with D, E, H, K, R, A, G, I, L, S, T, M, V, N, Q, F, W, Y, or C; Y251 replaced with D, E, H, K, R, N, Q, A, G, I, L, S, T, M, V, P, or C; N252 replaced with D, E, H, K, R, A, G, I, L, S, T, M, V, F, W, Y, P, or C; I253 replaced with D, E, H, K, R, N, Q, F, W, Y, P, or C; V254 replaced with D, E, H, K, R, N, Q, F, W, Y, P, or C; L255 replaced with D, E, H, K, R, N, Q, F, W, Y, P, or C; L256 replaced with D, E, H, K, R, N, Q, F, W, Y, P, or C; L257 replaced with D, E, H, K, R, N, Q, F, W, Y, P, or C; N258 replaced with D, E, H, K, R, A, G, I, L, S, T, M, V, F, W, Y, P, or C; T259 replaced with D, E, H, K, R, N, Q, F, W, Y, P, or C; F260 replaced with D, E, H, K, R, N, Q, A, G, I, L, S, T, M, V, P, or C; Q261 replaced with D, E, H, K, R, A, G, I, L, S, T, M, V, F, W, Y, P, or C; E262 replaced with H, K, R, A, G, I, L, S, T, M, V, N, Q, F, W, Y, P, or C; F263 replaced with D, E, H, K, R, N, Q, A, G, I, L, S, T, M, V, P, or C; F264 replaced with D, E, H, K, R, N, Q, A, G, I, L, S, T, M, V, P, or C; G265 replaced with D, E, H, K, R, N, Q, F, W, Y, P, or C; L266 replaced with D, E, H, K, R, N, Q, F, W, Y, P, or C; N267 replaced with D, E, H, K, R, A, G, I, L, S, T, M, V, F, W, Y, P, or C; N268 replaced with D, E, H, K, R, A, G, I, L, S, T, M, V, F, W, Y, P, or C; C269 replaced with D, E, H, K, R, A, G, I, L, S, T, M, V, N, Q, F, W, Y, or P; S270 replaced with D, E, H, K, R, N, Q, F, W, Y, P, or C; S271 replaced with D, E, H, K, R, N, Q, F, W, Y, P, or C; S272 replaced with D, E, H, K, R, N, Q, F, W, Y, P, or C; N273 replaced with D, E, H, K, R, A, G, I, L, S, T, M, V, F, W, Y, P, or C; R274 replaced with D, E, A, G, I, L, S, T, M, V, N, Q, F, W, Y, P, or C; L275 replaced with D, E, H, K, R, N, Q, F, W, Y, P, or C; D276 replaced with H, K, R, A, G, I, L, S, T, M, V, N, Q, F, W, Y, P, or C; Q277 replaced with D, E, H, K, R, A, G, I, L, S, T, M, V, F, W, Y, P, or C; A278 replaced with D, E, H, K, R, N, Q, F, W, Y, P, or C; M279 replaced with D, E, H, K, R, N, Q, F, W, Y, P, or C; Q280 replaced with D, E, H, K, R, A, G, I, L, S, T, M, V, F, W, Y, P, or C; V281 replaced with D, E, H, K, R, N, Q, F, W, Y, P, or C; T282 replaced with D, E, H, K, R, N, Q, F, W, Y, P, or C; E283 replaced with H, K, R, A, G, I, L, S, T, M, V, N, Q, F, W, Y, P, or C; T284 replaced with D, E, H, K, R, N, Q, F, W, Y, P, or C; L285 replaced with D, E, H, K, R, N, Q, F, W, Y, P, or C; G286 replaced with D, E, H, K, R, N, Q, F, W, Y, P, or C; M287 replaced with D, E, H, K, R, N, Q, F, W, Y, P, or C; T288 replaced with D, E, H, K, R, N, Q, F, W, Y, P, or C; H289 replaced with D, E, A, G, I, L, S, T, M, V, N, Q, F, W, Y, P, or C; C290 replaced with D, E, H, K, R, A, G, I, L, S, T, M, V, N, Q, F, W, Y, or P; C291 replaced with D, E, H, K, R, A, G, I, L, S, T, M, V, N, Q, F, W, Y, or P; I292 replaced with D, E, H, K, R, N, Q, F, W, Y, P, or C; N293 replaced with D, E, H, K, R, A, G, I, L, S, T, M, V, F, W, Y, P, or C; P294 replaced with D, E, H, K, R, A, G, I, L, S, T, M, V, N, Q, F, W, Y, or C; I295 replaced with D, E, H, K, R, N, Q, F, W, Y, P, or C; I296 replaced with D, E, H, K, R, N, Q, F, W, Y, P, or C; Y297 replaced with D, E, H, K, R, N, Q, A, G, I, L, S, T, M, V, P, or C; A298 replaced with D, E, H, K, R, N, Q, F, W, Y, P, or C; F299 replaced with D, E, H, K, R, N, Q, A, G, I, L, S, T, M, V, P, or C; V300 replaced with D, E, H, K, R, N, Q, F, W, Y, P, or C; G301 replaced with D, E, H, K, R, N, Q, F, W, Y, P, or C; E302 replaced with H, K, R, A, G, I, L, S, T, M, V, N, Q, F, W, Y, P, or C; K303 replaced with D, E, A, G, I, L, S, T, M, V, N, Q, F, W, Y, P, or C; F304 replaced with D, E, H, K, R, N, Q, A, G, I, L, S, T, M, V, P, or C; R305 replaced with D, E, A, G, I, L, S, T, M, V, N, Q, F, W, Y, P, or C; N306 replaced with D, E, H, K, R, A, G, I, L, S, T, M, V, F, W, Y, P, or C; Y307 replaced with D, E, H, K, R, N, Q, A, G, I, L, S, T, M, V, P, or C; L308 replaced with D, E, H, K, R, N, Q, F, W, Y, P, or C; L309 replaced with D, E, H, K, R, N, Q, F, W, Y, P, or C; V310 replaced with D, E, H, K, R, N, Q, F, W, Y, P, or C; F311 replaced with D, E, H, K, R, N, Q, A, G, I, L, S, T, M, V, P, or C; F312 replaced with D, E, H, K, R, N, Q, A, G, I, L, S, T, M, V, P, or C; Q313 replaced with D, E, H, K, R, A, G, I, L, S, T, M, V, F, W, Y, P, or C; K314 replaced with D, E, A, G, I, L, S, T, M, V, N, Q, F, W, Y, P, or C; H315 replaced with D, E, A, G, I, L, S, T, M, V, N, Q, F, W, Y, P, or C; I316 replaced with D, E, H, K, R, N, Q, F, W, Y, P, or C; A317 replaced with D, E, H, K, R, N, Q, F, W, Y, P, or C; K318 replaced with D, E, A, G, I, L, S, T, M, V, N, Q, F, W, Y, P, or C; R319 replaced with D, E, A, G, I, L, S, T, M, V, N, Q, F, W, Y, P, or C; F320 replaced with D, E, H, K, R, N, Q, A, G, I, L, S, T, M, V, P, or C; C321 replaced with D, E, H, K, R, A, G, I, L, S, T, M, V, N, Q, F, W, Y, or P; K322 replaced with D, E, A, G, I, L, S, T, M, V, N, Q, F, W, Y, P, or C; C323 replaced with D, E, H, K, R, A, G, I, L, S, T, M, V, N, Q, F, W, Y, or P; C324 replaced with D, E, H, K, R, A, G, I, L, S, T, M, V, N, Q, F, W, Y, or P; S325 replaced with D, E, H, K, R, N, Q, F, W, Y, P, or C; I326 replaced with D, E, H, K, R, N, Q, F, W, Y, P, or C; F327 replaced with D, E, H, K, R, N, Q, A, G, I, L, S, T, M, V, P, or C; Q328 replaced with D, E, H, K, R, A, G, I, L, S, T, M, V, F, W, Y, P, or C; Q329 replaced with D, E, H, K, R, A, G, I, L, S, T, M, V, F, W, Y, P, or C; E330 replaced with H, K, R, A, G, I, L, S, T, M, V, N, Q, F, W, Y, P, or C; A331 replaced with D, E, H, K, R, N, Q, F, W, Y, P, or C; P332 replaced with D, E, H, K, R, A, G, I, L, S, T, M, V, N, Q, F, W, Y, or C; E333 replaced with H, K, R, A, G, I, L, S, T, M, V, N, Q, F, W, Y, P, or C; R334 replaced with D, E, A, G, I, L, S, T, M, V, N, Q, F, W, Y, P, or C; A335 replaced with D, E, H, K, R, N, Q, F, W, Y, P, or C; S336 replaced with D, E, H, K, R, N, Q, F, W, Y, P, or C; S337 replaced with D, E, H, K, R, N, Q, F, W, Y, P, or C; V338 replaced with D, E, H, K, R, N, Q, F, W, Y, P, or C; Y339 replaced with D, E, H, K, R, N, Q, A, G, I, L, S, T, M, V, P, or C; T340 replaced with D, E, H, K, R, N, Q, F, W, Y, P, or C; R341 replaced with D, E, A, G, I, L, S, T, M, V, N, Q, F, W, Y, P, or C; S342 replaced with D, E, H, K, R, N, Q, F, W, Y, P, or C; T343 replaced with D, E, H, K, R, N, Q, F, W, Y, P, or C; G344 replaced with D, E, H, K, R, N, Q, F, W, Y, P, or C; E345 replaced with H, K, R, A, G, I, L, S, T, M, V, N, Q, F, W, Y, P, or C; Q346 replaced with D, E, H, K, R, A, G, I, L, S, T, M, V, F, W, Y, P, or C; E347 replaced with H, K, R, A, G, I, L, S, T, M, V, N, Q, F, W, Y, P, or C; I348 replaced with D, E, H, K, R, N, Q, F, W, Y, P, or C; S349 replaced with D, E, H, K, R, N, Q, F, W, Y, P, or C; V350 replaced with D, E, H, K, R, N, Q, F, W, Y, P, or C; G351 replaced with D, E, H, K, R, N, Q, F, W, Y, P, or C; and/or L352 replaced with D, E, H, K, R, N, Q, F, W, Y, P, or C.

Addition preferred non-conservative substitutions of G-protein Chemokine Receptor (CCR5) as encoded by the HDGNR10 deposited clone (SEQ ID NO:22) include: M1 replaced with D, E, H, K, R, N, Q, F, W, Y, P, or C; D2 replaced with H, K, R, A, G, I, L, S, T, M, V, N, Q, F, W, Y, P, or C; Y3 replaced with D, E, H, K, R, N, Q, A, G, I, L, S, T, M, V, P, or C; Q4 replaced with D, E, H, K, R, A, G, I, L, S, T, M, V, F, W, Y, P, or C; V5 replaced with D, E, H, K, R, N, Q, F, W, Y, P, or C; S6 replaced with D, E, H, K, R, N, Q, F, W, Y, P, or C; S7replaced with D, E, H, K, R, N, Q, F, W, Y, P, or C; P8 replaced with D, E, H, K, R, A, G, I, L, S, T, M, V, N, Q, F, W, Y, or C; I9 replaced with D, E, H, K, R, N, Q, F, W, Y, P, or C; Y10 replaced with D, E, H, K, R, N, Q, A, G, I, L, S, T, M, V, P, or C; D11 replaced with H, K, R, A, G, I, L, S, T, M, V, N, Q, F, W, Y, P, or C; I12 replaced with D, E, H, K, R, N, Q, F, W, Y, P, or C; N13 replaced with D, E, H, K, R, A, G, I, L, S, T, M, V, F, W, Y, P, or C; Y14 replaced with D, E, H, K, R, N, Q, A, G, I, L, S, T, M, V, P, or C; Y15 replaced with D, E, H, K, R, N, Q, A, G, I, L, S, T, M, V, P, or C; T16 replaced with D, E, H, K, R, N, Q, F, W, Y, P, or C; S17 replaced with D, E, H, K, R, N, Q, F, W, Y, P, or C; E18 replaced with H, K, R, A, G, I, L, S, T, M, V, N, Q, F, W, Y, P, or C; P19 replaced with D, E, H, K, R, A, G, I, L, S, T, M, V, N, Q, F, W, Y, or C; C20 replaced with D, E, H, K, R, A, G, I, L, S, T, M, V, N, Q, F, W, Y, or P; Q21 replaced with D, E, H, K, R, A, G, I, L, S, T, M, V, F, W, Y, P, or C; K22 replaced with D, E, A, G, I, L, S, T, M, V, N, Q, F, W, Y, P, or C; I23 replaced with D, E, H, K, R, N, Q, F, W, Y, P, or C; N24 replaced with D, E, H, K, R, A, G, I, L, S, T, M, V, F, W, Y, P, or C; V25 replaced with D, E, H, K, R, N, Q, F, W, Y, P, or C; K26 replaced with D, E, A, G, I, L, S, T, M, V, N, Q, F, W, Y, P, or C; Q27 replaced with D, E, H, K, R, A, G, I, L, S, T, M, V, F, W, Y, P, or C; I28 replaced with D, E, H, K, R, N, Q, F, W, Y, P, or C; A29 replaced with D, E, H, K, R, N, Q, F, W, Y, P, or C;

W, Y, P, or C; A30 replaced with D, E, H, K, R, N, Q, F, W, Y, P, or C; R31 replaced with D, E, A, G, I, L, S, T, M, V, N, Q, F, W, Y, P, or C; L32 replaced with D, E, H, K, R, N, Q, F, W, Y, P, or C; L33 replaced with D, E, H, K, R, N, Q, F, W, Y, P, or C; P34 replaced with D, E, H, K, R, A, G, I, L, S, T, M, V, N, Q, F, W, Y, or C; P35 replaced with D, E, H, K, R, A, G, I, L, S, T, M, V, N, Q, F, W, Y, or C; L36 replaced with D, E, H, K, R, N, Q, F, W, Y, P, or C; Y37 replaced with D, E, H, K, R, N, Q, A, G, I, L, S, T, M, V, P, or C; S38 replaced with D, E, H, K, R, N, Q, F, W, Y, P, or C; L39 replaced with D, E, H, K, R, N, Q, F, W, Y, P, or C; V40 replaced with D, E, H, K, R, N, Q, F, W, Y, P, or C; F41 replaced with D, E, H, K, R, N, Q, A, G, I, L, S, T, M, V, P, or C; I42 replaced with D, E, H, K, R, N, Q, F, W, Y, P, or C; F43 replaced with D, E, H, K, R, N, Q, A, G, I, L, S, T, M, V, P, or C; G44 replaced with D, E, H, K, R, N, Q, F, W, Y, P, or C; F45 replaced with D, E, H, K, R, N, Q, A, G, I, L, S, T, M, V, P, or C; V46 replaced with D, E, H, K, R, N, Q, F, W, Y, P, or C; G47 replaced with D, E, H, K, R, N, Q, F, W, Y, P, or C; N48 replaced with D, E, H, K, R, A, G, I, L, S, T, M, V, F, W, Y, P, or C; M49 replaced with D, E, H, K, R, N, Q, F, W, Y, P, or C; L50 replaced with D, E, H, K, R, N, Q, F, W, Y, P, or C; V51 replaced with D, E, H, K, R, N, Q, F, W, Y, P, or C; I52 replaced with D, E, H, K, R, N, Q, F, W, Y, P, or C; L53 replaced with D, E, H, K, R, N, Q, F, W, Y, P, or C; I54 replaced with D, E, H, K, R, N, Q, F, W, Y, P, or C; L55 replaced with D, E, H, K, R, N, Q, F, W, Y, P, or C; I56 replaced with D, E, H, K, R, N, Q, F, W, Y, P, or C; N57 replaced with D, E, H, K, R, A, G, I, L, S, T, M, V, F, W, Y, P, or C; C58 replaced with D, E, H, K, R, A, G, I, L, S, T, M, V, N, Q, F, W, Y, or P; K59 replaced with D, E, A, G, I, L, S, T, M, V, N, Q, F, W, Y, P, or C; R60 replaced with D, E, A, G, I, L, S, T, M, V, N, Q, F, W, Y, P, or C; L61 replaced with D, E, H, K, R, N, Q, F, W, Y, P, or C; K62 replaced with D, E, A, G, I, L, S, T, M, V, N, Q, F, W, Y, P, or C; S63 replaced with D, E, H, K, R, N, Q, F, W, Y, P, or C; M64 replaced with D, E, H, K, R, N, Q, F, W, Y, P, or C; T65 replaced with D, E, H, K, R, N, Q, F, W, Y, P, or C; D66 replaced with H, K, R, A, G, I, L, S, T, M, V, N, Q, F, W, Y, P, or C; I67 replaced with D, E, H, K, R, N, Q, F, W, Y, P, or C; Y68 replaced with D, E, H, K, R, N, Q, A, G, I, L, S, T, M, V, P, or C; L69 replaced with D, E, H, K, R, N, Q, F, W, Y, P, or C; L70 replaced with D, E, H, K, R, N, Q, F, W, Y, P, or C; N71 replaced with D, E, H, K, R, A, G, I, L, S, T, M, V, F, W, Y, P, or C; L72 replaced with D, E, H, K, R, N, Q, F, W, Y, P, or C; A73 replaced with D, E, H, K, R, N, Q, F, W, Y, P, or C; 174 replaced with D, E, H, K, R, N, Q, F, W, Y, P, or C; S75 replaced with D, E, H, K, R, N, Q, F, W, Y, P, or C; D76 replaced with H, K, R, A, G, I, L, S, T, M, V, N, Q, F, W, Y, P, or C; L77 replaced with D, E, H, K, R, N, Q, F, W, Y, P, or C; F78 replaced with D, E, H, K, R, N, Q, A, G, I, L, S, T, M, V, P, or C; F79 replaced with D, E, H, K, R, N, Q, A, G, I, L, S, T, M, V, P, or C; L80 replaced with D, E, H, K, R, N, Q, F, W, Y, P, or C; L81 replaced with D, E, H, K, R, N, Q, F, W, Y, P, or C; T82 replaced with D, E, H, K, R, N, Q, F, W, Y, P, or C; V83 replaced with D, E, H, K, R, N, Q, F, W, Y, P, or C; P84 replaced with D, E, H, K, R, A, G, I, L, S, T, M, V, N, Q, F, W, Y, or C; F85 replaced with D, E, H, K, R, N, Q, A, G, I, L, S, T, M, V, P, or C; W86 replaced with D, E, H, K, R, N, Q, A, G, I, L, S, T, M, V, P, or C; A87 replaced with D, E, H, K, R, N, Q, F, W, Y, P, or C; H88 replaced with D, E, A, G, I, L, S, T, M, V, N, Q, F, W, Y, P, or C; Y89 replaced with D, E, H, K, R, N, Q, A, G, I, L, S, T, M, V, P, or C; A90 replaced with D, E, H, K, R, N, Q, F, W, Y, P, or C; A91 replaced with D, E, H, K, R, N, Q, F, W, Y, P, or C; A92 replaced with D, E, H, K, R, N, Q, F, W, Y, P, or C; Q93 replaced with D, E, H, K, R, A, G, I, L, S, T, M, V, F, W, Y, P, or C; W94 replaced with D, E, H, K, R, N, Q, A, G, I, L, S, T, M, V, P, or C; D95 replaced with H, K, R, A, G, I, L, S, T, M, V, N, Q, F, W, Y, P, or C; F96 replaced with D, E, H, K, R, N, Q, A, G, I, L, S, T, M, V, P, or C; G97 replaced with D, E, H, K, R, N, Q, F, W, Y, P, or C; N98replaced with D, E, H, K, R, A, G, I, L, S, T, M, V, F, W, Y, P, or C; T99 replaced with D, E, H, K, R, N, Q, F, W, Y, P, or C; M100 replaced with D, E, H, K, R, N, Q, F, W, Y, P, or C; C101 replaced with D, E, H, K, R, A, G, I, L, S, T, M, V, N, Q, F, W, Y, or P; Q102 replaced with D, E, H, K, R, A, G, I, L, S, T, M, V, F, W, Y, P, or C; L103 replaced with D, E, H, K, R, N, Q, F, W, Y, P, or C; L104 replaced with D, E, H, K, R, N, Q, F, W, Y, P, or C; T105 replaced with D, E, H, K, R, N, Q, F, W, Y, P, or C; G106 replaced with D, E, H, K, R, N, Q, F, W, Y, P, or C; L107 replaced with D, E, H, K, R, N, Q, F, W, Y, P, or C; Y108 replaced with D, E, H, K, R, N, Q, A, G, I, L, S, T, M, V, P, or C; F109 replaced with D, E, H, K, R, N, Q, A, G, I, L, S, T, M, V, P, or C; I110 replaced with D, E, H, K, R, N, Q, F, W, Y, P, or C; G111 replaced with D, E, H, K, R, N, Q, F, W, Y, P, or C; F112 replaced with D, E, H, K, R, N, Q, A, G, I, L, S, T, M, V, P, or C; F113 replaced with D, E, H, K, R, N, Q, A, G, I, L, S, T, M, V, P, or C; S114 replaced with D, E, H, K, R, N, Q, F, W, Y, P, or C; G115 replaced with D, E, H, K, R, N, Q, F, W, Y, P, or C; I116 replaced with D, E, H, K, R, N, Q, F, W, Y, P, or C;F117 replaced with D, E, H, K, R, N, Q, A, G, I, L, S, T, M, V, P, or C; F118 replaced with D, E, H, K, R, N, Q, A, G, I, L, S, T, M, V, P, or C; I119 replaced with D, E, H, K, R, N, Q, F, W, Y, P, or C; I120 replaced with D, E, H, K, R, N, Q, F, W, Y, P, or C; L121 replaced with D, E, H, K, R, N, Q, F, W, Y, P, or C; L122 replaced with D, E, H, K, R, N, Q, F, W, Y, P, or C; T123 replaced with D, E, H, K, R, N, Q, F, W, Y, P, or C; I124 replaced with D, E, H, K, R, N, Q, F, W, Y, P, or C; D125 replaced with H, K, R, A, G, I, L, S, T, M, V, N, Q, F, W, Y, P, or C; R126 replaced with D, E, A, G, I, L, S, T, M, V, N, Q, F, W, Y, P, or C; Y127 replaced with D, E, H, K, R, N, Q, A, G, I, L, S, T, M, V, P, or C; L128 replaced with D, E, H, K, R, N, Q, F, W, Y, P, or C; A129 replaced with D, E, H, K, R, N, Q, F, W, Y, P, or C; V130 replaced with D, E, H, K, R, N, Q, F, W, Y, P, or C; V131 replaced with D, E, H, K, R, N, Q, F, W, Y, P, or C; H132 replaced with D, E, A, G, I, L, S, T, M, V, N, Q, F, W, Y, P, or C; A133 replaced with D, E, H, K, R, N, Q, F, W, Y, P, or C; V134 replaced with D, E, H, K, R, N, Q, F, W, Y, P, or C; F135 replaced with D, E, H, K, R, N, Q, A, G, I, L, S, T, M, V, P, or C; A136 replaced with D, E, H, K, R, N, Q, F, W, Y, P, or C; L137 replaced with D, E, H, K, R, N, Q, F, W, Y, P, or C; K138 replaced with D, E, A, G, I, L, S, T, M, V, N, Q, F, W, Y, P, or C; A139 replaced with D, E, H, K, R, N, Q, F, W, Y, P, or C; R140 replaced with D, E, A, G, I, L, S, T, M, V, N, Q, F, W, Y, P, or C; T141 replaced with D, E, H, K, R, N, Q, F, W, Y, P, or C; V142 replaced with D, E, H, K, R, N, Q, F, W, Y, P, or C; T143 replaced with D, E, H, K, R, N, Q, F, W, Y, P, or C; F144 replaced with D, E, H, K, R, N, Q, A, G, I, L, S, T, M, V, P, or C; G145 replaced with D, E, H, K, R, N, Q, F, W, Y, P, or C; V146 replaced with D, E, H, K, R, N, Q, F, W, Y, P, or C; V147 replaced with D, E, H, K, R, N, Q, F, W, Y, P, or C; T148 replaced with D, E, H, K, R, N, Q, F, W, Y, P, or C; S149 replaced with D, E, H, K, R, N, Q, F, W, Y, P, or C; V150 replaced with D, E, H, K, R, N, Q, F, W, Y, P, or C; I151 replaced with D, E, H, K, R, N, Q, F, W, Y, P, or C; T152 replaced with D, E, H, K, R, N, Q, F, W, Y, P, or C; W153 replaced with D, E, H, K, R, N, Q, A, G, I, L, S, T, M, V, P, or C; V154 replaced with D, E, H, K, R, N, Q, F, W, Y, P, or C; V155 replaced with D, E, H, K, R, N, Q, F, W, Y, P, or C; A156 replaced with D, E, H, K, R, N, Q, F, W, Y, P, or C; V157 replaced with D, E, H, K, R, N, Q, F, W, Y, P, or C; F158 replaced with D, E, H, K, R, N, Q, A, G, I, L, S, T, M, V, P, or C; A159 replaced with D, E, H, K, R, N, Q, F, W, Y, P, or C; S160 replaced with D, E, H, K, R, N, Q, F, W, Y, P, or C; L161 replaced with D, E, H, K, R, N, Q, F, W, Y, P, or C; P162 replaced with D, E, H, K, R, A, G, I, L, S, T, M, V, N, Q, F, W, Y, or C; G163 replaced with D, E, H, K, R, N, Q, F, W, Y, P, or C; I164 replaced with D, E, H, K, R, N, Q, F, W, Y, P, or C; I165 replaced with D, E, H, K, R, N, Q, F, W, Y, P, or C; F166 replaced with D, E, H, K, R, N, Q, A, G, I, L, S, T, M, V, P, or C; T167 replaced with D, E, H, K, R, N, Q, F, W, Y, P, or C; R168 replaced with D, E, A, G, I, L, S, T, M, V, N, Q, F, W, Y, P, or C; S169 replaced with D, E, H, K, R, N, Q, F, W, Y, P, or C; Q170 replaced with D, E, H, K, R, A, G, I, L, S, T, M, V, F, W, Y, P, or C; K171 replaced with D, E, A, G, I, L, S, T, M, V, N, Q, F, W, Y, P, or C; E172 replaced with H, K, R, A, G, I, L, S, T, M, V, N, Q, F, W, Y, P, or C; G173 replaced with D, E, H, K, R, N, Q, F, W, Y, P, or C; L174 replaced with D, E, H, K, R, N, Q, F, W, Y, P, or C; H175 replaced with D, E, A, G, I, L, S, T, M, V, N, Q, F, W, Y, P, or C; Y176 replaced with D, E, H, K, R, N, Q, A, G, I, L, S, T, M, V, P, or C; T177 replaced with D, E, H, K, R, N, Q, F, W, Y, P, or C; C178 replaced with D, E, H, K, R, A, G, I, L, S, T, M, V, N, Q, F, W, Y, or P; S179 replaced with D, E, H, K, R, N, Q, F, W, Y, P, or C; S180 replaced with D, E, H, K, R, N, Q, F, W, Y, P, or C; H181 replaced with D, E, A, G, I, L, S, T, M, V, N, Q, F, W, Y, P, or C; F182 replaced with D, E, H, K, R, N, Q, A, G, I, L, S, T, M, V, P, or C; P183 replaced with D, E, H, K, R, A, G, I, L, S, T, M, V, N, Q, F, W, Y, or C; Y184 replaced with D, E, H, K, R, N, Q, A, G, I, L, S, T, M, V, P, or C; S185 replaced with D, E, H, K, R, N, Q, F, W, Y, P, or C; Q186 replaced with D, E, H, K, R, A, G, I, L, S, T, M, V, F, W, Y, P, or C; Y187 replaced with D, E, H, K, R, N, Q, A, G, I, L, S, T, M, V, P, or C; Q188 replaced with D, E, H, K, R, A, G, I, L, S, T, M, V, F, W, Y, P, or C; F189 replaced with D, E, H, K, R, N, Q, A, G, I, L, S, T, M, V, P, or C; W190 replaced with D, E, H, K, R, N, Q, A, G, I, L, S, T, M, V, P, or C; K191 replaced with D, E, A, G, I, L, S, T, M, V, N, Q, F, W, Y, P, or C; N192 replaced with D, E, H, K, R, A, G, I, L, S, T, M, V, F, W, Y, P, or C; F193 replaced with D, E, H, K, R, N, Q, A, G, I, L, S, T, M, V, P, or C; Q194 replaced with D, E, H, K, R, A, G, I, L, S, T, M, V, F, W, Y, P, or C; T195 replaced with D, E, H, K, R, N, Q, F, W, Y, P, or C; L196 replaced with D, E, H, K, R, N, Q, F, W, Y, P, or C; K197 replaced with D, E, A, G, I, L, S, T, M, V, N, Q, F, W, Y, P, or C;I198 replaced with D, E, H, K, R, N, Q, F, W, Y, P, or C; V199 replaced with D, E, H, K, R, N, Q, F, W, Y, P, or C; I200 replaced with D, E, H, K, R, N, Q, F, W, Y, P, or C; L201 replaced with D, E, H, K, R, N, Q, F, W, Y, P, or C; G202 replaced with D, E, H, K, R, N, Q, F, W, Y, P, or C; L203 replaced with D, E, H, K, R, N, Q, F, W, Y, P, or C; V204 replaced with D, E, H, K, R, N, Q, F, W, Y, P, or C; L205 replaced with D, E, H, K, R, N, Q, F, W, Y, P, or C; P206 replaced with D, E, H, K, R, A, G, I, L, S, T, M, V, N, Q, F, W, Y, or C; L207 replaced with D, E, H, K, R, N, Q, F, W, Y, P, or C; L208 replaced with D, E, H, K, R, N, Q, F, W, Y, P, or C; V209 replaced with D, E, H, K, R, N, Q, F, W, Y, P, or C; M210 replaced with D, E, H, K, R, N, Q, F, W, Y, P, or C; V211 replaced with D, E, H, K, R, N, Q, F, W, Y, P, or C; I212 replaced with D, E, H, K, R, N, Q, F, W, Y, P, or C; C213 replaced with D, E, H, K, R, A, G, I, L, S, T, M, V, N, Q, F, W, Y, or P; Y214 replaced with D, E, H, K, R, N, Q, A, G, I, L, S, T, M, V, P, or C; S215 replaced with D, E, H, K, R, N, Q, F, W, Y, P, or C; G216 replaced with D, E, H, K, R, N, Q, F, W, Y, P, or C; I217 replaced with D, E, H, K, R, N, Q, F, W, Y, P, or C; L218 replaced with D, E, H, K, R, N, Q, F, W, Y, P, or C; K219 replaced with D, E, A, G, I, L, S, T, M, V, N, Q, F, W, Y, P, or C; T220 replaced with D, E, H, K, R, N, Q, F, W, Y, P, or C; L221 replaced with D, E, H, K, R, N, Q, F, W, Y, P, or C; L222 replaced with D, E, H, K, R, N, Q, F, W, Y, P, or C; R223 replaced with D, E, A, G, I, L, S, T, M, V, N, Q, F, W, Y, P, or C; C224 replaced with D, E, H, K, R, A, G, I, L, S, T, M, V, N, Q, F, W, Y, or P; R225 replaced with D, E, A, G, I, L, S, T, M, V, N, Q, F, W, Y, P, or C; N226 replaced with D, E, H, K, R, A, G, I, L, S, T, M, V, F, W, Y, P, or C; E227 replaced with H, K, R, A, G, I, L, S, T, M, V, N, Q, F, W, Y, P, or C; K228 replaced with D, E, A, G, I, L, S, T, M, V, N, Q, F, W, Y, P, or C; K229 replaced with D, E, A, G, I, L, S, T, M, V, N, Q, F, W, Y, P, or C; R230 replaced with D, E, A, G, I, L, S, T, M, V, N, Q, F, W, Y, P, or C; H231 replaced with D, E, A, G, I, L, S, T, M, V, N, Q, F, W, Y, P, or C; R232 replaced with D, E, A, G, I, L, S, T, M, V, N, Q, F, W, Y, P, or C; A233 replaced with D, E, H, K, R, N, Q, F, W, Y, P, or C; V234 replaced with D, E, H, K, R, N, Q, F, W, Y, P, or C; R235 replaced with D, E, A, G, I, L, S, T, M, V, N, Q, F, W, Y, P, or C; L236 replaced with D, E, H, K, R, N, Q, F, W, Y, P, or C; I237 replaced with D, E, H, K, R, N, Q, F, W, Y, P, or C; F238 replaced with D, E, H, K, R, N, Q, A, G, I, L, S, T, M, V, P, or C; T239 replaced with D, E, H, K, R, N, Q, F, W, Y, P, or C; I240 replaced with D, E, H, K, R, N, Q, F, W, Y, P, or C; M241 replaced with D, E, H, K, R, N, Q, F, W, Y, P, or C; I242 replaced with D, E, H, K, R, N, Q, F, W, Y, P, or C; V243 replaced with D, E, H, K, R, N, Q, F, W, Y, P, or C; Y244 replaced with D, E, H, K, R, N, Q, A, G, I, L, S, T, M, V, P, or C; F245 replaced with D, E, H, K, R, N, Q, A, G, I, L, S, T, M, V, P, or C; L246 replaced with D, E, H, K, R, N, Q, F, W, Y, P, or C; F247 replaced with D, E, H, K, R, N, Q, A, G, I, L, S, T, M, V, P, or C; W248 replaced with D, E, H, K, R, N, Q, A, G, I, L, S, T, M, V, P, or C; A249 replaced with D, E, H, K, R, N, Q, F, W, Y, P, or C; P250 replaced with D, E, H, K, R, A, G, I, L, S, T, M, V, N, Q, F, W, Y, or C; Y251 replaced with D, E, H, K, R, N, Q, A, G, I, L, S, T, M, V, P, or C; N252 replaced with D, E, H, K, R, A, G, I, L, S, T, M, V, F, W, Y, P, or C; I253 replaced with D, E, H, K, R, N, Q, F, W, Y, P, or C; V254 replaced with D, E, H, K, R, N, Q, F, W, Y, P, or C; L255 replaced with D, E, H, K, R, N, Q, F, W, Y, P, or C; L256 replaced with D, E, H, K, R, N, Q, F, W, Y, P, or C; L257 replaced with D, E, H, K, R, N, Q, F, W, Y, P, or C; N258 replaced with D, E, H, K, R, A, G, I, L, S, T, M, V, F, W, Y, P, or C; T259 replaced with D, E, H, K, R, N, Q, F, W, Y, P, or C; F260 replaced with D, E, H, K, R, N, Q, A, G, I, L, S, T, M, V, P, or C; Q261 replaced with D, E, H, K, R, A, G, I, L, S, T, M, V, F, W, Y, P, or C; E262 replaced with H, K, R, A, G, I, L, S, T, M, V, N, Q, F, W, Y, P, or C; F263 replaced with D, E, H, K, R, N, Q, A, G, I, L, S, T, M, V, P, or C; F264 replaced with D, E, H, K, R, N, Q, A, G, I, L, S, T, M, V, P, or C; G265 replaced with D, E, H, K, R, N, Q, F, W, Y, P, or C; L266 replaced with D, E, H, K, R, N, Q, F, W, Y, P, or C; N267 replaced with D, E, H, K, R, A, G, I, L, S, T, M, V, F, W, Y, P, or C; N268 replaced with D, E, H, K, R, A, G, I, L, S, T, M, V, F, W, Y, P, or C; C269 replaced with D, E, H, K, R, A, G, I, L, S, T, M, V, N, Q, F, W, Y, or P; S270 replaced with D, E, H, K, R, N, Q, F, W, Y, P, or C; S271 replaced with D, E, H, K, R, N, Q, F, W, Y, P, or C; S272 replaced with D, E, H, K, R, N, Q, F, W, Y, P, or C; N273 replaced with D, E, H, K, R, A, G, I, L, S, T, M, V, F, W, Y, P, or C; R274 replaced with D, E, A, G, I, L, S, T, M, V, N, Q, F, W, Y, P, or C; L275 replaced with D, E, H, K, R, N, Q, F, W, Y, P, or C; D276 replaced with H, K, R, A, G, I, L, S, T, M, V, N, Q, F, W, Y, P, or C; Q277 replaced with D, E, H, K, R, A, G, I, L, S, T, M, V, F, W, Y, P, or C;

A278 replaced with D, E, H, K, R, N, Q, F, W, Y, P, or C; M279 replaced with D, E, H, K, R, N, Q, F, W, Y, P, or C; Q280 replaced with D, E, H, K, R, A, G, I, L, S, T, M, V, F, W, Y, P, or C; V281 replaced with D, E, H, K, R, N, Q, F, W, Y, P, or C; T282 replaced with D, E, H, K, R, N, Q, F, W, Y, P, or C; E283 replaced with H, K, R, A, G, I, L, S, T, M, V, N, Q, F, W, Y, P, or C; T284 replaced with D, E, H, K, R, N, Q, F, W, Y, P, or C; L285 replaced with D, E, H, K, R, N, Q, F, W, Y, P, or C; G286 replaced with D, E, H, K, R, N, Q, F, W, Y, P, or C; M287 replaced with D, E, H, K, R, N, Q, F, W, Y, P, or C; T288 replaced with D, E, H, K, R, N, Q, F, W, Y, P, or C; H289 replaced with D, E, A, G, I, L, S, T, M, V, N, Q, F, W, Y, P, or C; C290 replaced with D, E, H, K, R, A, G, I, L, S, T, M, V, N, Q, F, W, Y, or P; C291 replaced with D, E, H, K, R, A, G, I, L, S, T, M, V, N, Q, F, W, Y, or P; I292 replaced with D, E, H, K, R, N, Q, F, W, Y, P, or C; N293 replaced with D, E, H, K, R, A, G, I, L, S, T, M, V, F, W, Y, P, or C; P294 replaced with D, E, H, K, R, A, G, I, L, S, T, M, V, N, Q, F, W, Y, or C; I295 replaced with D, E, H, K, R, N, Q, F, W, Y, P, or C; I296 replaced with D, E, H, K, R, N, Q, F, W, Y, P, or C; Y297 replaced with D, E, H, K, R, N, Q, A, G, I, L, S, T, M, V, P, or C; A298 replaced with D, E, H, K, R, N, Q, F, W, Y, P, or C; F299 replaced with D, E, H, K, R, N, Q, A, G, I, L, S, T, M, V, P, or C; V300 replaced with D, E, H, K, R, N, Q, F, W, Y, P, or C; G301 replaced with D, E, H, K, R, N, Q, F, W, Y, P, or C; E302 replaced with H, K, R, A, G, I, L, S, T, M, V, N, Q, F, W, Y, P, or C; K303 replaced with D, E, A, G, I, L, S, T, M, V, N, Q, F, W, Y, P, or C; F304 replaced with D, E, H, K, R, N, Q, A, G, I, L, S, T, M, V, P, or C; R305 replaced with D, E, A, G, I, L, S, T, M, V, N, Q, F, W, Y, P, or C; N306 replaced with D, E, H, K, R, A, G, I, L, S, T, M, V, F, W, Y, P, or C; Y307 replaced with D, E, H, K, R, N, Q, A, G, I, L, S, T, M, V, P, or C; L308 replaced with D, E, H, K, R, N, Q, F, W, Y, P, or C; L309 replaced with D, E, H, K, R, N, Q, F, W, Y, P, or C; V310 replaced with D, E, H, K, R, N, Q, F, W, Y, P, or C; F311 replaced with D, E, H, K, R, N, Q, A, G, I, L, S, T, M, V, P, or C; F312 replaced with D, E, H, K, R, N, Q, A, G, I, L, S, T, M, V, P, or C; Q313 replaced with D, E, H, K, R, A, G, I, L, S, T, M, V, F, W, Y, P, or C; K314 replaced with D, E, A, G, I, L, S, T, M, V, N, Q, F, W, Y, P, or C; H315 replaced with D, E, A, G, I, L, S, T, M, V, N, Q, F, W, Y, P, or C; I316 replaced with D, E, H, K, R, N, Q, F, W, Y, P, or C; A317 replaced with D, E, H, K, R, N, Q, F, W, Y, P, or C; K318 replaced with D, E, A, G, I, L, S, T, M, V, N, Q, F, W, Y, P, or C; R319 replaced with D, E, A, G, I, L, S, T, M, V, N, Q, F, W, Y, P, or C; F320 replaced with D, E, H, K, R, N, Q, A, G, I, L, S, T, M, V, P, or C; C321 replaced with D, E, H, K, R, A, G, I, L, S, T, M, V, N, Q, F, W, Y, or P; K322 replaced with D, E, A, G, I, L, S, T, M, V, N, Q, F, W, Y, P, or C; C323 replaced with D, E, H, K, R, A, G, I, L, S, T, M, V, N, Q, F, W, Y, or P; C324 replaced with D, E, H, K, R, A, G, I, L, S, T, M, V, N, Q, F, W, Y, or P; S325 replaced with D, E, H, K, R, N, Q, F, W, Y, P, or C; I326 replaced with D, E, H, K, R, N, Q, F, W, Y, P, or C; F327 replaced with D, E, H, K, R, N, Q, A, G, I, L, S, T, M, V, P, or C; Q328 replaced with D, E, H, K, R, A, G, I, L, S, T, M, V, F, W, Y, P, or C; Q329 replaced with D, E, H, K, R, A, G, I, L, S, T, M, V, F, W, Y, P, or C; E330 replaced with H, K, R, A, G, I, L, S, T, M, V, N, Q, F, W, Y, P, or C; A331 replaced with D, E, H, K, R, N, Q, F, W, Y, P, or C; P332 replaced with D, E, H, K, R, A, G, I, L, S, T, M, V, N, Q, F, W, Y, or C; E333 replaced with H, K, R, A, G, I, L, S, T, M, V, N, Q, F, W, Y, P, or C; R334 replaced with D, E, A, G, I, L, S, T, M, V, N, Q, F, W, Y, P, or C; A335 replaced with D, E, H, K, R, N, Q, F, W, Y, P, or C; S336 replaced with D, E, H, K, R, N, Q, F, W, Y, P, or C; S337 replaced with D, E, H, K, R, N, Q, F, W, Y, P, or C; V338 replaced with D, E, H, K, R, N, Q, F, W, Y, P, or C; Y339 replaced with D, E, H, K, R, N, Q, A, G, I, L, S, T, M, V, P, or C; T340 replaced with D, E, H, K, R, N, Q, F, W, Y, P, or C; R341 replaced with D, E, A, G, I, L, S, T, M, V, N, Q, F, W, Y, P, or C; S342 replaced with D, E, H, K, R, N, Q, F, W, Y, P, or C; T343 replaced with D, E, H, K, R, N, Q, F, W, Y, P, or C; E344 replaced with H, K, R, A, G, I, L, S, T, M, V, N, Q, F, W, Y, P, or C; E345 replaced with H, K, R, A, G, I, L, S, T, M, V, N, Q, F, W, Y, P, or C; Q346 replaced with D, E, H, K, R, A, G, I, L, S, T, M, V, F, W, Y, P, or C; E347 replaced with H, K, R, A, G, I, L, S, T, M, V, N, Q, F, W, Y, P, or C; I348 replaced with D, E, H, K, R, N, Q, F, W, Y, P, or C; S349 replaced with D, E, H, K, R, N, Q, F, W, Y, P, or C; V350 replaced with D, E, H, K, R, N, Q, F, W, Y, P, or C; G351 replaced with D, E, H, K, R, N, Q, F, W, Y, P, or C; and/or L352 replaced with D, E, H, K, R, N, Q, F, W, Y, P, or C.

The resulting constructs can be routinely screened for activities or functions described throughout the specification and known in the art. Preferably, the resulting constructs have an increased and/or decreased G-protein Chemokine Receptor (CCR5) activity or function, while the remaining G-protein Chemokine Receptor (CCR5) activities or functions are maintained. More preferably, the resulting constructs have more than one increased and/or decreased G-protein Chemokine Receptor (CCR5) activity or function, while the remaining G-protein Chemokine Receptor (CCR5) activities or functions are maintained.

Additionally, more than one amino acid (e.g., 2, 3, 4, 5, 6, 7, 8, 9 and 10) can be replaced with the substituted amino acids as described above (either conservative or nonconservative). The substituted amino acids can occur in the full length, mature, or proprotein form of G-protein Chemokine Receptor (CCR5) protein, as well as the N- and C-terminal deletion mutants, having the general formula m-n, listed below.

A further embodiment of the invention relates to a polypeptide which comprises the amino acid sequence of a G-protein Chemokine Receptor (CCR5) polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of a G-protein Chemokine Receptor (CCR5) polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIG. 1 or that encoded by the deposited clone or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

The present invention is also directed to polynucleotide fragments of the polynucleotides of the invention. In the present invention, a "polynucleotide fragment" refers to a short polynucleotide having a nucleic acid sequence which: is a portion of that contained in a deposited clone, or encoding the polypeptide encoded by deposited clone; is a portion of that shown in SEQ ID NO:1 or the complementary strand thereto, or is a portion of a polynucleotide sequence encoding the polypeptide of SEQ ID NO:2. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the HDGNR10 DNA sequence contained in a deposited clone or the nucleotide sequence shown in SEQ ID NO:1. In this context "about" includes the particularly recited value, a value larger or smaller by several (5, 4, 3, 2, or 1) nucleotides, at either terminus or at both termini. These nucleotide fragments have uses that include, but are not limited to, as diagnostic probes and primers as discussed herein. Of course, larger fragments (e.g., 50, 150, 500, 600, 1000 nucleotides) are preferred.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, or 1401 to the end of SEQ ID NO:1, or the complementary strand thereto, or the HDGNR10 DNA contained in the deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides. In the present invention, a "polypeptide fragment" refers to an amino acid sequence which is a portion of that contained in SEQ ID NO:2 or encoded by the HDGNR10 DNA contained in the deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Even if deletion of one or more amino acids from the N-terminus of a protein results in modification of loss of one or more biological functions of the protein, other functional activities (e.g., biological activities, ability to multimerize, ability to bind G-protein Chemokine Receptor (CCR5) ligand) may still be retained. For example, the ability of shortened G-protein Chemokine Receptor (CCR5) muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an G-protein Chemokine Receptor (CCR5) mutein with a large number of deleted N-terminal amino acid residues may retain some biological or immunogenic activities. In fact, peptides composed of as few as six G-protein Chemokine Receptor (CCR5) amino acid residues may often evoke an immune response.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids.

Accordingly, polypeptide fragments include the secreted G-protein Chemokine Receptor (CCR5) protein as well as the mature form. Further preferred polypeptide fragments include the secreted G-protein Chemokine Receptor (CCR5) protein or the mature form having a continuous series of deleted residues from the amino or the carboxy terminus, or both. For example, any number of amino acids, ranging from 1–60, can be deleted from the amino terminus of either the secreted G-protein Chemokine Receptor (CCR5) polypeptide or the mature form. Similarly, any number of amino acids, ranging from 1–30, can be deleted from the carboxy terminus of the secreted G-protein Chemokine Receptor (CCR5) protein or mature form. Furthermore, any combination of the above amino and carboxy terminus deletions are preferred. Similarly, polynucleotides encoding these polypeptide fragments are also preferred.

Particularly, N-terminal deletions of the G-protein Chemokine Receptor (CCR5) polypeptide can be described by the general formula m-352, where m is an integer from 2 to 346, where m corresponds to the position of the amino acid residue identified in SEQ ID NO:2 or the polypeptide encoded by the deposited clone. More in particular, the invention provides polynucleotides encoding polypeptides comprising, or alternatively consisting of, the amino acid sequence of residues of N-terminal deletions of the polypeptide of the invention shown as SEQ ID NO:2 including polypeptides comprising the amino acid sequence of residues: D-2 to L-352; Y-3 to L-352; Q-4 to L-352; V-5 to L-352; S-6 to L-352; S-7 to L-352; P-8 to L-352; I-9 to L-352; Y-10 to L-352; D-11 to L-352; I-12 to L-352; N-13 to L-352; Y-14 to L-352; Y-15 to L-352; T-16 to L-352; S-17 to L-352; E-18 to L-352; P-19 to L-352; C-20 to L-352; P-21 to L-352; K-22 to L-352; I-23 to L-352; N-24 to L-352; V-25 to L-352; K-26 to L-352; Q-27 to L-352; I-28 to L-352; A-29 to L-352; A-30 to L-352; R-31 to L-352; L-32 to L-352; L-33 to L-352; P-34 to L-352; P-35 to L-352; L-36 to L-352; Y-37 to L-352; S-38 to L-352; L-39 to L-352; V-40 to L-352; F-41 to L-352; I-42 to L-352; F-43 to L-352;G-44 to L-352; F-45 to L-352; V-46 to L-352; G-47 to L-352; N-48 to L-352; M-49 to L-352; L-50 to L-352; V-51 to L-352; I-52 to L-352; L-53 to L-352; L-54 to L-352; L-55 to L-352; I-56 to L-352; N-57 to L-352; C-58 to L-352; Q-59 to L-352; R-60 to L-352; L-61 to L-352; E-62 to L-352; S-63 to L-352; M-64 to L-352; T-65 to L-352; D-66 to L-352; I-67 to L-352; Y-68 to L-352; L-69 to L-352; L-70 to L-352; N-71 to L-352; L-72 to L-352; A-73 to L-352; I-74 to L-352; S-75 to L-352; D-76 to L-352; L-77 to L-352; F-78 to L-352; F-79 to L-352; L-80 to L-352; L-81 to L-352; T-82 to L-352; V-83 to L-352; P-84 to L-352; F-85to L-352; W-86 to L-352; A-87 to L-352; H-88 to L-352; Y-89 to L-352; A-90 to L-352; A-91 to L-352; A-92 to L-352; Q-93 to L-352; W-94 to L-352; D-95 to L-352; F-96 to L-352; G-97 to L-352; N-98 to L-352; T-99 to L-352; M-100 to L-352; C-101 to L-352; Q-102 to L-352; L-103 to L-352; L-104 to L-352; T-105 to L-352; G-106 to L-352; L-107 to L-352; Y-108 to L-352; F-109 to L-352; I-110 to L-352; G-111 to L-352; F-112 to L-352; F-113 to L-352; S-114 to L-352;G-115 to L-352; I-116 to L-352; F-117 to L-352; F-118 to L-352; I-119 to L-352; I-120 to L-352; L-121 to L-352; L-122 to L-352; T-123 to L-352; I-124 to L-352; D-125 to L-352; R-126 to L-352; Y-127 to L-352; L-128 to L-352; A-129 to L-352; I-130 to L-352; V-131 to L-352; H-132 to L-352; A-133 to L-352; V-134 to L-352; F-135 to L-352; A-136 to L-352; L-137 to L-352; K-138 to L-352; A-139 to L-352; R-140 to L-352; T-141 to L-352; V-142 to L-352; T-143 to L-352; F-144 to L-352; G-145 to L-352; V-146 to L-352; V-147 to L-352; T-148 to L-352; S-149 to L-352; V-150 to L-352; I-151 to L-352; T-152 to L-352; W-153 to L-352; V-154 to L-352; V-155 to L-352; A-156 to L-352; V-157 to L-352; F-158 to L-352; A-159 to L-352; S-160 to L-352; L-161 to L-352; P-162 to L-352; G-163 to L-352; I-164 to L-352; I-165 to L-352; F-166 to L-352; T-167 to L-352; R-168 to L-352; S-169 to L-352; Q-170 to L-352; K-171 to L-352; E-172 to L-352; G-173 to L-352; L-174 to L-352; H-175 to L-352; Y-176 to L-352; T-177 to L-352; C-178 to L-352; S-179 to L-352; S-180 to L-352; H-181 to L-352; F-182 to L-352; P-183 to L-352; Y-184 to L-352; S-185 to L-352; Q-186 to L-352; Y-187 to L-352; Q-188 to L-352; F-189 to L-352; W-190 to L-352; K-191 to L-352; N-192 to L-352; F-193 to L-352; Q-194 to L-352; T-195 to L-352; L-196 to L-352; K-197 to L-352; I-198 to L-352; V-199 to L-352; I-200 to L-352; L-201 to L-352; G-202 to L-352; L-203 to L-352; V-204 to L-352; L-205 to L-352; P-206 to L-352; L-207 to L-352; L-208 to L-352; V-209 to L-352; M-210 to L-352; V-211 to L-352; I-212 to L-352; C-213 to L-352; Y-214 to L-352; S-215 to L-352; G-216 to L-352; I-217 to L-352; L-218 to L-352; K-219 to L-352; T-220 to L-352; L-221 to L-352; L-222 to L-352; R-223 to L-352; C-224 to L-352; R-225 to L-352; N-226 to L-352; E-227 to L-352; K-228 to L-352; K-229 to L-352; R-230 to L-352; H-231 to L-352; R-232 to L-352; A-233 to L-352; V-234 to L-352; R-235 to L-352; L-236 to L-352; I-237 to L-352; F-238 to L-352; T-239 to L-352; I-240 to L-352; M-241 to L-352; I-242 to L-352; V-243 to L-352; Y-244 to L-352; F-245 to L-352; L-246 to L-352; F-247 to L-352; W-248 to L-352; A-249 to L-352; P-250 to L-352; Y-251 to L-352; N-252 to L-352; I-253 to L-352; V-254 to L-352; L-255 to L-352; L-256 to L-352; L-257 to L-352; N-258 to L-352; T-259 to L-352; F-260 to L-352; Q-261 to L-352; E-262 to L-352; F-263 to L-352; F-264 to L-352; G-265 to L-352; L-266 to L-352; N-267 to L-352; N-268 to L-352; C-269 to L-352; S-270 to L-352; S-271 to L-352; S-272 to L-352; N-273 to L-352; R-274 to L-352; L-275 to L-352; D-276 to L-352; Q-277 to L-352; A-278 to L-352; M-279 to L-352; Q-280 to L-352; V-281 to L-352; T-282 to L-352; E-283 to L-352; T-284 to L-352; L-285 to L-352; G-286 to L-352; M-287 to L-352; T-288 to L-352; H-289 to L-352; C-290 to L-352; C-291 to L-352; I-292 to L-352; N-293 to L-352; P-294 to L-352; I-295 to L-352; I-296 to L-352; Y-297 to L-352; A-298 to L-352; F-299 to L-352; V-300 to L-352; G-301 to L-352; E-302 to L-352; K-303 to L-352; F -304 to L-352; R-305 to L-352; N-306 to L-352; Y-307 to L-352; L-308 to L-352; L-309 to L-352; V-310 to L-352; F-311 to L-352; F-312 to L-352; Q-313 to L-352; K-314 to L-352; H-315 to L-352; I-316 to L-352; A-317 to L-352; K-318 to L-352; R-319 to L-352; F-320 to L-352; C-321 to L-352; K-322 to L-352; C-323 to L-352; C-324 to L-352; S-325 to L-352; I-326 to L-352; F-327 to L-352; Q-328 to L-352; Q-329 to L-352; E-330 to L-352; A-331 to L-352; P-332 to L-352; E-333 to L-352; R-334 to L-352; A-335 to L-352; S-336 to L-352; S-337 to L-352; V-338 to L-352; Y-339 to L-352; T-340 to L-352; R-341 to L-352; S-342 to L-352; T-343 to L-352; G-344 to L-352; E-345 to L-352; Q-346 to L-352; and/or E-347 to L-352 of SEQ ID NO:2. Polynucleotides encoding these polypeptides are also encompassed by the invention.

In addition, the invention provides polynucleotides encoding polypeptides comprising, or alternatively consisting of, the amino acid sequence of residues of N-terminal deletions of the polypeptide of the invention encoded by the deposited HDGNR10 clone (SEQ ID NO:22) including polypeptides comprising the amino acid sequence of residues: D-2 to L-352; Y-3 to L-352; Q-4 to L-352; V-5 to L-352; S-6 to L-352; S-7 to L-352; P-8 to L-352; I-9 to L-352; Y-10 to L-352; D-11 to L-352; I-12 to L-352; N-13 to L-352; Y-14 to L-352; Y-15 to L-352; T-16 to L-352; S-17 to L-352; E-18 to L-352; P-19 to L-352; C-20 to L-352; Q-21 to L-352; K-22 to L-352; I-23 to L-352; N-24 to L-352; V-25 to L-352; K-26 to L-352; Q-27 to L-352; I-28 to L-352; A-29 to L-352; A-30 to L-352; R-31 to L-352; L-32 to L-352; L-33 to L-352; P-34 to L-352; P-35 to L-352; L-36 to L-352; Y-37 to L-352; S-38 to L-352; L-39 to L-352; V-40 to L-352; F-41 to L-352; I-42 to L-352; F-43 to L-352;G-44 to L-352; F-45 to L-352; V-46 to L-352; G-47 to L-352; N-48 to L-352; M-49 to L-352; L-50 to L-352; V-51 to L-352; I-52 to L-352; L-53 to L-352; I-54to L-352; L-55 to L-352; I-56 to L-352; N-57 to L-352; C-58 to L-352; K-59 to L-352; R-60 to L-352; L-61 to L-352; K-62 to L-352; S-63 to L-352; M-64 to L-352; T-65 to L-352; D-66 to L-352; I-67 to L-352; Y-68 to L-352; L-69 to L-352; L-70 to L-352; N-71 to L-352; L-72 to L-352; A-73 to L-352; I-74 to L-352; S-75 to L-352; D-76 to L-352; L-77 to L-352; F-78 to L-352; F-79 to L-352; L-80 to L-352; L-81 to L-352; T-82 to L-352; V-83 to L-352; P-84 to L-352; F-85to L-352; W-86 to L-352; A-87 to L-352; H-88 to L-352; Y-89 to L-352; A-90 to L-352; A-91 to L-352; A-92 to L-352; Q-93 to L-352; W-94 to L-352; D-95 to L-352; F-96 to L-352; G-97 to L-352; N-98 to L-352; T-99 to L-352; M-100 to L-352; C-101 to L-352; Q-102 to L-352; L-103 to L-352; L-104 to L-352; T-105 to L-352; G-106 to L-352; L-107 to L-352; Y-108 to L-352; F-109 to L-352; C-101 to L-352; G-121 to L-352; F-112 to L-352; F-113 to L-352; S-114 to L-352;G-115 to L-352; I-116 to L-352; F-117 to L-352; F-118 to L-352; I-119 to L-352; I-120 to L-352; L-121 to L-352; L-122 to L-352; T-123 to L-352; I-124 to L-352; D-125 to L-352; R-126 to L-352; Y-127 to L-352; L-128 to L-352; A-129 to L-352; V-130 to L-352; V-131 to L-352; H-132 to L-352; A-133 to L-352; V-134 to L-352; F-135 to L-352; A-136 to L-352; L-137 to L-352; K-138 to L-352; A-139 to L-352; R-140 to L-352; T-141 to L-352; V-142 to L-352; T-143 to L-352; F-144 to L-352; G-145 to L-352; V-146 to L-352; V-147 to L-352; T-148 to L-352; S-149 to L-352; V-150 to L-352; I-151 to L-352; T-152 to L-352; W-153 to L-352; V-154 to L-352; V-155 to L-352; A-156 to L-352; V-157 to L-352; F-158 to L-352; A-159 to L-352; S-160 to L-352; L-161 to L-352; P-162 to L-352; G-163 to L-352; I-164 to L-352; I-165 to L-352; F-166 to L-352; T-167 to L-352; R-168 to L-352; S-169 to L-352; Q-170 to L-352; K-171 to L-352; E-172 to L-352; G-173 to L-352; L-174 to L-352; H-175 to L-352; Y-176 to L-352; T-177 to L-352; C-178 to L-352; S-179 to L-352; S-180 to L-352; H-181 to L-352; F-182 to L-352; P-183 to L-352; Y-184 to L-352; S-185 to L-352; Q-186 to L-352; Y-187 to L-352; Q-188 to L-352; F-189 to L-352; W-190 to L-352; K-191 to L-352; N-192 to L-352; F-193 to L-352; Q-194 to L-352; T-195 to L-352; L-196 to L-352; K-197 to L-352; I-198 to L-352; V-199 to L-352; I-200 to L-352; L-201 to L-352; G-202 to L-352; L-203 to L-352; V-204 to L-352; L-205 to L-352; P-206 to L-352; L-207 to L-352; L-208 to L-352; V-209 to L-352; M-210 to L-352; V-211 to L-352; I-212 to L-352; C-213 to L-352; Y-214 to L-352; S-215 to L-352; G-216 to L-352; I-217 to L-352; L-218 to L-352; K-219 to L-352; T-220 to L-352; L-221 to L-352; L-222 to L-352; R-223 to L-352; C-224 to L-352; R -225 to L-352; N-226 to L-352; E-227 to L-352; K-228 to L-352;K-229 to L-352; R-230 to L-352; H-231 to L-352; R-232 to L-352; A-233 to L-352; V-234 to L-352; R-235 to L-352; L-236 to L-352; I-237 to L-352; F-238 to L-352; T-239 to L-352; I-240 to L-352; M-241 to L-352; I-242 to L-352; V-243 to L-352; Y-244 to L-352; F-245 to L-352; L-246 to L-352; F-247 to L-352; W-248 to L-352; A-249 to L-352; P-250 to L-352; Y-251 to L-352; N-252 to L-352; I-253 to L-352; V-254 to L-352; L-255 to L-352; L-256 to L-352; L-257 to L-352; N-258 to L-352; T-259 to L-352; F-260 to L-352; Q-261 to L-352; E-262 to L-352; F-263 to L-352; F-264 to L-352; G-265 to L-352; L-266 to L-352; N-267 to L-352; N-268 to L-352; C-269 to L-352; S-270 to L-352; S-271 to L-352; S-272 to L-352; N-273 to L-352; R-274 to L-352; L-275 to L-352; D-276 to L-352; Q-277 to L-352; A-278 to L-352; M-279 to L-352; Q-280 to L-352; V-281 to L-352; T-282 to L-352; E-283 to L-352; T-284 to L-352; L-285 to L-352; G-286 to L-352; M-287 to L-352; T-288 to L-352; H-289 to L-352; C-290 to L-352; C-291 to L-352; I-292 to L-352; N-293 to L-352; P-294 to L-352; I-295 to L-352; I-296 to L-352; Y-297 to L-352; A-298 to L-352; F-299 to L-352; V-300 to L-352; G-301 to L-352; E-302 to L-352; K-303 to L-352; F-304 to L-352;R-305 to L-352; N-306 to L-352; Y-307 to L-352; L-308 to L-352; L-309 to L-352; V-310 to L-352; F-311 to L-352; F-312 to L-352; Q-313 to L-352; K-314 to L-352; H-315 to L-352; I-316 to L-352; A-317 to L-352; K-318 to L-352; R-319 to L-352; F-320 to L-352; C-321 to L-352; K-322 to L-352; C-323 to L-352; C-324 to L-352; S-325 to L-352; I-326 to L-352; F-327 to L-352; Q-328 to L-352; Q-329 to L-352; E-330 to L-352; A-331 to L-352; P-332 to L-352; E-333 to L-352; R-334 to L-352; A-335 to L-352; S-336 to L-352; S-337 to L-352; V-338 to L-352; Y-339 to L-352; T-340 to L-352; R-341 to L-352; S-342 to L-352; T-343 to L-352; E-344 to L-352; E-345 to L-352; Q-346 to L-352; and/or E-347 to L-352 of SEQ ID NO:22. Polynucleotides encoding these polypeptides are also encompassed by the invention.

The present application is also directed to nucleic acid molecules comprising, or alternatively, consisting of, a polynucleotide sequence at least 90%, 92%, 95%, 96%, 97%, 98%, or 99% identical to the polynucleotide sequence encoding the G-protein Chemokine Receptor (CCR5) polypeptide described above. The present invention also encompasses the above polynucleotide sequences fused to a heterologous polynucleotide sequence.

Also as mentioned above, even if deletion of one or more amino acids from the C-terminus of a protein results in modification of loss of one or more biological functions of the protein, other functional activities (e.g., biological activities, ability to multimerize, ability to bind G-protein Chemokine Receptor (CCR5) ligand) may still be retained. For example the ability of the shortened G-protein Chemokine Receptor (CCR5) mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an G-protein Chemokine Receptor (CCR5) mutein with a large number of deleted C-terminal amino acid residues may retain some biological or immunogenic activities. In fact, peptides composed of as few as six G-protein Chemokine Receptor (CCR5) amino acid residues may often evoke an immune response.

Accordingly, the present invention further provides polypeptides having one or more residues deleted from the carboxy terminus of the amino acid sequence of the G-protein Chemokine Receptor (CCR5) polypeptide shown in FIG. 1 (SEQ ID NO:2) or of the polypeptide encoded by the deposited clone, as described by the general formula 1-n, where n is an integer from 6 to 346, where n corresponds to the position of amino acid residue identified in SEQ ID NO:2 or in the polypeptide encoded by the deposited clone. More in particular, the invention provides polynucleotides encoding polypeptides comprising, or alternatively consisting of, the amino acid sequence of residues of D-2 to G-351; D-2 to V-350; D-2 to S-349; D-2 to I-348; D-2 to E-347; D-2 to Q-346; D-2 to E-345; D-2 to G-344; D-2 to T-343; D-2to S-342; D-2 to R-341; D-2 to T-340; D-2 to Y-339; D-2 to V-338; D-2 to S-337; D-2 to S-336; D-2 to A-335; D-2 to R-334; D-2 to E-333; D-2 to P-332; D-2 to A-331; D-2 to E-330; D-2 to Q-329; D-2 to Q-328; D-2 to F-327; D-2 to I-326; D-2 to S-325; D-2 to C-324; D-2 to C-323; D-2 to K-322; D-2 to C-321; D-2 to F-320; D-2 to R-319; D-2 to K-318; D-2 to A-317; D-2 to I-316; D-2 to H-315; D-2 to K-314; D-2 to Q-313; D-2 to F-312; D-2 to F-311; D-2 to V-310; D-2 to L-309; D-2 to L-308; D-2 to Y-307; D-2 to N-306; D-2 to R-305; D-2 to F-304; D-2 to K-303; D-2 to E-302; D-2 to G-301; D-2 to V-300; D-2 to F-299; D-2 to A-298; D-2 to Y-297; D-2 to I-296; D-2 to I-295; D-2 to P-294; D-2 to N-293; D-2 to I-292; D-2 to C-291; D-2 to C-290; D-2 to H-289; D-2 to T-288; D-2 to M-287; D-2 to G-286; D-2 to L-285; D-2 to T-284; D-2 to E-283; D-2 to T-282; D-2 to V-281; D-2 to Q-280; D-2 to M-279; D-2 to A-278; D-2 to Q-277; D-2 to D-276; D-2 to L-275; D-2 to R-274; D-2 to N-273; D-2 to S-272; D-2 to S-271; D-2 to S-270; D-2 to C-269; D-2 to N-268; D-2 to N-267; D-2 to L-266; D-2 to G-265; D-2 to F-264; D-2 to F-263; D-2 to E-262; D-2 to Q-261; D-2 to F-260; D-2 to T-259; D-2 to N-258; D-2 to L-257; D-2 to L-256; D-2 to L-255; D-2 to V-254; D-2 to I-253; D-2 to N-252; D-2 to Y-251; D-2 to P-250; D-2 to A-249; D-2 to W-248; D-2 to F-247; D-2 to L-246; D-2 to F-245; D-2 to Y-244; D-2 to V-243; D-2 to I-242; D-2 to M-241; D-2 to I-240; D-2 to T-239; D-2 to F-238; D-2 to I-237; D-2 to L-236; D-2 to R-235; D-2 to V-234; D-2 to A-233; D-2 to R-232; D-2 to H-231; D-2 to R-230; D-2 to K-229; D-2 to K-228; D-2 to E-227; D-2 to N-226; D-2 to R-225; D-2 to C-224; D-2 to R-223; D-2 to L-222; D-2 to L-221; D-2 to T-220; D-2 to K-219; D-2 to L-218; D-2 to I-217; D-2 to G-216; D-2 to S-215; D-2 to Y-214; D-2 to C-213; D-2 to I-212; D-2 to V-211; D-2 to M-210; D-2 to V-209; D-2 to L-208; D-2 to L-207; D-2 to P-206; D-2 to L-205; D-2 to V-204; D-2 to L-203; D-2 to G-202; D-2 to L-201; D-2 to I-200; D-2 to V-199; D-2 to I-198; D-2 to K-197; D-2 to L-196; D-2 to T-195; D-2 to Q-194; D-2 to F-193; D-2 to N-192; D-2 to K-191; D-2 to W-190; D-2 to F-189; D-2 to Q-188; D-2 to Y-187; D-2 to Q-186; D-2 to S-185; D-2 to Y-184; D-2 to P-183; D-2 to F-182; D-2 to I-181; D-2 to S-180; D-2 to S-179; D-2 to C-178; D-2 to T-177; D-2 to Y-176; D-2 to H-175; D-2 to L-174; D-2 to G-173; D-2 to E-172; D-2 to K-171; D-2 to Q-170; D-2 to S-169; D-2 to R-168; D-2 to T-167; D-2 to F-166; D-2 to I-165; D-2 to I-164; D-2 to G-163; D-2 to P-162; D-2 to L-161; D-2 to S-160; D-2 to A-159; D-2 to F-158; D-2 to V-157; D-2 to A-156; D-2 to V-155; D-2 to V-154; D-2 to W-153; D-2 to T-152; D-2 to I-151; D-2 to V-150; D-2 to S-149; D-2 to T-148; D-2 to V-147; D-2 to V-146; D-2 to G-145; D-2 to F-144; D-2 to T-143; D-2 to V-142; D-2 to T-141; D-2 to R-140; D-2 to A-139; D-2 to K-138; D-2 to L-137; D-2 to A-136; D-2 to F-135; D-2 to V-134; D-2 to A-133; D-2 to H-132; D-2 to V-131; D-2 to I-130; D-2 to A-129; D-2 to L-128; D-2 to Y-127; D-2 to R-126; D-2 to D-125; D-2 to I-124; D-2 to T-123; D-2 to L-122; D-2 to L-121; D-2 to I-120; D-2 to I-119; D-2 to F-118; D-2 to F-117; D-2 to I-116; D-2 G-115; D-2 to S-114; D-2 to F-113; D-2 to F-112; D-2 to G-111; D-2 to I-110; D-2 to F-109; D-2 to Y-108; D-2 to L-107; D-2 to G-106; D-2 to T-105; D-2 to L-104; D-2 to L-103; D-2 to Q-102; D-2 to C-101; D-2 to M-100; D-2 to T-99; D-2 to N-98; D-2 to G-97; D-2 to F-96; D-2 to D-95; D-2 to W-94; D-2 to Q-93; D-2 to A-92; D-2 to A-91; D-2 to A-90; D-2 to Y-89; D-2 to H-88; D-2 to A-87; D-2 to W-86; D-2 to F-85; D-2 to P-84; D-2 to V-83; D-2 to T-82; D-2 to L-81; D-2 to L-80; D-2 to F-79; D-2 to F-78; D-2 to L-77; D-2 to D-76; D-2 to S-75; D-2 to I-74; D-2 to A-73; D-2 to L-72; D-2 to N-71; D-2 to L-70; D-2 to L-69; D-2 to Y-68; D-2 to I-67; D-2 to D-66; D-2 to T-65; D-2 to M-64; D-2 to S-63; D-2 to E-62; D-2 to L-61; D-2 to R-60; D-2 to Q-59; D-2 to C-58; D-2 to N-57; D-2 to I-56; D-2 to L-55; D-2 to I-54; D-2 to L-53; D-2 to I-52; D-2 to V-51; D-2 to L-50; D-2 to M-49; D-2 to N-48;D-2 to G-47; D-2 to V-46; D-2 to F-45; D-2 to G-44; D-2 to F-43; D-2 to I-42; D-2 to F-41; D-2 to V-40; D-2 to L-39; D-2 to S-38; D-2 to Y-37; D-2 to L-36; D-2 to P-35; D-2 to P-34; D-2 to L-33; D-2 to L-32; D-2 to R-31; D-2 to A-30; D-2 to A-29; D-2 to I-28; D-2 to Q-27; D-2 to K-26; D-2 to V-25; D-2 to N-24; D-2 to I-23; D-2 to K-22; D-2 to P-21; D-2 to C-20; D-2 to P-19; D-2 to E-18; D-2 to S-17; D-2 to T-16; D-2 to Y-15; D-2 to Y-14; D-2 to N-13; D-2 to I-12; D-2 to D-11; D-2 to Y-10; D-2 to I-9; and/or D-2 to P-8 of SEQ ID NO:2. Moreover, a methionine may be added to the N-terminus of each of these C-terminal contructs. Polynucleotides encoding these polypeptides are also encompassed by the invention.

Additionally, the invention provides polynucleotides encoding polypeptides comprising, or alternatively consisting of, the amino acid sequence of residues of D-2 to G-351; D-2 to V-350; D-2 to S-349; D-2 to I-348; D-2 to E-347; D-2 to Q-346; D-2 to E-345; D-2 to E-344; D-2 to T-343; D-2 to S-342; D-2 to R-341; D-2 to T-340; D-2 to Y-339; D-2 to V-338; D-2 to S-337; D-2 to S-336; D-2 to A-335; D-2 to R-334; D-2 to E-333; D-2 to P-332; D-2 to A-331; D-2 to E-330; D-2 to Q-329; D-2 to Q-328; D-2 to F-327; D-2 to I-326; D-2 to S-325; D-2 to C-324; D-2 to C-323; D-2 to K-322; D-2 to C-321; D-2 to F-320; D-2 to R-319; D-2 to K-318; D-2 to A-317; D-2 to I-316; D-2 to H-315; D-2 to K-314; D-2 to Q-313; D-2 to F-312; D-2 to F-311; D-2 to V-310; D-2 to L-309; D-2 to L-308; D-2 to Y-307; D-2 to N-306; D-2 to R-305; D-2 to F-304; D-2 to K-303; D-2 to E-302; D-2 to G-301; D-2 to V-300; D-2 to F-299; D-2 to A-298; D-2 to Y-297; D-2 to I-296; D-2 to I-295; D-2 to P-294; D-2 to N-293; D-2 to I-292; D-2 to C-291; D-2 to C-290; D-2 to H-289; D-2 to T-288; D-2 to M-287; D-2 to G-286; D-2 to L-285; D-2 to T-284; D-2 to E-283; D-2 to T-282; D-2 to V-281; D-2 to Q-280; D-2 to M-279; D-2 to A-278; D-2 to Q-277; D-2 to D-276; D-2 to L-275; D-2 to R-274; D-2 to N-273; D-2 to S-272; D-2 to S-271; D-2 to S-270; D-2 to C-269; D-2 to N-268; D-2 to N-267; D-2 to L-266; D-2 to G-265; D-2 to F-264; D-2 to F-263; D-2 to E-262; D-2 to Q-261; D-2 to F-260; D-2 to T-259; D-2 to N-258; D-2 to L-257; D-2 to L-256; D-2 to L-255; D-2 to V-254; D-2 to I-253; D-2 to N-252; D-2 to Y-251; D-2 to P-250; D-2 to A-249; D-2 to W-248; D-2 to F-247; D-2 to L-246; D-2 to F-245; D-2 to Y-244; D-2 to V-243; D-2 to I-242; D-2 to M-241; D-2 to I-240; D-2 to T-239; D-2 to F-238; D-2 to I-237; D-2 to L-236; D-2 to R-235; D-2 to V-234; D-2 to A-233; D-2 to R-232; D-2 to H-231; D-2 to R-230; D-2 to K-229; D-2 to K-228; D-2 to E-227; D-2 to N-226; D-2 to R-225; D-2 to C-224; D-2 to R-223; D-2 to L-222; D-2 to L-221; D-2 to T-220; D-2 to K-219; D-2 to L-218; D-2 to I-217; D-2 to G-216; D-2 to S-215; D-2 to Y-214; D-2 to C-213; D-2 to I-212; D-2 to V-211; D-2 to M-210; D-2 to V-209; D-2 to L-208; D-2 to L-207; D-2 to P-206; D-2 to L-205; D-2 to V-204; D-2 to L-203; D-2 to G-202; D-2 to L-201; D-2 to I-200; D-2 to V-199; D-2 to I-198; D-2 to K-197; D-2 to L-196; D-2 to T-195; D-2 to Q-194; D-2 to F-193; D-2 to N-192; D-2 to K-191; D-2 to W-190; D-2 to F-189; D-2 to Q-188; D-2 to Y-187; D-2 to Q-186; D-2 to S-185; D-2 to Y-184; D-2 to P-183; D-2 to F-182; D-2 to H-181; D-2 to S-180; D-2 to S-179; D-2 to C-178; D-2 to T-177; D-2 to Y-176; D-2 to H-175; D-2 to L-174; D-2 to G-173; D-2 to E-172; D-2 to K-171; D-2 to Q-170; D-2 to S-169; D-2 to R-168; D-2 to T-167; D-2 to F-166; D-2 to I-165; D-2 to I-164; D-2 to G-163; D-2 to P-162; D-2 to L-161; D-2 to S-160; D-2 to A-159; D-2 to F-158; D-2 to V-157; D-2 to A-156; D-2 to V-155; D-2 to V-154; D-2 to W-153; D-2 to T-152; D-2 to I-151; D-2 to V-150; D-2 to S-149; D-2 to T-148; D-2 to V-147; D-2 to V-146; D-2 to G-145; D-2 to F-144; D-2 to T-143; D-2 to V-142; D-2 to T-141; D-2 to R-140; D-2 to A-139; D-2 to K-138; D-2 to L-137; D-2 to A-136; D-2 to F-135; D-2 to V-134; D-2 to A-133; D-2 to H-132; D-2 to V-131; D-2 to V-130; D-2 to A-129; D-2 to L-128; D-2 to Y-127; D-2 to R-126; D-2 to D-125; D-2 to I-124; D-2 to T-123; D-2 to L-122; D-2 to L-121; D-2 to I-120; D-2 to I-119; D-2 to F-118; D-2 to F-117; D-2 to I-116; D-2 to G-115; D-2 to S-114; D-2 to F-113; D-2 to F-112; D-2 to G-111; D-2 to I-110; D-2 to F-109; D-2 to Y-108; D-2 to L-107; D-2 to G-106; D-2 to T-105; D-2 to L-104; D-2 to L-103; D-2 to Q-102; D-2 to C-101; D-2 to M-100; D-2 to T-99; D-2 to N-98; D-2 to G-97; D-2 to F-96; D-2 to D-95; D-2 to W-94; D-2 to Q-93; D-2 to A-92; D-2 to A-91; D-2 to A-90; D-2 to Y-89; D-2 to H-88; D-2 to A-87; D-2 to W-86; D-2 to F-85; D-2 to P-84; D-2 to V-83; D-2 to T-82; D-2 to L-81; D-2 to L-80; D-2 to F-79; D-2 to F-78; D-2 to L-77; D-2 to D-76; D-2 to S-75; D-2 to I-74; D-2 to A-73; D-2 to L-72; D-2 to N-71; D-2 to L-70; D-2 to L-69; D-2 to Y-68; D-2 to I-67; D-2 to D-66; D-2 to T-65; D-2 to M-64; D-2 to S-63; D-2 to K-62; D-2 to L-61; D-2 to R-60; D-2 to K-59; D-2 to C-58; D-2 to N-57; D-2 to I-56; D-2 to L-55; D-2 to I-54; D-2 to L-53; D-2 to I-52; D-2 to V-51; D-2 to L-50; D-2 to M-49; D-2 to N-48; D-2 to G-47; D-2 to V-46; D-2 to F-45; D-2 to G-44; D-2 to F-43; D-2 to I-42; D-2 to F-41; D-2 to V-40; D-2 to L-39; D-2 to S-38; D-2 to Y-37; D-2 to L-36; D-2 to P-35; D-2 to P-34; D-2 to L-33; D-2 to L-32; D-2 to R-31; D-2 to A-30; D-2 to A-29; D-2 to I-28; D-2 to Q-27; D-2 to K-26; D-2 to V-25; D-2 to N-24; D-2 to I-23; D-2 to K-22; D-2 to Q-21; D-2 to C-20; D-2 to P-19; D-2 to E-18; D-2 to S-17; D-2 to T-16; D-2 to Y-15; D-2 to Y-14; D-2 to N-13; D-2 to I-12; D-2 to D-11; D-2 to Y-10; D-2 to I-9; and/or D-2 to P-8 of SEQ ID NO:22. Moreover, a methionine may be added to the N-terminus of each of these C-terminal contructs. Polynucleotides encoding these polypeptides are also encompassed by the invention.

The present application is also directed to nucleic acid molecules comprising, or alternatively, consisting of, a polynucleotide sequence at least 90%, 92%, 95%, 96%, 97%, 98%, or 99% identical to the polynucleotide sequence encoding the G-protein Chemokine Receptor (CCR5) polypeptide described above. The present invention also encompasses the above polynucleotide sequences fused to a heterologous polynucleotide sequence.

In addition, any of the above listed N- or C-terminal deletions can be combined to produce a N- and C-terminal deleted G-protein Chemokine Receptor (CCR5) polypeptide. The invention also provides polypeptides having one or more amino acids deleted from both the amino and the carboxyl termini, which may be described generally as having residues m–n of SEQ ID NO:2 or of the polypeptide encoded by the deposited clone, where n and m are integers as described above. Polynucleotides encoding these polypeptides are also encompassed by the invention.

Also included are a nucleotide sequence encoding a polypeptide consisting of a portion of the complete G-protein Chemokine Receptor (CCR5) amino acid sequence encoded by the clone contained in ATCC Deposit No. 97183, where this portion excludes any integer of amino acid residues from 1 to about 342 amino acids from the amino terminus of the complete amino acid sequence encoded by the clone contained in ATCC Deposit No. 97183, or any integer of amino acid residues from 1 to about 342 amino acids from the carboxy terminus, or any combination of the above amino terminal and carboxy terminal deletions, of the complete amino acid sequence encoded by the clone contained in ATCC Deposit No. 97183. Polynucleotides encoding all of the above deletion mutant polypeptide forms also are provided.

The present application is also directed to proteins containing polypeptides at least 90%, 92%, 93%, 94%, 95%, 96%, 97%, 98% or 99% identical to the G-protein Chemokine Receptor (CCR5) polypeptide sequence set forth herein m-n. In preferred embodiments, the application is directed to proteins containing polypeptides at least 90%, 95%, 96%, 97%, 98% or 99% identical to polypeptides having the amino acid sequence of the specific G-protein Chemokine Receptor (CCR5) N- and C-terminal deletions recited herein. Polynucleotides encoding these polypeptides are also encompassed by the invention.

Additional preferred polypeptide fragments comprise, or alternatively consist of, the amino acid sequence of residues: M-1 to Y-15; D-2 to T-16; Y-3 to S-17; Q-4 to E-18; V-5 to P-19; S-6 to C-20; S-7 to P-21; P-8 to K-22; I-9 to I-23; Y-10 to N-24; D-11 to V-25; I-12 to K-26; N-13 to Q-27; Y-14 to I-28; Y-15 to A-29; T-16 to A-30; S-17 to R-31; E-18 to L-32; P-19 to L-33; C-20 to P-34; P-21 to P-35; K-22 to L-36; I-23 to Y-37; N-24 to S-38; V-25 to L-39; K-26 to V-40; Q-27to F-41; I-28 to I-42; A-29 to F-43; A-30 to G-44; R-31 to F-45; L-32 to V-46; L-33 to G-47; P-34 to N-48; P-35 to M-49; L-36 to L-50; Y-37 to V-51; S-38 to I-52; L-39 to L-53; V-40 to I-54; F-41 to L-55; I-42 to I-56; F-43 to N-57; G-44 to C-58; F-45 to Q-59; V-46 to R-60; G-47 to L-61; N-48 to E-62; M-49 to S-63; L-50 to M-64; V-51 to T-65; I-52 to D-66; L-53 to I-67; I-54 to Y-68; L-55 to L-69; I-56 to L-70; N-57 to N-71; C-58 to L-72; Q-59 to A-73; R-60 to I-74; L-61 to S-75; E-62 to D-76; S-63 to L-77; M-64 to F-78; T-65 to F-79; D-66 to L-80; I-67 to L-81; Y-68 to T-82; L-69 to V-83; L-70to P-84; N-71 to F-85; L-72 to W-86; A-73 to A-87; I-74 to H-88; S-75 to Y-89; D-76 to A-90; L-77 to A-91; F-78 to A-92; F-79 to Q-93; L-80 to W-94; L-81 to D-95; T-82 to F-96; V-83 to G-97; P-84 to N-98; F-85 to T-99; W-86 to M-100; A-87 to C-101; H-88 to Q-102; Y-89 to L-103; A-90 to L-104; A-91 to T-105; A-92 to G-106; Q-93 to L-107; W-94 to Y-108; D-95 to F-109; F-96 to I-10; G-97 to G-111; N-98 to F-112; T-99 to F-113; M-100 to S-114; C-101 to G-115; Q-102 to I-116; L-103 to F-117; L-104 to F-118; T-105 to I-119; G-106 to I-120; L-107 to L-121; Y-108 to L-122; F-109 to T-123; I-110 to I-124; G-111 to D-125; F-112 to R-126; F-113 to Y-127; S-114 to L-128; G-115 to A-129; I-116 to I-130; F-117 to V-131; F-118 to H-132; I-119 to A-133; I-120 to V-134; L-121 to F-135; L-122 to A-136; T-123 to L-137; I-124 to K-138; D-125 to A-139; R-126 to R-140; Y-127 to T-141; L-128 to V-142; A-129 to T-143; I-130 to F-144; V-131 to G-145; H-132 to V-146; A-133 to V-147; V-134 to T-148; F-135 to S-149; A-136 to V-150; L-137 to I-151; K-138 to T-152; A-139 to W-153; R-140 to V-154; T-141 to V-155; V-142 to A-156; T-143 to V-157; F-144 to F-158; G-145 to A-159; V-146 to S-160; V-147 to L-161; T-148 to P-162; S-149 to G-163; V-150 to I-164; I-151 to I-165; T-152 to F-166; W-153 to T-167; V-154 to R-168; V-155 to S-169; A-156 to Q-170; V-157 to K-171; F-158 to E-172; A-159 to G-173; S-160 to L-174; L-161 to H-175; P-162 to Y-176; G-163 to T-177; I-164 to C-178; I-165 to S-179; F-166 to S-180; T-167 to H-181; R-168 to F-182; S-169 to P-183; Q-170 to Y-184; K-171 to S-185; E-172 to Q-186; G-173 to Y-187; L-174 to Q-188; H-175 to F-189; Y-176 to W-190; T-177 to K-191; C-178 to N-192; S-179 to F-193; S-180 to Q-194; H-181 to T-195; F-182 to L-196; P-183 to K-197; Y-184 to I-198; S-185 to V-199; Q-186 to I-200; Y-187 to L-201; Q-188 to G-202; F-189 to L-203; W-190 to V-204; K-191 to L-205; N-192 to P-206; F-193 to L-207; Q-194 to L-208; T-195 to V-209; L-196 to M-210; K-197 to V-211; I-198 to I-212; V-199 to C-213; I-200 to Y-214; L-201 to S-215; G-202 to G-216; L-203 to I-217; V-204 to L-218; L-205 to K-219; P-206 to T-220; L-207 to L-221; L-208 to L-222; V-209 to R-223; M-210 to C-224; V-211 to R-225; I-212 to N-226; C-213 to E-227; Y-214 to K-228; S-215 to K-229; G-216 to R-230; I-217 to H-231; L-218 to R-232; K-219 to A-233; T-220 to V-234; L-221 to R-235; L-222 to L-236; R-223 to I-237; C-224 to F-238; R-225 to T-239; N-226 to I-240; E-227 to M-241; K-228 to I-242; K-229 to V-243; R-230 to Y-244; H-231 to F-245; R-232 to L-246; A-233 to F-247; V-234 to W-248; R-235 to A-249; L-236 to P-250; I-237 to Y-251; F-238 to N-252; T-239 to I-253; I-240 to V-254; M-241 to L-255; I-242 to L-256; V-243 to L-257; Y-244 to N-258; F-245 to T-259; L-246 to F-260; F-247 to Q-261; W-248 to E-262; A-249 to F-263; P-250 to F-264; Y-251 to G-265; N-252 to L-266; I-253 to N-267; V-254 to N-268; L-255 to C-269; L-256 to S-270; L-257 to S-271; N-258 to S-272; T-259 to N-273; F-260 to R-274; Q-261 to L-275; E-262 to D-276; F-263 to Q-277; F-264 to A-278; G-265 to M-279; L-266 to Q-280; N-267 to V-281; N-268 to T-282; C-269 to E-283; S-270 to T-284; S-271 to L-285; S-272 to G-286; N-273 to M-287; R-274 to T-288; L-275 to H-289; D-276 to C-290; Q-277 to C-291; A-278 to I-292; M-279 to N-293; Q-280 to P-294; V-281 to I-295; T-282 to I-296; E-283 to Y-297; T-284 to A-298; L-285 to F-299; G-286 to V-300; M-287 to G-301; T-288 to E-302; H-289 to K-303; C-290 to F-304; C-291 to R-305; I-292 to N-306; N-293 to Y-307; P-294 to L-308; I-295 to L-309; I-296 to V-310; Y-297 to F-311; A-298 to F-312; F-299 to Q-313; V-300 to K-314; G-301 to H-315; E-302 to I-316; K-303 to A-317; F-304 to K-318; R-305 to R-319; N-306 to F-320; Y-307 to C-321; L-308 to K-322; L-309 to C-323; V-310 to C-324; F-311 to S-325; F-312 to I-326; Q-313 to F-327; K-314 to Q-328; H-315 to Q-329; I-316 to E-330; A-317 to A-331; K-318 to P-332; R-319 to E-333; F-320 to R-334; C-321 to A-335; K-322 to S-336; C-323 to S-337; C-324 to V-338; S-325 to Y-339; I-326 to T-340; F-327 to R-341; Q-328 to S-342; Q-329 to T-343; E-330 to G-344; A-331 to E-345; P-332 to Q-346; E-333 to E-347;

R-334 to I-348; A-335 to S-349; S-336 to V-350; S-337 to G-351; and/or V-338 to L-352 of SEQ ID NO:2.

Additional preferred polypeptide fragments comprise, or alternatively consist of, the amino acid sequence of residues: M-1 to Y-15; D-2 to T-16; Y-3 to S-17; Q-4 to E-18; V-5 to P-19; S-6 to C-20; S-7 to Q-21; P-8 to K-22; I-9 to I-23; Y-10 to N-24; D-11 to V-25; I-12 to K-26; N-13 to Q-27; Y-14 to I-28; Y-15 to A-29; T-16 to A-30; S-17 to R-31; E-18 to L-32; P-19 to L-33; C-20 to P-34; Q-21 to P-35; K-22 to L-36; I-23 to Y-37; N-24 to S-38; V-25 to L-39; K-26 to V-40; Q-27 to F-41; I-28 to I-42; A-29 to F-43; A-30 to G-44; R-31 to F-45; L-32 to V-46; L-33 to G-47; P-34 to N-48; P-35 to M-49; L-36 to L-50; Y-37 to V-51; S-38 to I-52; L-39 to L-53; V-40 to I-54; F-41 to L-55; I-42 to I-56; F-43 to N-57; G-44 to C-58; F-45 to K-59; V-46 to R-60; G-47 to L-61; N-48 to K-62; M-49 to S-63; L-50 to M-64; V-51 to T-65; I-52 to D-66; L-53 to I-67; I-54 to Y-68; L-55 to L-69; I-56 to L-70; N-57 to N-71; C-58 to L-72; K-59 to A-73; R-60 to I-74; L-61 to S-75; K-62 to D-76; S-63 to L-77; M-64 to F-78; T-65 to F-79; D-66 to L-80; I-67 to L-81; Y-68 to T-82; L-69 to V-83; L-70 to P-84; N-71 to F-85; L-72 to W-86; A-73 to A-87; I-74 to H-88; S-75 to Y-89; D-76 to A-90; L-77 to A-91; F-78 to A-92; F-79 to Q-93; L-80 to W-94; L-81 to D-95; T-82 to F-96; V-83 to G-97; P-84 to N-98; F-85 to T-99; W-86 to M-100; A-87 to C-101; H-88 to Q-102; Y-89 to L-103; A-90 to L-104; A-91 to T-105; A-92 to G-106; Q-93 to L-107; W-94 to Y-108; D-95 to F-109; F-96 to I-110; G-97 to G-111; N-98 to F-112; T-99 to F-113; M-100 to S-114; C-101 to G-115; Q-102 to I-116; L-103 to F-117; L-104 to F-118; T-105 to I-119; G-106 to I-120; L-107 to L-121; Y-108 to L-122; F-109 to T-123; I-110 to I-124; G-111 to D-125; F-112 to R-126; F-113 to Y-127; S-114 to L-128; G-115 to A-129; I-116 to V-130; F-117 to V-131; F-118 to H-132; I-119 to A-133; I-120 to V-134; L-121 to F-135; L-122 to A-136; T-123 to L-137; I-124 to K-138; D-125 to A-139; R-126 to R-140; Y-127 to T-141; L-128 to V-142; A-129 to T-143; V-130 to F-144; V-131 to G-145; H-132 to V-146; A-133 to V-147; V-134 to T-148; F-135 to S-149; A-136 to V-150; L-137 to I-151; K-138 to T-152; A-139 to W-153; R-140 to V-154; T-141 to V-155; V-142 to A-156; T-143 to V-157; F-144 to F-158; G-145 to A-159; V-146 to S-160; V-147 to L-161; T-148 to P-162; S-149 to G-163; V-150 to I-164; I-151 to I-165; T-152 to F-166; W-153 to T-167; V-154 to R-168; V-155 to S-169; A-156 to Q-170; V-157 to K-171; F-158 to E-172; A-159 to G-173; S-160 to L-174; L-161 to H-175; P-162 to Y-176; G-163 to T-177; I-164 to C-178; I-165 to S-179; F-166 to S-180; T-167 to H-181; R-168 to F-182; S-169 to P-183; Q-170 to Y-184; K-171 to S-185; E-172 to Q-186; G-173 to Y-187; L-174 to Q-188; H-175 to F-189; Y-176 to W-190; T-177 to K-191; C-178 to N-192; S-179 to F-193; S-180 to Q-194; H-181 to T-195; F-182 to L-196; P-183 to K-197; Y-184 to I-198; S-185 to V-199; Q-186 to I-200; Y-187 to L-201; Q-188 to G-202; F-189 to L-203; W-190 to V-204; K-191 to L-205; N-192 to P-206; F-193 to L-207; Q-194 to L-208; T-195 to V-209; L-196 to M-210; K-197 to V-211; I-198 to I-212; V-199 to C-213; I-200 to Y-214; L-201 to S-215; G-202 to G-216; L-203 to I-217; V-204 to L-218; L-205 to K-219; P-206 to T-220; L-207 to L-221; L-208 to L-222; V-209 to R-223; M-210 to C-224; V-211 to R-225; I-212 to N-226; C-213 to E-227; Y-214 to K-228; S-215 to K-229; G-216 to R-230; I-217 to H-231; L-218 to R-232; K-219 to A-233; T-220 to V-234; L-221 to R-235; L-222 to L-236; R-223 to I-237; C-224 to F-238; R-225 to T-239; N-226 to I-240; E-227 to M-241; K-228 to I-242; K-229 to V-243; R-230 to Y-244; H-231 to F-245; R-232 to L-246; A-233 to F-247; V-234 to W-248; R-235 to A-249; L-236 to P-250; I-237 to Y-251; F-238 to N-252; T-239 to I-253; I-240 to V-254; M-241 to L-255; I-242 to L-256; V-243 to L-257; Y-244 to N-258; F-245 to T-259; L-246 to F-260; F-247 to Q-261; W-248 to E-262; A-249 to F-263; P-250 to F-264; Y-251 to G-265; N-252 to L-266; I-253 to N-267; V-254 to N-268; L-255 to C-269; L-256 to S-270; L-257 to S-271; N-258 to S-272; T-259 to N-273; F-260 to R-274; Q-261 to L-275; E-262 to D-276; F-263 to Q-277; F-264 to A-278; G-265 to M-279; L-266 to Q-280; N-267 to V-281; N-268 to T-282; C-269 to E-283; S-270 to T-284; S-271 to L-285; S-272 to G-286; N-273 to M-287; R-274 to T-288; L-275 to H-289; D-276 to C-290; Q-277 to C-291; A-278 to I-292; M-279 to N-293; Q-280 to P-294; V-281 to I-295; T-282 to I-296; E-283 to Y-297; T-284 to A-298; L-285 to F-299; G-286 to V-300; M-287 to G-301; T-288 to E-302; H-289 to K-303; C-290 to F-304; C-291 to R-305; I-292 to N-306; N-293 to Y-307; P-294 to L-308; I-295 to L-309; I-296 to V-310; Y-297 to F-311; A-298 to F-312; F-299 to Q-313; V-300 to K-314; G-301 to H-315; E-302 to I-316; K-303 to A-317; F-304 to K-318; R-305 to R-319; N-306 to F-320; Y-307 to C-321; L-308 to K-322; L-309 to C-323; V-310 to C-324; F-311 to S-325; F-312 to I-326; Q-313 to F-327; K-314 to Q-328; H-315 to Q-329; I-316 to E-330; A-317 to A-331; K-318 to P-332; R-319 to E-333; F-320 to R-334; C-321 to A-335; K-322 to S-336; C-323 to S-337; C-324 to V-338; S-325 to Y-339; I-326 to T-340; F-327 to R-341; Q-328 to S-342; Q-329 to T-343; E-330 to E-344; A-331 to E-345; P-332 to Q-346; E-333 to E-347; R-334 to I-348; A-335 to S-349; S-336 to V-350; S-337 to G-351; and/or V-338 to L-352 of SEQ ID NO:22.

These polypeptide fragments may retain the biological activity of G-protein Chemokine Receptor (CCR5) polypeptides of the invention and/or may be useful to generate or screen for antibodies, as described further below. Polynucleotides encoding these polypeptide fragments are also encompassed by the invention.

The present application is also directed to nucleic acid molecules comprising, or alternatively, consisting of, a polynucleotide sequence at least 90%, 92%, 95%, 96%, 97%, 98%, or 99% identical to the polynucleotide sequence encoding the G-protein Chemokine Receptor (CCR5) polypeptide described above. The present invention also encompasses the above polynucleotide sequences fused to a heterologous polynucleotide sequence.

Additionally, the present application is also directed to proteins containing polypeptides at least 90%, 92%, 93%, 94%, 95%, 96%, 97%, 98% or 99% identical to the G-protein Chemokine Receptor (CCR5) polypeptide fragments set forth above. Polynucleotides encoding these polypeptides are also encompassed by the invention.

Preferably, the polynucleotide fragments of the invention encode a polypeptide which demonstrates a G-protein Chemokine Receptor (CCR5) functional activity. By a polypeptide demonstrating a G-protein Chemokine Receptor (CCR5) "functional activity" is meant, a polypeptide capable of displaying one or more known functional activities associated with a full-length (complete) G-protein Chemokine Receptor (CCR5) protein. Such functional activities include, but are not limited to, biological activity, antigenicity [ability to bind (or compete with a G-protein Chemokine Receptor (CCR5) polypeptide for binding) to an anti-G-protein Chemokine Receptor (CCR5) antibody], immunogenicity (ability to generate antibody which binds to a G-protein Chemokine Receptor (CCR5) polypeptide), ability to form multimers with G-protein Chemokine Receptor (CCR5) polypeptides of the invention, and ability to bind to a receptor or ligand for a G-protein Chemokine Receptor (CCR5) polypeptide.

The functional activity of G-protein Chemokine Receptor (CCR5) polypeptides, and fragments, variants derivatives, and analogs thereof, can be assayed by various methods.

For example, in one embodiment where one is assaying for the ability to bind or compete with full-length G-protein Chemokine Receptor (CCR5) polypeptide for binding to anti-G-protein Chemokine Receptor (CCR5) antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a G-protein Chemokine Receptor (CCR5) ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94–123. In another embodiment, physiological correlates of G-protein Chemokine Receptor (CCR5) binding to its substrates (signal transduction) can be assayed.

In addition, assays described herein (see Examples) and otherwise known in the art may routinely be applied to measure the ability of G-protein Chemokine Receptor (CCR5) polypeptides and fragments, variants derivatives and analogs thereof to elicit G-protein Chemokine Receptor (CCR5) related biological activity (either in vitro or in vivo). Other methods will be known to the skilled artisan and are within the scope of the invention.

Among the especially preferred fragments of the invention are fragments characterized by structural or functional attributes of G-protein Chemokine Receptor. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) G-protein Chemokine Receptor (CCR5) (SEQ ID NO:2) or encoded by the deposited clone. Certain preferred regions are those set out in FIG. 3 and include, but are not limited to, regions of the aforementioned types identified by analysis of the amino acid sequence depicted in FIG. 1 (SEQ ID NO:2) or encoded by the deposited clone, such preferred regions include; Gamier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of G-protein Chemokine Receptor. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of G-protein Chemokine Receptor.

The data representing the structural or functional attributes of G-protein Chemokine Receptor (CCR5) set forth in FIG. 1 or encoded by the deposited clone and/or Table 1, as described above, was generated using the various modules and algorithms of the DNA*STAR set on default parameters. In a preferred embodiment, the data presented in columns VIII, IX, XIII, and XIV of Table 1 can be used to determine regions of G-protein Chemokine Receptor (CCR5) which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table 1, be represented or identified by using tabular representations of the data presented in FIG. 3. The DNA*STAR computer algorithm used to generate FIG. 3 (set on the original default parameters) was used to present the data in FIG. 3 in a tabular format (See Table 1). The tabular format of the data in FIG. 3 may be used to easily determine specific boundaries of a preferred region.

The above-mentioned preferred regions set out in FIG. 3 and in Table 1 include, but are not limited to, regions of the aforementioned types identified by analysis of the amino acid sequence set out in FIG. 1 or encoded by the deposited clone. As set out in FIG. 3 and in Table 1, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

TABLE I

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.24 | 0.06 | . | * | . | 0.05 | 1.68 |
| Asp | 2 | . | . | B | B | . | . | . | 0.33 | 0.27 | . | * | . | −0.30 | 0.98 |
| Tyr | 3 | . | . | B | B | . | . | . | 0.42 | 0.23 | . | * | . | −0.15 | 1.02 |
| Gln | 4 | . | . | B | B | . | . | . | 0.60 | 0.19 | . | * | . | −0.15 | 1.38 |
| Val | 5 | . | . | B | B | . | . | . | 0.10 | 0.00 | . | * | F | 0.00 | 1.28 |
| Ser | 6 | . | . | B | B | . | . | . | 0.46 | 0.69 | * | * | F | −0.45 | 0.57 |
| Ser | 7 | . | . | B | B | . | . | . | 0.46 | 0.69 | * | * | F | −0.45 | 0.52 |
| Pro | 8 | . | . | B | B | . | . | . | −0.19 | 0.29 | * | * | F | 0.00 | 1.17 |
| Ile | 9 | . | . | B | B | . | . | . | −0.19 | 0.33 | * | * | . | −0.30 | 0.61 |
| Tyr | 10 | . | . | B | B | . | . | . | 0.42 | 0.34 | * | . | . | −0.30 | 0.73 |
| Asp | 11 | . | . | B | . | . | T | . | 0.48 | 0.71 | . | . | . | −0.20 | 0.74 |
| Ile | 12 | . | . | B | . | . | T | . | 0.47 | 1.04 | . | . | . | −0.05 | 1.66 |
| Asn | 13 | . | . | B | . | . | T | . | 0.38 | 0.84 | * | . | . | −0.05 | 1.53 |
| Tyr | 14 | . | . | B | . | . | T | . | 1.27 | 0.47 | * | . | . | −0.05 | 1.23 |
| Tyr | 15 | . | . | . | B | T | . | . | 1.30 | 0.47 | . | * | . | −0.05 | 3.03 |
| Thr | 16 | . | . | . | B | T | . | . | 0.63 | 0.21 | . | * | F | 0.65 | 2.91 |
| Ser | 17 | . | . | . | B | T | . | . | 1.31 | 0.39 | . | * | F | 0.75 | 1.00 |
| Glu | 18 | . | . | B | . | . | . | . | 1.36 | 0.06 | . | * | F | 0.80 | 0.98 |
| Pro | 19 | . | . | . | . | T | . | . | 0.71 | −0.70 | . | * | F | 2.50 | 1.36 |
| Cys | 20 | . | . | . | . | T | T | . | 0.96 | −0.50 | . | * | F | 2.50 | 0.71 |
| Pro | 21 | . | . | . | . | T | T | . | 0.41 | −0.49 | . | * | F | 2.25 | 0.66 |
| Lys | 22 | . | . | . | . | T | T | . | 0.76 | 0.16 | . | * | F | 1.40 | 0.32 |
| Ile | 23 | A | . | . | . | . | T | . | 0.76 | −0.27 | * | * | F | 1.50 | 1.19 |
| Asn | 24 | A | A | . | . | . | . | . | 0.08 | −0.44 | . | * | F | 0.85 | 1.33 |
| Val | 25 | A | A | . | . | . | . | . | 0.16 | −0.19 | . | * | . | 0.30 | 0.47 |
| Lys | 26 | . | A | B | . | . | . | . | −0.22 | 0.31 | . | * | . | −0.30 | 0.67 |
| Gln | 27 | . | A | B | . | . | . | . | −0.16 | 0.13 | * | * | . | −0.30 | 0.42 |
| Ile | 28 | . | A | B | . | . | . | . | −0.08 | −0.27 | * | * | . | 0.45 | 1.11 |
| Ala | 29 | . | A | B | . | . | . | . | −0.89 | −0.23 | * | * | . | 0.30 | 0.46 |
| Ala | 30 | . | A | B | . | . | . | . | −0.24 | 0.46 | * | * | . | −0.60 | 0.22 |
| Arg | 31 | . | A | B | . | . | . | . | −0.50 | 0.49 | * | * | . | −0.60 | 0.48 |
| Leu | 32 | . | A | B | . | . | . | . | −1.31 | 0.23 | * | * | . | −0.30 | 0.74 |
| Leu | 33 | . | A | B | . | . | . | . | −0.67 | 0.41 | * | * | . | −0.60 | 0.60 |
| Pro | 34 | . | . | . | . | . | T | C | −0.38 | 0.67 | * | * | F | 0.15 | 0.48 |
| Pro | 35 | . | . | . | . | T | T | . | −0.60 | 1.06 | * | * | F | 0.35 | 0.78 |
| Leu | 36 | . | . | B | . | . | T | . | −1.57 | 1.06 | * | * | . | −0.20 | 0.78 |
| Tyr | 37 | . | . | B | . | . | T | . | −1.46 | 1.01 | . | . | . | −0.20 | 0.38 |
| Ser | 38 | . | . | B | B | . | . | . | −1.53 | 1.37 | . | . | . | −0.60 | 0.21 |
| Leu | 39 | . | . | B | B | . | . | . | −2.02 | 1.63 | . | . | . | −0.60 | 0.18 |
| Val | 40 | . | . | B | B | . | . | . | −2.16 | 1.73 | . | . | . | −0.60 | 0.10 |
| Phe | 41 | . | . | B | B | . | . | . | −2.04 | 1.40 | . | . | . | −0.60 | 0.07 |
| Ile | 42 | . | . | B | B | . | . | . | −2.66 | 1.80 | . | . | . | −0.60 | 0.08 |
| Phe | 43 | . | . | B | B | . | . | . | −2.70 | 1.76 | . | . | . | −0.60 | 0.08 |
| Gly | 44 | . | . | B | B | . | . | . | −1.89 | 1.54 | . | . | . | −0.60 | 0.09 |
| Phe | 45 | . | . | . | B | T | . | . | −1.63 | 1.16 | . | . | . | −0.20 | 0.20 |
| Val | 46 | . | . | . | B | . | . | C | −1.74 | 1.09 | . | . | . | −0.40 | 0.23 |
| Gly | 47 | . | . | . | B | . | . | C | −1.71 | 0.99 | . | . | . | −0.40 | 0.19 |
| Asn | 48 | A | . | . | B | . | . | . | −1.90 | 1.20 | . | . | . | −0.60 | 0.16 |
| Met | 49 | A | . | . | B | . | . | . | −2.37 | 1.10 | . | . | . | −0.60 | 0.15 |
| Leu | 50 | A | . | . | B | . | . | . | −2.56 | 1.14 | . | . | . | −0.60 | 0.13 |
| Val | 51 | . | . | B | B | . | . | . | −2.51 | 1.40 | . | . | . | −0.60 | 0.06 |
| Ile | 52 | . | . | B | B | . | . | . | −3.06 | 1.69 | . | . | . | −0.60 | 0.05 |
| Leu | 53 | . | . | B | B | . | . | . | −3.06 | 1.76 | . | . | . | −0.60 | 0.04 |
| Ile | 54 | . | . | B | B | . | . | . | −3.12 | 1.47 | . | * | . | −0.60 | 0.09 |
| Leu | 55 | . | . | B | B | . | . | . | −2.31 | 1.40 | * | . | . | −0.60 | 0.07 |
| Ile | 56 | . | . | B | B | . | . | . | −1.34 | 1.11 | * | . | . | −0.60 | 0.14 |
| Asn | 57 | . | . | B | B | . | . | . | −1.27 | 0.43 | . | * | . | −0.60 | 0.39 |
| Cys | 58 | . | A | B | B | . | . | . | −0.46 | 0.43 | . | . | . | −0.60 | 0.39 |
| Gln | 59 | A | A | . | B | . | . | . | 0.13 | −0.26 | * | . | . | 0.30 | 0.96 |
| Arg | 60 | A | A | . | B | . | . | . | 0.34 | −0.56 | . | . | F | 0.75 | 0.80 |
| Leu | 61 | A | A | . | B | . | . | . | 0.92 | −0.34 | . | . | F | 0.60 | 1.47 |
| Glu | 62 | . | A | B | B | . | . | . | 0.92 | −0.43 | . | * | F | 0.60 | 1.23 |
| Ser | 63 | . | A | B | . | . | . | . | 0.70 | −0.83 | * | * | F | 0.90 | 1.05 |
| Met | 64 | . | A | B | B | . | . | . | 0.46 | −0.14 | * | * | F | 0.45 | 0.89 |
| Thr | 65 | . | A | B | B | . | . | . | −0.47 | −0.07 | . | * | F | 0.45 | 0.80 |
| Asp | 66 | A | A | . | B | . | . | . | −0.47 | 0.61 | . | * | . | −0.60 | 0.50 |
| Ile | 67 | A | A | . | B | . | . | . | −0.47 | 0.91 | . | . | . | −0.60 | 0.41 |
| Tyr | 68 | A | A | . | B | . | . | . | −0.98 | 0.70 | . | . | . | −0.60 | 0.46 |
| Leu | 69 | A | A | . | B | . | . | . | −0.97 | 0.90 | . | . | . | −0.60 | 0.23 |
| Leu | 70 | A | A | . | B | . | . | . | −1.54 | 1.40 | . | * | . | −0.60 | 0.33 |
| Asn | 71 | A | A | . | B | . | . | . | −1.84 | 1.40 | . | . | . | −0.60 | 0.15 |
| Leu | 72 | . | A | B | B | . | . | . | −0.96 | 1.03 | * | . | . | −0.60 | 0.24 |
| Ala | 73 | A | A | . | B | . | . | . | −1.52 | 0.34 | * | . | . | −0.30 | 0.48 |
| Ile | 74 | A | A | . | B | . | . | . | −1.41 | 0.34 | . | . | . | −0.30 | 0.25 |
| Ser | 75 | A | A | . | B | . | . | . | −1.30 | 0.73 | . | * | . | −0.60 | 0.26 |
| Asp | 76 | A | A | . | B | . | . | . | −2.11 | 0.83 | . | . | . | −0.60 | 0.22 |
| Leu | 77 | . | A | B | B | . | . | . | −2.11 | 1.01 | . | . | . | −0.60 | 0.26 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Phe | 78 | . | A | B | B | . | . | . | −1.83 | 1.01 | . | . | . | −0.60 | 0.16 |
| Phe | 79 | . | A | B | B | . | . | . | −1.80 | 1.11 | . | . | . | −0.60 | 0.14 |
| Leu | 80 | . | A | B | B | . | . | . | −1.71 | 1.76 | . | * | . | −0.60 | 0.13 |
| Leu | 81 | . | A | B | B | . | . | . | −2.41 | 1.50 | . | * | . | −0.60 | 0.22 |
| Thr | 82 | . | A | B | B | . | . | . | −1.89 | 1.50 | . | * | . | −0.60 | 0.22 |
| Val | 83 | . | A | . | B | . | . | C | −1.78 | 1.63 | . | * | . | −0.40 | 0.29 |
| Pro | 84 | A | A | . | B | . | . | . | −1.11 | 1.44 | . | * | . | −0.60 | 0.35 |
| Phe | 85 | A | A | . | B | . | . | . | −0.54 | 1.26 | . | . | . | −0.60 | 0.33 |
| Trp | 86 | A | A | . | B | . | . | . | −0.32 | 1.53 | . | * | . | −0.60 | 0.70 |
| Ala | 87 | A | A | . | B | . | . | . | −0.60 | 1.39 | . | . | . | −0.60 | 0.45 |
| His | 88 | A | A | . | B | . | . | . | −0.33 | 1.46 | . | . | . | −0.60 | 0.53 |
| Tyr | 89 | A | A | . | B | . | . | . | −0.12 | 1.17 | . | . | . | −0.60 | 0.51 |
| Ala | 90 | A | A | . | B | . | . | . | 0.29 | 0.66 | . | * | . | −0.60 | 0.87 |
| Ala | 91 | A | A | . | . | . | . | . | 0.58 | 1.07 | . | * | . | −0.60 | 0.67 |
| Ala | 92 | A | A | . | . | . | . | . | 0.47 | 0.57 | . | * | . | −0.60 | 0.72 |
| Gln | 93 | A | A | . | . | . | . | . | 0.16 | 0.60 | . | * | . | −0.60 | 0.62 |
| Trp | 94 | A | A | . | . | . | . | . | 0.40 | 0.53 | . | * | . | −0.60 | 0.60 |
| Asp | 95 | . | . | . | . | T | T | . | 0.68 | 0.43 | . | * | . | 0.20 | 0.96 |
| Phe | 96 | . | . | . | . | T | T | . | 0.67 | 0.41 | . | * | . | 0.20 | 0.80 |
| Gly | 97 | . | . | . | . | T | T | . | 0.59 | 0.63 | * | * | F | 0.35 | 0.75 |
| Asn | 98 | . | . | . | . | T | T | . | 0.59 | 0.29 | * | * | F | 0.65 | 0.24 |
| Thr | 99 | . | . | . | B | T | . | . | 0.07 | 0.69 | * | . | . | −0.20 | 0.48 |
| Met | 100 | . | . | . | B | T | . | . | −0.74 | 0.59 | * | . | . | −0.20 | 0.40 |
| Cys | 101 | . | . | B | B | . | . | . | −0.36 | 0.84 | * | . | . | −0.60 | 0.21 |
| Gln | 102 | . | . | B | B | . | . | . | −0.36 | 0.93 | * | . | . | −0.60 | 0.21 |
| Leu | 103 | . | . | B | B | . | . | . | −1.17 | 0.87 | * | . | . | −0.60 | 0.21 |
| Leu | 104 | . | . | B | B | . | . | . | −1.10 | 0.94 | . | . | . | −0.60 | 0.32 |
| Thr | 105 | . | . | B | B | . | . | . | −1.20 | 1.13 | * | . | . | −0.60 | 0.29 |
| Gly | 106 | . | . | B | B | . | . | . | −1.42 | 1.51 | * | . | . | −0.60 | 0.30 |
| Leu | 107 | . | . | B | B | . | . | . | −1.77 | 1.51 | . | . | . | −0.60 | 0.26 |
| Tyr | 108 | . | . | B | B | . | . | . | −1.66 | 1.26 | . | . | . | −0.60 | 0.18 |
| Phe | 109 | . | . | B | B | . | . | . | −1.54 | 1.56 | . | . | . | −0.60 | 0.15 |
| Ile | 110 | . | . | B | B | . | . | . | −1.53 | 1.91 | . | . | . | −0.60 | 0.16 |
| Gly | 111 | . | . | B | B | . | . | . | −1.53 | 1.61 | . | . | . | −0.60 | 0.14 |
| Phe | 112 | . | . | B | B | . | . | . | −1.61 | 1.29 | . | . | . | −0.60 | 0.16 |
| Phe | 113 | . | . | B | B | . | . | . | −2.07 | 1.19 | . | . | . | −0.60 | 0.16 |
| Ser | 114 | . | . | . | B | . | . | C | −2.07 | 1.29 | . | . | . | −0.40 | 0.14 |
| Gly | 115 | . | . | . | B | . | . | C | −2.07 | 1.64 | . | . | . | −0.40 | 0.14 |
| Ile | 116 | . | . | . | B | . | . | C | −2.61 | 1.54 | . | . | . | −0.40 | 0.11 |
| Phe | 117 | . | . | B | B | . | . | . | −2.72 | 1.44 | . | . | . | −0.60 | 0.06 |
| Phe | 118 | . | . | B | B | . | . | . | −2.83 | 1.74 | . | . | . | −0.60 | 0.05 |
| Ile | 119 | . | . | B | B | . | . | . | −2.84 | 2.00 | . | . | . | −0.60 | 0.06 |
| Ile | 120 | . | . | B | B | . | . | . | −3.39 | 1.80 | . | * | . | −0.60 | 0.10 |
| Leu | 121 | . | . | B | B | . | . | . | −2.50 | 1.70 | * | . | . | −0.60 | 0.08 |
| Leu | 122 | . | . | B | B | . | . | . | −1.69 | 0.91 | * | . | . | −0.60 | 0.18 |
| Thr | 123 | A | . | . | B | . | . | . | −1.23 | 0.23 | * | . | . | −0.30 | 0.52 |
| Ile | 124 | A | . | . | B | . | . | . | −1.16 | 0.30 | * | . | . | −0.30 | 0.98 |
| Asp | 125 | A | . | . | . | . | T | . | −0.86 | 0.30 | * | . | F | 0.25 | 0.98 |
| Arg | 126 | A | . | . | . | . | T | . | −0.93 | 0.11 | * | . | . | 0.10 | 0.69 |
| Tyr | 127 | A | . | . | . | . | T | . | −0.98 | 0.31 | * | . | . | 0.10 | 0.69 |
| Leu | 128 | A | . | . | . | . | T | . | −0.70 | 0.27 | * | . | . | 0.10 | 0.30 |
| Ala | 129 | A | . | . | B | . | . | . | −0.40 | 0.77 | * | . | . | −0.60 | 0.21 |
| Ile | 130 | A | . | . | B | . | . | . | −1.26 | 1.27 | * | . | . | −0.60 | 0.14 |
| Val | 131 | A | . | . | B | . | . | . | −2.07 | 1.16 | * | . | . | −0.60 | 0.12 |
| His | 132 | A | . | . | B | . | . | . | −2.41 | 1.26 | . | . | . | −0.60 | 0.11 |
| Ala | 133 | A | . | . | B | . | . | . | −2.41 | 1.26 | . | * | . | −0.60 | 0.15 |
| Val | 134 | A | . | . | B | . | . | . | −1.78 | 1.26 | . | * | . | −0.60 | 0.17 |
| Phe | 135 | A | . | . | B | . | . | . | −1.48 | 0.61 | . | * | . | −0.60 | 0.25 |
| Ala | 136 | A | . | . | B | . | . | . | −0.51 | 0.61 | . | * | . | −0.60 | 0.25 |
| Leu | 137 | A | . | . | B | . | . | . | −0.79 | 0.11 | . | * | . | −0.30 | 0.65 |
| Lys | 138 | A | . | . | B | . | . | . | −1.06 | −0.04 | . | * | F | 0.60 | 1.09 |
| Ala | 139 | A | . | . | B | . | . | . | −0.51 | −0.19 | . | * | F | 0.45 | 0.80 |
| Arg | 140 | A | . | . | B | . | . | . | −0.51 | −0.20 | . | * | F | 0.60 | 1.40 |
| Thr | 141 | . | . | B | B | . | . | . | −0.27 | −0.10 | . | * | F | 0.45 | 0.61 |
| Val | 142 | . | . | B | B | . | . | . | −0.31 | 0.33 | . | * | . | −0.30 | 0.59 |
| Thr | 143 | . | . | B | B | . | . | . | −1.21 | 0.47 | . | * | . | −0.60 | 0.23 |
| Phe | 144 | . | . | B | B | . | . | . | −0.93 | 1.11 | . | . | . | −0.60 | 0.12 |
| Gly | 145 | . | . | B | B | . | . | . | −1.34 | 1.11 | . | . | . | −0.60 | 0.23 |
| Val | 146 | . | . | B | B | . | . | . | −1.89 | 0.86 | . | . | . | −0.60 | 0.21 |
| Val | 147 | . | . | B | B | . | . | . | −1.92 | 1.01 | . | . | . | −0.60 | 0.18 |
| Thr | 148 | . | . | B | B | . | . | . | −1.92 | 0.91 | . | . | . | −0.60 | 0.13 |
| Ser | 149 | . | . | B | B | . | . | . | −1.51 | 0.97 | * | . | . | −0.60 | 0.25 |
| Val | 150 | . | . | B | B | . | . | . | −2.02 | 1.24 | * | . | . | −0.60 | 0.35 |
| Ile | 151 | . | . | B | B | . | . | . | −2.02 | 1.24 | * | . | . | −0.60 | 0.18 |
| Thr | 152 | . | . | B | B | . | . | . | −1.76 | 1.40 | * | . | . | −0.60 | 0.10 |
| Trp | 153 | . | . | B | B | . | . | . | −2.30 | 1.51 | * | . | . | −0.60 | 0.14 |
| Val | 154 | . | . | B | B | . | . | . | −2.70 | 1.51 | * | . | . | −0.60 | 0.14 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Val | 155 | . | . | B | B | . | . | . | −2.43 | 1.61 | * | . | . | −0.60 | 0.09 |
| Ala | 156 | . | . | B | B | . | . | . | −1.84 | 1.63 | * | . | . | −0.60 | 0.08 |
| Val | 157 | . | . | B | B | . | . | . | −2.34 | 1.10 | . | . | . | −0.60 | 0.15 |
| Phe | 158 | . | . | B | B | . | . | . | −2.27 | 1.14 | . | . | . | −0.60 | 0.17 |
| Ala | 159 | . | . | B | B | . | . | . | −1.76 | 0.93 | . | . | . | −0.60 | 0.25 |
| Ser | 160 | . | . | . | B | . | . | C | −1.79 | 0.86 | . | . | . | −0.40 | 0.34 |
| Leu | 161 | . | . | . | B | . | . | C | −2.09 | 0.90 | . | . | . | −0.40 | 0.27 |
| Pro | 162 | . | . | . | B | . | . | C | −1.93 | 0.80 | . | . | . | −0.40 | 0.19 |
| Gly | 163 | . | . | . | B | T | . | . | −1.54 | 1.09 | * | . | . | −0.20 | 0.12 |
| Ile | 164 | . | . | B | B | . | . | . | −0.84 | 1.19 | . | . | . | −0.60 | 0.22 |
| Ile | 165 | . | . | B | B | . | . | . | −0.84 | 0.50 | . | * | . | −0.60 | 0.27 |
| Phe | 166 | . | . | B | B | . | . | . | −0.03 | 0.46 | . | . | . | −0.26 | 0.37 |
| Thr | 167 | . | . | B | . | . | T | . | 0.22 | 0.43 | * | . | F | 0.63 | 0.91 |
| Arg | 168 | . | . | B | . | . | T | . | 0.57 | −0.26 | * | . | F | 2.02 | 2.60 |
| Ser | 169 | . | . | . | . | . | T | C | 1.11 | −0.94 | * | . | F | 2.86 | 5.21 |
| Gln | 170 | . | . | . | . | T | T | . | 1.19 | −1.30 | * | . | F | 3.40 | 3.57 |
| Lys | 171 | . | . | . | . | T | . | . | 1.86 | −1.10 | * | . | F | 2.86 | 1.50 |
| Glu | 172 | . | . | . | . | T | . | . | 1.92 | −0.60 | * | . | F | 2.52 | 1.53 |
| Gly | 173 | . | . | . | B | T | . | . | 1.50 | −0.23 | * | * | F | 1.68 | 1.38 |
| Leu | 174 | . | . | B | B | . | . | . | 1.13 | −0.14 | . | . | . | 0.64 | 1.00 |
| His | 175 | . | . | B | B | . | . | . | 0.83 | 0.43 | . | . | . | −0.60 | 0.31 |
| Tyr | 176 | . | . | B | B | . | . | . | 0.49 | 0.81 | . | . | . | −0.60 | 0.42 |
| Thr | 177 | . | . | B | B | . | . | . | 0.46 | 0.77 | . | * | . | −0.60 | 0.68 |
| Cys | 178 | . | . | B | . | . | T | . | 0.10 | 0.59 | . | * | . | −0.20 | 0.68 |
| Ser | 179 | . | . | . | . | T | T | . | 0.70 | 0.87 | . | * | . | 0.20 | 0.38 |
| Ser | 180 | . | . | . | . | T | T | . | 0.49 | 0.54 | . | . | . | 0.20 | 0.40 |
| His | 181 | . | . | . | . | T | T | . | 0.43 | 0.81 | . | . | . | 0.35 | 1.18 |
| Phe | 182 | . | . | . | . | . | T | C | 0.74 | 0.63 | . | . | . | 0.15 | 1.18 |
| Pro | 183 | . | . | . | . | T | T | . | 1.17 | 0.64 | . | . | . | 0.35 | 1.52 |
| Tyr | 184 | . | . | . | . | T | T | . | 1.47 | 1.01 | . | * | . | 0.35 | 1.75 |
| Ser | 185 | . | . | . | . | T | T | . | 1.07 | 0.91 | . | . | . | 0.35 | 3.50 |
| Gln | 186 | . | . | B | B | . | . | . | 0.81 | 0.91 | * | . | . | −0.45 | 1.96 |
| Tyr | 187 | . | . | . | B | T | . | . | 1.56 | 1.40 | * | . | . | −0.05 | 1.31 |
| Gln | 188 | . | . | . | B | T | . | . | 1.77 | 0.64 | * | . | . | −0.05 | 1.96 |
| Phe | 189 | . | . | . | B | T | . | . | 1.31 | 0.66 | * | * | . | −0.05 | 1.82 |
| Trp | 190 | . | . | . | B | T | . | . | 1.61 | 1.04 | * | * | . | −0.05 | 1.01 |
| Lys | 191 | . | . | B | B | . | . | . | 1.30 | 0.69 | * | * | . | −0.45 | 1.01 |
| Asn | 192 | . | . | . | B | T | . | . | 0.73 | 0.77 | * | . | . | −0.05 | 1.68 |
| Phe | 193 | . | . | . | B | T | . | . | 0.78 | 0.67 | * | * | . | −0.05 | 1.32 |
| Gln | 194 | A | . | . | B | . | . | . | 0.59 | −0.24 | * | . | F | 0.60 | 1.32 |
| Thr | 195 | . | . | . | B | . | . | C | 0.02 | 0.44 | * | * | F | −0.25 | 0.57 |
| Leu | 196 | . | . | B | B | . | . | . | −0.91 | 0.69 | * | . | . | −0.60 | 0.49 |
| Lys | 197 | . | . | B | B | . | . | . | −1.72 | 0.59 | . | . | . | −0.60 | 0.20 |
| Ile | 198 | . | . | B | B | . | . | . | −1.37 | 0.87 | * | . | . | −0.60 | 0.11 |
| Val | 199 | . | . | B | B | . | . | . | −2.18 | 0.81 | * | * | . | −0.60 | 0.14 |
| Ile | 200 | . | . | B | B | . | . | . | −2.72 | 0.81 | . | * | . | −0.60 | 0.06 |
| Leu | 201 | . | . | B | B | . | . | . | −2.72 | 1.46 | . | * | . | −0.60 | 0.06 |
| Gly | 202 | . | . | B | B | . | . | . | −2.98 | 1.46 | . | * | . | −0.60 | 0.07 |
| Leu | 203 | . | . | B | B | . | . | . | −2.90 | 1.24 | . | . | . | −0.60 | 0.15 |
| Val | 204 | . | . | B | B | . | . | . | −2.86 | 1.24 | . | . | . | −0.60 | 0.15 |
| Leu | 205 | . | . | B | B | . | . | . | −2.82 | 1.24 | . | . | . | −0.60 | 0.12 |
| Pro | 206 | . | . | B | B | . | . | . | −2.61 | 1.46 | . | . | . | −0.60 | 0.11 |
| Leu | 207 | . | . | B | B | . | . | . | −3.12 | 1.39 | . | . | . | −0.60 | 0.15 |
| Leu | 208 | . | . | B | B | . | . | . | −3.20 | 1.39 | . | . | . | −0.60 | 0.13 |
| Val | 209 | . | . | B | B | . | . | . | −3.01 | 1.39 | . | . | . | −0.60 | 0.06 |
| Met | 210 | . | . | B | B | . | . | . | −2.44 | 1.53 | . | . | . | −0.60 | 0.04 |
| Val | 211 | . | . | B | B | . | . | . | −2.53 | 1.60 | . | . | . | −0.60 | 0.07 |
| Ile | 212 | . | . | B | B | . | . | . | −2.07 | 1.30 | . | . | . | −0.60 | 0.13 |
| Cys | 213 | . | . | B | . | . | T | . | −2.14 | 1.09 | . | . | . | −0.20 | 0.13 |
| Tyr | 214 | . | . | B | . | . | T | . | −2.10 | 1.16 | . | . | . | −0.20 | 0.13 |
| Ser | 215 | . | . | B | . | . | T | . | −1.46 | 1.20 | . | . | . | −0.20 | 0.15 |
| Gly | 216 | . | . | B | . | . | T | . | −0.91 | 0.51 | * | . | . | −0.20 | 0.55 |
| Ile | 217 | . | . | B | B | . | . | . | −0.83 | 0.43 | . | . | . | −0.60 | 0.51 |
| Leu | 218 | . | . | B | B | . | . | . | −0.98 | 0.36 | * | * | . | −0.30 | 0.31 |
| Lys | 219 | . | . | B | B | . | . | . | −0.62 | 0.66 | * | * | F | −0.45 | 0.26 |
| Thr | 220 | . | . | B | B | . | . | . | −0.99 | 0.23 | * | * | . | −0.30 | 0.73 |
| Leu | 221 | . | . | B | B | . | . | . | −0.53 | 0.11 | * | * | . | −0.30 | 0.47 |
| Leu | 222 | A | . | . | B | . | . | . | 0.36 | −0.57 | * | * | . | 0.60 | 0.46 |
| Arg | 223 | A | . | . | B | . | . | . | 1.17 | −0.17 | * | * | . | 0.30 | 0.52 |
| Cys | 224 | A | . | . | . | . | T | . | 1.17 | −0.66 | . | * | . | 1.15 | 1.08 |
| Arg | 225 | A | . | . | . | . | T | . | 1.52 | −1.34 | * | * | F | 1.30 | 2.63 |
| Asn | 226 | A | . | . | . | . | T | . | 2.44 | −2.03 | * | * | F | 1.30 | 2.68 |
| Glu | 227 | A | . | . | . | . | T | . | 3.22 | −2.03 | . | * | F | 1.30 | 9.80 |
| Lys | 228 | A | . | . | . | . | . | . | 3.22 | −2.10 | . | * | F | 1.10 | 6.81 |
| Lys | 229 | A | . | . | . | . | . | . | 3.30 | −2.10 | * | * | F | 1.10 | 8.29 |
| Arg | 230 | A | . | . | . | . | . | . | 2.33 | −2.00 | * | . | F | 1.10 | 4.83 |
| His | 231 | A | . | . | B | . | . | . | 2.44 | −1.36 | * | * | . | 0.75 | 1.79 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 232 | A | . | . | B | . | . | . | 1.63 | −1.36 | * | . | . | 0.75 | 1.76 |
| Ala | 233 | A | . | . | B | . | . | . | 0.70 | −0.67 | * | * | . | 0.60 | 0.74 |
| Val | 234 | A | . | . | B | . | . | . | −0.04 | 0.01 | * | . | . | −0.30 | 0.38 |
| Arg | 235 | A | . | . | B | . | . | . | −0.47 | 0.30 | * | * | . | −0.30 | 0.17 |
| Leu | 236 | . | . | B | B | . | . | . | −1.32 | 0.79 | * | * | . | −0.60 | 0.24 |
| Ile | 237 | . | . | B | B | . | . | . | −2.03 | 0.97 | * | * | . | −0.60 | 0.23 |
| Phe | 238 | . | . | B | B | . | . | . | −2.33 | 0.94 | * | * | . | −0.60 | 0.11 |
| Thr | 239 | . | . | B | B | . | . | . | −2.33 | 1.63 | * | * | . | −0.60 | 0.10 |
| Ile | 240 | . | . | B | B | . | . | . | −2.69 | 1.59 | * | * | . | −0.60 | 0.10 |
| Met | 241 | . | . | B | B | . | . | . | −2.58 | 1.66 | . | . | . | −0.60 | 0.19 |
| Ile | 242 | . | . | B | B | . | . | . | −2.50 | 1.66 | . | . | . | −0.60 | 0.11 |
| Val | 243 | . | . | B | B | . | . | . | −2.50 | 1.86 | . | . | . | −0.60 | 0.13 |
| Tyr | 244 | . | . | B | B | . | . | . | −2.48 | 1.96 | . | . | . | −0.60 | 0.12 |
| Phe | 245 | . | . | B | B | . | . | . | −2.18 | 2.26 | . | . | . | −0.60 | 0.17 |
| Leu | 246 | . | . | B | B | . | . | . | −1.79 | 2.07 | . | . | . | −0.60 | 0.24 |
| Phe | 247 | . | . | . | B | T | . | . | −1.14 | 1.86 | . | . | . | −0.20 | 0.23 |
| Trp | 248 | . | . | . | B | . | . | C | −0.29 | 1.86 | . | * | . | −0.40 | 0.42 |
| Ala | 249 | . | . | . | . | . | T | C | −0.93 | 1.47 | . | . | . | 0.00 | 0.82 |
| Pro | 250 | . | . | . | . | . | T | C | −1.09 | 1.47 | . | * | . | 0.00 | 0.67 |
| Tyr | 251 | . | . | . | . | T | T | . | −1.09 | 1.33 | . | . | . | 0.20 | 0.47 |
| Asn | 252 | . | . | B | . | . | T | . | −1.20 | 1.10 | . | * | . | −0.20 | 0.38 |
| Ile | 253 | . | . | B | B | . | . | . | −1.72 | 1.29 | . | * | . | −0.60 | 0.20 |
| Val | 254 | . | . | B | B | . | . | . | −1.13 | 1.54 | . | * | . | −0.60 | 0.11 |
| Leu | 255 | . | . | B | B | . | . | . | −1.23 | 1.19 | * | . | . | −0.60 | 0.11 |
| Leu | 256 | . | . | B | B | . | . | . | −1.69 | 1.27 | * | . | . | −0.60 | 0.22 |
| Leu | 257 | . | . | B | B | . | . | . | −1.69 | 1.37 | * | . | . | −0.60 | 0.26 |
| Asn | 258 | . | . | B | B | . | . | . | −0.80 | 1.13 | * | . | . | −0.60 | 0.54 |
| Thr | 259 | A | . | . | B | . | . | . | −0.64 | 0.44 | * | . | . | −0.45 | 1.14 |
| Phe | 260 | A | . | . | B | . | . | . | −0.53 | 0.54 | * | . | . | −0.45 | 1.20 |
| Gln | 261 | . | . | B | B | . | . | . | −0.07 | 0.64 | * | . | . | −0.60 | 0.64 |
| Glu | 262 | . | . | B | B | . | . | . | −0.07 | 0.67 | * | . | . | −0.60 | 0.44 |
| Phe | 263 | . | . | B | . | . | . | . | −0.07 | 0.87 | * | . | . | −0.40 | 0.42 |
| Phe | 264 | . | . | . | . | T | . | . | 0.24 | 0.49 | . | . | . | 0.00 | 0.39 |
| Gly | 265 | . | . | . | . | T | . | . | 0.28 | 0.49 | . | . | . | 0.00 | 0.36 |
| Leu | 266 | . | . | . | . | T | . | . | −0.02 | 1.06 | . | . | . | 0.00 | 0.22 |
| Asn | 267 | . | . | . | . | T | . | . | −0.32 | 0.66 | . | . | . | 0.00 | 0.35 |
| Asn | 268 | . | . | . | . | T | . | . | 0.08 | 0.26 | . | . | F | 0.45 | 0.47 |
| Cys | 269 | . | . | . | . | T | T | . | 0.78 | 0.21 | * | * | F | 0.65 | 0.76 |
| Ser | 270 | . | . | . | . | T | T | . | 1.23 | −0.07 | * | * | F | 1.25 | 0.76 |
| Ser | 271 | . | . | . | . | T | T | . | 1.23 | −0.47 | . | * | F | 1.25 | 0.93 |
| Ser | 272 | . | . | . | . | . | T | C | 1.23 | −0.19 | * | * | F | 1.20 | 1.43 |
| Asn | 273 | . | A | . | . | T | . | . | 1.23 | −0.76 | . | * | F | 1.30 | 1.79 |
| Arg | 274 | . | A | . | . | T | . | . | 1.31 | −0.74 | * | * | F | 1.30 | 2.31 |
| Leu | 275 | A | A | . | . | . | . | . | 1.01 | −0.63 | * | * | F | 0.90 | 1.74 |
| Asp | 276 | A | A | . | . | . | . | . | 1.31 | −0.40 | * | * | F | 0.60 | 1.07 |
| Gln | 277 | A | A | . | . | . | . | . | 0.76 | −0.40 | * | * | . | 0.30 | 0.95 |
| Ala | 278 | A | . | . | B | . | . | . | 0.44 | 0.24 | * | * | . | −0.30 | 0.85 |
| Met | 279 | . | . | B | B | . | . | . | 0.33 | 0.04 | * | * | . | −0.30 | 0.74 |
| Gln | 280 | . | . | B | B | . | . | . | 0.83 | 0.04 | * | * | . | −0.30 | 0.74 |
| Val | 281 | . | . | B | B | . | . | . | 0.02 | 0.13 | * | . | . | −0.15 | 1.05 |
| Thr | 282 | A | . | . | B | . | . | . | −0.32 | 0.31 | * | . | F | −0.15 | 0.88 |
| Glu | 283 | A | . | . | B | . | . | . | −0.33 | 0.13 | * | . | F | −0.15 | 0.50 |
| Thr | 284 | A | . | . | B | . | . | . | −0.04 | 0.34 | . | * | F | −0.15 | 0.67 |
| Leu | 285 | A | . | . | B | . | . | . | −0.08 | 0.19 | . | . | . | −0.30 | 0.67 |
| Gly | 286 | . | . | . | B | T | . | . | 0.11 | 0.20 | . | . | . | 0.10 | 0.52 |
| Met | 287 | . | . | . | B | T | . | . | −0.24 | 0.77 | . | . | . | −0.20 | 0.19 |
| Thr | 288 | . | . | B | B | . | . | . | −1.13 | 0.86 | . | . | . | −0.60 | 0.13 |
| His | 289 | . | . | B | B | . | . | . | −0.82 | 0.86 | . | . | . | −0.60 | 0.09 |
| Cys | 290 | . | . | B | B | . | . | . | −0.22 | 0.83 | . | . | . | −0.60 | 0.15 |
| Cys | 291 | . | . | B | B | . | . | . | −0.77 | 0.64 | . | . | . | −0.60 | 0.16 |
| Ile | 292 | . | . | B | B | . | . | . | −1.06 | 0.84 | . | . | . | −0.60 | 0.08 |
| Asn | 293 | . | . | B | B | . | . | . | −0.99 | 1.03 | * | * | . | −0.60 | 0.11 |
| Pro | 294 | . | . | B | B | . | . | . | −1.54 | 1.21 | * | . | . | −0.60 | 0.31 |
| Ile | 295 | . | A | B | B | . | . | . | −1.58 | 1.14 | * | . | . | −0.60 | 0.44 |
| Ile | 296 | . | A | B | B | . | . | . | −1.77 | 1.24 | * | . | . | −0.60 | 0.24 |
| Tyr | 297 | . | A | B | B | . | . | . | −1.22 | 1.49 | * | . | . | −0.60 | 0.11 |
| Ala | 298 | . | A | B | B | . | . | . | −1.22 | 1.49 | . | . | . | −0.60 | 0.16 |
| Phe | 299 | . | A | B | B | . | . | . | −0.97 | 0.80 | . | . | . | −0.60 | 0.40 |
| Val | 300 | . | A | B | B | . | . | . | −0.78 | 0.11 | * | * | . | −0.30 | 0.51 |
| Gly | 301 | A | A | . | B | . | . | . | 0.22 | 0.14 | * | * | F | −0.15 | 0.44 |
| Glu | 302 | A | A | . | . | . | . | . | 0.47 | −0.36 | * | * | F | 0.45 | 0.99 |
| Lys | 303 | A | A | . | . | . | . | . | 0.81 | −0.74 | * | * | F | 0.90 | 2.14 |
| Phe | 304 | A | . | . | . | . | T | . | 0.70 | −0.63 | * | * | F | 1.30 | 3.39 |
| Arg | 305 | A | . | . | . | . | T | . | 0.74 | −0.37 | * | * | . | 0.85 | 1.62 |
| Asn | 306 | A | . | . | . | . | T | . | 0.23 | 0.31 | * | * | . | 0.10 | 0.67 |
| Tyr | 307 | A | . | . | . | . | T | . | −0.47 | 0.96 | * | * | . | −0.20 | 0.57 |
| Leu | 308 | A | . | . | B | . | . | . | −1.21 | 0.96 | * | * | . | −0.60 | 0.25 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 309 | A | . | . | B | . | . | . | −0.51 | 1.74 | * | * | . | −0.60 | 0.14 |
| Val | 310 | A | . | . | B | . | . | . | −0.58 | 1.74 | . | . | . | −0.60 | 0.15 |
| Phe | 311 | A | . | . | B | . | . | . | −0.61 | 0.99 | * | . | . | −0.60 | 0.36 |
| Phe | 312 | A | . | . | B | . | . | . | −1.26 | 0.80 | * | . | . | −0.60 | 0.60 |
| Gln | 313 | A | . | . | B | . | . | . | −1.03 | 0.80 | * | . | . | −0.60 | 0.57 |
| Lys | 314 | A | . | . | B | . | . | . | −0.18 | 0.66 | * | . | . | −0.60 | 0.66 |
| His | 315 | A | A | . | . | . | . | . | 0.79 | −0.13 | * | * | . | 0.45 | 1.53 |
| Ile | 316 | A | A | . | . | . | . | . | 0.79 | −0.91 | * | . | . | 0.75 | 1.73 |
| Ala | 317 | A | A | . | . | . | . | . | 0.82 | −0.53 | * | . | . | 0.88 | 0.75 |
| Lys | 318 | A | A | . | . | . | . | . | 0.87 | 0.04 | * | . | . | 0.26 | 0.30 |
| Arg | 319 | . | A | . | . | T | . | . | 0.16 | −0.46 | * | . | . | 1.54 | 0.84 |
| Phe | 320 | . | A | . | . | T | . | . | −0.48 | −0.57 | * | . | . | 2.12 | 0.45 |
| Cys | 321 | . | . | . | . | T | T | . | 0.11 | −0.50 | * | . | . | 2.80 | 0.12 |
| Lys | 322 | . | . | . | . | T | T | . | −0.19 | −0.11 | * | . | . | 2.22 | 0.08 |
| Cys | 323 | . | . | . | . | T | T | . | −0.93 | 0.57 | * | . | . | 1.04 | 0.07 |
| Cys | 324 | . | . | . | . | T | T | . | −1.04 | 0.57 | * | . | . | 0.76 | 0.11 |
| Ser | 325 | . | A | . | . | T | . | . | −0.34 | 0.40 | * | . | . | 0.38 | 0.09 |
| Ile | 326 | . | A | B | . | . | . | . | 0.32 | 0.80 | * | . | . | −0.60 | 0.30 |
| Phe | 327 | . | A | B | . | . | . | . | −0.31 | 0.23 | * | . | . | −0.30 | 0.97 |
| Gln | 328 | A | A | . | . | . | . | . | 0.14 | 0.16 | . | . | F | −0.15 | 0.73 |
| Gln | 329 | A | A | . | . | . | . | . | 0.81 | 0.20 | . | * | F | 0.00 | 1.61 |
| Glu | 330 | A | A | . | . | . | . | . | 1.22 | −0.49 | . | * | F | 0.60 | 3.22 |
| Ala | 331 | . | A | . | . | . | . | C | 1.52 | −1.27 | . | * | F | 1.10 | 3.64 |
| Pro | 332 | A | A | . | . | . | . | . | 1.92 | −1.17 | * | * | F | 0.90 | 2.13 |
| Glu | 333 | A | A | . | . | . | . | . | 1.62 | −1.19 | * | * | F | 0.90 | 1.64 |
| Arg | 334 | A | A | . | . | . | . | . | 0.77 | −0.80 | * | . | F | 0.90 | 2.18 |
| Ala | 335 | A | A | . | B | . | . | . | 0.52 | −0.66 | * | * | F | 0.90 | 1.05 |
| Ser | 336 | . | A | B | B | . | . | . | 0.80 | −0.33 | * | * | F | 0.45 | 0.95 |
| Ser | 337 | . | . | B | B | . | . | . | 1.12 | 0.16 | * | . | F | −0.15 | 0.70 |
| Val | 338 | . | . | B | B | . | . | . | 0.82 | 0.16 | * | * | . | −0.15 | 1.35 |
| Tyr | 339 | . | . | B | B | . | . | . | 0.40 | 0.04 | * | * | F | 0.30 | 1.35 |
| Thr | 340 | . | . | B | B | . | . | . | 0.64 | 0.14 | * | * | F | 0.60 | 1.46 |
| Arg | 341 | . | . | . | B | . | . | C | 0.94 | 0.19 | . | * | F | 1.10 | 1.94 |
| Ser | 342 | . | . | . | . | . | T | C | 1.24 | −0.46 | . | * | F | 2.40 | 2.15 |
| Thr | 343 | . | . | . | . | . | T | C | 2.10 | −0.81 | . | * | F | 3.00 | 2.58 |
| Gly | 344 | . | . | . | . | . | T | C | 1.46 | −1.30 | . | * | F | 2.70 | 2.28 |
| Glu | 345 | . | . | . | . | . | T | C | 1.47 | −0.61 | . | * | F | 2.40 | 1.19 |
| Gln | 346 | . | . | B | B | . | . | . | 0.50 | −0.61 | . | * | F | 1.50 | 1.11 |
| Glu | 347 | . | . | B | B | . | . | . | 0.46 | −0.46 | . | * | F | 0.75 | 0.83 |
| Ile | 348 | . | . | B | B | . | . | . | −0.04 | −0.46 | . | * | F | 0.45 | 0.47 |
| Ser | 349 | . | . | B | B | . | . | . | −0.09 | 0.23 | . | * | . | −0.30 | 0.23 |
| Val | 350 | . | . | B | B | . | . | . | −0.48 | 0.26 | . | * | . | −0.30 | 0.17 |
| Gly | 351 | . | . | B | B | . | . | . | −0.87 | 0.69 | . | * | . | −0.60 | 0.30 |
| Leu | 352 | A | . | . | B | . | . | . | −1.26 | 0.43 | . | * | . | −0.60 | 0.29 |

Among highly preferred fragments in this regard are those that comprise regions of G-protein Chemokine Receptor (CCR5) that combine several structural features, such as several of the features set out above.

Other preferred polypeptide fragments are biologically active G-protein Chemokine Receptor (CCR5) fragments. Biologically active fragments are those exhibiting activity similar, but not necessarily identical, to an activity of the G-protein Chemokine Receptor (CCR5) polypeptide. The biological activity of the fragments may include an improved desired activity, or a decreased undesirable activity. Polynucleotides encoding these polypeptide fragments are also encompassed by the invention.

However, many polynucleotide sequences, such as EST sequences, are publicly available and accessible through sequence databases. Some of these sequences are related to SEQ ID NO:1 or to the deposited clone and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1400 of SEQ ID NO:1, b is an integer of 15 to 1414, where both a and b correspond to the positions of nucleotide residues shown in SEQ ID NO:1 or of the deposited clone, and where the b is greater than or equal to a +14.

Epitopes and Antibodies

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in ATCC Deposit No: 97183 or encoded by a polynucleotide that hybridizes to the complement of the sequence of SEQ ID NO:1 or contained in ATCC Deposit No: 97183 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1 or the sequence of the deposited clone), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic. Either the full-length protein or an antigenic peptide fragment can be used. Regions having a high antigenicity index are shown in Table 1 and FIG. 3.

Antibodies are preferably prepared from these regions or from discrete fragments in these regions. However, antibodies can be prepared from any region of the peptide as described herein. A preferred fragment produces an antibody that diminishes or completely prevents ligand binding. Antibodies can be developed against the entire receptor or portions of the receptor, for example, the intracellular carboxy terminal domain, the amino terminal extracellular domain, the entire transmembrane domain or specific transmembrane segments, any of the intracellular or extracellular loops, or any portions of these regions. Antibodies may also be developed against specific functional sites, such as the site of ligand binding, the site of G-protein coupling, or sites that are glycosylated, phosphorylated, myristoylated, or amidated.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)). These fragments are not to be construed, however, as encompassing any fragments which may be disclosed prior to the invention.

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde.

Epitope bearing peptides of the invention may also be synthesized as multiple antigen peptides (MAPs), first described by J. P. Tam in *Proc. Natl. Acad. Sci. U.S.A.* 85:5409 which is incorporated by reference herein in its entirety. MAPs consist of multiple copies of a specific peptide attached to a non-immunogenic lysine core. Map peptides usually contain four or eight copies of the peptide often referred to as MAP-4 or MAP-8 peptides. By way of non-limiting example, MAPs may be synthesized onto a lysine core matrix attached to a polyethylene glycol-polystyrene (PEG-PS) support. The peptide of interest is synthesized onto the lysine residues using 9-fluorenylmethoxycarbonyl (Fmoc) chemistry. For example, Applied Biosystems (Foster City, Calif.) offers MAP resins, such as, for example, the Fmoc Resin 4 Branch and the Fmoc Resin 8 Branch which can be used to synthesize MAPs. Cleavage of MAPs from the resin is performed with standard trifloroacetic acid (TFA)-based cocktails known in the art. Purification of MAPs, except for desalting, is not necessary. MAP peptides may be used as an immunizing vaccine which elicits antibodies that recognize both the MAP and the native protein from which the peptide was derived.

Epitope bearing peptides of the invention may also be incorporated into a coat protein of a virus which can then be used as an immunogen or a vaccine with which to immunize animals, including humans, in order encourage the production of anti-epitope antibodies. For example, the V3 loop of the gp120 glycoprotein of the human immunodeficiency virus type 1 (HIV-1) has been engineered to be expressed on the surface of rhinovirus. Immunization with this rhinovirus displaying the V3 loop peptide yielded apparently effective mimics of the HIV-1 immunogens (as measured by their ability to be neutralized by anti-HIV-1 antibodies as well as their ability to elicit the production of antibodies capable of neutralizing HIV-1 in cell culture). This techniques of using engineered viral particles as an immunogen is described in more detail in Smith et al., Behring Inst Mitt Feb;(98):

229–39 (1997), Smith et al, J Virol 72:651–9 (1998), and Zhang et al., Biol Chem 380:365–74 (1999), which are hereby incorporated by reference herein in their entireties.

Epitope bearing polypeptides of the invention may be modified, for example, by the addition of amino acids at the amino- and/or carboxy-termini of the peptide. Such modifications may be performed, for example, to alter the conformation of the epitope bearing polypeptide such that the epitope will have a conformation more closely related to the structure of the epitope in the native protein. An example of a modified epitope-bearing polypeptide of the invention is a polypeptide in which one or more cysteine residues have been added to the polypeptide to allow for the formation of a disulfide bond between two cysteines, resulting in a stable loop structure of the epitope bearing polypeptide under non-reducing conditions. Disulfide bonds may form between a cysteine residue added to the polypeptide and a cysteine residue of the naturally occurring epitope, or may form between two cysteines which have both been added to the naturally occurring epitope bearing polypeptide. Additionally, it is possible to modify one or more amino acid residues of the naturally occurring epitope bearing polypeptide by substituting them with cysteines to promote the formation of disulfide bonded loop structures. Cyclic thioether molecules of synthetic peptides may be routinely generated using techniques known in the art and are described in PCT publication WO 97/46251, incorporated in its entirety by reference herein. Other modifications of epitope-bearing polypeptides contemplated by this invention include biotinylation.

Animals such as rabbits, rats and mice are immunized with either free or carrier-coupled peptides or MAP peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2 or of the polypeptide encoded by the deposited clone, and/or an epitope, of the present invention (as determined by immunoassays well known in the art for assaying specific antibody-antigen binding).

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the heavy and the light chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk J *Mol. Biol.* 196:901–917 (1987); Chothia et al. Nature 342:878–883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann Clin. Exp. Immunol. 79: 315–321 (1990), Kostelny et al. J *Immunol.* 148:1547 1553 (1992). In addition, bispecific antibodies may be formed as "diabodies" (Holliger et al. "'Diabodies': small bivalent and bispecific antibody fragments" PNAS USA 90:6444–6448 (1993)) or "Janusins" (Traunecker et al. "Bispecific single chain molecules (Janusins) target cytotoxic lymphocytes on HIV infected cells" *EMBO J* 10:3655–3659 (1991) and Traunecker et al. "Janusin: new molecular design for bispecific reagents" *Int J Cancer Suppl* 7:51–52 (1992)).

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly-made antibodies (i.e., intrabodies), and epitope-binding fragments of any of the above. The term "antibody," as used herein, refers to immunoglobulin molecules and immunologically active portions or fragments of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In a preferred embodiment, the immunoglobulin is an IgM isotype.

In a preferred embodiment, the immunoglobulin is an IgG1 isotype. In another preferred embodiment, the immunoglobulin is an IgG2 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdfv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Preferred epitopes of the invention include: Thr16-Val25, Gln59-Thr65, Thr167-Leu174, Ser 179-Ser185, Leu222-Ala233, Asn268-Gln277, His315-Ser325, Glu330-Ser336, Tyr339-Ile348 of SEQ ID NO:2 or of the polypeptide encoded by the deposited clone, as well as polynucleotides that encode these epitopes. Even more preferred epitopes of the invention include peptides corresponding the extracellular loops of the G-protein Chemokine Receptor (CCR5) of the invention or fragments and variants thereof, e.g., amino acids 89–102, 167–195 and/or 261–274 of SEQ ID NO:2 or of the polypeptide encoded by the deposited clone. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, monkey, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein).

The antibodies of the invention (including molecules comprising, or alternatively consisting of, antibody fragments or variants thereof) may bind immunospecifically to that immunospecifically bind to a polypeptide or polypeptide fragment or variant of human G-protein Chemokine Receptor (CCR5) (SEQ ID NO:2 or of the polypeptide encoded by the deposited clone) and/or monkey G-protein Chemokine Receptor (CCR5). Preferably, the antibodies of the invention bind immunospecifically to human G-protein Chemokine Receptor. Preferably, the antibodies of the invention bind immunospecifically to human and monkey G-protein Chemokine Receptor. Also preferably, the antibodies of the invention bind immunospecifically to human G-protein Chemokine Receptor (CCR5) and murine G-protein Chemokine Receptor. More preferably, antibodies of the invention, bind immunospecifically and with higher affinity to human G-protein Chemokine Receptor (CCR5) than to murine G-protein Chemokine Receptor.

In preferred embodiments, the antibodies of the present invention (including molecules comprising, or alternatively consisting of, antibody fragments or variants thereof), immunospecifically bind to G-protein Chemokine Receptor (CCR5) and do not cross-react with any other antigens. In preferred embodiments, the antibodies of the invention immunospecifically bind to G-protein Chemokine Receptor (CCR5) and do not cross-react with other chemokine receptors such as, for example, US28, CCR1, CCR2, CCR3, CCR4, CCR6, CCR7, CCR8, CCR9, CXCR1, CXCR2, CXCR3, CXCR4, and/or CXCR5.

In other preferred embodiments, the antibodies of the invention immunospecifically bind to G-protein Chemokine Receptor (CCR5) and cross-react with other chemokine receptors such as, for example, US28, CCR1, CCR2, CCR3, CCR4, CCR6, CCR7, CCR8, CCR9, CXCR1, CXCR2, CXCR3, CXCR4, and/or CXCR5. In more preferred embodiments, the antibodies of the invention immunospecifically bind to G-protein Chemokine Receptor (CCR5) and do cross-react with CCR3 and/or CXCR4.

In a preferred embodiment, antibodies of the invention preferentially bind G-protein Chemokine Receptor (CCR5) (SEQ ID NO:2 or of the polypeptide encoded by the deposited clone), or fragments and variants thereof relative to their ability to bind other antigens, (such as, for example, other chemokine receptors).

By way of non-limiting example, an antibody may be considered to bind a first antigen preferentially if it binds said first antigen with a dissociation constant ($K_D$) that is less than the antibody's $K_D$ for the second antigen. In another non-limiting embodiment, an antibody may be considered to bind a first antigen preferentially if it binds said first antigen with an affinity that is at least one order of magnitude less than the antibody's KD for the second antigen. In another non-limiting embodiment, an antibody may be considered to bind a first antigen preferentially if it binds said first antigen with an affinity that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if it binds said first antigen with an affinity that is at least one order of magnitude less than the antibody's $k_{off}$ for the second antigen. In another non-limiting embodiment, an antibody may be considered to bind a first antigen preferentially if it binds said first antigen with an affinity that is at least two orders of magnitude less than the antibody's $k_{off}$ for the second antigen.

Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M. More preferred binding affinities include those with a dissociation constant or Kd less than $5\times10^{-5}$ M, $10^{-5}$ M, $5\times10^{-6}$ M, $10^{-6}$ M, $5\times10^{-7}$ M, $10^{7}$ M, $5\times10^{-8}$ M or $10^{-8}$ M. Even more preferred binding affinities include those with a dissociation constant or Kd less than $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $^{10-12}$ M, $5\times10^{-13}$ M, $10^{-13}$ M, $5\times10^{-14}$ M, $10^{-14}$ M, $5\times10^{-15}$ M, or $10^{-15}$ M.

In specific embodiments, antibodies of the invention bind B-protein Chemokine Receptor (CCR5) polypeptides or fragments or variants thereof with an off rate ($k_{off}$) of less than or equal to $5\times10^{-2}$ $sec^{-1}$, $10^{-2}$ $sec^{-1}$, $5\times10^{-3}$ $sec^{-1}$ or $10^{-3}$ $sec^{-1}$. More preferably, antibodies of the invention bind G-protein Chemokine Receptor (CCR5) polypeptides or fragments or variants thereof with an off rate ($k_{off}$) less than or equal to $5\times10^{-4}$ $sec^{-1}$, $10^{-4}$ $sec^{-1}$, $5\times10^{-5}$ $sec^{-1}$, or $10^{-5}$ $sec^{-1}$ $5\times10^{-6}$ $sec^{-1}$, $10^{-6}$ $sec^{-1}$, $5\times10^{-7}$ $sec^{-1}$ or $10^{-7}$ $sec^{-1}$.

In other embodiments, antibodies of the invention bind G-protein Chemokine Receptor (CCR5) polypeptides or fragments or variants thereof with an on rate ($k_{on}$) of greater than or equal to $10^{3}$ $M^{-1}$ $sec^{-1}$, $5\times10^{3}$ $M^{-1}$ $sec^{-1}$, $10^{4}$ $M^{-1}$ $sec^{-1}$ or $5\times10^{4}$ $M^{-1}$ $sec^{-1}$. More preferably, antibodies of the invention bind G-protein Chemokine Receptor (CCR5) polypeptides or fragments or variants thereof with an on rate ($k_{on}$) greater than or equal to $10^{5}$ $M^{-1}$ $sec^{-1}$, $5\times10^{5}$ $M^{-1}$ $sec^{-1}$, $10^{6}$ $M^{-1}$ sec−1, or $5\times10^{6}$ $M^{-1}$ $sec^{-1}$ or $10^{7}$ $M^{-1}$ $sec^{-1}$.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7):3170–3179 (1998); Prat et al., J. Cell. Sci. 111(Pt2): 237–247 (1998); Pitard et al., J. Immunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

In one embodiment of the present invention, antibodies that immunospecifically bind to a G-protein Chemokine Receptor (CCR5) or a fragment or variant thereof, comprise a polypeptide having the amino acid sequence of any one of the heavy chains expressed by an anti-G-protein Chemokine Receptor(CCR5) antibody expressing cell line of the invention and/or any one of the light chains expressed by an anti-G-protein Chemokine Receptor(CCR5) antibody expressing cell line of the invention. In another embodiment of the present invention, antibodies that immunospecifically bind to a G-protein Chemokine Receptor (CCR5) or a fragment or variant thereof, comprise a polypeptide having the amino acid sequence of any one of the VH domains of a heavy chain expressed by an anti-G-protein Chemokine Receptor(CCR5) antibody expressing cell line of the invention and/or any one of the VL domains of a light chain expressed by an anti-G-protein Chemokine Receptor(CCR5) antibody expressing cell line of the invention. In preferred embodiments, antibodies of the present invention comprise the amino acid sequence of a VH domain and VL domain expressed by a single anti-G-protein Chemokine Receptor (CCR5) antibody expressing cell line of the invention. In alternative embodiments, antibodies of the present invention comprise the amino acid sequence of a VH domain and a VL domain expressed by two different anti-G-protein Chemokine Receptor(CCR5) antibody expressing cell lines of the invention. Molecules comprising, or alternatively consisting of, antibody fragments or variants of the VH and/or VL domains expressed by an anti-G-protein Chemokine Receptor(CCR5) antibody expressing cell line of the invention that immunospecifically bind to a G-protein Chemokine Receptor (CCR5) are also encompassed by the invention, as are nucleic acid molecules encoding these VH and VL domains, molecules, fragments and/or variants.

The present invention also provides antibodies that immunospecifically bind to a polypeptide, or polypeptide fragment or variant of a G-protein Chemokine Receptor (CCR5), wherein said antibodies comprise, or alternatively consist of, a polypeptide having an amino acid sequence of any one, two, three, or more of the VH CDRs contained in a heavy chain expressed by one or more anti-G-protein Chemokine Receptor (CCR5) antibody expressing cell lines of the invention. In particular, the invention provides antibodies that immunospecifically bind a G-protein Chemokine Receptor (CCR5), comprising, or alternatively consisting of, a polypeptide having the amino acid sequence of a VH CDR1 contained in a heavy chain expressed by one or more anti-G-protein Chemokine Receptor (CCR5) antibody expressing cell lines of the invention. In another embodiment, antibodies that immunospecifically bind a G-protein Chemokine Receptor (CCR5), comprise, or alternatively consist of, a polypeptide having the amino acid sequence of a VH CDR2 contained in a heavy chain expressed by one or more anti-G-protein Chemokine Receptor (CCR5) antibody expressing cell lines of the invention. In a preferred embodiment, antibodies that immunospecifically bind a G-protein Chemokine Receptor (CCR5), comprise, or alternatively consist of a polypeptide having the amino acid sequence of a VH CDR3 contained in a heavy chain expressed by one or more anti-G-protein Chemokine Receptor (CCR5) antibody expressing cell lines of the invention. Molecules comprising, or alternatively consisting of, these antibodies, or antibody fragments or variants thereof, that immunospecifically bind to G-protein Chemokine Receptor (CCR5) or a G-protein Chemokine Receptor (CCR5) fragment or variant thereof are also encompassed by the invention, as are nucleic acid molecules encoding these antibodies, molecules, fragments and/or variants.

The present invention also provides antibodies that immunospecifically bind to a polypeptide, or polypeptide fragment or variant of a G-protein Chemokine Receptor (CCR5), wherein said antibodies comprise, or alternatively consist of, a polypeptide having an amino acid sequence of any one, two, three, or more of the VL CDRs contained in a light chain expressed by one or more anti-G-protein Chemokine Receptor (CCR5) antibody expressing cell lines of the invention. In particular, the invention provides antibodies that immunospecifically bind a G-protein Chemokine Receptor (CCR5), comprising, or alternatively consisting of, a polypeptide having the amino acid sequence of a VL CDR1 contained in a light expressed by one or more anti-G-protein Chemokine Receptor (CCR5) antibody expressing cell lines of the invention. In another embodiment, antibodies that immunospecifically bind a G-protein Chemokine Receptor (CCR5), comprise, or alternatively consist of, a polypeptide having the amino acid sequence of a VL CDR2 contained in a light chain expressed by one or more more anti-G-protein Chemokine Receptor (CCR5) antibody expressing cell lines of the invention. In a preferred embodiment, antibodies that immunospecifically bind a G-protein Chemokine Receptor (CCR5), comprise, or alternatively consist of a polypeptide having the amino acid sequence of a VL CDR3 contained in a light chain expressed by one or more anti-G-protein Chemokine Receptor (CCR5) antibody expressing cell lines of the invention. Molecules comprising, or alternatively consisting of, these antibodies, or antibody fragments or variants thereof, that immunospecifically bind to G-protein Chemokine Receptor (CCR5) or a G-protein Chemokine Receptor (CCR5) fragment or variant thereof are also encompassed by the invention, as are nucleic acid molecules encoding these antibodies, molecules, fragments and/or variants.

The present invention also provides antibodies (including molecules comprising, or alternatively consisting of, antibody fragments or variants) that immunospecifically bind to a G-protein Chemokine Receptor (CCR5) polypeptide or polypeptide fragment or variant of a G-protein Chemokine Receptor (CCR5), wherein said antibodies comprise, or alternatively consist of, one, two, three, or more VH CDRs and one, two, three or more VL CDRs, as contained in a heavy chain or light chain expressed by one or more anti-G-protein Chemokine Receptor (CCR5) antibody expressing cell lines of the invention. In particular, the invention provides for antibodies that immunospecifically bind to a polypeptide or polypeptide fragment or variant of a G-protein Chemokine Receptor (CCR5), wherein said antibodies comprise, or alternatively consist of, a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof, of the VH CDRs and VL CDRs contained in a light chain or light chain expressed by one or more anti-G-protein Chemokine Receptor (CCR5) antibody expressing cell lines of the invention. In a preferred embodiment, one or more of these combinations are from a single anti-G-protein Chemokine Receptor (CCR5) antibody expressing cell line of the invention. Molecules comprising, or alternatively consisting of, fragments or variants of these antibodies, that immunospecifically bind to G-protein Chemokine Receptor (CCR5) are also encompassed by the invention, as are nucleic acid molecules encoding these antibodies, molecules, fragments or variants.

The present invention also provides for nucleic acid molecules, generally isolated, encoding an antibody of the invention (including molecules comprising, or alternatively consisting of, antibody fragments or variants thereof). In a specific embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of a heavy chain expressed by an anti-G-protein Chemokine Receptor(CCR5) antibody expressing cell line of the invention and a VL domain having an amino acid sequence of a light chain expressed by an anti-G-protein Chemokine Receptor(CCR5) antibody expressing cell line of the invention. In another embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of a heavy chain expressed by an anti-G-protein Chemokine Receptor(CCR5) antibody expressing cell line of the invention or a VL domain having an amino acid sequence of a light chain expressed by an anti-G-protein Chemokine Receptor(CCR5) antibody expressing cell line of the invention.

The present invention also provides antibodies that comprise, or alternatively consist of, variants (including derivatives) of the antibody molecules (e.g., the VH domains and/or VL domains) described herein, which antibodies immunospecifically bind to a G-protein Chemokine Receptor (CCR5) or fragment or variant thereof. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid subsitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind a G-protein Chemokine Receptor).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind a G-protein Chemokine Receptor) can be determined using techniques described herein or by routinely modifying techniques known in the art.

In a specific embodiment, an antibody of the invention (including a molecule comprising, or alternatively consisting of, an antibody fragment or variant thereof), that immunospecifically binds G-protein Chemokine Receptor (CCR5) polypeptides or fragments or variants thereof, comprises, or alternatively consists of, an amino acid sequence encoded by a nucleotide sequence that hybridizes to a nucleotide sequence that is complementary to that encoding one of the VH or VL domains expressed by one or more anti-G-protein Chemokine Receptor (CCR5) antibody expressing cell lines of the invention. under stringent conditions, e.g., hybridization to filter-bound DNA in 6× sodium chloride/sodium citrate (SSC) at about 45° C. followed by one or more washes in 0.2×SSC/0.1% SDS at about 50–65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds. , 1989*, Current Protocols in Molecular Biology, Vol.* 1, Green Publishing Associates, Inc. and John Wiley & Sons, Inc., New York at pages 6.3.1–6.3.6 and 2.10.3). Nucleic acid molecules encoding these antibodies are also encompassed by the invention.

It is well known within the art that polypeptides, or fragments or variants thereof, with similar amino acid sequences often have similar structure and many of the same biological activities. Thus, in one embodiment, an antibody (including a molecule comprising, or alternatively consisting of, an antibody fragment or variant thereof), that immunospecifically binds to a G-protein Chemokine Receptor (CCR5) polypeptide or fragments or variants of a G-protein Chemokine Receptor (CCR5) polypeptide, comprises, or alternatively consists of, a VH domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VH domain of a heavy chain expressed by an anti-G-protein Chemokine Receptor(CCR5) antibody expressing cell line of the invention.

In another embodiment, an antibody (including a molecule comprising, or alternatively consisting of, an antibody fragment or variant thereof), that immunospecifically binds to a G-protein Chemokine Receptor (CCR5) polypeptide or fragments or variants of a G-protein Chemokine Receptor (CCR5) polypeptide, comprises, or alternatively consists of, a VL domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VL domain of a light chain expressed by an anti-G-protein Chemokine Receptor(CCRS) antibody expressing cell line of the invention.

The invention also encompasses antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ability to bind to G-protein Chemokine Receptor (CCR5) (e.g., G-protein Chemokine Receptor (CCR5) expressed on a cell surface, membrane-embedded G-protein Chemokine Receptor (CCR5), and/or a fragment or variant of G-protein Chemokine Receptor (CCR5)); the ability to substantially inhibit or abolish the binding of the G-protein Chemokine Receptor (CCR5) to a G-protein Chemokine Receptor (CCR5) ligand (e.g. MIP1-beta, see, e.g., Example 61); the ability to downregulate G-protein Chemokine Receptor (CCR5) expression on the surface of cells; the ability to inhibit or abolish G-protein Chemokine Receptor (CCR5) mediated biological activity (e.g., HIV binding to, infection (entry into/fusion), and/or replication in, G-protein Chemokine Receptor (CCR5) expressing cells (see, e.g., Example 60), the ability to inhibit or abolish MIP1-beta induced chemotaxis of peripheral blood mononuclear cells PBMC (or other G-protein Chemokine Receptor (CCR5) expressing cells), or the ability to induce an intracellular calcium flux in G-protein Chemokine Receptor (CCR5) expressing cells, (see, e.g., Example 63). Optionally, the antibodies of the invention will bind to the same epitope as at least one of the antibodies specifically referred to herein. Such epitope binding can be routinely determined using assays known in the art.

The present invention also provides for antibodies (including molecules comprising, or alternatively consisting of, antibody fragments or variants thereof), that neutralize G-protein Chemokine Receptor (CCR5), said antibodies comprising, or alternatively consisting of, a portion (e.g., VH CDR1, VH CDR2, VH CDR3, VL CDR1, VL CDR2, and/or VL CDR3) of a VH or VL domain of an antibody of the invention. An antibody that "neutralizes G-protein Chemokine Receptor (CCR5) or a fragment or variant thereof" is, for example, an antibody that diminishes or abolishes the ability of G-protein Chemokine Receptor (CCR5) or a fragment or variant thereof to bind to its ligand (e.g., HIV and MIP1-beta); that diminishes or abolishes MIP1-beta induced chemotaxis of PBMC or other CCR5 expressing cell; and/or that abolishes or inhibits the G-protein Chemokine Receptor (CCR5) signaling cascade (e.g., calcium flux initiated by an activated G-protein Chemokine Receptor (CCR5), see, e.g., Example 63). In one embodiment, an antibody that neutralizes G-protein Chemokine Receptor (CCR5), comprises, or alternatively consists of, a polypeptide having the amino acid sequence of a VH domain of an antibody of the invention, or a fragment or variant thereof and a VL domain of an antibody of the invention, or a fragment or variant thereof. In another embodiment, an antibody that neutralizes G-protein Chemokine Receptor (CCR5), comprises, or alternatively consists of, a polypeptide having the amino acid sequence of a VH domain and a VL domain from a single antibody (or scFv or Fab fragment) of the invention, or fragments or variants thereof. In one embodiment, an antibody that neutralizes G-protein Chemokine Receptor (CCR5), comprises, or alternatively consists of, a polypeptide having the amino acid sequence of a VH domain of an antibody of the invention, or a fragment or variant thereof. In another embodiment, an antibody that neutralizes G-protein Chemokine Receptor (CCR5), comprises, or alternatively consists of, a polypeptide having the amino acid sequence of a VL domain of an antibody of the invention, or a fragment or variant thereof. In another embodiment, an antibody that neutralizes G-protein Chemokine Receptor (CCR5) or a fragment or variant thereof, comprises, or alternatively consists of, a polypeptide having the amino acid sequence of a VH CDR domain of an antibody of the invention, or a fragment or variant thereof. In a preferred embodiment, an antibody that neutralizes G-protein Chemokine Receptor (CCR5) or a fragment or variant thereof, comprises, or alternatively consists of, a polypeptide having the amino acid sequence of a VH CDR3 of an antibody of the invention, or a fragment or variant thereof. In another embodiment, an antibody that neutralizes G-protein Chemokine Receptor (CCR5) or a fragment or variant thereof, comprises, or alternatively consists of, a polypeptide having the amino acid sequence of a VL CDR of an antibody of the invention, or a fragment or variant thereof. In another preferred embodiment, an antibody that neutralizes G-protein Chemokine Receptor (CCR5) or a fragment or variant thereof, comprises, or alternatively consists of, a polypeptide having the amino acid sequence of a VL CDR3 of an antibody of the invention, or a fragment or variant thereof. Nucleic acid molecules encoding these antibodies are also encompassed by the invention.

The present invention also provides for antibodies (including molecules comprising, or alternatively consisting of, antibody fragments or variants thereof), that reduces or abolishes the ability of HIV viruses, particularly those that utilize G-protein Chemokine Receptor (CCR5) as a co-receptor, to bind to, infect (enter into/fuse with), and/or replicate in G-protein Chemokine Receptor (CCR5) expressing cells, as determined by any method known in the art such as, for example, the assays described Example 60. Said antibodies may comprise, or alternatively consist of, a portion (e.g., VH CDR1, VH CDR2, VH CDR3, VL CDR1, VL CDR2, or VL CDR3) of a VH or VL domain having an amino acid sequence of an antibody of the invention or a fragment or variant thereof. In one embodiment, an antibody that reduces or abolishes the ability of HIV viruses, particularly those that utilize G-protein Chemokine Receptor (CCR5) as a co-receptor, to bind to, infect (enter into/fuse with), and/or replicate in G-protein Chemokine Receptor (CCR5) expressing cells, comprises, or alternatively consists of, a polypeptide having the amino acid sequence of a VH domain of an antibody of the invention, or a fragment or variant thereof and a VL domain of an antibody of the invention, or a fragment or variant thereof. In another embodiment, an antibody that reduces or abolishes the ability of HIV viruses, particularly those that utilize G-protein Chemokine Receptor (CCR5) as a co-receptor, to bind to, infect (enter into/fuse with), and/or replicate in G-protein Chemokine Receptor (CCR5) expressing cells, comprises, or alternatively consists of, a polypeptide having the amino acid sequence of a VH domain and a VL domain from a single antibody (or scFv or Fab fragment) of the invention, or fragments or variants thereof. In one embodiment, an antibody that reduces or abolishes the ability of HIV viruses, particularly those that utilize G-protein Chemokine Receptor (CCR5) as a co-receptor, to bind to, infect (enter into/fuse with), and/or replicate in G-protein Chemokine Receptor (CCR5) expressing cells, comprises, or alternatively consists of, a polypeptide having the amino acid sequence of a VH domain of an antibody of the invention, or a fragment or variant thereof. In another embodiment, an antibody that reduces or abolishes the ability of HIV viruses, particularly those that utilize G-protein Chemokine Receptor (CCR5) as a co-receptor, to bind to, infect (enter into/fuse with), and/or replicate in G-protein Chemokine Receptor (CCR5) expressing cells, comprises, or alternatively consists of, a polypeptide having the amino acid sequence of a VL domain of an antibody of the invention, or a fragment or variant thereof. In a preferred embodiment, an antibody that reduces or abolishes the ability of HIV viruses, particularly those that utilize G-protein Chemokine Receptor (CCR5) as a co-receptor, to bind to, infect (enter into/fuse with), and/or replicate in G-protein Chemokine Receptor (CCR5) expressing cells, comprises, or alternatively consists of, a polypeptide having the amino acid sequence of a VH CDR3 of an antibody of the invention, or a fragment or variant thereof. In another preferred embodiment, an antibody that reduces or abolishes the ability of HIV viruses, particularly those that utilize G-protein Chemokine Receptor (CCR5) as a co-receptor, to bind to, infect (enter into/fuse with), and/or replicate in G-protein Chemokine Receptor (CCR5) expressing cells, comprises, or alternatively consists of, a polypeptide having the amino acid sequence of a VL CDR3 of an antibody of the invention, or a fragment or variant thereof. Nucleic acid molecules encoding these antibodies are also encompassed by the invention.

The present invention also provides for antibodies (including molecules comprising, or alternatively consisting of, antibody fragments or variants thereof), that inhibits or abolishes MIP1-beta induced chemotaxis of peripheral blood mononuclear cells PBMC or other G-protein Chemokine Receptor (CCR5) expressing cells, as determined by any method known in the art such as, for example, the assays described in Example 62. Said antibodies may comprise, or alternatively consist of, a portion (e.g., VH CDR1, VH CDR2, VH CDR3, VL CDR1, VL CDR2, or VL CDR3) of a VH or VL domain having an amino acid sequence of an antibody of the invention or a fragment or variant thereof. In one embodiment, an antibody that inhibits or abolishes MIP1-beta induced chemotaxis of peripheral blood mononuclear cells PBMC or other G-protein Chemokine Receptor (CCR5) expressing cells, comprises, or alternatively consists of, a polypeptide having the amino acid sequence of a VH domain of an antibody of the invention, or a fragment or variant thereof and a VL domain of an antibody of the invention, or a fragment or variant thereof. In another embodiment, an antibody that inhibits or abolishes MIP1-beta induced chemotaxis of peripheral blood mononuclear cells PBMC or other G-protein Chemokine Receptor (CCR5) expressing cells, comprises, or alternatively consists of, a polypeptide having the amino acid sequence of a VH domain and a VL domain from a single antibody (or scFv or Fab fragment) of the invention, or fragments or variants thereof. In one embodiment, an antibody that inhibits or abolishes MIP1-beta induced chemotaxis of peripheral blood mononuclear cells PBMC or other G-protein Chemokine Receptor (CCR5) expressing cells, comprises, or alternatively consists of, a polypeptide having the amino acid sequence of a VH domain of an antibody of the invention, or a fragment or variant thereof. In another embodiment, an antibody that inhibits or abolishes MIP1-beta induced chemotaxis of peripheral blood mononuclear cells PBMC or other G-protein Chemokine Receptor (CCR5) expressing cells, comprises, or alternatively consists of, a polypeptide having the amino acid sequence of a VL domain of an antibody of the invention, or a fragment or variant thereof. In a preferred embodiment, an antibody that inhibits or abolishes MIP1-beta induced chemotaxis of peripheral blood mononuclear cells PBMC or other G-protein Chemokine Receptor (CCR5) expressing cells, comprises, or alternatively consists of, a polypeptide having the amino acid sequence of a VH CDR3 of an antibody of the invention, or a fragment or variant thereof. In another preferred embodiment, an antibody that inhibits or abolishes MIP1-beta induced chemotaxis of peripheral blood mononuclear cells PBMC or other G-protein Chemokine Receptor (CCR5) expressing cells, comprises, or alternatively consists of, a polypeptide having the amino acid sequence of a VL CDR3 of an antibody of the invention, or a fragment or variant thereof. Nucleic acid molecules encoding these antibodies are also encompassed by the invention.

The present invention also provides for antibodies (including molecules comprising, or alternatively consisting of, antibody fragments or variants thereof), that downregulates the cell-surface expression of G-protein Chemokine Receptor (CCR5), as determined by any method known in the art such as, for example, FACS analysis/the assays described in Examples 61 or 63. By way of a non-limiting hypothesis, such down regulation may be the result of antibody induced internalization of G-protein Chemokine Receptor (CCR5). Said antibodies may comprise, or alternatively consist of, a portion (e.g., VH CDR1, VH CDR2, VH CDR3, VL CDR1, VL CDR2, or VL CDR3) of a VH or VL domain having an amino acid sequence of an antibody of the invention or a fragment or variant thereof. In one embodiment, an antibody that downregulates the cell-surface expression of G-protein Chemokine Receptor (CCR5), comprises, or alternatively consists of, a polypeptide having the amino acid sequence of a VH domain of an antibody of the invention, or a fragment or variant thereof and a VL domain of an antibody of the invention, or a fragment or variant thereof. In another embodiment, an antibody that downregulates the cell-surface expression of G-protein Chemokine Receptor (CCR5), comprises, or alternatively consists of, a polypeptide having the amino acid sequence of a VH domain and a VL domain from a single antibody (or scFv or Fab fragment) of the invention, or fragments or variants thereof. In one embodiment, an antibody that downregulates the cell-surface expression of G-protein Chemokine Receptor (CCR5), comprises, or alternatively consists of, a polypeptide having the amino acid sequence of a VH domain of an antibody of the invention, or a fragment or variant thereof. In another embodiment, an antibody that downregulates the cell-surface expression of G-protein Chemokine Receptor (CCR5), comprises, or alternatively consists of, a polypeptide having the amino acid sequence of a VL domain of an antibody of the invention, or a fragment or variant thereof. In a preferred embodiment, an antibody that downregulate the cell-surface expression of G-protein Chemokine Receptor (CCR5), comprises, or alternatively consists of, a polypeptide having the amino acid sequence of a VH CDR3 of an antibody of the invention, or a fragment or variant thereof. In another preferred embodiment, an antibody that downregulates the cell-surface expression of G-protein Chemokine Receptor (CCR5), comprises, or alternatively consists of, a polypeptide having the amino acid sequence of a VL CDR3 of an antibody of the invention, or a fragment or variant thereof. Nucleic acid molecules encoding these antibodies are also encompassed by the invention.

The present invention also provides for antibodies (including molecules comprising, or alternatively consisting of, antibody fragments or variants thereof), that enhance the activity of G-protein Chemokine Receptor (CCR5), said antibodies comprising, or alternatively consisting of, a portion (e.g., VH CDR1, VH CDR2, VH CDR3, VL CDR1, VL CDR2, or VL CDR3) of a VH or VL domain of an antibody of the invention, or a fragment or variant thereof. By way of non-limiting example, an antibody that "enhances the activity of G-protein Chemokine Receptor (CCR5) or a fragment or variant thereof" is an antibody increases the ability of G-protein Chemokine Receptor (CCR5) to bind to stimulate chemotaxis of PBMC (or other G-protein Chemokine Receptor (CCR5) expressing cells), and/or to stimulate the G-protein Chemokine Receptor (CCR5) signaling cascade (e.g., to initiate an intracellular calcium flux, See Example 63). In one embodiment, an antibody that that enhances the activity of G-protein Chemokine Receptor (CCR5), comprises, or alternatively consists of, a polypeptide having the amino acid sequence of a VH domain of an antibody of the invention, or a fragment or variant thereof and a VL domain of an antibody of the invention, or a fragment or variant thereof. In another embodiment, an antibody that enhances the activity of G-protein Chemokine Receptor (CCR5), comprises, or alternatively consists of, a polypeptide having the amino acid sequence of a VH domain and a VL domain from a single antibody (or scFv or Fab fragment) of the invention, or fragments or variants thereof. In one embodiment, an antibody that enhances the activity of G-protein Chemokine Receptor (CCR5) or a fragment or variant thereof, comprises, or alternatively consists of, a polypeptide having the amino acid sequence of a VH domain of an antibody of the invention, or a fragment or variant thereof. In another embodiment, an antibody that enhances the activity of G-protein Chemokine Receptor (CCR5) or a fragment or variant thereof, comprises, or alternatively consists of, a polypeptide having the amino acid sequence of a VL domain of an antibody of the invention, or a fragment or variant thereof. In another embodiment, an antibody that enhances the activity of G-protein Chemokine Receptor (CCR5) or a fragment or variant thereof, comprises, or alternatively consists of, a polypeptide having the amino acid sequence of a VH CDR domain referred to in Table 2, or a fragment or variant thereof. In a preferred embodiment, an antibody that enhances the activity of G-protein Chemokine Receptor (CCR5) or a fragment or variant thereof, comprises, or alternatively consists of, a polypeptide having the amino acid sequence of a VH CDR3 of an antibody of the invention, or a fragment or variant thereof. In another embodiment, an antibody that enhances G-protein Chemokine Receptor (CCR5) or a fragment or variant thereof, comprises, or alternatively consists of, a polypeptide having the amino acid sequence of a VL CDR domain of an antibody of the invention, or a fragment or variant thereof. In another preferred embodiment, an antibody that enhances the activity of G-protein Chemokine Receptor (CCR5) or a fragment or variant thereof, comprises, or alternatively consists of, a polypeptide having the amino acid sequence of a VL CDR3 of an antibody of the invention, or a fragment or variant thereof. Nucleic acid molecules encoding these antibodies are also encompassed by the invention.

The present invention also provides for fusion proteins comprising, or alternatively consisting of, an antibody (including molecules comprising, or alternatively consisting of, antibody fragments or variants thereof), that immunospecifically binds to G-protein Chemokine Receptor (CCR5), and a heterologous polypeptide. Preferably, the heterologous polypeptide to which the antibody is fused to is useful for function or is useful to target the G-protein Chemokine Receptor (CCR5) expressing cells, including but not limited to, MIP-1-beta; a CD4 binding polypeptide such as an anti-CD4 antibody; a CXCR4 binding polypeptides such as stromal derived factor 1-alpha (SDF1-alpha); and/or a CCR3 binding protein, such as MIP1-alpha). In an alternative preferred embodiment, the heterologous polypeptide to which the antibody is fused to is useful for T cell, macrophage, and/or monocyte cell function or is useful to target the antibody to a T cell, macrophage, or monocyte, including but not limited to, MIP-1-beta; a CD4 binding polypeptide such as an anti-CD4 antibody; a CXCR4 binding polypeptides such as stromal derived factor 1-alpha (SDF1-alpha); and/or a CCR3 binding protein, such as MIP1-alpha). In one embodiment, a fusion protein of the invention comprises, or alternatively consists of, a polypeptide having the amino acid sequence of any one or more of the VH domains of an antibody of the invention or the amino acid sequence of any one or more of the VL domains of an antibody of the invention or fragments or variants thereof, and a heterologous polypeptide sequence. In another embodiment, a fusion protein of the present invention comprises, or alternatively consists of, a polypeptide having the amino acid sequence of any one, two, three, or more of the VH CDRs of an antibody of the invention, or the amino acid sequence of any one, two, three, or more of the VL CDRs of an antibody of the invention, or fragments or variants thereof, and a heterologous polypeptide sequence. In a preferred embodiment, the fusion protein comprises, or alternatively consists of, a polypeptide having the amino acid sequence of, a VH CDR3 of an antibody of the invention, or fragment or variant thereof, and a heterologous polypeptide sequence, which fusion protein immunospecifically binds to G-protein Chemokine Receptor (CCR5). In another embodiment, a fusion protein comprises, or alternatively consists of a polypeptide having the amino acid sequence of at least one VH domain of an antibody of the invention and the amino acid sequence of at least one VL domain of an antibody of the invention or fragments or variants thereof, and a heterologous polypeptide sequence. Preferably, the VH and VL domains of the fusion protein correspond to a single antibody (or scFv or Fab fragment) of the invention. In yet another embodiment, a fusion protein of the invention comprises, or alternatively consists of a polypeptide having the amino acid sequence of any one, two, three or more of the VH CDRs of an antibody of the invention and the amino acid sequence of any one, two, three or more of the VL CDRs of an antibody of the invention, or fragments or variants thereof, and a heterologous polypeptide sequence. Preferably, two, three, four, five, six, or more of the VHCDR(s) or VLCDR(s) correspond to single antibody (or scFv or Fab fragment) of the invention. Nucleic acid molecules encoding these fusion proteins are also encompassed by the invention.

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

By way of another non-limiting example, antibodies of the invention may be administered to individuals as a form of passive immunization. Alternatively, antibodies of the present invention may be used for epitope mapping to identify the epitope(s) bound by the antibody. Epitopes identified in this way may, in turn, for example, be used as vaccine candidates, i.e., to immunize an individual to elicit antibodies against the naturally occurring forms of G-protein Chemokine Receptor.

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody. For example, but not by way of limitation, the antibody derivatives include antibodies that have been modified, e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 or P3X63-AG8.653 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Another well known method for producing both polyclonal and monoclonal human B cell lines is transformation using Epstein Barr Virus (EBV). Protocols for generating EBV-transformed B cell lines are commonly known in the art, such as, for example, the protocol outlined in Chapter 7.22 of Current Protocols in Immunology, Coligan et al., Eds., 1994, John Wiley & Sons, NY, which is hereby incorporated in its entirety by reference herein. The source of B cells for transformation is commonly human peripheral blood, but B cells for transformation may also be derived from other sources including, but not limited to, lymph nodes, tonsil, spleen, tumor tissue, and infected tissues. Tissues are generally made into single cell suspensions prior to EBV transformation. Additionally, steps may be taken to either physically remove or inactivate T cells (e.g., by treatment with cyclosporin A) in B cell-containing samples, because T cells from individuals seropositive for anti-EBV antibodies can suppress B cell immortalization by EBV. In general, the sample containing human B cells is inoculated with EBV, and cultured for 3–4 weeks. A typical source of EBV is the culture supernatant of the B95-8 cell line (ATCC #VR-1492). Physical signs of EBV transformation can generally be seen towards the end of the 3–4 week culture period. By phase-contrast microscopy, transformed cells may appear large, clear, hairy and tend to aggregate in tight clusters of cells. Initially, EBV lines are generally polyclonal. However, over prolonged periods of cell cultures, EBV lines may become monoclonal or polyclonal as a result of the selective outgrowth of particular B cell clones. Alternatively, polyclonal EBV transformed lines may be subcloned (e.g., by limiting dilution culture) or fused with a suitable fusion partner and plated at limiting dilution to obtain monoclonal B cell lines. Suitable fusion partners for EBV transformed cell lines include mouse myeloma cell lines (e.g., SP2/0, X63-Ag8.653), heteromyeloma cell lines (human x mouse; e.g., SPAM-8, SBC-H20, and CB-F7), and human cell lines (e.g., GM 1500, SKO-007, RPMI 8226, and KR-4). Thus, the present invention also provides a method of generating polyclonal or monoclonal human antibodies against polypeptides of the invention or fragments thereof, comprising EBV-transformation of human B cells.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CHI domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182: 41–50 (1995); Ames et al., J. Immunol. Methods 184: 177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5): 489–498 (1991); Studnicka et al., Protein Engineering 7(6): 805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, which are incorporated by reference herein in their entirety. In addition, companies such as Abgenix, Inc. (Fremont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby activate or block its biological activity.

Intrabodies are antibodies, often scFvs, that expressed from a recombinant nucleic acid molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies of the invention can be produced using methods known in the art, such as those disclosed and reviewed in Chen et al., *Hum. Gene Ther.* 5:595–601 (1994); Marasco, W. A., *Gene Ther.* 4:11–15 (1997); Rondon and Marasco, *Annu. Rev. Microbiol.* 51:257–283 (1997); Proba et al., *J. Mol. Biol.* 275:245–253 (1998); Cohen et al., *Oncogene* 17:2445–2456 (1998); Ohage and Steipe, *J. Mol. Biol.* 291:1119–1128 (1999); Ohage et al., *J. Mol. Biol.* 291:1129–1134 (1999); Wirtz and Steipe, *Protein Sci.* 8:2245–2250 (1999); Zhu et al., *J. Immunol. Methods* 231:207–222 (1999); and references cited therein. In particular, a CCR5 intrabody has been produced by Steinberger et al., *Proc. Natl. Acad. Sci. USA* 97:805–810 (2000).

XenoMouse Technology

Antibodies in accordance with the invention are preferably prepared by the utilization of a transgenic mouse that has a substantial portion of the human antibody producing genome inserted but that is rendered deficient in the production of endogenous, murine, antibodies (e.g., XenoMouse strains available from Abgenix Inc., Fremont, Calif.). Such mice, then, are capable of producing human immunoglobulin molecules and antibodies and are deficient in the production of murine immunoglobulin molecules and antibodies. Technologies utilized for achieving the same are disclosed in the patents, applications, and references disclosed herein.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B cell development. Furthermore, such a strategy could provide an ideal source for production of fully human monoclonal antibodies (Mabs) an important milestone towards fulfilling the promise of antibody therapy in human disease.

Fully human antibodies are expected to minimize the immunogenic and allergic responses intrinsic to mouse or mouse-derivatized monoclonal antibodies and thus to increase the efficacy and safety of the administered antibodies. The use of fully human antibodies can be expected to provide a substantial advantage in the treatment of chronic and recurring human diseases, such as cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Monoclonal antibodies with the desired specificity could be readily produced and selected.

This general strategy was demonstrated in connection with the generation of the first XenoMouse™ strains as published in 1994. See Green et al. *Nature Genetics* 7:13–21 (1994). The XenoMouse™ strains were engineered with yeast artificial chromosomes (YACS) containing 245 kb and 10 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human monoclonal antibodies. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. *Nature Genetics* 15:146–156 (1997), Green and Jakobovits *J Exp. Med.* 188:483–495 (1998), Green, *Journal of Immunological Methods* 231: 11–23 (1999) and U.S. patent application Ser. No. 08/759,620, filed Dec. 3, 1996, the disclosures of which are hereby incorporated by reference.

Such approach is further discussed and delineated in U.S. patent application Ser. No. 07/466,008, filed Jan. 12, 1990, Ser. No. 07/710,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/471,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996. See also Mendez et al. *Nature Genetics* 15:146–156 (1997) and Green and Jakobovits *J Exp. Med.* 188:483 495 (1998). See also European Patent No., EP 0 471 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against G-protein Chemokine Receptor (CCR5) polypeptides in order to vitiate concerns and/or effects of HAMA or HACA responses.

Monoclonal antibodies specific for G-protein Chemokine Receptor (CCR5) polypeptides were prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 571–681 (1981)). Briefly, XenoMouse™ mice were immunized with cells transfected with a G-protein Chemokine Receptor (CCR5) expression vector (for details, see Example 54). After immunization, the splenocytes of such mice were extracted and fused with a suitable myeloma cell line. Any suitable myeloma cell line may be employed in accordance with the present invention; however, it is preferable to employ the parent myeloma cell line (P3X63-AG8.653), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the G-protein Chemokine Receptor (CCR5) polypeptides.

The present invention is directed to fully human antibodies, generally isolated, that immunospecifically bind G-protein Chemokine Receptor (CCR5) polypeptides. Essentially, XenoMouse lines of mice from Abgenix, Inc. (Fremont, Calif.) expressing human antibodies were immunized with G-protein Chemokine Receptor (CCR5) expressing cells (for details of immunization protocols, see Example 54); spleen and/or lymph node cells (containing B-cells) were recovered from the mice that had high titers of anti-G-protein Chemokine Receptor (CCR5) antibodies; and such recovered cells were fused with a myeloid-type cell line to prepare immortal hybridoma cell lines. Hybridoma cell lines were screened to select and identify hybridoma cell lines that produced antibodies specific to the immunogen. We utilized these techniques in accordance with the present invention for the preparation of antibodies specific to G-protein Chemokine Receptor (CCR5) polypeptides. Herein, we describe the production of multiple hybridoma cell lines that produce antibodies specific to G-protein Chemokine Receptor (CCR5) polypeptides. Further, we provide a characterization of the antibodies produced by such cell lines.

The antibodies derived from hybridoma cell lines discussed herein are listed in Table 2. Preferred antibodies of the invention include, antibodies expressed by the following cell lines: XF11.1D8, XF11.4D10, XF11.4C4, XF11.5H1, XF11.1G8, XF22.3C9.6, XF22.9E6, XF27/28.7D5, XF27/28.18B5, XF27/28.25G10, XF27/28.36A12, XF27/28.36F11, XF27/28.43E2, and XF27/28.55G4. XenoMouse strains of mice from Abgenix, Inc. express human kappa light chains with either human IgG1, IgG2, or IgG4. Each of the XenoMouse strains can also produce antibodies of the human IgM isotype. The IgG2 expressing strain was used to make the cell lines and antibodies of the present invention, thus each of the antibodies produced by cell lines are either fully human IgG2 heavy chains with human kappa light chains or IgM heavy chains with human kappa light chains. These hybridoma cell lines were deposited with the American Type Culture Collection ("ATCC") on the date listed in Table 2, and given ATCC Deposit Numbers listed in Table 2. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

Hybridoma XF11.1D8 was deposited at the ATCC on Feb. 7, 2001 and given ATCC Deposit Number PTA-3030. Hybridoma XF11.4D10 was deposited at the ATCC on Feb. 7, 2001 and given ATCC Deposit Number PTA-3026. Hybridoma XF11.4C4 was deposited at the ATCC on Feb. 7, 2001 and given ATCC Deposit Number PTA-3028. Hybridoma XF11.5H1 was deposited at the ATCC on Feb. 7, 2001 and given ATCC Deposit Number PTA-3029. Hybridoma XF11.1G8 was deposited at the ATCC on Feb. 7, 2001 and given ATCC Deposit Number PTA-3027. Hybridoma XF3.5F1 was deposited at the ATCC on Mar. 2, 2001 and given ATCC Deposit Number PTA-3147. Hybridoma XF11.1F8 was deposited at the ATCC on Mar. 2, 2001 and given ATCC Deposit Number PTA-3150. Hybridoma XF3.6A2 was deposited at the ATCC on Mar. 2, 2001 and given ATCC Deposit Number PTA-3148. Hybridoma XF3.10B8 was deposited at the ATCC on Mar. 2, 2001 and given ATCC Deposit Number PTA-3151. Hybridoma XF22.3C9.6 was deposited at the ATCC on Sep. 12, 2001 and given ATCC Deposit Number PTA-3702. Hybridoma XF22.9E6 was deposited at the ATCC on Nov. 14, 2001 and given ATCC Deposit Number PTA-3859. Hybridoma XF27/28.7D5 was deposited at the ATCC on Feb. 1, 2002 and given ATCC Deposit Number PTA-4049. Hybridoma XF27/28.18B5 was deposited at the ATCC on Feb. 1, 2002 and given ATCC Deposit Number PTA-4050. Hybridoma XF27/28.25G10 was deposited at the ATCC on Feb. 1, 2002 and given ATCC Deposit Number PTA-4051. Hybridoma XF27/28.36A12 was deposited at the ATCC on Feb. 1, 2002 and given ATCC Deposit Number PTA-4052. Hybridoma XF27/28.36F11 was deposited at the ATCC on Feb. 1, 2002 and given ATCC Deposit Number PTA-4053. Hybridoma XF27/28.43E2 was deposited at the ATCC on Feb. 1, 2002 and given ATCC Deposit Number PTA-4054. The ATCC Deposit Numbers and the Hybridoma designations are also presented in Table 2.

TABLE 2

Hybridoma Cell Lines Expressing anti-G-protein Chemokine Receptor (CCR5) Receptor Antibodies

| Hybridoma | ATCC Deposit Number | ATCC Deposit Date |
|---|---|---|
| XF11.1D8 | PTA-3030 | Feb. 7, 2001 |
| XF11.4D10 | PTA-3026 | Feb. 7, 2001 |
| XF11.4C4 | PTA-3028 | Feb. 7, 2001 |
| XF11.5H1 | PTA-3029 | Feb. 7, 2001 |
| XF11.1G8 | PTA-3027 | Feb. 7, 2001 |
| XF3.5F1 | PTA-3147 | Mar. 2, 2001 |
| XF11.1F8 | PTA-3150 | Mar. 2, 2001 |
| XF3.6A2 | PTA-3148 | Mar. 2, 2001 |
| XF3.10B8 | PTA-3151 | Mar. 2, 2001 |
| XF22.3C9.6 | PTA-3702 | Sep. 12, 2001 |
| XF22.9E6 | PTA-3859 | Nov. 14, 2001 |
| XF27/28.7D5 | PTA-4049 | Feb. 1, 2002 |
| XF27/28.18B5 | PTA-4050 | Feb. 1, 2002 |
| XF27/28.25G10 | PTA-4051 | Feb. 1, 2002 |
| XF27/28.36A12 | PTA-4052 | Feb. 1, 2002 |
| XF27/28.36F11 | PTA-4053 | Feb. 1, 2002 |
| XF27/28.43E2 | PTA-4054 | Feb. 1, 2002 |
| XF27/28.55G4 | | |

In one embodiment, the present invention provides hybridoma cell lines expressing an antibody of the invention. In specific embodiments, the hybridoma cell line of the invention is XF11.1D8. In another specific embodiment, the hybridoma cell line of the invention is XF11.4D10. In another specific embodiment, the hybridoma cell line of the invention is XF11.4C4. In another specific embodiment, the hybridoma cell line of the invention is XF11.5H1. In another specific embodiment, the hybridoma cell line of the invention is XF11.1G8. In another specific embodiment, the hybridoma cell line of the invention is XF3.5F1. In another specific embodiment, the hybridoma cell line of the invention is XF11.1F8. In another specific embodiment, the hybridoma cell line of the invention is XF3.6A2. In another specific embodiment, the hybridoma cell line of the invention is XF3.10B8. In another specific embodiment, the hybridoma cell line of the invention is XF22.3C9.6. In another specific embodiment, the hybridoma cell line of the invention is XF22.9E6. In another specific embodiment, the hybridoma cell line of the invention is XF27/28.7D5. In another specific embodiment, the hybridoma cell line of the invention is XF27/28.18B5. In another specific embodiment, the hybridoma cell line of the invention is XF27/28.25G10. In another specific embodiment, the hybridoma cell line of the invention is XF27/28.36A12. In another specific embodiment, the hybridoma cell line of the invention is XF27/28.36F11. In another specific embodiment, the hybridoma cell line of the invention is XF27/28.43E2. In another specific embodiment, the hybridoma cell line of the invention is XF27/28.55G4.

The present invention encompasses antibodies (including molecules comprising, or alternatively consisting of, antibody fragments or variants thereof) that immunospecifically bind to a G-protein Chemokine Receptor (CCR5) polypeptide or a fragment, variant, or fusion protein thereof. A G-protein Chemokine Receptor (CCR5) polypeptide includes, but is not limited to, the G-protein Chemokine Receptor (CCR5) polypeptide of SEQ ID NO:2 or the polypeptide encoded by the DNA in clone HDGNR10 contained in ATCC Deposit 97183 deposited Jun. 1, 1995; G-protein Chemokine Receptor (CCR5) may be produced through recombinant expression of nucleic acids encoding the polypeptides of SEQ ID NOS:2 or the HDGNR10 DNA in ATCC Deposit Number 97183).

In one embodiment of the present invention, antibodies that immunospecifically bind to a G-protein Chemokine Receptor (CCR5) or a fragment or variant thereof, comprise a polypeptide having the amino acid sequence of any one of the heavy chains expressed by at least one of the cell lines referred to in Table 2 and/or any one of the light chains expressed by at least one of the cell lines referred to in Table 2. In another embodiment of the present invention, antibodies that immunospecifically bind to a G-protein Chemokine Receptor (CCR5) or a fragment or variant thereof, comprise a polypeptide having the amino acid sequence of any one of the VH domains of a heavy chain expressed by at least one of the cell lines referred to in Table 2 and/or any one of the VL domains of a light chain expressed by at least one of the cell lines referred to in Table 2. In preferred embodiments, antibodies of the present invention comprise the amino acid sequence of a VH domain and VL domain expressed by the same cell line selected from the group consisting of cell lines referred to in Table 2 In alternative embodiments, antibodies of the present invention comprise the amino acid sequence of a VH domain and a VL domain from different cell lines referred to in Table 2. Molecules comprising, or alternatively consisting of, antibody fragments or variants of the VH and/or VL domains expressed by at least one of the cell lines referred to in Table 2 that immunospecifically bind to a G-protein Chemokine Receptor (CCR5) are also encompassed by the invention, as are nucleic acid molecules encoding these VH and VL domains, molecules, fragments and/or variants.

The present invention also provides antibodies that immunospecifically bind to a polypeptide, or polypeptide fragment or variant of a G-protein Chemokine Receptor (CCR5), wherein said antibodies comprise, or alternatively consist of, a polypeptide having an amino acid sequence of any one, two, three, or more of the VH CDRs contained in a heavy chain expressed by one or more cell lines referred to in Table 2. In particular, the invention provides antibodies that immunospecifically bind a G-protein Chemokine Receptor (CCR5), comprising, or alternatively consisting of, a polypeptide having the amino acid sequence of a VH CDR1 contained in a heavy chain expressed by one or more cell lines referred to in Table 2. In another embodiment, antibodies that immunospecifically bind a G-protein Chemokine Receptor (CCR5), comprise, or alternatively consist of, a polypeptide having the amino acid sequence of a VH CDR2 contained in a heavy chain expressed by one or more cell lines referred to in Table 2. In a preferred embodiment, antibodies that immunospecifically bind a G-protein Chemokine Receptor (CCR5), comprise, or alternatively consist of a polypeptide having the amino acid sequence of a VH CDR3 contained in a heavy chain expressed by one or more cell lines referred to in Table 2. Molecules comprising, or alternatively consisting of, these antibodies, or antibody fragments or variants thereof, that immunospecifically bind to G-protein Chemokine Receptor (CCR5) or a G-protein Chemokine Receptor (CCR5) fragment or variant thereof are also encompassed by the invention, as are nucleic acid molecules encoding these antibodies, molecules, fragments and/or variants.

The present invention also provides antibodies that immunospecifically bind to a polypeptide, or polypeptide fragment or variant of a G-protein Chemokine Receptor (CCR5), wherein said antibodies comprise, or alternatively consist of, a polypeptide having an amino acid sequence of any one, two, three, or more of the VL CDRs contained in a light chain expressed by one or more cell lines referred to in Table 2. In particular, the invention provides antibodies that immunospecifically bind a G-protein Chemokine Receptor (CCR5), comprising, or alternatively consisting of, a polypeptide having the amino acid sequence of a VL CDR1 contained in a light chain expressed by one or more cell lines referred to in Table 2. In another embodiment, antibodies that immunospecifically bind a G-protein Chemokine Receptor (CCR5), comprise, or alternatively consist of, a polypeptide having the amino acid sequence of a VL CDR2 contained in a light chain expressed by one or more cell lines referred to in Table 2. In a preferred embodiment, antibodies that immunospecifically bind a G-protein Chemokine Receptor (CCR5), comprise, or alternatively consist of a polypeptide having the amino acid sequence of a VL CDR3 contained in a light chain expressed by one or more cell lines referred to in Table 2. Molecules comprising, or alternatively consisting of, these antibodies, or antibody fragments or variants thereof, that immunospecifically bind to G-protein Chemokine Receptor (CCR5) or a G-protein Chemokine Receptor (CCR5) fragment or variant thereof are also encompassed by the invention, as are nucleic acid molecules encoding these antibodies, molecules, fragments and/or variants.

The present invention also provides antibodies (including molecules comprising, or alternatively consisting of, antibody fragments or variants) that immunospecifically bind to a G-protein Chemokine Receptor (CCR5) polypeptide or polypeptide fragment or variant of a G-protein Chemokine Receptor (CCR5), wherein said antibodies comprise, or alternatively consist of, one, two, three, or more VH CDRs and one, two, three or more VL CDRs, as contained in a heavy chain or light chain expressed by one or more cell lines referred to in Table 2. In particular, the invention provides for antibodies that immunospecifically bind to a polypeptide or polypeptide fragment or variant of a G-protein Chemokine Receptor (CCR5), wherein said antibodies comprise, or alternatively consist of, a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof, of the VH CDRs and VL CDRs contained in a heavy chain or light chain expressed by one or more cell lines referred to in Table 2. In a preferred embodiment, one or more of these combinations are from the same scFv as disclosed in Table 2. Molecules comprising, or alternatively consisting of, fragments or variants of these antibodies, that immunospecifically bind to G-protein Chemokine Receptor (CCR5) are also encompassed by the invention, as are nucleic acid molecules encoding these antibodies, molecules, fragments or variants.

Nucleic Acid Molecules Encoding Anti-G-protein Chemokine Receptor (CCR5) Antibodies Corresponding to Antibodies Derived from Xenomouse Strains.

The present invention also provides for nucleic acid molecules, generally isolated, encoding an antibody of the invention (including molecules comprising, or alternatively consisting of, antibody fragments or variants thereof). In a specific embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of a heavy chain expressed by at least one of the cell lines referred to in Table 2 and a VL domain having an amino acid sequence of a light chain expressed by at least one of the cell lines referred to in Table 2. In another embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of a heavy chain expressed by at least one of the cell lines referred to in Table 2 or a VL domain having an amino acid sequence of a light chain expressed by at least one of the cell lines referred to in Table 2.

The present invention also provides antibodies that comprise, or alternatively consist of, variants (including derivatives) of the antibody molecules (e.g., the VH domains and/or VL domains) described herein, which antibodies immunospecifically bind to a G-protein Chemokine Receptor (CCR5) or fragment or variant thereof. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid subsitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind a G-protein Chemokine Receptor).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind a G-protein Chemokine Receptor) can be determined using techniques described herein or by routinely modifying techniques known in the art.

In a specific embodiment, an antibody of the invention (including a molecule comprising, or alternatively consisting of, an antibody fragment or variant thereof), that immunospecifically binds G-protein Chemokine Receptor (CCR5) polypeptides or fragments or variants thereof, comprises, or alternatively consists of, an amino acid sequence encoded by a nucleotide sequence that hybridizes to a nucleotide sequence that is complementary to that encoding one of the VH or VL domains expressed by one or more cell lines referred to in Table 2. under stringent conditions, e.g., hybridization to filter-bound DNA in 6× sodium chloride/sodium citrate (SSC) at about 45° C. followed by one or more washes in 0.2×SSC/0.1% SDS at about 50–65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds. , 1989*, Current Protocols in Molecular Biology*, Vol. I, Green Publishing Associates, Inc. and John Wiley & Sons, Inc., New York at pages 6.3.1–6.3.6 and 2.10.3). Nucleic acid molecules encoding these antibodies are also encompassed by the invention.

It is well known within the art that polypeptides, or fragments or variants thereof, with similar amino acid sequences often have similar structure and many of the same biological activities. Thus, in one embodiment, an antibody (including a molecule comprising, or alternatively consisting of, an antibody fragment or variant thereof), that immunospecifically binds to a G-protein Chemokine Receptor (CCR5) polypeptide or fragments or variants of a G-protein Chemokine Receptor (CCR5) polypeptide, comprises, or alternatively consists of, a VH domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VH domain of a heavy chain expressed by at least one of the cell lines referred to in Table 2.

In another embodiment, an antibody (including a molecule comprising, or alternatively consisting of, an antibody fragment or variant thereof), that immunospecifically binds to a G-protein Chemokine Receptor (CCR5) polypeptide or fragments or variants of a G-protein Chemokine Receptor (CCR5) polypeptide, comprises, or alternatively consists of, a VL domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VL domain of a light chain expressed by at least one of the cell lines referred to in Table 2.

Polynucleotides Encoding Antibodies

Antibodies of the invention (including antibody fragments or variants) can be produced by any method known in the art. For example, it will be appreciated that antibodies in accordance with the present invention can be expressed in cell lines other than hybridoma cell lines. Sequences encoding the cDNAs or genomic clones for the particular antibodies can be used for transformation of a suitable mammalian or nonmammalian host cells or to generate phage display libraries, for example. Additionally, polypeptide antibodies of the invention may be chemically synthesized or produced through the use of recombinant expression systems.

One way to produce the antibodies of the invention would be to clone the VH and/or VL domains expressed by any one or more of the hybridoma cell lines referred to in Table 2. In order to isolate the VH and VL domains from the hybridoma cell lines, PCR primers including VH or VL nucleotide sequences (See Example 55), may be used to amplify the expressed VH and VL sequences contained in total RNA isolated from hybridoma cell lines. The PCR products may then be cloned using vectors, for example, which have a PCR product cloning site consisting of a 5' and 3' single T nucleotide overhang, that is complementary to the overhanging single adenine nucleotide added onto the 5' and 3' end of PCR products by many DNA polymerases used for PCR reactions. The VH and VL domains can then be sequenced using conventional methods known in the art.

The cloned VH and VL genes may be placed into one or more suitable expression vectors. By way of non-limiting example, PCR primers including VH or VL nucleotide sequences, a restriction site, and a flanking sequence to protect the restriction site may be used to amplify the VH or VL sequences. Utilizing cloning techniques known to those of skill in the art, the PCR amplified VH domains may be cloned into vectors expressing the appropriate immunoglobulin constant region, e.g., the human IgG1 or IgG4 constant region for VH domains, and the human kappa or lambda constant regions for kappa and lambda VL domains, respectively. Preferably, the vectors for expressing the VH or VL domains comprise a promoter suitable to direct expression of the heavy and light chains in the chosen expression system, a secretion signal, a cloning site for the immunoglobulin variable domain, immunoglobulin constant domains, and a selection marker such as neomycin. The VH and VL domains may also be cloned into a single vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art (See, for example, Guo et al., J. Clin. Endocrinol. Metab. 82:925–31 (1997), and Ames et al., J. Immunol. Methods 184:177–86 (1995) which are herein incorporated in their entireties by reference).

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2 or a polypeptide encoded by the deposited clone.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence (See Example 55) or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

For some uses, such as for in vitro affinity maturation of an antibody of the invention, it may be useful to express the VH and VL domains of the heavy and light chains of one or more antibodies of the invention as single chain antibodies or Fab fragments in a phage display library. For example, the cDNAs encoding the VH and VL domains of one or more antibodies of the invention may be expressed in all possible combinations using a phage display library, allowing for the selection of VH/VL combinations that bind a G-protein Chemokine Receptor (CCR5) polypeptides with preferred binding characteristics such as improved affinity or improved off rates. Additionally, VH and VL segments—the CDR regions of the VH and VL domains of one or more antibodies of the invention, in particular, may be mutated in vitro. Expression of VH and VL domains with "mutant" CDRs in a phage display library allows for the selection of VH/VL combinations that bind a G-protein Chemokine Receptor (CCR5) receptor polypeptides with preferred binding characteristics such as improved affinity or improved off rates.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues) or synthetic cDNA libraries. The DNA encoding the VH and VL domains are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest (i.e., a G-protein Chemokine Receptor polypeptide or a fragment thereof) can be selected or identified with antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280(1994); PCT application No. PCT/GB91/O1 134; PCT publications WO 90/02809; WO 91/10737; WO 92/01047; WO 92/18719; WO 93/1 1236; WO 95/15982; WO 95/20401; WO97/13844; and U.S. Pat. Nos. 5,698,426; 5,223,409; 5,403,484; 5,580,717; 5,427,908; 5,750,753; 5,821,047; 5,571,698; 5,427,908; 5,516,717; 5,780,225; 5,658,727; 5,735,743 and 5,969,108; each of which is incorporated herein by reference in its entirety.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242: 1038–1041 (1988)).

Methods of Producing Antibodies

The antibodies of the invention can be produced by any method known in the art for the synthesis of antibodies, in particular, by chemical synthesis, by intracellular immunization (i.e., intrabody technology), or preferably, by recombinant expression techniques. Methods of producing antibodies include, but are not limited to, hybridoma technology, EBV transformation, and other methods discussed herein as well as through the use recombinant DNA technology, as discussed below.

Recombinant expression of an antibody of the invention, or fragment, derivative, variant or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia). transformed with recombinant yeast expression vectors containing antibody coding sequences; insect cell systems infected with recombinant virus expression vectors (e.g., *baculovirus*) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors are the availability of cell lines (e.g., the murine myeloma cell line, NSO) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. Vectors that use glutamine synthase as the selectable marker include, but are not limited to, the pEE6 expression vector described in Stephens and Cockett, *Nucl. Acids. Res* 17:7110 (1989). A glutamine synthase expression system and components thereof are detailed in PCT publications: WO87/04462; WO86/05807; WO89101036; WO89/10404; and WO91/06657 which are incorporated in their entireties by reference herein. Additionally, glutamine synthase expression vectors that may be used according to the present invention are commercially available from suppliers, including, for example Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are incorporated in their entireties by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Antibody Conjugates

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Polypeptides and/or antibodies of the present invention (including fragments or variants thereof) may be fused to either the N- or C-terminal end of the heterologous protein (e.g., immunoglobulin Fc polypeptide or human serum albumin polypeptide). Antibodies of the invention may also be fused to albumin (including but not limited to recombinant human serum albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. In a preferred embodiment, polypeptides and/or antibodies of the present invention (including fragments or variants thereof) are fused with the mature form of human serum albumin (i.e., amino acids 1–585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polynucleotides encoding fusion proteins of the invention are also encompassed by the invention. Such fusion proteins may, for example, facilitate purification and may increase half-life in vivo. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992);

Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:2 or of the polypeptide encoded by the deposited clone may be fused or conjugated to the above antibody portions to increase the in vivo half life of the polypeptides or for use in immunoassays using methods known in the art. Further, the polypeptides corresponding to SEQ ID NO: 2 or to the polypeptide encoded by the deposited clone may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331: 84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{121}I$, $^{123}I$, $^{125}I$, $^{131}I$), carbon ($^{14}C$), sulfur ($^{35}S$), tritium ($^{3}H$), indium ($^{111}In$, $^{112}In$, $^{113m}In$, $^{115m}In$), technetium ($^{99}Tc$, $^{99m}Tc$), thallium ($^{201}Ti$), gallium ($^{68}Ga$, $^{67}Ga$), palladium ($^{103}$ Pd), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, and $^{97}Ru$;

In specific embodiments, G-protein Chemokine Receptor (CCR5) polypeptides of the invention are attached to macrocyclic chelators useful for conjugating radiometal ions, including but not limited to, $^{111}In$, $^{177}Lu$, $^{90}Y$, $^{166}Ho$, and $^{153}Sm$, to polypeptides. In a preferred embodiment, the radiometal ion associated with the macrocyclic chelators attached to G-protein Chemokine Receptor (CCR5) polypeptides of the invention is $^{111}In$. In another preferred embodiment, the radiometal ion associated with the macrocyclic chelator attached to G-protein Chemokine Receptor (CCR5) polypeptides of the invention is $^{90}Y$. In specific embodiments, the macrocyclic chelator is 1,4,7,10-tetraazacyclododecane-N,N',N'',N'''-tetraacetic acid (DOTA). In other specific embodiments, the DOTA is attached to the G-protein Chemokine Receptor (CCR5) polypeptide of the invention via a linker molecule. Examples of linker molecules useful for conjugating DOTA to a polypeptide are commonly known in the art—see, for example, DeNardo et al., Clin Cancer Res. 4(10):2483–90, 1998; Peterson et al., Bioconjug. Chem. 10(4):553–7, 1999; and Zimmerman et al, Nucl. Med. Biol. 26(8):943–50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties. Though U.S. Pat. Nos. 5,652,361 and 5,756,065 focus on conjugating chelating agents to antibodies, one skilled in the art could readily adapt the methods disclosed therein in order to conjugate chelating agents to other polypeptides.

A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The antibody conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell,* 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as BIAcore analysis (see, e.g., Example 59), FACS (Fluorescence activated cell sorter) analysis (see, e.g., Example 54), immunofluorescence (see, e.g., Example 56), immunocytochemistry, western blots (see Examples 64 and 65), radioimmunoassays, ELISA (enzyme linked immunosorbent assay) (See, e.g., Example 54), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$), or fragment or variant thereof, with the antibody of interest in the presence of increasing amounts of unlabeled antigen, and the detection of the antibody bound to the labeled antigen. The affinity of the antibody of interest for a G-protein Chemokine Receptor (CCR5) and the binding off-rates can be determined from the data by scatchard plot analysis. Competition with a second antibody can also be determined using radioimmunoassays. In this case, the G-protein Chemokine Receptor (CCR5) is incubated with antibody of interest conjugated to a labeled compound (e.g., compound labeled with $^{3}H$ or $^{125}I$) in the presence of increasing amounts of an unlabeled second antibody. This kind of competitive assay between two antibodies, may also be used to determine if two antibodies bind the same or different epitopes.

In a preferred embodiment, BIAcore kinetic analysis is used to determine the binding on and off rates of antibodies (including antibody fragments or variants thereof) to a G-protein Chemokine Receptor (CCR5), or fragments of a G-protein Chemokine Receptor (CCR5). BIAcore kinetic analysis comprises analyzing the binding and dissociation of antibodies from chips with immobilized G-protein Chemokine Receptors (CCR5) on their surface as described in Example 59.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy, anti-tumor agents, and anti-retroviral agents (see Example 28, below). In a highly preferred embodiment, antibodies of the invention may be administered alone or in combination with and anti-retroviral agents (see Example 28, below). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M. More preferred binding affinities include those with a dissociation constant or Kd less than $5\times10^{-5}$ M, $10^{-5}$ M, $5\times10^{-6}$ M, $10^{-6}$M, $5\times10^{-7}$M, $10^{7}$ M, $5\times10^{-8}$ M or $10^{-8}$ M. Even more preferred binding affinities include those with a dissociation constant or Kd less than $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $^{10-12}$ M, $5\times10^{-13}$ M, $10^{-13}$ M, $5\times10^{-14}$ M, $10^{-14}$ M, $5\times10^{-15}$ M, or $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342: 435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell . Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (NRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any G-protein Chemokine Receptor (CCR5) polypeptide can be used to generate fusion proteins. For example, the G-protein Chemokine Receptor (CCR5) polypeptide, when fused to a second protein, can be used as an antigenic tag. Antibodies raised against the G-protein Chemokine Receptor (CCR5) polypeptide can be used to indirectly detect the second protein by binding to the G-protein Chemokine Receptor. Moreover, because secreted proteins target cellular locations based on trafficking signals, the G-protein Chemokine Receptor (CCR5) polypeptides can be used as targeting molecules once fused to other proteins.

Examples of domains that can be fused to G-protein Chemokine Receptor (CCR5) polypeptides include not only heterologous signal sequences, but also other heterologous functional regions. The fusion does not necessarily need to be direct, but may occur through linker sequences.

In certain preferred embodiments, G-protein Chemokine Receptor (CCR5) proteins of the invention comprise fusion proteins wherein the G-protein Chemokine Receptor (CCR5) polypeptides are those described above as m-n. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

Moreover, fusion proteins may also be engineered to improve characteristics of the G-protein Chemokine Receptor (CCR5) polypeptide. For instance, a region of additional amino acids, particularly charged amino acids, may be added to the N-terminus of the G-protein Chemokine Receptor (CCR5) polypeptide to improve stability and persistence during purification from the host cell or subsequent handling and storage. Also, peptide moieties may be added to the G-protein Chemokine Receptor (CCR5) polypeptide to facilitate purification. Such regions may be removed prior to final preparation of the G-protein Chemokine Receptor (CCR5) polypeptide. The addition of peptide moieties to facilitate handling of polypeptides are familiar and routine techniques in the art.

As one of skill in the art will appreciate, polypeptides of the present invention and the epitope-bearing fragments thereof described above, can be combined with heterologous polypeptide sequences. For example, polypeptides of the present invention (including fragments or variants thereof), may be fused with the constant domain of immunoglobulins (IgA, IgE, IgG, IgM), or portions thereof (CH1, CH2, CH3, or any combination thereof and portions thereof, resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1–585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1–z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270: 9459–9471 (1995).)

Moreover, the G-protein Chemokine Receptor (CCR5) polypeptides can be fused to marker sequences, such as a peptide which facilitates purification of G-protein Chemokine Receptor. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the G-protein Chemokine Receptor (CCR5) polynucleotides or the polypeptides.

Vectors, Host Cells, and Protein Production

The present invention also relates to vectors containing the G-protein Chemokine Receptor (CCR5) polynucleotide, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

G-protein Chemokine Receptor (CCR5) polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The G-protein Chemokine Receptor (CCR5) polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418, glutamine synthase or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, NSO, COS, 293, and Bowes melanoma cells; and plant cells. Appropriate culture mediums and conditions for the above-described host cells are known in the art.

Vectors which use glutamine synthase (GS) or DHFR as the selectable markers can be amplified in the presence of the drugs methionine sulphoximine or methotrexate, respectively. The availability of drugs which inhibit the function of the enzymes encoded by these selectable markers allows for selection of cell lines in which the vector sequences have been amplified after integration into the host cell's DNA. An advantage of glutamine synthase based vectors are the availability of cell lines (e.g., the murine myeloma cell line, NSO) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. Vectors that use glutamine synthase as the selectable marker include the pEE6 expression vector described in Stephens and Cockett, Nucl. Acids. Res 17:7110 (1989). A glutamine synthase expression system and components thereof are detailed in PCT publications: WO87/04462; WO86/05807; WO89/01036; WO89/10404; and WO91/06657 which are hereby incorporated in their entireties by reference herein. Additionally, glutamine synthase expression vectors that may be used according to the present invention are commercially available from suppliers including, for example, Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are herein incorporated by reference.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that G-protein Chemokine Receptor (CCR5) polypeptides may in fact be expressed by a host cell lacking a recombinant vector.

G-protein Chemokine Receptor (CCR5) polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

G-protein Chemokine Receptor (CCR5) polypeptides, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the G-protein Chemokine Receptor (CCR5) polypeptides may be glycosylated or may be non-glycosylated. In addition, G-protein Chemokine Receptor (CCR5) polypeptides may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express G-protein Chemokine Receptor (CCR5) protein in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., *Mol. Cell. Biol.* 5:1111–21 (1985); Koutz, P. J, et al., *Yeast* 5:167–77 (1989); Tschopp, J. F., et al., *Nucl. Acids Res.* 15:3859–76 (1987). Thus, a heterologous coding sequence, such as, for example, a G-protein Chemokine Receptor (CCR5) polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a G-protein Chemokine Receptor (CCR5) polypeptide of the invention, as set forth herein, in a *Pichea* yeast system essentially as described in "*Pichia* Protocols: Methods in Molecular Biology," D. R. Higgins and J. Cregg, eds. The Humana Press, Totowa, N.J., 1998. This expression vector allows expression and secretion of a G-protein Chemokine Receptor (CCR5) protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a G-protein Chemokine Receptor (CCR5) polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., G-protein Chemokine Receptor (CCR5) coding sequence), and/or to include genetic material (e.g., heterologous polynucleotide sequences) that is operably associated with G-protein Chemokine Receptor (CCR5) polynucleotides of the invention, and which activates, alters, and/or amplifies endogenous G-protein Chemokine Receptor (CCR5) polynucleotides. For example, techniques known in the art may be used to operably associate heterologous control regions (e.g., promoter and/or enhancer) and endogenous G-protein Chemokine Receptor (CCR5) polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., *Nature,* 310:105–111 (1984)). For example, a polypeptide corresponding to a fragment of a G-protein Chemokine Receptor (CCR5) polypeptide can be synthesized by use of a peptide synthesizer. Furthermore, if desired, nonclassical amino acids or chemical amino acid analogs can be introduced as a substitution or addition into the G-protein Chemokine Receptor (CCR5) polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, omithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses G-protein Chemokine Receptor (CCR5) polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The G-protein Chemokine Receptor (CCR5) polypeptides of the invention may be in monomers or multimers (i.e., dimers, trimers, tetramers and higher multimers). Accordingly, the present invention relates to monomers and multimers of the G-protein Chemokine Receptor (CCR5) polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2 or encoded by the HDGNR10 DNA contained in the deposited clone (including fragments, variants, splice variants, and fusion proteins, corresponding to these as described herein). These homomers may contain G-protein Chemokine Receptor (CCR5) polypeptides having identical or different amino acid sequences. In a specific embodiment, a homomer of the invention is a multimer containing only G-protein Chemokine Receptor (CCR5) polypeptides having an identical amino acid sequence. In another specific embodiment, a homomer of the invention is a multimer containing G-protein Chemokine Receptor (CCR5) polypeptides having different amino acid sequences. In specific embodiments, the multimer of the invention is a homodimer (e.g., containing G-protein Chemokine Receptor (CCR5) polypeptides having identical or different amino acid sequences) or a homotrimer (e.g., containing G-protein Chemokine Receptor (CCR5) polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the G-protein Chemokine Receptor (CCR5) polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the G-protein Chemokine Receptor (CCR5) polypeptides of the invention. Such covalent associations may involve one or more amino acid residues contained in the polypeptide sequence (e.g., that recited in SEQ ID NO:2, or contained in the polypeptide encoded by the clone HDGNR10). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a G-protein Chemokine Receptor (CCR5) fusion protein. In one example, covalent associations are between the heterologous sequence contained in a fusion protein of the invention (see, e.g., U.S. Pat. No. 5,478,925). In a specific example, the covalent associations are between the heterologous sequence contained in a G-protein Chemokine Receptor-Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

Uses of the G-protein Chemokine Receptor (CCR5) Polynucleotides

The G-protein Chemokine Receptor (CCR5) polynucleotides identified herein can be used in numerous ways as reagents. The following description should be considered exemplary and utilizes known techniques.

There exists an ongoing need to identify new chromosome markers, since few chromosome marking reagents, based on actual sequence data (repeat polymorphisms), are presently available.

Briefly, sequences can be mapped to chromosomes by preparing PCR primers (preferably 15–25 bp) from the sequences shown in SEQ ID NO:1 or from the deposited clone. Primers can be selected using computer analysis so that primers do not span more than one predicted exon in the genomic DNA. These primers are then used for PCR screening of somatic cell hybrids containing individual human chromosomes. Only those hybrids containing the human G-protein Chemokine Receptor (CCR5) gene corresponding to the SEQ ID NO:1 or to the deposited clone will yield an amplified fragment.

Similarly, somatic hybrids provide a rapid method of PCR mapping the polynucleotides to particular chromosomes. Three or more clones can be assigned per day using a single thermal cycler. Moreover, sublocalization of the G-protein Chemokine Receptor (CCR5) polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the G-protein Chemokine Receptor (CCR5) polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the G-protein Chemokine Receptor (CCR5) polynucleotides can be used individually (to mark a single chromosome or a single site on that chromosome) or in panels (for marking multiple sites and/or multiple chromosomes). Preferred polynucleotides correspond to the noncoding regions of the cDNAs or genomic clone because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the G-protein Chemokine Receptor (CCR5) polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the G-protein Chemokine Receptor (CCR5) polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using G-protein Chemokine Receptor (CCR5) polynucleotides. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an individual and comparing the measured gene expression level with a standard level of polynucleotide expression level, whereby an increase or decrease in the gene expression level compared to the standard is indicative of a disorder.

In still another embodiment, the invention includes a kit for analyzing samples for the presence of proliferative and/or cancerous polynucleotides derived from a test subject. In a general embodiment, the kit includes at least one polynucleotide probe containing a nucleotide sequence that will specifically hybridize with a polynucleotide of the present invention and a suitable container. In a specific embodiment, the kit includes two polynucleotide probes defining an internal region of the polynucleotide of the present invention, where each probe has one strand containing a 31'mer-end internal to the region. In a further embodiment, the probes may be useful as primers for polymerase chain reaction amplification.

Where a diagnosis of a disorder, has already been made according to conventional methods, the present invention is useful as a prognostic indicator, whereby patients exhibiting enhanced or depressed polynucleotide of the present invention expression will experience a worse clinical outcome relative to patients expressing the gene at a level nearer the standard level.

By "measuring the expression level of polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or niRNA level, the standard being taken from a second biological sample obtained from an individual not having the disorder or being determined by averaging levels from a population of individuals not having a disorder. As will be appreciated in the art, once a standard polypeptide level or mRNA level is known, it can be used repeatedly as a standard for comparison.

By "biological sample" is intended any biological sample obtained from an individual, body fluid, cell line, tissue culture, or other source which contains the polypeptide of the present invention or mRNA. As indicated, biological samples include body fluids (such as semen, lymph, sera, plasma, urine, synovial fluid and spinal fluid) which contain the polypeptide of the present invention, and other tissue sources found to express the polypeptide of the present invention. Methods for obtaining tissue biopsies and body fluids from mammals are well known in the art. Where the biological sample is to include mRNA, a tissue biopsy is the preferred source.

The method(s) provided above may preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including cancerous diseases and conditions. Such a method is described in U.S. Pat. Nos. 5,858,659 and 5,856,104. The U.S. patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L.Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point ($T_m$) by 8°–20° C., vs. 4°–16° C. for the DNA/DNA 15-mer duplex. Also, the absence of charge groups in PNA means that hybridization can be done at low ionic strengths and reduce possible interference by salt during the analysis.

The present invention is useful for detecting cancer in mammals. In particular the invention is useful during diagnosis of pathological cell proliferative neoplasias which include, but are not limited to: acute myelogenous leukemias including acute monocytic leukemia, acute myeloblastic leukemia, acute promyelocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

Pathological cell proliferative disorders are often associated with inappropriate activation of proto-oncogenes. (Gelmann, E. P. et al., "The Etiology of Acute Leukemia: Molecular Genetics and Viral Oncology," in Neoplastic Diseases of the Blood, Vol 1., Wiemik, P. H. et al. eds., 161–182 (1985)). Neoplasias are now believed to result from the qualitative alteration of a normal cellular gene product, or from the quantitative modification of gene expression by insertion into the chromosome of a viral sequence, by chromosomal translocation of a gene to a more actively transcribed region, or by some other mechanism. (Gelmann et al., supra) It is likely that mutated or altered expression of specific genes is involved in the pathogenesis of some leukemias, among other tissues and cell types.

(Gelmann et al., supra) Indeed, the human counterparts of the oncogenes involved in some animal neoplasias have been amplified or translocated in some cases of human leukemia and carcinoma. (Gelmann et al., supra)

For example, c-myc expression is highly amplified in the non-lymphocytic leukemia cell line HL-60. When HL-60 cells are chemically induced to stop proliferation, the level of c-myc is found to be downregulated. (International Publication Number WO 91/15580) However, it has been shown that exposure of HL-60 cells to a DNA construct that is complementary to the 5' end of c-myc or c-myb blocks translation of the corresponding mRNAs which downregulates expression of the c-myc or c-myb proteins and causes arrest of cell proliferation and differentiation of the treated cells. (International Publication Number WO 91/15580; Wickstrom et al., Proc. Natl. Acad. Sci. 85:1028 (1988); Anfossi et al., Proc. Natl. Acad. Sci. 86:3379 (1989)). However, the skilled artisan would appreciate the present invention's usefulness would not be limited to treatment of proliferative diseases, disorders, and/or conditions of hematopoietic cells and tissues, in light of the numerous cells and cell types of varying origins which are known to exhibit proliferative phenotypes.

In addition to the foregoing, a G-protein Chemokine Receptor (CCR5) polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression,CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

G-protein Chemokine Receptor (CCR5) polynucleotides are also useful in gene therapy. One goal of gene therapy is to insert a normal gene into an organism having a defective gene, in an effort to correct the genetic defect. G-protein Chemokine Receptor (CCR5) offers a means of targeting such genetic defects in a highly accurate manner. Another goal is to insert a new gene that was not present in the host genome, thereby producing a new trait in the host cell.

The G-protein Chemokine Receptor (CCR5) polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The G-protein Chemokine Receptor (CCR5) polynucleotides can be used as additional DNA markers for RFLP.

The G-protein Chemokine Receptor (CCR5) polynucleotides can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once a unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, synovial fluid, amniotic fluid, breast milk, lymph, pulmonary sputum or surfactant, urine, fecal matter, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, G-protein Chemokine Receptor (CCR5) polynucleotides can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from G-protein Chemokine Receptor (CCR5) sequences. Panels of such reagents can identify tissue by species and/or by organ type. In a similar fashion, these reagents can be used to screen tissue cultures for contamination.

Because G-protein Chemokine Receptor (CCR5) is expressed in macrophages and memory T cells, G-protein Chemokine Receptor (CCR5) polynucleotides are useful as hybridization probes for differential identification of the tissue(s) or cell type(s) present in a biological sample. Similarly, polypeptides and antibodies directed to G-protein Chemokine Receptor (CCR5) polypeptides are useful to provide immunological probes for differential identification of the tissue(s) or cell type(s). In addition, for a number of diseases, disorders, and/or conditions of the above tissues or cells, or in which these cells play a role, significantly higher or lower levels of G-protein Chemokine Receptor (CCR5) gene expression may be detected in certain tissues (e.g., cancerous and wounded tissues) or bodily fluids (e.g., serum, plasma, urine, synovial fluid or spinal fluid) taken from an individual having such a disorder, relative to a "standard" G-protein Chemokine Receptor (CCR5) gene expression level, i.e., the G-protein Chemokine Receptor (CCR5) expression level in healthy tissue from an individual not having the immune system-related disorder.

Thus, the invention provides a diagnostic method of a disorder, which involves: (a) assaying G-protein Chemokine Receptor (CCR5) gene expression level in cells or body fluid of an individual; (b) comparing the G-protein Chemokine Receptor (CCR5) gene expression level with a standard G-protein Chemokine Receptor (CCR5) gene expression level, whereby an increase or decrease in the assayed G-protein Chemokine Receptor (CCR5) gene expression level compared to the standard expression level is indicative of disorder in the immune system or related to the immune system.

In a further embodiment, the invention provides a method of using G-protein Chemokine Receptor (CCR5) polynucleotides, or fragments or variants thereof as a vaccine to elicit an immune response to G-protein Chemokine Receptor. In a preferred embodiment, the invention provides a method of using G-protein Chemokine Receptor (CCR5) polynucleotides, or fragments or variants thereof as a DNA vaccine to elicit a humoral (antibody-mediated) immune response to G-protein Chemokine Receptor. In other highly preferred embodiments, the invention provides a method of using G-protein Chemokine Receptor (CCR5) polynucleotides comprising the nucleotide sequence of one or more extracellular loops of G-protein Chemokine Receptor (CCR5) (i.e., amino acids 89–102, 167–195 and/or 261–274 of SEQ ID NO:2 or of the polypeptide encoded by the deposited clone (SEQ ID NO:22)) as a DNA vaccine to elicit immune response to G-protein Chemokine Receptor. In other highly preferred embodiments, the invention provides a method of using G-protein Chemokine Receptor (CCR5) polynucleotides comprising the nucleotide sequence of the first extracellular loop of G-protein Chemokine Receptor (CCR5) (i.e., amino acids 89–102 of SEQ ID NO:2 or of the polypeptide encoded by the deposited clone (SEQ ID NO:22)) as a DNA vaccine to elicit an immune response to G-protein Chemokine Receptor (CCR5). In other highly preferred embodiments, the invention provides a method of using G-protein Chemokine Receptor (CCR5) polynucleotides comprising the nucleotide sequence of the second extracellular loop of G-protein Chemokine Receptor (CCR5) (i.e., amino acids 167–195 of SEQ ID NO:2 or of the polypeptide encoded by the deposited clone (SEQ ID NO:22)) as a DNA vaccine to elicit an immune response to G-protein Chemokine Receptor (CCR5). In other highly preferred embodiments, the invention provides a method of using G-protein Chemokine Receptor (CCR5) polynucleotides comprising the nucleotide sequence of the third extracellular loop of G-protein Chemokine Receptor (CCR5) (i.e., 261–274 of SEQ ID NO:2 or of the polypeptide encoded by the deposited clone (SEQ ID NO:22)) as a DNA vaccine to elicit an immune response to G-protein Chemokine Receptor (CCR5).

In other highly preferred embodiments, the invention provides a method of using G-protein Chemokine Receptor (CCR5) polynucleotides comprising the nucleotide sequence of one or more extracellular loops of G-protein Chemokine Receptor (CCR5) (i.e., amino acids 89–102, 167–195 and/or 261–274 of SEQ ID NO:2 or of the polypeptide encoded by the deposited clone (SEQ ID NO:22)) as a DNA vaccine to elicit a humoral immune response to G-protein Chemokine Receptor. In other highly preferred embodiments, the invention provides a method of using C-protein Chemokine Receptor (CCR5) polynucleotides comprising the nucleotide sequence of the first extracellular loop of G-protein Chemokine Receptor (CCR5) (i.e., amino acids 89–102 of SEQ ID NO:2 or of the polypeptide encoded by the deposited clone (SEQ ID NO:22)) as a DNA vaccine to elicit a humoral immune response to G-protein Chemokine Receptor (CCR5). In other highly preferred embodiments, the invention provides a method of using G-protein Chemokine Receptor (CCR5) polynucleotides comprising the nucleotide sequence of the second extracellular loop of G-protein Chemokine Receptor (CCR5) (i.e., amino acids 167–195 of SEQ ID NO:2 or of the polypeptide encoded by the deposited clone (SEQ ID NO:22)) as a DNA vaccine to elicit a humoral immune response to G-protein Chemokine Receptor (CCR5). In other highly preferred embodiments, the invention provides a method of using G-protein Chemokine Receptor (CCR5) polynucleotides comprising the nucleotide sequence of the third extracellular loop of G-protein Chemokine Receptor (CCR5) (i.e., 261–274 of SEQ ID NO:2 or of the polypeptide encoded by the deposited clone (SEQ ID NO:22)) as a DNA vaccine to elicit a humoral immune response to G-protein Chemokine Receptor (CCR5).

In another embodiment, the present invention provides a DNA vaccine comprising, or alternatively consisting of, a G-protein Chemokine Receptor (CCR5) polynucleotide, or fragment or variant thereof. In another preferred embodiment, the present invention provides a DNA vaccine comprising, or alternatively consisting of, a G-protein Chemokine Receptor (CCR5) polynucleotide encoding the nucleotide sequence of one or more extracellular loops of G-protein Chemokine Receptor (CCR5) (i.e., amino acids 89–102, 167–195 and/or 261–274 of SEQ ID NO:2 or of the polypeptide encoded by the deposited clone (SEQ ID NO:22)). In another preferred embodiment, the present invention provides a DNA vaccine comprising, or alternatively consisting of, a G-protein Chemokine Receptor (CCR5) polynucleotide encoding the nucleotide sequence of the first extracellular loop of G-protein Chemokine Receptor (CCR5) (i.e., amino acids 89–102, of SEQ ID NO:2 or of the polypeptide encoded by the deposited clone (SEQ ID NO:22)). In another preferred embodiment, the present invention provides a DNA vaccine comprising, or alternatively consisting of, a G-protein Chemokine Receptor (CCR5) polynucleotide encoding the nucleotide sequence of the second extracellular loop of G-protein Chemokine Receptor (CCR5) (i.e., amino acids 167–195 of SEQ ID NO:2 or of the polypeptide encoded by the deposited clone (SEQ ID NO:22)). In another preferred embodiment, the present invention provides a DNA vaccine comprising, or alternatively consisting of, a G-protein Chemokine Receptor (CCR5) polynucleotide encoding the nucleotide sequence of the third extracellular loop of G-protein Chemokine Receptor (CCR5) (i.e., amino acids 261–274 of SEQ ID NO:2 or of the polypeptide encoded by the deposited clone (SEQ ID NO:22)).

In highly preferred embodiments, the vaccines described above are administered to an animal, including humans, to prevent viral infection. In even more highly preferred embodiments, the vaccines described above are administered to an animal, including humans, to prevent HIV infection. In still other highly preferred embodiments, the vaccines described above are administered to an animal, including humans, to prevent poxvirus infection. In still other highly preferred embodiments, the vaccines described above are administered to an animal, including humans, to prevent cytomegalovirus infection.

In the very least, the G-protein Chemokine Receptor (CCR5) polynucleotides can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of G-Protein Chemokine Receptor (CCR5) Polypeptides

G-protein Chemokine Receptor (CCR5) polypeptides can be used in numerous ways. The following description should be considered exemplary and utilizes known techniques.

G-protein Chemokine Receptor (CCR5) polypeptides can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying G-protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of G-protein Chemokine Receptor (CCR5) polypeptide in cells or body fluid of an individual; (b) comparing the level of gene expression with a standard gene expression level, whereby an increase or decrease in the assayed G-protein Chemokine Receptor (CCR5) polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, G-protein Chemokine Receptor (CCR5) polypeptides can be used to treat, prevent, and/or diagnose disease. For example, patients can be administered G-protein Chemokine Receptor (CCR5) polypeptides in an effort to replace absent or decreased levels of the G-protein Chemokine Receptor (CCR5) polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to G-protein Chemokine Receptor (CCR5) polypeptides can also be used to treat, prevent, and/or diagnose disease. For example, administration of an antibody directed to a G-protein Chemokine Receptor (CCR5) polypeptide can bind and reduce overproduction of the polypeptide. Similarly, administration of an antibody can activate the polypeptide, such as by binding to a polypeptide bound to a membrane (receptor).

In a further embodiment, the invention provides a method of using G-protein Chemokine Receptor (CCR5) polypeptides, or fragments or variants as a vaccine to elicit an immune response to G-protein Chemokine Receptor. In a preferred embodiment, the invention provides a method of using G-protein Chemokine Receptor (CCR5) polypeptides, or fragments or variants thereof as a vaccine to elicit a humoral (antibody-mediated) immune response to G-protein Chemokine Receptor. In other highly preferred embodiments, the invention provides a method of using G-protein Chemokine Receptor (CCR5) polypeptides comprising the amino acid sequence of one or more extracellular loops of G-protein Chemokine Receptor (CCR5) (i.e., amino acids 89–102, 167–195 and/or 261–274 of SEQ ID NO:2 or of the polypeptide encoded by the deposited clone (SEQ ID NO:22)) as a vaccine to elicit an immune response to G-protein Chemokine Receptor. In other highly preferred embodiments, the invention provides a method of using G-protein Chemokine Receptor (CCR5) polypeptides comprising the amino acid sequence of the first extracellular loop of G-protein Chemokine Receptor (CCR5) (i.e., amino acids 89–102 of SEQ ID NO:2 or of the polypeptide encoded by the deposited clone (SEQ ID NO:22)) as a vaccine to elicit an immune response to G-protein Chemokine Receptor (CCR5). In other highly preferred embodiments, the invention provides a method of using G-protein Chemokine Receptor (CCR5) polypeptides comprising the amino acid sequence of the second extracellular loop of G-protein Chemokine Receptor (CCR5) (i.e., amino acids 167–195 of SEQ ID NO:2 or of the polypeptide encoded by the deposited clone (SEQ ID NO:22)) as a vaccine to elicit an immune response to G-protein Chemokine Receptor (CCR5). In other highly preferred embodiments, the invention provides a method of using G-protein Chemokine Receptor (CCR5) polypeptides comprising the amino acid sequence of the third extracellular loop of G-protein Chemokine Receptor (CCR5) (i.e., 261–274 of SEQ ID NO:2 or of the polypeptide encoded by the deposited clone (SEQ ID NO:22)) as a vaccine to elicit an immune response to G-protein Chemokine Receptor (CCR5).

In other highly preferred embodiments, the invention provides a method of using G-protein Chemokine Receptor (CCR5) polypeptides comprising the amino acid sequence of one or more extracellular loops of G-protein Chemokine Receptor (CCR5) (i.e., amino acids 89–102, 167–195 and/or 261–274 of SEQ ID NO:2 or of the polypeptide encoded by the deposited clone (SEQ ID NO:22)) as a vaccine to elicit a humoral immune response to G-protein Chemokine Receptor. In other highly preferred embodiments, the invention provides a method of using G-protein Chemokine Receptor (CCR5) polypeptides comprising the amino acid sequence of the first extracellular loop of G-protein Chemokine Receptor (CCR5) (i.e., amino acids 89–102 of SEQ ID NO:2 or of the polypeptide encoded by the deposited clone (SEQ ID NO:22)) as a vaccine to elicit a humoral immune response to G-protein Chemokine Receptor (CCR5). In other highly preferred embodiments, the invention provides a method of using G-protein Chemokine Receptor (CCR5) polypeptides comprising the amino acid sequence of the second extracellular loop of G-protein Chemokine Receptor (CCR5) (i.e., amino acids 167–195 of SEQ ID NO:2 or of the polypeptide encoded by the deposited clone (SEQ ID NO:22)) as a vaccine to elicit a humoral immune response to G-protein Chemokine Receptor (CCR5). In other highly preferred embodiments, the invention provides a method of using G-protein Chemokine Receptor (CCR5) polypeptides comprising the amino acid sequence of the third extracellular loop of G-protein Chemokine Receptor (CCR5) (i.e., 261–274 of SEQ ID NO:2 or of the polypeptide encoded by the deposited clone (SEQ ID NO:22)) as a vaccine to elicit a humoral immune response to G-protein Chemokine Receptor (CCR5).

In another embodiment, the present invention provides a vaccine comprising, or alternatively consisting of, a G-protein Chemokine Receptor (CCR5) polypeptide, or fragment or variant thereof. In another preferred embodiment, the present invention provides a vaccine comprising, or alternatively consisting of, a G-protein Chemokine Receptor (CCR5) polypeptide encoding the amino acid sequence of one or more extracellular loops of G-protein Chemokine Receptor (CCR5) (i.e., amino acids 89–102, 167–195 and/or 261–274 of SEQ ID NO:2 or of the polypeptide encoded by the deposited clone (SEQ ID NO:22)). In another preferred embodiment, the present invention provides a vaccine comprising, or alternatively consisting of, a G-protein Chemokine Receptor (CCR5) polypeptide encoding the amino acid sequence of the first extracellular loop of G-protein Chemokine Receptor (CCR5) (i.e., amino acids 89–102, of SEQ ID NO:2 or of the polypeptide encoded by the deposited clone (SEQ ID NO:22)). In another preferred embodiment, the present invention provides a vaccine comprising, or alternatively consisting of, a G-protein Chemokine Receptor (CCR5) polypeptide encoding the amino acid sequence of the second extracellular loop of G-protein Chemokine Receptor (CCR5) (i.e., amino acids 167–195 of SEQ ID NO:2 or of the polypeptide encoded by the deposited clone (SEQ ID NO:22)). In another preferred embodiment, the present invention provides a vaccine comprising, or alternatively consisting of, a G-protein Chemokine Receptor (CCR5) polypeptide encoding the amino acid sequence of the third extracellular loop of G-protein Chemokine Receptor (CCR5) (i.e., amino acids 261–274 of SEQ ID NO:2 or of the polypeptide encoded by the deposited clone (SEQ ID NO:22)).

In highly preferred embodiments, the vaccines described above are administered to an animal, including humans, to prevent viral infection. In even more highly preferred embodiments, the vaccines described above are administered to an animal, including humans, to prevent HIV infection. In still other highly preferred embodiments, the vaccines described above are administered to an animal, including humans, to prevent poxvirus infection. In still other highly preferred embodiments, the vaccines described above are administered to an animal, including humans, to prevent cytomegalovirus infection.

At the very least, the G-protein Chemokine Receptor (CCR5) polypeptides can be used as molecular weight markers on SDS-PAGE gels or on molecular sieve gel filtration columns using methods well known to those of skill in the art. G-protein Chemokine Receptor (CCR5) polypeptides can also be used to raise antibodies, which in turn are used to measure protein expression from a recombinant cell, as a way of assessing transformation of the host cell. Moreover, G-protein Chemokine Receptor (CCR5) polypeptides can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of the G-protein Chemokine Receptor (CCR5) polypeptide of the present invention. This method requires a polynucleotide which codes for a G-protein Chemokine Receptor (CCR5) polypeptide operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a G-protein Chemokine Receptor (CCR5) polynucleotide ex vivo, with the engineered cells then being provided to a patient to be treated with the polypeptide. Such methods are well-known in the art. For example, see Belldegrun, A., et al., J. Natl. Cancer Inst. 85: 207–216 (1993); Ferrantini, M. et al., Cancer Research 53: 1107–1112 (1993); Ferrantini, M. et al., J. Immunology 153: 4604–4615 (1994); Kaido, T., et al., Int. J. Cancer 60: 221–229 (1995); Ogura, H., et al., Cancer Research 50: 5102–5106 (1990); Santodonato, L., et al., Human Gene Therapy 7:1–10 (1996); Santodonato, L., et al., Gene Therapy 4:1246–1255 (1997); and Zhang, J.-F. et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the G-protein Chemokine Receptor (CCR5) polynucleotide constructs can be delivered by any method that delivers injectable materials to the cells of an animal, such as, injection into the interstitial space of tissues (heart, muscle, skin, lung, liver, and the like). The G-protein Chemokine Receptor (CCR5) polynucleotide constructs may be delivered in a pharmaceutically acceptable liquid or aqueous carrier.

In one embodiment, the G-protein Chemokine Receptor (CCR5) polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the G-protein Chemokine Receptor (CCR5) polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The G-protein Chemokine Receptorpolynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of G-protein Chemokine Receptor (CCR5) polynucleotide sequence. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for G-protein Chemokine Receptor.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The G-protein Chemokine Receptor (CCR5) polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked G-protein Chemokine Receptor (CCR5) DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called “gene guns”. These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the G-protein Chemokine Receptor (CCR5) polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA (1987) 84:7413–7416, which is herein incorporated by reference); mRNA (Malone et al., Proc. Natl. Acad. Sci. USA (1989) 86:6077–6081, which is herein incorporated by reference); and purified transcription factors (Debs et al., J. Biol. Chem. (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl Acad. Sci. USA (1987) 84:7413–7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., Proc. Natl. Acad. Sci. USA 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology (1983), 101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta (1975) 394:483; Wilson et al., Cell (1979) 17:77); ether injection (Deamer, D. and Bangham, A., Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); detergent dialysis (Enoch, H. and Strittmatter, P., Proc. Natl. Acad. Sci. USA (1979) 76:145); and reverse-phase evaporation (REV) (Fraley et al., J. Biol. Chem. (1980) 255: 10431; Szoka, F. and Papahadjopoulos, D., Proc. Natl. Acad. Sci. USA (1978) 75:145; Schaefer-Ridder et al., Science (1982) 215:166), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding G-protein Chemokine Receptor. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding G-protein Chemokine Receptor. Such retroviral vector particles then may be employed, to transduce eukaryotic cells, either in vitro or in vivo. The transduced eukaryotic cells will express G-protein Chemokine Receptor.

In certain other embodiments, cells are engineered, ex vivo or in vivo, with G-protein Chemokine Receptor (CCR5) polynucleotide contained in an adenovirus vector. Adenovirus can be manipulated such that it encodes and expresses G-protein Chemokine Receptor (CCR5), and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) Am. Rev. Respir. Dis,109:233–238). Finally, adenovirus mediated gene transfer has been demonstrated in a number of instances including transfer of alpha-1-antitrypsin and CFTR to the lungs of cotton rats (Rosenfeld, M. A. et al. (1991) Science 252:431–434; Rosenfeld et al., (1992) Cell 68:143–155). Furthermore, extensive studies to attempt to establish adenovirus as a causative agent in human cancer were uniformly negative (Green, M. et al. (1979) Proc. Natl. Acad. Sci. USA 76:6606).

Suitable adenoviral vectors useful in the present invention are described, for example, in Kozarsky and Wilson, Curr. Opin. Genet. Devel. 3:499–503 (1993); Rosenfeld et al., Cell 68:143–155 (1992); Engelhardt et al., Human Genet. Ther. 4:759–769 (1993); Yang et al., Nature Genet. 7:362–369 (1994); Wilson et al., Nature 365:691–692 (1993); and U.S. Pat. No. 5,652,224, which are herein incorporated by reference. For example, the adenovirus vector Ad2 is useful and can be grown in human 293 cells.

These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The G-protein Chemokine Receptor (CCR5) polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the G-protein Chemokine Receptor (CCR5) polynucleotide construct. These viral particles are then used to transduce eukaryotic cells, either ex vivo or in vivo. The transduced cells will contain the G-protein Chemokine Receptor (CCR5) polynucleotide construct integrated into its genome, and will express G-protein Chemokine Receptor.

Another method of gene therapy involves operably associating heterologous control regions and endogenous polynucleotide sequences (e.g. encoding G-protein Chemokine Receptor) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the G-protein Chemokine Receptor (CCR5) desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous G-protein Chemokine Receptor (CCR5) sequence is placed under the control of the promoter. The promoter then drives the expression of the endogenous G-protein Chemokine Receptor (CCR5) sequence.

The polynucleotides encoding G-protein Chemokine Receptor (CCR5) may be administered along with other polynucleotides encoding an angiogenic protein. Examples of angiogenic proteins include, but are not limited to, acidic and basic fibroblast growth factors, VEGF-1, VEGF-2, VEGF-3, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

In one preferred embodiment, the polynucleotide encoding G-protein Chemokine Receptor (CCR5) contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189: 11277–11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities of G-Protein Chemokine Receptor

G-protein Chemokine Receptor (CCR5) polynucleotides or polypeptides, or agonists or antagonists of G-protein Chemokine Receptor (CCR5), can be used in assays to test for one or more biological activities. If G-protein Chemokine Receptor (CCR5) polynucleotides or polypeptides, or agonists or antagonists of G-protein Chemokine Receptor (CCR5), do exhibit activity in a particular assay, it is likely that G-protein Chemokine Receptor (CCR5) may be involved in the diseases associated with the biological activity. Therefore, G-protein Chemokine Receptor (CCR5) could be used to treat, prevent, and/or diagnose the associated disease.

Ligands of the G-protein Chemokine Receptor (CCR5) include MIP-1alpha, MIP-1beta, MCP-1, MCP-2, MCP-3, MCP-4, RANTES, and Eotaxin. The G-protein Chemokine Receptor (CCR5) is also a major co-receptor for HIV, and may be also be recognized by other infectious agents, such as other viruses, to allow entry into the cell. Thus, G-protein Chemokine Receptor (CCR5) polynucleotides, polypeptides, agonists and antagonists thereof are useful for treating, preventing and diagnosing diseases associated with any of the above ligands, such as the diseases disclosed herein. In highly preferred embodiments, G-protein Chemokine Receptor (CCR5) polynucleotides, polypeptides, agonists and antagonists thereof are useful for treating, preventing and diagnosing HIV infection and/or conditions associated with HIV infection, as described in the section entitled "Treatment and prevention of HIV Infection."

G-protein Chemokine Receptor (CCR5) is predominantly expressed on monocytes and T-cells. Expression of G-protein Chemokine Receptor (CCR5) is found on microglial, dendritic and some hematopoietic stem cells. Activation of G-protein Chemokine Receptor (CCR5) on macrophages and lymphocytes by G-protein Chemokine Receptor (CCR5) ligands (especially, RANTES, MIP-1beta and MIP-1alpha) primarily results in chemoattraction of these cell types to sites of inflammation, often sites of infection. G-protein Chemokine Receptor (CCR5) may also be involved in the induction of chemotaxis in NK cells, eosinophils and basophils. Activation of G-protein Chemokine Receptor (CCR5) on macrophages and lymphocytes by G-protein Chemokine Receptor (CCR5) ligands (especially, RANTES, MIP-1beta and MIP-1alpha) can promote interactions between T-cells and antigen presenting cells (e.g., dendritic cells, macrophages and B cells.) G-protein Chemokine Receptor (CCR5) may also be involved in cell sticking and migration through blood vessels via adhesion molecules in transit to site of inflammation. Accordingly, compositions of the invention (including polynucleotides, polypeptides and antibodies of the invention, and fragments and variants thereof) may be used in the diagnosis, prognosis, prevention, and/or treatment of diseases and/or disorders associated with defects in the biological activities of G-protein Chemokine Receptor (CCR5) such as those described above.

In preferred embodiments, compositions of the invention (including polynucleotides, polypeptides and antibodies of the invention, and fragments and variants thereof) may be used in the diagnosis, prognosis, prevention, and/or treatment of diseases and/or disorders relating to immune function (e.g., viral infection (especially HIV infection, poxvirus infection and/or cytomegalovirus infection); autoimmune diseases (such as Rheumatoid Arthritis, Grave's disease and Multiple Sclerosis); immune cell chemotaxis; inflammatory conditions; and/or as described in "Immune Activity") and neoplastic disorders such as those described under "Hyperproliferative Disorders" below).

G-protein Chemokine Receptor (CCR5) polynucleotides, polypeptides, agonists and antagonists (including antibodies) of the invention are useful in the diagnosis, prognosis, prevention, and/or treatment of diseases and/or disorders associated with activities that include, but are not limited to, immune cell chemoattraction, immune cell activation, antigen presentation, inflammation, and viral infection.

More generally, G-protein Chemokine Receptor (CCR5) polynucleotides, polypeptides, agonists and antagonists (including antibodies) of the invention may be useful for the diagnosis, prognosis, prevention, and/or treatment of diseases and/or disorders described below.

Treatment and Prevention of HIV Infection. As CCR5 is HIV co-receptor for macrophage tropic HIV it has major impact on HIV infection and disease progression, especially early in HIV infection when HIV is predominantly of R5 macrophage-tropic strains. Therefore, G-protein Chemokine Receptor (CCR5) polynucleotides or polypeptides, or agonists (including antibodies) or antagonists (including antibodies) of G-protein Chemokine Receptor (CCR5), may be used to diagnose, treat, prevent, and/or ameliorate HIV infection.

In specific embodiments, G-protein Chemokine Receptor (CCR5) polynucleotides or polypeptides, or agonists (including antibodies) or antagonists (including antibodies) of G-protein Chemokine Receptor (CCR5), may be used to diagnose, treat, prevent, and/or ameliorate diseases, disorders or conditions associated with HIV infection. Conditions associated with HIV infection include, but are not limited to, *Pneumocystis carinii* pneumonia, Wasting syndrome, Kaposi's sarcoma, Esophageal candidiasis, and pulmonary Candidiasis, disseminated or extrapulmonary *Mycobacterium avium-intracellulare* complex, disseminated or extrapulmonary *Mycobacterium kansasii*, Cytomegalovirus disease, Cytomegalovirus retinitis, HIV encephalopathy, Herpes simplex disease, extrapulmonary Cryptococcosis, Toxoplasmosis of brain, chronic Cryptosporidiosis, chronic intestinal Cryptosporidiosis, immunoblastic lymphoma, extrapulmonary *Mycobacterium tuberculosis*, pulmonary *Mycobacterium tuberculosis*, Mycobacterial disease, extrapulmonary Mycobacterial disease, Burkitt's lymphoma, progressive multifocal leukoencephalopathy, primary brain lymphoma, chronic Isosporiasis, chronic intestinal Isosporiasis, disseminated or extrapulmonary Coccidioidomycosis, *Salmonella septicemia*, multiple or recurrent bacterial infections, invasive cervical carcinoma, disseminated or extrapulmonary Histoplasmosis, Lymphoid interstitial pneumonia, pulmonary lymphoid hyperplasia, recurrent pneumonia, severe immunosuppression and/or AIDS dementia.

In preferred embodiments, G-protein Chemokine Receptor (CCR5) polynucleotides or polypeptides, or agonists (including antibodies) or antagonists (including antibodies) of G-protein Chemokine Receptor (CCR5), may be used to diagnose, treat, prevent, and/or ameliorate opportunistic infections (e.g., Herpes virus infection, *Mycobacterium Tuberculosis* infection, or cytomegalovirus infection) associated with HIV infection.

In preferred embodiments, G-protein Chemokine Receptor (CCR5) polynucleotides or polypeptides, or agonists (including antibodies) or antagonists (including antibodies) of G-protein Chemokine Receptor (CCR5), may be used to diagnose, treat, prevent, and/or ameliorate opportunistic *Pneumocystis carinii* infection associated with HIV infection.

In preferred embodiments, G-protein Chemokine Receptor (CCR5) polynucleotides or polypeptides, or agonists (including antibodies) or antagonists (including antibodies) of G-protein Chemokine Receptor (CCR5), may be used to diagnose, treat, prevent, and/or ameliorate Kaposi's sarcoma associated with HIV infection.

In other preferred embodiments, G-protein Chemokine Receptor (CCR5) polynucleotides or polypeptides, or agonists (including antibodies) or antagonists (including antibodies) of G-protein Chemokine Receptor (CCR5), may be used to diagnose, treat, prevent, and/or ameliorate the early stages of HIV infection.

In other embodiments, G-protein Chemokine Receptor (CCR5) polynucleotides or polypeptides, or agonists (including antibodies) or antagonists (including antibodies) of G-protein Chemokine Receptor (CCR5), may be used to diagnose, treat, prevent, and/or ameliorate the late stages of HIV infection.

In other embodiments, G-protein Chemokine Receptor (CCR5) polynucleotides or polypeptides, or agonists (including antibodies) or antagonists (including antibodies) of G-protein Chemokine Receptor (CCR5), may be used to diagnose, treat, prevent, and/or ameliorate the late stages of HIV infection.

In still other embodiments, G-protein Chemokine Receptor (CCR5) polynucleotides or polypeptides, or agonists (including antibodies) or antagonists (including antibodies) of G-protein Chemokine Receptor (CCR5) are used as a prophylatic to prevent HIV infection in persons who have an HIV-infected sexual partner or persons with reason to believe they have been exposed to HIV, (e.g., persons who have been stuck with a needle that had previously been in contact with the biological fluid of another individual (or animal), or rape victims).

In still other embodiments, G-protein Chemokine Receptor (CCR5) polynucleotides or polypeptides, or agonists (including antibodies) or antagonists (including antibodies) of G-protein Chemokine Receptor (CCR5) are used as a prophylatic to prevent maternal-fetal transmission of HIV.

Immune Activity. G-protein Chemokine Receptor (CCR5) polynucleotides or polypeptides, or agonists or antagonists of G-protein Chemokine Receptor (CCR5), may be useful in treating diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, G-protein Chemokine Receptor (CCR5) polynucleotides or polypeptides, or agonists or antagonists of G-protein Chemokine Receptor (CCR5), can be used as a marker or detector of a particular immune system disease or disorder.

The G-protein Chemokine Receptor (CCR5) polynucleotides and/or polypeptides of the present invention and/or agonists or antagonists thereof may be used to modulate hematopoietic activity (the formation of blood cells). For example, the G-protein Chemokine Receptor (CCR5) polynucleotides and/or polypeptides of the present invention and/or agonists or antagonists thereof may be used to increase the quantity of all or subsets of blood cells, such as, for example, erythrocytes, lymphocytes (B or T cells), myeloid cells (e.g., basophils, eosinophils, neutrophils, mast cells, macrophages) and platelets. The ability to decrease the quantity of blood cells or subsets of blood cells may be useful in the prevention, detection, diagnosis and/or treatment of anemias and leukopenias described below. Alternatively, the G-protein Chemokine Receptor (CCR5) polynucleotides and/or polypeptides of the present invention and/or agonists or antagonists thereof may be used to decrease the quantity of all or subsets of blood cells, such as, for example, erythrocytes, lymphocytes (B or T cells), myeloid cells (e.g., basophils, eosinophils, neutrophils, mast cells, macrophages) and platelets. The ability to decrease the quantity of blood cells or subsets of blood cells may be useful in the prevention, detection, diagnosis and/or treatment of leukocytoses, such as, for example eosinophilia.

G-protein Chemokine Receptor (CCR5) polynucleotides or polypeptides, or agonists or antagonists of G-protein Chemokine Receptor (CCR5), may be useful in treating, preventing, and/or diagnosing diseases, disorders, and/or conditions of hematopoietic cells. G-protein Chemokine Receptor (CCR5) polynucleotides or polypeptides, or agonists or antagonists of G-protein Chemokine Receptor (CCR5), could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to, blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, leukopenia, neutropenia, anemia or hemoglobinuria. Alternatively, G-protein Chemokine Receptor (CCR5) polynucleotides and/or polypeptides of the invention, and/or agonists or antagonists thereof could be used to increase differentiation and proliferation of hematopoietic cells, including the pluripotent stem cells, in an effort to treat or prevent those diseases, disorders, and/or conditions associated with an increase in certain (or many) types of hematopoietic cells, including but not limited to, histiocytosis.

In another embodiment, a G-protein Chemokine Receptor (CCR5) polypeptide of the invention, or polynucleotides, antibodies, agonists, or antagonists corresponding to that G-protein Chemokine Receptor (CCR5) polypeptide, may be used to treat diseases and disorders of the immune system and/or to inhibit or enhance an immune response generated by cells associated with the tissue(s) in which the polypeptide of the invention is expressed.

G-protein Chemokine Receptor (CCR5) polynucleotides and/or polypeptides of the invention, and/or agonists or antagonists thereof may be useful in treating, preventing, diagnosing, and/or prognosing immunodeficiencies, including both congenital and acquired immunodeficiencies. Examples of B cell immunodeficiencies in which immunoglobulin levels B cell function and/or B cell numbers are decreased include: X-linked agammaglobulinemia (Bruton's disease), X-linked infantile agammaglobulinemia, X-linked immunodeficiency with hyper IgM, non X-linked immunodeficiency with hyper IgM, X-linked lymphoproliferative syndrome (XLP), agammaglobulinemia including congenital and acquired agammaglobulinemia, adult onset agammaglobulinemia, late-onset agammaglobulinemia, dysgammaglobulinemia, hypogammaglobulinemia, unspecified hypogammaglobulinemia, recessive agammaglobulinemia (Swiss type), Selective IgM deficiency, selective IgA deficiency, selective IgG subclass deficiencies, IgG subclass deficiency (with or without IgA deficiency), Ig deficiency with increased IgM, IgG and IgA deficiency with increased IgM, antibody deficiency with normal or elevated Igs, Ig heavy chain deletions, kappa chain deficiency, B cell lymphoproliferative disorder (BLPD), common variable immunodeficiency (CVID), common variable immunodeficiency (CVI) (acquired), and transient hypogammaglobulinemia of infancy.

In specific embodiments, ataxia-telangiectasia or conditions associated with ataxia-telangiectasia are treated, prevented, diagnosed, and/or prognosing using the polypeptides or polynucleotides of the invention, and/or agonists or antagonists thereof.

Examples of congenital immunodeficiencies in which T cell and/or B cell function and/or number is decreased include, but are not limited to: DiGeorge anomaly, severe combined immunodeficiencies (SCID) (including, but not limited to, X-linked SCID, autosomal recessive SCID, adenosine deaminase deficiency, purine nucleoside phosphorylase (PNP) deficiency, Class II MHC deficiency (Bare lymphocyte syndrome), Wiskott-Aldrich syndrome, and ataxia telangiectasia), thymic hypoplasia, third and fourth pharyngeal pouch syndrome, 22q11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity.

In specific embodiments, DiGeorge anomaly or conditions associated with DiGeorge anomaly are treated, prevented, diagnosed, and/or prognosed using polypeptides or polynucleotides of the invention, or antagonists or agonists thereof.

Other immunodeficiencies that may be treated, prevented, diagnosed, and/or prognosed using polypeptides or polynucleotides of the invention, and/or agonists or antagonists thereof, include, but are not limited to, chronic granulomatous disease, Chédiak-Higashi syndrome, myeloperoxidase deficiency, leukocyte glucose-6-phosphate dehydrogenase deficiency, X-linked lymphoproliferative syndrome (XLP), leukocyte adhesion deficiency, complement component deficiencies (including C1, C2, C3, C4, C5, C6, C7, C8 and/or C9 deficiencies), reticular dysgenesis, thymic alymphoplasia-aplasia, immunodeficiency with thymoma, severe congenital leukopenia, dysplasia with immunodeficiency, neonatal neutropenia, short limbed dwarfism, and Nezelof syndrome-combined immunodeficiency with Igs.

In a preferred embodiment, the immunodeficiencies and/or conditions associated with the immunodeficiencies recited above are treated, prevented, diagnosed and/or prognosed using G-protein Chemokine Receptor (CCR5) polynucleotides and/or polypeptides of the invention, and/or agonists or antagonists thereof.

In a preferred embodiment G-protein Chemokine Receptor (CCR5) polynucleotides and/or polypeptides of the invention, and/or agonists or antagonists thereof could be used as an agent to boost immunoresponsiveness among immunodeficient individuals. In specific embodiments, G-protein Chemokine Receptor (CCR5) polynucleotides and/or polypeptides of the invention, and/or agonists or antagonists thereof could be used as an agent to boost immunoresponsiveness among B cell and/or T cell immunodeficient individuals.

Moreover, G-protein Chemokine Receptor (CCR5) polynucleotides or polypeptides, or agonists or antagonists of G-protein Chemokine Receptor (CCR5), can also be used to modulate hemostatic (the stopping of bleeding) or thrombolytic activity (clot formation). For example, by increasing hemostatic or thrombolytic activity, G-protein Chemokine Receptor (CCR5) polynucleotides or polypeptides, or agonists or antagonists of G-protein Chemokine Receptor (CCR5), could be used to treat or prevent blood coagulation diseases, disorders, and/or conditions (e.g., afibrinogenemia, factor deficiencies), blood platelet diseases, disorders, and/or conditions (e.g. thrombocytopenia), or wounds resulting from trauma, surgery, or other causes. Alternatively, G-protein Chemokine Receptor (CCR5) polynucleotides or polypeptides, or agonists or antagonists of G-protein Chemokine Receptor (CCR5), that can decrease hemostatic or thrombolytic activity could be used to inhibit or dissolve clotting. These molecules could be important in the treatment or prevention of heart attacks (infarction), strokes, or scarring.

G-protein Chemokine Receptor (CCR5) polynucleotides or polypeptides, or agonists or antagonists of G-protein Chemokine Receptor (CCR5), may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of G-protein Chemokine Receptor (CCR5) polynucleotides or polypeptides, or agonists or antagonists of G-protein Chemokine Receptor (CCR5), that can inhibit an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by G-protein Chemokine Receptor (CCR5) include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by G-protein Chemokine Receptor (CCR5) polynucleotides or polypeptides, or agonists or antagonists of G-protein Chemokine Receptor. Moreover, these molecules can be used to treat anaphylaxis, hypersensitivity to an antigenic molecule, or blood group incompatibility.

Additionally, G-protein Chemokine Receptor (CCR5) polypeptides or polynucleotides of the invention, and/or agonists or antagonists thereof, may be used to treat, prevent, diagnose and/or prognose IgE-mediated allergic reactions. Such allergic reactions include, but are not limited to, asthma, rhinitis, and eczema. In specific embodiments, G-protein Chemokine Receptor (CCR5) polynucleotides and/or polypeptides of the invention, and/or agonists or antagonists thereof may be used to modulate IgE concentrations in vitro or in vivo.

G-protein Chemokine Receptor (CCR5) polynucleotides or polypeptides, or agonists or antagonists of G-protein Chemokine Receptor (CCR5), may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of G-protein Chemokine Receptor (CCR5) polynucleotides or polypeptides, or agonists or antagonists of G-protein Chemokine Receptor (CCR5), that inhibits an immune response, particularly the proliferation, differentiation, or chemotaxis of T-cells, may be an effective therapy in preventing organ rejection or GVHD. In specific embodiments, polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing experimental allergic and hyperacute xenograft rejection.

Similarly, G-protein Chemokine Receptor (CCR5) polynucleotides or polypeptides, or agonists or antagonists of G-protein Chemokine Receptor (CCR5), may also be used to modulate inflammation. For example, since polypeptides, antibodies, or polynucleotides of the invention, and/or agonists or antagonists of the invention may inhibit the activation, proliferation and/or differentiation of cells involved in an inflammatory response, these molecules can be used to prevent and/or treat chronic and acute inflammatory conditions. Such inflammatory conditions include, but are not limited to, for example, inflammation associated with infection (e.g., septic shock, sepsis, or systemic inflammatory response syndrome), ischemia-reperfusion injury, endotoxin lethality, complement-mediated hyperacute rejection, nephritis, cytokine or chemokine induced lung injury, inflammatory bowel disease, Crohn's disease, over production of cytokines (e.g., TNF or IL-1.), respiratory disorders (e.g., asthma and allergy); gastrointestinal disorders (e.g., inflammatory bowel disease); cancers (e.g., gastric, ovarian, lung, bladder, liver, and breast); CNS disorders (e.g., multiple sclerosis; ischemic brain injury and/or stroke, traumatic brain injury, neurodegenerative disorders (e.g., Parkinson's disease and Alzheimer's disease); AIDS-related dementia; and prion disease); cardiovascular disorders (e.g., atherosclerosis, myocarditis, cardiovascular disease, and cardiopulmonary bypass complications); as well as many additional diseases, conditions, and disorders that are characterized by inflammation (e.g., hepatitis, rheumatoid arthritis, gout, trauma, pancreatitis, sarcoidosis, dermatitis, renal ischemia-reperfusion injury, Grave's disease, systemic lupus erythematosus, diabetes mellitus, and allogenic transplant rejection).

Because inflammation is a fundamental defense mechanism, inflammatory disorders can effect virtually any tissue of the body. Accordingly, polynucleotides, polypeptides, and antibodies of the invention, as well as agonists or antagonists thereof, have uses in the treatment of tissue-specific inflammatory disorders, including, but not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myosititis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, sclerochoroiditis, scrotitis, sinusitis, spondylitis, steatitis, stomatitis, synovitis, syringitis, tendonitis, tonsillitis, urethritis, and vaginitis.

In other embodiments, the G-protein Chemokine Receptor (CCR5) polynucleotides and/or polypeptides of the present invention and/or agonists or antagonists thereof may be useful as an agent to enhance the migration, phagocytosis, superoxide production, antibody dependent cellular cytotoxicity of neutrophils, eosionophils and macrophages.

In another embodiment, the G-protein Chemokine Receptor (CCR5) polynucleotides and/or polypeptides of the present invention and/or agonists or antagonists thereof may be useful in diagnosing, prognosing, preventing, and/or treating diseases and disorders characterized by or associated with increased or decreased numbers of white blood cells. Leukopenia occurs when the number of white blood cells decreases below normal. Leukopenias include, but are not limited to, neutropenia and lymphocytopenia. An increase in the number of white blood cells compared to normal is known as leukocytosis. The body generates increased numbers of white blood cells during infection. Thus, leukocytosis may simply be a normal physiological parameter that reflects infection. Alternatively, leukocytosis may be an indicator of injury or other disease such as cancer. Leokocytoses, include but are not limited to, eosinophilia, and accumulations of macrophages. In specific embodiments, the G-protein Chemokine Receptor (CCR5) polynucleotides and/or polypeptides of the present invention and/or agonists or antagonists thereof may be useful in diagnosing, prognosing, preventing, and/or treating leukopenia. In other specific embodiments, the G-protein Chemokine Receptor (CCR5) polynucleotides and/or polypeptides of the present invention and/or agonists or antagonists thereof may be useful in diagnosing, prognosing, preventing, and/or treating leukocytosis.

Leukopenia may be a generalized decreased in all types of white blood cells, or may be a specific depletion of particular types of white blood cells. Thus, in specific embodiments, the G-protein Chemokine Receptor (CCR5) polynucleotides and/or polypeptides of the present invention and/or agonists or antagonists thereof may be useful in diagnosing, prognosing, preventing, and/or treating decreases in neutrophil numbers, known as neutropenia. Neutropenias that may be diagnosed, prognosed, prevented, and/or treated by the G-protein Chemokine Receptor (CCR5) polynucleotides and/or polypeptides of the present invention and/or agonists or antagonists thereof include, but are not limited to, infantile genetic agranulocytosis, familial neutropenia, cyclic neutropenia, neutropenias resulting from or associated with dietary deficiencies (e.g., vitamin B 12 deficiency or folic acid deficiency), neutropenias resulting from or associated with drug treatments (e.g., antibiotic regimens such as penicillin treatment, sulfonamide treatment, anticoagulant treatment, anticonvulsant drugs, anti-thyroid drugs, and cancer chemotherapy), and neutropenias resulting from increased neutrophil destruction that may occur in association with some bacterial or viral infections, allergic disorders, autoimmune diseases, conditions in which an individual has an enlarged spleen (e.g., Felty syndrome, malaria and sarcoidosis), and some drug treatment regimens.

The G-protein Chemokine Receptor (CCR5) polynucleotides and/or polypeptides of the present invention and/or agonists or antagonists thereof may be useful in diagnosing, prognosing, preventing, and/or treating lymphocytopenias (decreased numbers of B and/or T lymphocytes), including, but not limited lymphocytopenias resulting from or associated with stress, drug treatments (e.g., drug treatment with corticosteroids, cancer chemotherapies, and/or radiation therapies), AIDS and/or other diseases such as, for example, cancer, rheumatoid arthritis, systemic lupus erythematosus, chronic infections, some viral infections and/or hereditary disorders (e.g., DiGeorge syndrome, Wiskott-Aldrich Syndrome, severe combined immunodeficiency, ataxia telangiectasia).

The G-protein Chemokine Receptor (CCR5) polynucleotides and/or polypeptides of the present invention and/or agonists or antagonists thereof may be useful in diagnosing, prognosing, preventing, and/or treating diseases and disorders associated with macrophage numbers and/or macrophage function including, but not limited to, Gaucher's disease, Niemann-Pick disease, Letterer-Siwe disease and Hand-Schuller-Christian disease.

In another embodiment, the G-protein Chemokine Receptor (CCR5) polynucleotides and/or polypeptides of the present invention and/or agonists or antagonists thereof may be useful in diagnosing, prognosing, preventing, and/or treating diseases and disorders associated with eosinophil numbers and/or eosinophil function including, but not limited to, idiopathic hypereosinophilic syndrome, eosinophilia-myalgia syndrome, and Hand-Schuller-Christian disease.

In yet another embodiment, the G-protein Chemokine Receptor (CCR5) polynucleotides and/or polypeptides of the present invention and/or agonists or antagonists thereof may be useful in diagnosing, prognosing, preventing, and/or treating leukemias and lymphomas including, but not limited to, acute lymphocytic (lymphoblastic) leukemia (ALL), acute myeloid (myelocytic, myelogenous, myeloblastic, or myelomonocytic) leukemia, chronic lymphocytic leukemia (e.g., B cell leukemias, T cell leukemias, Sezary syndrome, and Hairy cell leukemia), chronic myelocytic (myeloid, myelogenous, or granulocytic) leukemia, Hodgkin's lymphoma, non-hodgkin's lymphoma, Burkitt's lymphoma, and mycosis fungoides.

In other embodiments, polypeptides, antibodies, or polynucleotides of the invention, and/or agonists or antagonists thereof, are useful to diagnose, prognose, prevent, and/or treat immune complex diseases, including, but not limited to, serum sickness, post streptococcal glomerulonephritis, polyarteritis nodosa, and immune complex-induced vasculitis.

Polypeptides, antibodies, polynucleotides and/or agonists or antagonists of the invention can be used to treat, detect, and/or prevent infectious agents. For example, by increasing the immune response, particularly increasing the proliferation activation and/or differentiation of B and/or T cells, infectious diseases may be treated, detected, and/or prevented. The immune response may be increased by either enhancing an existing immune response, or by initiating a new immune response. Alternatively, G-protein Chemokine Receptor (CCR5) polynucleotides and/or polypeptides of the invention, and/or agonists or antagonists thereof may also directly inhibit the infectious agent (refer to section of application listing infectious agents, etc), without necessarily eliciting an immune response.

In another embodiment, G-protein Chemokine Receptor (CCR5) polynucleotides and/or polypeptides of the invention, and/or agonists or antagonists thereof are used as a vaccine adjuvant that enhances immune responsiveness to an antigen. In a specific embodiment, G-protein Chemokine Receptor (CCR5) polynucleotides and/or polypeptides of the invention, and/or agonists or antagonists thereof are used as an adjuvant to enhance tumor-specific immune responses.

In another specific embodiment, G-protein Chemokine Receptor (CCR5) polynucleotides and/or polypeptides of the invention, and/or agonists or antagonists thereof are used as an adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, respiratory syncytial virus, Dengue, rotavirus, Japanese B encephalitis, influenza A and B, parainfluenza, measles, cytomegalovirus, rabies, Junin, Chikungunya, Rift Valley Fever, herpes simplex, and yellow fever.

In another specific embodiment, G-protein Chemokine Receptor (CCR5) polynucleotides and/or polypeptides of the invention, and/or agonists or antagonists thereof are used as an adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B.

In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae*, Group B *streptococcus, Shigella* spp., Enterotoxigenic *Escherichia coli*, Enterohemorrhagic *E. coli*, and *Borrelia burgdorferi.*

In another specific embodiment, G-protein Chemokine Receptor (CCR5) polynucleotides and/or polypeptides of the invention, and/or agonists or antagonists thereof are used as an adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to Plasmodium (malaria) or Leishmania.

In another specific embodiment, G-protein Chemokine Receptor (CCR5) polynucleotides and/or polypeptides of the invention, and/or agonists or antagonists thereof may also be employed to treat infectious diseases including silicosis, sarcoidosis, and idiopathic pulmonary fibrosis; for example, by preventing the recruitment and activation of mononuclear phagocytes.

In another specific embodiment, G-protein Chemokine Receptor (CCR5) polynucleotides and/or polypeptides of the invention, and/or agonists or antagonists thereof are used as an antigen for the generation of antibodies to inhibit or enhance immune mediated responses against polypeptides of the invention.

In one embodiment, G-protein Chemokine Receptor (CCR5) polynucleotides and/or polypeptides of the invention, and/or agonists or antagonists thereof are administered to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production and immunoglobulin class switching (e.g., IgG, IgA, IgM, and IgE), and/or to increase an immune response.

In another specific embodiment, G-protein Chemokine Receptor (CCR5) polynucleotides and/or polypeptides of the invention, and/or agonists or antagonists thereof are used as a stimulator of B cell responsiveness to pathogens.

In another specific embodiment, G-protein Chemokine Receptor (CCRS) polynucleotides and/or polypeptides of the invention, and/or agonists or antagonists thereof are used as an activator of T cells.

In another specific embodiment, G-protein Chemokine Receptor (CCR5) polynucleotides and/or polypeptides of the invention, and/or agonists or antagonists thereof are used as an agent that elevates the immune status of an individual prior to their receipt of immunosuppressive therapies.

In another specific embodiment, G-protein Chemokine Receptor (CCR5) polynucleotides and/or polypeptides of the invention, and/or agonists or antagonists thereof are used as an agent to induce higher affinity antibodies.

In another specific embodiment, G-protein Chemokine Receptor (CCR5) polynucleotides and/or polypeptides of the invention, and/or agonists or antagonists thereof are used as an agent to increase serum immunoglobulin concentrations.

In another specific embodiment, G-protein Chemokine Receptor (CCR5) polynucleotides and/or polypeptides of the invention, and/or agonists or antagonists thereof are used as an agent to accelerate recovery of immunocompromised individuals.

In another specific embodiment, G-protein Chemokine Receptor (CCR5) polynucleotides and/or polypeptides of the invention, and/or agonists or antagonists thereof are used as an agent to boost immunoresponsiveness among aged populations and/or neonates.

In another specific embodiment, G-protein Chemokine Receptor (CCR5) polynucleotides and/or polypeptides of the invention, and/or agonists or antagonists thereof are used as an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

In another specific embodiment, G-protein Chemokine Receptor (CCR5) polynucleotides and/or polypeptides of the invention, and/or agonists or antagonists thereof are used as an agent to boost immunoresponsiveness among individuals having an acquired loss of B cell function. Conditions resulting in an acquired loss of B cell function that may be ameliorated or treated by administering the polypeptides, antibodies, polynucleotides and/or agonists or antagonists thereof, include, but are not limited to, HIV Infection, AIDS, bone marrow transplant, and B cell chronic lymphocytic leukemia (CLL).

In another specific embodiment, G-protein Chemokine Receptor (CCR5) polynucleotides and/or polypeptides of the invention, and/or agonists or antagonists thereof are used as an agent to boost immunoresponsiveness among individuals having a temporary immune deficiency. Conditions resulting in a temporary immune deficiency that may be ameliorated or treated by administering the polypeptides, antibodies, polynucleotides and/or agonists or antagonists thereof, include, but are not limited to, recovery from viral infections (e.g., influenza), conditions associated with malnutrition, recovery from infectious mononucleosis, or conditions associated with stress, recovery from measles, recovery from blood transfusion, and recovery from surgery.

In another specific embodiment, G-protein Chemokine Receptor (CCR5) polynucleotides and/or polypeptides of the invention, and/or agonists or antagonists thereof are used as a regulator of antigen presentation by monocytes, dendritic cells, and/or B-cells. In one embodiment, G-protein Chemokine Receptor (CCR5) polynucleotides and/or polypeptides of the invention, and/or agonists or antagonists thereof enhance antigen presentation or antagonizes antigen presentation in vitro or in vivo. Moreover, in related embodiments, said enhancement or antagonism of antigen presentation may be useful as an anti-tumor treatment or to modulate the immune system.

In another specific embodiment, G-protein Chemokine Receptor (CCR5) polynucleotides and/or polypeptides of the invention, and/or agonists or antagonists thereof are used as an agent to direct an individual's immune system towards development of a humoral response (i.e. TH2) as opposed to a TH1 cellular response.

In another specific embodiment, G-protein Chemokine Receptor (CCR5) polynucleotides and/or polypeptides of the invention, and/or agonists or antagonists thereof are used as a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

In another specific embodiment, G-protein Chemokine Receptor (CCR5) polynucleotides and/or polypeptides of the invention, and/or agonists or antagonists thereof are used as a stimulator of B cell production in pathologies such as AIDS, chronic lymphocyte disorder and/or Common Variable Immunodificiency.

In another specific embodiment, G-protein Chemokine Receptor (CCR5) polynucleotides and/or polypeptides of the invention, and/or agonists or antagonists thereof are used as a therapy for generation and/or regeneration of lymphoid tissues following surgery, trauma or genetic defect. In another specific embodiment, G-protein Chemokine Receptor (CCR5) polynucleotides and/or polypeptides of the invention, and/or agonists or antagonists thereof are used in the pretreatment of bone marrow samples prior to transplant.

In another specific embodiment, G-protein Chemokine Receptor (CCR5) polynucleotides and/or polypeptides of the invention, and/or agonists or antagonists thereof are used as a gene-based therapy for genetically inherited disorders resulting in immuno-incompetence/immunodeficiency such as observed among SCID patients.

In another specific embodiment, G-protein Chemokine Receptor (CCR5) polynucleotides and/or polypeptides of the invention, and/or agonists or antagonists thereof are used as a means of activating monocytes/macrophages to defend against parasitic diseases that effect monocytes such as Leishmania.

In another specific embodiment, G-protein Chemokine Receptor (CCR5) polynucleotides and/or polypeptides of the invention, and/or agonists or antagonists thereof are used as a means of regulating secreted cytokines that are elicited by polypeptides of the invention.

In another embodiment, G-protein Chemokine Receptor (CCR5) polynucleotides and/or polypeptides of the invention, and/or agonists or antagonists thereof are used in one or more of the applications described herein, as they may apply to veterinary medicine.

In another specific embodiment, G-protein Chemokine Receptor (CCR5) polynucleotides and/or polypeptides of the invention, and/or agonists or antagonists thereof are used as a means of blocking various aspects of immune responses to foreign agents or self. Examples of diseases or conditions in which blocking of certain aspects of immune responses may be desired include autoimmune disorders such as lupus, and arthritis, as well as immunoresponsiveness to skin allergies, inflammation, bowel disease, injury and diseases/disorders associated with pathogens.

In another specific embodiment, G-protein Chemokine Receptor (CCR5) polynucleotides and/or polypeptides of the invention, and/or agonists or antagonists thereof are used as a therapy for preventing the B cell proliferation and Ig secretion associated with autoimmune diseases such as idiopathic thrombocytopenic purpura, systemic lupus erythematosus and multiple sclerosis.

In another specific embodiment, G-protein Chemokine Receptor (CCR5) polynucleotides and/or polypeptides of the invention, and/or agonists or antagonists thereof are used as a inhibitor of B and/or T cell migration in endothelial cells. This activity disrupts tissue architecture or cognate responses and is useful, for example in disrupting immune responses, and blocking sepsis.

In another specific embodiment, G-protein Chemokine Receptor (CCR5) polynucleotides and/or polypeptides of the invention, and/or agonists or antagonists thereof are used as a therapy for chronic hypergammaglobulinemia evident in such diseases as monoclonal gammopathy of undetermined significance (MGUS), Waldenstrom's disease, related idiopathic monoclonal gammopathies, and plasmacytomas.

In another specific embodiment, G-protein Chemokine Receptor (CCR5) polynucleotides and/or polypeptides of the invention, and/or agonists or antagonists thereof may be employed for instance to inhibit polypeptide chemotaxis and activation of macrophages and their precursors, and of neutrophils, basophils, B lymphocytes and some T-cell subsets, e.g., activated and CD8 cytotoxic T cells and natural killer cells, in certain autoimmune and chronic inflammatory and infective diseases. Examples of autoimmune diseases are described herein and include multiple sclerosis, and insulin-dependent diabetes.

The G-protein Chemokine Receptor (CCR5) polynucleotides and/or polypeptides of the invention, and/or agonists or antagonists thereof may also be employed to treat idiopathic hyper-eosinophilic syndrome by, for example, preventing eosinophil production and migration.

In another specific embodiment, G-protein Chemokine Receptor (CCR5) polynucleotides and/or polypeptides of the invention, and/or agonists or antagonists thereof are used to enhance or inhibit complement mediated cell lysis.

In another specific embodiment, G-protein Chemokine Receptor (CCR5) polynucleotides and/or polypeptides of the invention, and/or agonists or antagonists thereof are used to enhance or inhibit antibody dependent cellular cytotoxicity.

In another specific embodiment, G-protein Chemokine Receptor (CCR5) polynucleotides and/or polypeptides of the invention, and/or agonists or antagonists thereof may also be employed for treating atherosclerosis, for example, by preventing monocyte infiltration in the artery wall.

In another specific embodiment, G-protein Chemokine Receptor (CCR5) polynucleotides and/or polypeptides of the invention, and/or agonists or antagonists thereof may be employed to treat adult respiratory distress syndrome (ARDS).

In another specific embodiment, G-protein Chemokine Receptor (CCR5) polynucleotides and/or polypeptides of the invention, and/or agonists or antagonists thereof may be useful for stimulating wound and tissue repair, stimulating angiogenesis, and/or stimulating the repair of vascular or lymphatic diseases or disorders. Additionally, agonists and antagonists of the invention may be used to stimulate the regeneration of mucosal surfaces.

In a specific embodiment, polynucleotides or polypeptides, and/or agonists thereof are used to diagnose, prognose, treat, and/or prevent a disorder characterized by primary or acquired immunodeficiency, deficient serum immunoglobulin production, recurrent infections, and/or immune system dysfunction. Moreover, polynucleotides or polypeptides, and/or agonists thereof may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pneumocystis carnii. Other diseases and disorders that may be prevented, diagnosed, prognosed, and/or treated with polynucleotides or polypeptides, and/or agonists of the present invention include, but are not limited to, HIV infection, HTLV-BLV infection, lymphopenia, phagocyte bactericidal dysfunction anemia, thrombocytopenia, and hemoglobinuria.

In another embodiment, G-protein Chemokine Receptor (CCR5) polynucleotides and/or polypeptides of the invention, and/or agonists or antagonists thereof are used to treat, and/or diagnose an individual having common variable immunodeficiency disease ("CVID"; also known as "acquired agammaglobulinemia" and "acquired hypogammaglobulinemia") or a subset of this disease.

In a specific embodiment, G-protein Chemokine Receptor (CCR5) polynucleotides and/or polypeptides of the invention, and/or agonists or antagonists thereof may be used to diagnose, prognose, prevent, and/or treat cancers or neoplasms including immune cell or immune tissue-related cancers or neoplasms. Examples of cancers or neoplasms that may be prevented, diagnosed, or treated by G-protein Chemokine Receptor (CCR5) polynucleotides and/or polypeptides of the invention, and/or agonists or antagonists thereof include, but are not limited to, acute myelogenous leukemia, chronic myelogenous leukemia, Hodgkin's disease, non-Hodgkin's lymphoma, acute lymphocytic anemia (ALL) Chronic lymphocyte leukemia, plasmacytomas, multiple myeloma, Burkitt's lymphoma, EBV-transformed diseases, and/or diseases and disorders described in the section entitled "Hyperproliferative Disorders" elsewhere herein.

In another specific embodiment, G-protein Chemokine Receptor (CCR5) polynucleotides and/or polypeptides of the invention, and/or agonists or antagonists thereof are used as a therapy for decreasing cellular proliferation of Large B-cell Lymphomas.

In another specific embodiment, G-protein Chemokine Receptor (CCR5) polynucleotides and/or polypeptides of the invention, and/or agonists or antagonists thereof are used as a means of decreasing the involvement of B cells and Ig associated with Chronic Myelogenous Leukemia.

In specific embodiments, the compositions of the invention are used as an agent to boost immunoresponsiveness among B cell immunodeficient individuals, such as, for example, an individual who has undergone a partial or complete splenectomy.

Antagonists of the invention include, for example, binding and/or inhibitory antibodies, antisense nucleic acids, ribozymes or soluble forms of the polypeptides of the present invention (e.g., Fc fusion protein). Agonists of the invention include, for example, binding or stimulatory antibodies, and soluble forms of the polypeptides (e.g., Fc fusion proteins). G-protein Chemokine Receptor (CCR5) polynucleotides and/or polypeptides of the invention, and/or agonists or antagonists thereof may be employed in a composition with a pharmaceutically acceptable carrier, e.g., as described herein.

In another embodiment, G-protein Chemokine Receptor (CCR5) polynucleotides and/or polypeptides of the invention, and/or agonists or antagonists thereof are administered to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741). Administration of G-protein Chemokine Receptor (CCR5) polynucleotides and/or polypeptides of the invention, and/or agonists or antagonists thereof to such animals is useful for the generation of monoclonal antibodies against the G-protein Chemokine Receptor (CCR5) polynucleotides and/or polypeptides of the invention, and/or agonists or antagonists thereof.

Chemotaxis. G-protein Chemokine Receptor (CCR5) polynucleotides or polypeptides, or agonists or antagonists of G-protein Chemokine Receptor (CCR5), may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

G-protein Chemokine Receptor (CCR5) polynucleotides or polypeptides, or agonists or antagonists of G-protein Chemokine Receptor (CCR5), may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that G-protein Chemokine Receptor (CCR5) polynucleotides or polypeptides, or agonists or antagonists of G-protein Chemokine Receptor (CCR5), may inhibit chemotactic activity. These molecules could also be used to treat, prevent, and/or diagnose diseases, disorders, and/or conditions. Thus, G-protein Chemokine Receptor (CCR5) polynucleotides or polypeptides, or agonists or antagonists of G-protein Chemokine Receptor (CCR5), could be used as an inhibitor of chemotaxis.

Infectious Disease. G-protein Chemokine Receptor (CCR5) polynucleotides or polypeptides, or agonists or antagonists of G-protein Chemokine Receptor (CCR5), can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, G-protein Chemokine Receptor (CCR5) polynucleotides or polypeptides, or agonists or antagonists of G-protein Chemokine Receptor (CCR5), may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovavifidae, Parvoviridae, Picomaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. Polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

In highly preferred embodiments, G-protein Chemokine Receptor (CCR5) polynucleotides and/or polypeptides of the present invention and/or agonists or antagonists thereof, are used to diagnose, treat, prevent or ameliorate HIV infection.

In other highly preferred embodiments, G-protein Chemokine Receptor (CCR5) polynucleotides and/or polypeptides of the present invention and/or agonists or antagonists thereof, are used to diagnose, treat, prevent or ameliorate Cytomegalovirus infections.

In other highly preferred embodiments, G-protein Chemokine Receptor (CCR5) polynucleotides and/or polypeptides of the present invention and/or agonists or antagonists thereof, are used to diagnose, treat, prevent or ameliorate Poxviridae infections.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium, Mycobacterium, Norcardia*), *Cryptococcus neoformans, Aspergillosis, Bacillaceae* (e.g., *Anthrax, Clostridium*), *Bacteroidaceae, Blastomycosis, Bordetella, Borrelia* (e.g., *Borrelia burgdorferi*), *Brucellosis, Candidiasis, Campylobacter, Coccidioidomycosis, Cryptococcosis, Dermatocycoses, E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), *Erysipelothrix, Helicobacter, Legionellosis, Leptospirosis, Listeria, Mycoplasmatales, Mycobacterium leprae, Vibrio cholerae*, Neisseriaceae (e.g., Acinetobacter, Gonorrhea, Menigococcal), *Meisseria meningitidis, Pasteurellacea* Infections (e.g., *Actinobacillus, Heamophilus* (e.g., *Heamophilus influenza* type B), *Pasteurella*), *Pseudomonas, Rickettsiaceae, Chlamydiaceae, Syphilis, Shigella* spp., *Staphylococcal, Meningiococcal, Pneumococcal* and *Streptococcal* (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: *Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis*, and *Trichomonas* and *Sporozoans* (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Neurological Diseases.

Nervous system diseases, disorders, and/or conditions, which can be treated with the G-protein Chemokine Receptor (CCR5) compositions of the invention (e.g., G-protein Chemokine Receptor (CCR5) polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wemicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the G-protein Chemokine Receptor (CCR5) polypeptides, polynucleotides, or agonists or antagonists of the invention are used to protect neural cells from the damaging effects of cerebral hypoxia. According to this embodiment, the G-protein Chemokine Receptor (CCR5) compositions of the invention are used to treat, prevent, and/or diagnose neural cell injury associated with cerebral hypoxia. In one aspect of this embodiment, the G-protein Chemokine Receptor (CCR5) polypeptides, polynucleotides, or agonists or antagonists of the invention are used to treat, prevent, and/or diagnose neural cell injury associated with cerebral ischemia. In another aspect of this embodiment, the G-protein Chemokine Receptor (CCR5) polypeptides, polynucleotides, or agonists or antagonists of the invention are used to treat, prevent, and/or diagnose neural cell injury associated with cerebral infarction.

In another aspect of this embodiment, the G-protein Chemokine Receptor (CCR5) polypeptides, polynucleotides, or agonists or antagonists of the invention are used to treat, prevent, and/or diagnose neural cell injury associated with a stroke. In another aspect of this embodiment, the G-protein Chemokine Receptor (CCR5) polypeptides, polynucleotides, or agonists or antagonists of the invention are used to treat, prevent, and/or diagnose cerebral neural cell injury associated with a stroke.

In a further aspect of this embodiment, the G-protein Chemokine Receptor (CCR5) polypeptides, polynucleotides, or agonists or antagonists of the invention are used to treat, prevent, and/or diagnose neural cell injury associated with a heart attack.

In another aspect of this embodiment, the G-protein Chemokine Receptor (CCR5) polypeptides, polynucleotides, or agonists or antagonists of the invention are used to treat, prevent, and/or diagnose cerebral neural cell injury associated with a heart attack.

The compositions of the invention which are useful for treating, preventing, and/or diagnosing a nervous system disorder may be selected by testing for biological activity in promoting the survival or differentiation of neurons. For example, and not by way of limitation, G-protein Chemokine Receptor (CCR5) compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Further, G-protein Chemokine Receptor (CCR5) polypeptides or polynucleotides of the invention may play a role in neuronal survival; synapse formation; conductance; neural differentiation, etc. Thus, compositions of the invention (including G-protein Chemokine Receptor (CCR5) polynucleotides and/or polypeptides, and/or agonists or antagonists thereof) may be used to diagnose and/or treat or prevent diseases or disorders associated with these roles, including, but not limited to, learning and/or cognition disorders. The compositions of the invention may also be useful in the treatment or prevention of neurodegenerative disease states and/or behavioral disorders. Such neurodegenerative disease states and/or behavioral disorders include, but are not limited to, Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, compositions of the invention may also play a role in the treatment, prevention and/or detection of developmental disorders associated with the developing embryo, or sexually-linked disorders.

Additionally, G-protein Chemokine Receptor (CCR5) polynucleotides and/or polypeptides, and/or agonists or antagonists thereof, may be useful in protecting neural cells from diseases, damage, disorders, or injury, associated with cerebrovascular disorders including, but not limited to, carotid artery diseases (e.g., carotid artery thrombosis, carotid stenosis, or Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis (e.g., carotid artery thrombosis, sinus thrombosis, or Wallenberg's Syndrome), cerebral hemorrhage (e.g., epidural or subdural hematoma, or subarachnoid hemorrhage), cerebral infarction, cerebral ischemia (e.g., transient cerebral ischemia, Subclavian Steal Syndrome, or vertebrobasilar insufficiency), vascular dementia (e.g., multi-infarct), leukomalacia, periventricular, and vascular headache (e.g., cluster headache or migraines).

In accordance with yet a further aspect of the present invention, there is provided a process for utilizing G-protein Chemokine Receptor (CCR5) polynucleotides and/or polypeptides, and/or agonists or antagonists thereof, for therapeutic purposes, for example, to stimulate neurological cell proliferation and/or differentiation. Therefore, polynucleotides, polypeptides, agonists and/or antagonists of the invention may be used to treat and/or detect neurologic diseases. Moreover G-protein Chemokine Receptor (CCR5) polynucleotides and/or polypeptides, and/or agonists or antagonists thereof, can be used as a marker or detector of a particular nervous system disease or disorder.

Examples of neurologic diseases which can be treated or detected with the G-protein Chemokine Receptor (CCR5) polynucleotides and/or polypeptides of the present invention, and/or agonists or antagonists thereof, include brain diseases, such as metabolic brain diseases which includes phenylketonuria such as maternal phenylketonuria, pyruvate carboxylase deficiency, pyruvate dehydrogenase complex deficiency, Wernicke's Encephalopathy, brain edema, brain neoplasms such as cerebellar neoplasms which include infratentorial neoplasms, cerebral ventricle neoplasms such as choroid plexus neoplasms, hypothalamic neoplasms, supratentorial neoplasms, canavan disease, cerebellar diseases such as cerebellar ataxia which include spinocerebellar degeneration such as ataxia telangiectasia, cerebellar dyssynergia, Friederich's Ataxia, Machado-Joseph Disease, olivopontocerebellar atrophy, cerebellar neoplasms such as infratentorial neoplasms, diffuse cerebral sclerosis such as encephalitis periaxialis, globoid cell leukodystrophy, metachromatic leukodystrophy and subacute sclerosing panencephalitis.

Additional neurologic diseases which can be treated or detected with the G-protein Chemokine Receptor (CCR5) polynucleotides and/or polypeptides of the present invention, and/or agonists or antagonists thereof, include cerebrovascular disorders (such as carotid artery diseases which include carotid artery thrombosis, carotid stenosis and Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thrombosis, sinus thrombosis and Wallenberg's Syndrome, cerebral hemorrhage such as epidural hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache and migraine.

Additional neurologic diseases which can be treated or detected with the G-protein Chemokine Receptor (CCR5) polynucleotides and/or polypeptides of the present invention, and/or agonists or antagonists thereof, include dementia such as AIDS Dementia Complex, presenile dementia such as Alzheimer's Disease and Creutzfeldt-Jakob Syndrome, senile dementia such as Alzheimer's Disease and progressive supranuclear palsy, vascular dementia such as multi-infarct dementia, encephalitis which include encephalitis periaxialis, viral encephalitis such as epidemic encephalitis, Japanese Encephalitis, St. Louis Encephalitis, tick-borne encephalitis and West Nile Fever, acute disseminated encephalomyelitis, meningoencephalitis such as uveomeningoencephalitic syndrome, Postencephalitic Parkinson Disease and subacute sclerosing panencephalitis, encephalomalacia such as periventricular leukomalacia, epilepsy such as generalized epilepsy which includes infantile spasms, absence epilepsy, myoclonic epilepsy which includes MERRF Syndrome, tonic-clonic epilepsy, partial epilepsy such as complex partial epilepsy, frontal lobe epilepsy and temporal lobe epilepsy, post-traumatic epilepsy, status epilepticus such as Epilepsia Partialis Continua, and Hallervorden-Spatz Syndrome.

Additional neurologic diseases which can be treated or detected with the G-protein Chemokine Receptor (CCR5) polynucleotides and/or polypeptides of the present invention, and/or agonists or antagonists thereof, include hydrocephalus such as Dandy-Walker Syndrome and normal pressure hydrocephalus, hypothalamic diseases such as hypothalamic neoplasms, cerebral malaria, narcolepsy which includes cataplexy, bulbar poliomyelitis, cerebri pseudotumor, Rett Syndrome, Reye's Syndrome, thalamic diseases, cerebral toxoplasmosis, intracranial tuberculoma and Zellweger Syndrome, central nervous system infections such as AIDS Dementia Complex, Brain Abscess, subdural empyema, encephalomyelitis such as Equine Encephalomyelitis, Venezuelan Equine Encephalomyelitis, Necrotizing Hemorrhagic Encephalomyelitis, Visna, and cerebral malaria.

Additional neurologic diseases which can be treated or detected with the G-protein Chemokine Receptor (CCR5) polynucleotides and/or polypeptides of the present invention, and/or agonists or antagonists thereof, include meningitis such as arachnoiditis, aseptic meningtitis such as viral meningtitis which includes lymphocytic choriomeningitis, Bacterial meningtitis which includes Haemophilus Meningtitis, Listeria Meningtitis, Meningococcal Meningtitis such as Waterhouse-Friderichsen Syndrome, Pneumococcal Meningtitis and meningeal tuberculosis, fungal meningitis such as Cryptococcal Meningtitis, subdural effusion, meningoencephalitis such as uvemeningoencephalitic syndrome, myelitis such as transverse myelitis, neurosyphilis such as tabes dorsalis, poliomyelitis which includes bulbar poliomyelitis and postpoliomyelitis syndrome, prion diseases (such as Creutzfeldt-Jakob Syndrome, Bovine Spongiform Encephalopathy, Gerstmann-Straussler Syndrome, Kuru, Scrapie), and cerebral toxoplasmosis.

Additional neurologic diseases which can be treated or detected with the G-protein Chemokine Receptor (CCR5) polynucleotides and/or polypeptides of the present invention, and/or agonists or antagonists thereof, include central nervous system neoplasms such as brain neoplasms that include cerebellar neoplasms such as infratentorial neoplasms, cerebral ventricle neoplasms such as choroid plexus neoplasms, hypothalamic neoplasms and supratentorial neoplasms, meningeal neoplasms, spinal cord neoplasms which include epidural neoplasms, demyelinating diseases such as Canavan Diseases, diffuse cerebral sceloris which includes adrenoleukodystrophy, encephalitis periaxialis, globoid cell leukodystrophy, diffuse cerebral sclerosis such as metachromatic leukodystrophy, allergic encephalomyelitis, necrotizing hemorrhagic encephalomyelitis, progressive multifocal leukoencephalopathy, multiple sclerosis, central pontine myelinolysis, transverse myelitis, neuromyelitis optica, Scrapie, Swayback, Chronic Fatigue Syndrome, Visna, High Pressure Nervous Syndrome, Meningism, spinal cord diseases such as amyotonia congenita, amyotrophic lateral sclerosis, spinal muscular atrophy such as Werdnig-Hoffmann Disease, spinal cord compression, spinal cord neoplasms such as epidural neoplasms, syringomyelia, Tabes Dorsalis, Stiff-Man Syndrome, mental retardation such as Angelman Syndrome, Cri-du-Chat Syndrome, De Lange's Syndrome, Down Syndrome, Gangliosidoses such as gangliosidoses G(M1), Sandhoff Disease, Tay-Sachs Disease, Hartnup Disease, homocystinuria, Laurence-Moon-Biedl Syndrome, Lesch-Nyhan Syndrome, Maple Syrup Urine Disease, mucolipidosis such as fucosidosis, neuronal ceroid-lipofuscinosis, oculocerebrorenal syndrome, phenylketonuria such as maternal phenylketonuria, Prader-Willi Syndrome, Rett Syndrome, Rubinstein-Taybi Syndrome, Tuberous Sclerosis, WAGR Syndrome, nervous system abnormalities such as holoprosencephaly, neural tube defects such as anencephaly which includes hydrangencephaly, Arnold-Chairi Deformity, encephalocele, meningocele, meningomyelocele, spinal dysraphism such as spina bifida cystica and spina bifida occulta.

Additional neurologic diseases which can be treated or detected with the G-protein Chemokine Receptor (CCR5) polynucleotides and/or polypeptides of the present invention, and/or agonists or antagonists thereof, include hereditary motor and sensory neuropathies which include Charcot-Marie Disease, Hereditary optic atrophy, Refsum's Disease, hereditary spastic paraplegia, Werdnig-Hoffmann Disease, Hereditary Sensory and Autonomic Neuropathies such as Congenital Analgesia and Familial Dysautonomia, Neurologic manifestations (such as agnosia that include Gerstmann's Syndrome, Amnesia such as retrograde amnesia, apraxia, neurogenic bladder, cataplexy, communicative disorders such as hearing disorders that includes deafness, partial hearing loss, loudness recruitment and tinnitus, language disorders such as aphasia which include agraphia, anomia, broca aphasia, and Wernicke Aphasia, Dyslexia such as Acquired Dyslexia, language development disorders, speech disorders such as aphasia which includes anomia, broca aphasia and Wernicke Aphasia, articulation disorders, communicative disorders such as speech disorders which include dysarthria, echolalia, mutism and stuttering, voice disorders such as aphonia and hoarseness, decerebrate state, delirium, fasciculation, hallucinations, meningism, movement disorders such as angelman syndrome, ataxia, athetosis, chorea, dystonia, hypokinesia, muscle hypotonia, myoclonus, tic, torticollis and tremor, muscle hypertonia such as muscle rigidity such as stiffman syndrome, muscle spasticity, paralysis such as facial paralysis which includes Herpes Zoster Oticus, Gastroparesis, Hemiplegia, ophthalmoplegia such as diplopia, Duane's Syndrome, Horner's Syndrome, Chronic progressive external ophthalmoplegia such as Kearns Syndrome, Bulbar Paralysis, Tropical Spastic Paraparesis, Paraplegia such as Brown-Sequard Syndrome, quadriplegia, respiratory paralysis and vocal cord paralysis, paresis, phantom limb, taste disorders such as ageusia and dysgeusia, vision disorders such as amblyopia, blindness, color vision defects, diplopia, hemianopsia, scotoma and subnormal vision, sleep disorders such as hypersomnia which includes Kleine-Levin Syndrome, insomnia, and somnambulism, spasm such as trismus, unconsciousness such as coma, persistent vegetative state and syncope and vertigo, neuromuscular diseases such as amyotonia congenita, amyotrophic lateral sclerosis, Lambert-Eaton Myasthenic Syndrome, motor neuron disease, muscular atrophy such as spinal muscular atrophy, Charcot-Marie Disease and Werdnig-Hoffmann Disease, Postpoliomyelitis Syndrome, Muscular Dystrophy, Myasthenia Gravis, Myotonia Atrophica, Myotonia Confenita, Nemaline Myopathy, Familial Periodic Paralysis, Multiplex Paramyloclonus, Tropical Spastic Paraparesis and Stiff-Man Syndrome, peripheral nervous system diseases such as acrodynia, amyloid neuropathies, autonomic nervous system diseases such as Adie's Syndrome, Barre-Lieou Syndrome, Familial Dysautonomia, Horner's Syndrome, Reflex Sympathetic Dystrophy and Shy-Drager Syndrome, Cranial Nerve Diseases such as Acoustic Nerve Diseases such as Acoustic Neuroma which includes Neurofibromatosis 2, Facial Nerve Diseases such as Facial Neuralgia,Melkersson-Rosenthal Syndrome, ocular motility disorders which includes amblyopia, nystagmus, oculomotor nerve paralysis, ophthalmoplegia such as Duane's Syndrome, Homer's Syndrome, Chronic Progressive External Ophthalmoplegia which includes Kearns Syndrome, Strabismus such as Esotropia and Exotropia, Oculomotor Nerve Paralysis, Optic Nerve Diseases such as Optic Atrophy which includes Hereditary Optic Atrophy, Optic Disk Drusen, Optic Neuritis such as Neuromyelitis Optica, Papilledema, Trigeminal Neuralgia, Vocal Cord Paralysis, Demyelinating Diseases such as Neuromyelitis Optica and Swayback, and Diabetic neuropathies such as diabetic foot.

Additional neurologic diseases which can be treated or detected with the G-protein Chemokine Receptor (CCR5) polynucleotides and/or polypeptides of the present invention, and/or agonists or antagonists thereof, include nerve compression syndromes such as carpal tunnel syndrome, tarsal tunnel syndrome, thoracic outlet syndrome such as cervical rib syndrome, ulnar nerve compression syndrome, neuralgia such as causalgia, cervico-brachial neuralgia, facial neuralgia and trigeminal neuralgia, neuritis such as experimental allergic neuritis, optic neuritis, polyneuritis, polyradiculoneuritis and radiculities such as polyradiculitis, hereditary motor and sensory neuropathies such as Charcot-Marie Disease, Hereditary Optic Atrophy, Refsum's Disease, Hereditary Spastic Paraplegia and Werdnig-Hoffmann Disease, Hereditary Sensory and Autonomic Neuropathies which include Congenital Analgesia and Familial Dysautonomia, POEMS Syndrome, Sciatica, Gustatory Sweating and Tetany).

Hyperproliferative Disorders.

G-protein Chemokine Receptor (CCR5) polynucleotides or polypeptides, or agonists or antagonists of G-protein Chemokine Receptor (CCR5), can be used to treat, prevent, and/or diagnose hyperproliferative diseases, disorders, and/or conditions, including neoplasms. G-protein Chemokine Receptor (CCR5) polynucleotides or polypeptides, or agonists or antagonists of G-protein Chemokine Receptor (CCR5), may inhibit the proliferation of the disorder through direct or indirect interactions. Alternatively, G-protein Chemokine Receptor (CCR5) polynucleotides or polypeptides, or agonists or antagonists of G-protein Chemokine Receptor (CCR5), may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by G-protein Chemokine Receptor (CCR5) polynucleotides or polypeptides, or agonists or antagonists of G-protein Chemokine Receptor (CCR5), include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by G-protein Chemokine Receptor (CCR5) polynucleotides or polypeptides, or agonists or antagonists of G-protein Chemokine Receptor. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating cell proliferative diseases, disorders, and/or conditions by inserting into an abnormally proliferating cell a polynucleotide of the present invention, wherein said polynucleotide represses said expression.

Another embodiment of the present invention provides a method of treating cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more preferably an adenoviral vector (See G J. Nabel, et. al., PNAS 1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M. More preferred binding affinities include those with a dissociation constant or Kd less than $5\times10^{-5}$ M, $10^{-5}$ M,$5\times10^{-6}$ M, $10^{-6}$ M, $5\times10^{-7}$ M, $10^{7}$ M, $5\times10^{-8}$ M or $10^{-8}$ M. Even more preferred binding affinities include those with a dissociation constant or Kd less than $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$M $5\times10^{-13}$ M, $10^{-13}$ M $5\times10^{-14}$ M, $10^{-14}$ M, $5\times10^{-15}$ M, or $10^{-15}$ M.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph IB, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155–61 (1998), which is hereby incorporated by reference)).

Polypeptides, including G-protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, anti-inflammatory proteins (See for example, Mutat Res 400 (1–2):447–55 (1998), Med Hypotheses. 50(5):423–33 (1998), Chem Biol Interact. Apr 24;111–112:23–34 (1998), J Mol Med. 76(6):402–12 (1998), Int J Tissue React;20(1): 3–15 (1998), which are all hereby incorporated by reference).

Polypeptides, including G-protein fusions to, or fragments thereof, of the present invention are useful in inhibiting the metastasis of proliferative cells or tissues. Inhibition may occur as a direct result of administering polypeptides, or antibodies directed to said polypeptides as described elsewere herein, or indirectly, such as activating the expression of proteins known to inhibit metastasis, for example alpha 4 integrins, (See, e.g., Curr Top Microbiol Immunol 1998;231:125–41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders.

G-protein Chemokine Receptor (CCR5) polynucleotides or polypeptides, or agonists or antagonists of G-protein Chemokine Receptor (CCR5), encoding G-protein Chemokine Receptor (CCR5) may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

G-protein Chemokine Receptor (CCR5) polynucleotides or polypeptides, or agonists or antagonists of G-protein Chemokine Receptor (CCR5), are especially effective for the treatment of critical limb ischemia and coronary disease.

G-protein Chemokine Receptor (CCR5) polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. G-protein Chemokine Receptor (CCR5) polypeptides may be administered as part of a Therapeutic, described in more detail below. Methods of delivering G-protein Chemokine Receptor (CCR5) polynucleotides are described in more detail herein.

Treatment of Carbohydrate Metabolism Disorders.

In specific embodiments, the polynucleotides and/or polypeptides corresponding to this gene and/or agonists or antagonists of those polypeptides (including antibodies) as well as fragments and variants of those polynucleotides, polypeptides, agonists and antagonists, may be used to diagnose, prognose, treat, prevent, or ameliorate diseases and disorders associated with aberrant glucose metabolism or glucose uptake into cells.

In a specific embodiment, the polynucleotides and/or polypeptides corresponding to this gene and/or agonists and/or antagonists thereof may be used to diagnose, prognose, treat, prevent, and/or ameliorate type I diabetes mellitus (insulin dependent diabetes mellitus, IDDM).

In another embodiment, the polynucleotides and/or polypeptides corresponding to this gene and/or agonists and/or antagonists thereof may be used to diagnose, prognose, treat, prevent, and/or ameliorate type II diabetes mellitus (insulin resistant diabetes mellitus).

Additionally, in other embodiments, the polynucleotides and/or polypeptides corresponding to this gene and/or antagonists thereof (especially neutralizing or antagonistic antibodies) may be used to diagnose, prognose, treat, prevent, and/or ameliorate conditions associated with (type I or type II) diabetes mellitus, including, but not limited to, diabetic ketoacidosis, diabetic coma, nonketotic hyperglycemic-hyperosmolar coma, seizures, mental confusion, drowsiness, cardiovascular disease (e.g., heart disease, atherosclerosis, microvascular disease, hypertension, stroke, and other diseases and disorders as described in the "Cardiovascular Disorders" section), dyslipidemia, kidney disease (e.g., renal failure and nephropathy) nerve damage, neuropathy, vision impairment (e.g., diabetic retinopathy and blindness), ulcers and impaired wound healing, infections (e.g., infectious diseases and disorders as described in the "Infectious Diseases" section, especially of the urinary tract and skin), carpal tunnel syndrome and Dupuytren's contracture.

In other embodiments, the polynucleotides and/or polypeptides corresponding to this gene and/or agonists or antagonists thereof are administered to an animal, preferably a mammal, and most preferably a human, in order to regulate the animal's weight. In specific embodiments the polynucleotides and/or polypeptides corresponding to this gene and/or agonists or antagonists thereof are administered to an animal, preferably a mammal, and most preferably a human, in order to control the animal's weight by modulating a biochemical pathway involving insulin. In still other embodiments the polynucleotides and/or polypeptides corresponding to this gene and/or agonists or antagonists thereof are administered to an animal, preferably a mammal, and most preferably a human, in order to control the animal's weight by modulating a biochemical pathway involving insulin-like growth factor.

Anti-Angiogenesis Activity.

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., *Biotech.* 9:630–634 (1991); Folkman et al., *N. Engl. J. Med.,* 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J. Opthalmol.* 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)).Thus, the present invention provides a method of treating an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat or prevent a cancer or tumor. Cancers which may be treated with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases;

melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat, prevent, and/or diagnose superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, comeal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., bums), and is preferably initiated after the proliferative phase has had time to progress (approximately 14 days after the initial injury), but before hypertrophic scar or keloid development. As noted above, the present invention also provides methods for treating neovascular diseases of the eye, including for example, corneal neovascularization, neovascular glaucoma, proliferative diabetic retinopathy, retrolental fibroplasia and macular degeneration.

Moreover, ocular diseases, disorders, and/or conditions associated with neovascularization which can be treated with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Thus, within one aspect of the present invention methods are provided for treating neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated with be treated with the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (Helicobacter pylori), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Binding Activity.

G-protein Chemokine Receptor (CCR5) polypeptides may be used to screen for molecules that bind to G-protein Chemokine Receptor (CCR5) or for molecules to which G-protein Chemokine Receptor (CCR5) binds. The binding of G-protein Chemokine Receptor (CCR5) and the molecule may activate (agonist), increase, inhibit (antagonist), or decrease activity of the G-protein Chemokine Receptor (CCR5) or the molecule bound. Examples of such molecules include antibodies, oligonucleotides, proteins (e.g., receptors),or small molecules.

Preferably, the molecule is closely related to the natural ligand of G-protein Chemokine Receptor (CCR5), e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which G-protein Chemokine Receptor (CCR5) binds, or at least, a fragment of the receptor capable of being bound by G-protein Chemokine Receptor (CCR5) (e.g., active site). In either case, the molecule can be rationally designed using known techniques.

Preferably, the screening for these molecules involves producing appropriate cells which express G-protein Chemokine Receptor (CCR5), either as a secreted protein or on the cell membrane. Preferred cells include cells from mammals, yeast, Drosophila, or *E. coli*. Cells expressing G-protein Chemokine Receptor (CCR5) (or cell membrane containing the expressed polypeptide) are then preferably contacted with a test compound potentially containing the molecule to observe binding, stimulation, or inhibition of activity of either G-protein Chemokine Receptor (CCR5) or the molecule.

The assay may simply test binding of a candidate compound toG-protein Chemokine Receptor (CCR5), wherein binding is detected by a label, or in an assay involving competition with a labeled competitor. Further, the assay may test whether the candidate compound results in a signal generated by binding to G-protein Chemokine Receptor.

Alternatively, the assay can be carried out using cell-free preparations, polypeptide/molecule affixed to a solid support, chemical libraries, or natural product mixtures. The assay may also simply comprise the steps of mixing a candidate compound with a solution containing G-protein Chemokine Receptor (CCR5), measuring G-protein Chemokine Receptor/molecule activity or binding, and comparing the G-protein Chemokine Receptor/molecule activity or binding to a standard.

Preferably, an ELISA assay can measure G-protein Chemokine Receptor (CCR5) level or activity in a sample (e.g., biological sample) using a monoclonal or polyclonal antibody. The antibody can measure G-protein Chemokine Receptor (CCR5) level or activity by either binding, directly or indirectly, to G-protein Chemokine Receptor (CCR5) or by competing with G-protein Chemokine Receptor (CCR5) for a substrate.

Additionally, the ligands to which G-protein Chemokine Receptor (CCR5) binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of G-protein Chemokine Receptor (CCR5) thereby effectively generating agonists and antagonists of G-protein Chemokine Receptor. See generally, U.S. Pat. Nos. 5,605,793, 5,811,238, 5,830,721, 5,834,252, and 5,837,458, and Patten, P. A., et al., *Curr. Opinion Biotechnol.* 8:724–33 (1997); Harayama, S. *Trends Biotechnol.* 16(2):76–82 (1998); Hansson, L. O., et al., *J. Mol. Biol.* 287:265–76 (1999); and Lorenzo, M. M. and Blasco, R. *Biotechniques* 24(2):308–13 (1998) (each of these patents and publications are hereby incorporated by reference). In one embodiment, alteration of G-protein Chemokine Receptor (CCR5) polynucleotides and corresponding polypeptides may be achieved by DNA shuffling. DNA shuffling involves the assembly of two or more DNA segments into a desired G-protein Chemokine Receptor (CCR5) molecule by homologous, or site-specific, recombination. In another embodiment, G-protein Chemokine Receptor (CCR5) polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of G-protein Chemokine Receptor (CCR5) may be recombined with one or more components, motifs, sections, parts, domains, fragments, etc. of one or more heterologous molecules. In preferred embodiments, the heterologous molecules are G-protein Chemokine Receptor (CCR5) family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active G-protein Chemokine Receptor (CCR5) fragments. Biologically active fragments are those exhibiting activity similar, but not necessarily identical, to an activity of the G-protein Chemokine Receptor (CCR5) polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and $^3$[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of $^3$[H] thymidine in each case. The amount of fibroblast cell proliferation is measured by liquid scintillation chromatography which measures the incorporation of $^3$[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the G-protein Chemokine Receptor (CCR5) is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to G-protein Chemokine Receptor (CCR5) comprising the steps of: (a) incubating a candidate binding compound with G-protein Chemokine Receptor; and (b) determining if binding has occurred. Moreover, the invention includes a method of identifying agonists/antagonists comprising the steps of: (a) incubating a candidate compound with G-protein Chemokine Receptor (CCR5), (b) assaying a biological activity , and (b) determining if a biological activity of G-protein Chemokine Receptor (CCR5) has been altered.

Also, one could identify molecules bind G-protein Chemokine Receptor (CCR5) experimentally by using the beta-pleated sheet regions disclosed in FIG. 3 and Table 1. Accordingly, specific embodiments of the invention are directed to polynucleotides encoding polypeptides which comprise, or alternatively consist of, the amino acid sequence of each beta pleated sheet regions disclosed in FIG. 3/Table 1. Additional embodiments of the invention are directed to polynucleotides encoding G-protein Chemokine Receptor (CCR5) polypeptides which comprise, or alternatively consist of, any combination or all of the beta pleated sheet regions disclosed in FIG. 3/Table 1. Additional preferred embodiments of the invention are directed to polypeptides which comprise, or alternatively consist of, the G-protein Chemokine Receptor (CCR5) amino acid sequence of each of the beta pleated sheet regions disclosed in FIG. 3/Table 1. Additional embodiments of the invention are directed to G-protein Chemokine Receptor (CCR5) polypeptides which comprise, or alternatively consist of, any combination or all of the beta pleated sheet regions disclosed in FIG. 3/Table 1.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNase, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Thus, the polypeptides can be used to identify compounds that modulate receptor activity. Both the receptor protein and appropriate variants and fragments can be used in high-throughput screens to assay candidate compounds for the ability to bind to the receptor. These compounds can be further screened against a functional receptor to determine the effect of the compound on the receptor activity. Compounds can be identified that activate (agonist) or inactivate (antagonist) the receptor to a desired degree.

The terms "agonist" and "antagonist" represent compounds that enhance or diminish a response. As one form of an agonist, the compound binds to the same site as the endogenous compound and produces the same type of signal, usually of equal or greater magnitude than the endogenous agent. Another form of agonist binds to a different site than the first agonist, producing no signal by itself, however, an enhanced signal is generated when the endogenous agent also binds to its site. This is called an allosteric action. One form of antagonist binds to the site used by the endogenous agent and diminishes or blocks the signal generated by the endogenous agent. Another form of antagonist binds to an allosteric site, similar to the second form of agonist, but produces a diminished signal generated by the endogenous agent. A third form of antagonist dissolves in the membrane or crosses the membrane and intercepts the signal generated by the endogenous agent within the membrane or on the intracellular side. An antagonist, accordingly, encompasses negative agonists or "inverse agonists", having a negative intrinsic activity that reduces the receptor signal activity relative to the signaling activity measured in the absence of the inverse agonist. Such an antagonist is distinguished from an antagonist having no intrinsic activity and no effect on the receptor's basal activity. Thus, for example, an inverse agonist could alter the receptor confirmation, thereby reducing or eliminating interaction with a ligand. See, Milligan et al., *TIPS* 16:10 (1995).

The receptor polypeptides can be used to screen a compound for the ability to stimulate or inhibit interaction between the receptor protein and a target molecule that normally interacts with the receptor protein. The target can be ligand or a component of the signal pathway with which the receptor protein normally interacts (for example, a G-protein or other interactor involved in cAMP or phosphatidylinositol turnover and/or adenylate cyclase, or phospholipase C activation). The assay includes the steps of combining the receptor protein with a candidate compound under conditions that allow the receptor protein or fragment to interact with the target molecule, and to detect the formation of a complex between the protein and the target or to detect the biochemical consequence of the interaction with the receptor protein and the target, such as any of the associated effects of signal transduction, such as ion flux, G-protein phosphorylation, cyclic AMP or phosphatidylinositol turnover, and adenylate cyclase or phospholipase C activation.

The receptor polypeptides are useful in cell based assays when they are overexpressed in a cell. Accordingly, such cells overexpressing the receptor are useful to identify compounds that are capable of modulating or compensating for the overexpression. Cells overexpressing the receptor can be derived from natural sources or can be created by routine recombinant methods.

The receptor polypeptides are also useful for screening compounds in a cell based assay when constitutively activated on a cell. Such cells expressing constitutively activated receptors are useful for screening compounds that modulate receptor activation. Such cells can be derived from natural sources or can be created by recombinant means that are well known in the art. For example, see Scheer et al., *J. Receptor Signal Transduction Res.* 17:57–73 (1997); U.S. Pat. No. 5,750,353.

Candidate compounds include, for example, (1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; (2) phosphopeptides (e.g., members of random and partially degenerate, directed phosphopeptide libraries, see, e.g., Songyang et al., *Cell* 72:767–778 (1993)); (3) antibodies (e.g., polyclonal, monoclonal, humanized, anti-idiotypic, chimeric, intrabodies, and single chain antibodies, as well as Fab, $F(ab)_2$, Fab expression library fragments, and epitope-binding fragments of antibodies); and (4) small organic and inorganic molecules (e.g., molecules obtained from combinatorial and natural product libraries).

One candidate compound is a soluble full-length receptor or fragment that competes for ligand binding. Other candidate compounds include mutant receptors or appropriate fragments containing mutations that affect receptor function and thus compete for ligand. Accordingly, a fragment that competes for ligand, for example with a higher affinity, or a fragment that binds ligand but does not allow release, is encompassed by the invention.

The invention provides other end points to identify compounds that modulate (stimulate or inhibit) receptor activity. The assays typically involve an assay of events in the signal transduction pathway that indicate receptor activity. Thus, the expression of genes that are up- or down-regulated in response to the receptor protein dependent signal cascade can be assayed. In one embodiment, the regulatory region of such genes can be operably linked to a marker that is easily detectable, such as luciferase. Alternatively, phosphorylation of the receptor protein, or a receptor protein target, could also be measured.

It is also understood that a disorder caused by aberrant levels or mutations in the protein can be used as a basis for an endpoint. Accordingly, specific deviations in the development or course of the disorder in response to a compound that acts on the receptor can serve as an endpoint.

Any of the biological or biochemical functions mediated by the receptor can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric receptor proteins in which the amino terminal extracellular domain, or parts thereof, the entire transmembrane domain or subregions, such as any of the seven transmembrane segments or any of the intracellular or extracellular loops, and the carboxy terminal intracellular domain, or parts thereof, can be replaced by heterologous domains or subregions. For example, a G-protein-binding region can be used that interacts with a different G-protein than that which is recognized by the native receptor. Accordingly, a different set of signal transduction components is available as an end-point assay for activation. Alternatively, the entire transmembrane portion or subregions (such as transmembrane segments or intracellular or extracellular loops) can be replaced with the entire transmembrane portion or subregions specific to a host cell that is different from the host cell from which the amino terminal extracellular domain and/or the G-protein binding region are derived. This allows for assays to be performed in other than the specific host cell from which the receptor is derived. Alternatively, the amino terminal extracellular domain (and/or other ligand-binding regions) could be replaced by a domain (and/or other binding region) binding a different ligand, thus, providing an assay for test compounds that interact with the heterologous amino terminal extracellular domain (or region) but still cause signal transduction. Finally, activation can be detected by a reporter gene containing an easily detectable coding region operably linked to a transcriptional regulatory sequence that is part of the native signal transduction pathway.

The receptor polypeptides are also useful in competition binding assays in methods designed to discover compounds that interact with the receptor. Thus, a compound is exposed to a receptor polypeptide under conditions that allow the compound to bind or to otherwise interact with the polypeptide. Soluble receptor polypeptide is also added to the mixture. If the test compound interacts with the soluble receptor polypeptide, it decreases the amount of complex formed or activity from the receptor target. This type of assay is particularly useful in cases in which compounds are sought that interact with specific regions of the receptor. Thus, the soluble polypeptide that competes with the target receptor region is designed to contain peptide sequences corresponding to the target region.

To perform cell-free drug screening assays, it is desirable to immobilize either the receptor protein, or fragment, or its target molecule to facilitate separation of complexes from uncomplexed forms of one or both of the proteins, as well as to accommodate automation of the assay.

Techniques for immobilizing G-proteins on matrices can be used in the drug screening assays. In one embodiment, a fusion protein can be provided which adds a domain that allows the protein to be bound to a matrix. For example, glutathione-Stransferase/G-protein Chemokine Receptor (CCR5) fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of receptor-binding protein found in the bead fraction quantitated from the gel using standard electrophoretic techniques, For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a receptor-binding protein and a candidate compound are incubated in the receptor protein-presenting wells and the amount of complex trapped in the well can be quantitated. Methods for detecting such complexes, in addition to those described above for the GST-immobilized complexes, include immunodetection of complexes using antibodies reactive with the receptor protein target molecule, or which are reactive with receptor protein and compete with the target molecule; as well as enzyme-linked assays which rely on detecting an enzymatic activity associated with the target molecule.

Modulators of receptor protein activity identified according to these drug screening assays can be used to treat a subject with a disorder mediated by the receptor pathway, by treating cells that express the receptor protein. These methods of treatment include the steps of administering the modulators of protein activity in a pharmaceutical composition as described herein, to a subject in need of such treatment.

Antisense and Ribozyme (Antagonists)

In specific embodiments, antagonists according to the present invention are nucleic acids corresponding to the sequences contained in SEQ ID NO:1, or the complementary strand thereof, and/or to nucleotide sequences contained in the deposited clone 97183. In one embodiment, antisense sequence is generated internally, by the organism, in another embodiment, the antisense sequence is separately administered (see, for example, O'Connor, J., Neurochem. 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCI pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the G-protein Chemokine Receptor (CCR5) antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the G-protein Chemokine Receptor (CCR5) antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding G-protein Chemokine Receptor (CCR5), or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of a G-protein Chemokine Receptor (CCR5) gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded G-protein Chemokine Receptor (CCR5) antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a G-protein Chemokine Receptor (CCR5) RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of G-protein Chemokine Receptor (CCR5) shown in FIGS. 1A–B or within the coding region of the deposited clone could be used in an antisense approach to inhibit translation of endogenous G-protein Chemokine Receptor (CCR5) mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of G-protein Chemokine Receptor (CCR5) mRNA or within the coding region of the deposited clone, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the G-protein Chemokine Receptor (CCR5) coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy G-protein Chemokine Receptor (CCR5) mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of G-protein Chemokine Receptor (CCR5) (FIGS. 1A–B or the sequence of the deposited clone). Preferably, the ribozyme is engineered so that the cleavage recognition site is located near the 5' end of the G-protein Chemokine Receptor (CCR5) mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express G-protein Chemokine Receptor (CCR5) in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous G-protein Chemokine Receptor (CCR5) messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Use of Transmembrane Fragments as Antagonists/Inhibitors

In specific embodiments, the present invention relates to modulating, especially inhibiting, biological activities of G-protein Chemokine Receptor (CCR5) by exposing it to molecules which interfere with correct receptor assembly. In particular, the invention relates to isolated fragments or peptides of the transmembrane domain of G-protein Chemokine Receptor (CCR5) that inhibit G-protein Chemokine Receptor mediated signal transduction or ligand-binding. In certain embodiments, charged residues are added at one terminus of the fragment to promote correct orientation of the fragment in the membrane.

It has been demonstrated that G-protein coupled receptor (GPCR) transmembrane (TM) domain segments interact in a specific way during the assembly of receptor molecules. These interactions do not lead to a rigid structure because some flexibility is required for conformational changes following ligand binding, which allow the molecule to signal from the cell surface to the intracellular parts. It was also demonstrated for several GPCRs that the transmembrane domain is involved in ligand binding and thus it contains openings that allow penetration of the ligands. Reports that expression of missing transmembrane domains rescues inactive truncated V2 vasopressin, beta-adrenergic and muscarinic M3 receptors (Schoneberg et al. *EMBO J.* 15:1283 (1996); Wong et al., *J. Biol. Chem.* 265:6219 (1990); Monnot et al., *J. Biol. Chem.* 271:1507 (1996); Gudermann et al., *Annu. Rev. Neurosci.* 20:399 (1997); Osuga et al., *J. Biol. Chem.* 272:25006 (1997)) suggested peptide derived from the sixth transmembrane domain of P2-adrenergic receptor was found to inhibit receptor activation and dimerization (Hebert et al., *J. Biol. Chem.*, 271(27):16384–92 (1996)). Thus, GPCR function can be rescued by targeting intramembrane interactions of GPCRs.

Additionally, GPCR function can be inhibited by targeting intramembrane interactions. For example, fragments corresponding to predicted TM segments of CCR5, which functions as a coreceptor during entry of HIV into cells, yielded potent inhibition of HIV entry without apparent toxicity to the cells. (See WO 99/43711) The usefulness of the method was also demonstrated by specifically targeting CXCR4, which functions as a co-receptor during the cell entry of T-cell tropic strains of HIV-1. Fragments containing 20–25 amino acid residues inhibited receptor signaling and HIV-1 infection in vitro at concentration as low as 0.2 micromolar. (See WO 99/43711).

The hydrophobic and/or amphipathic nature of the transmembrane fragments allows their penetration into the bilayer. Further, orientation inside the membrane can be controlled by addition of charged residues to the terminus that is exposed at the extracellular side of the membrane in the intact receptor. Insertion into the membrane is tested by fluorescent microscopy of labeled peptide analogs using methodology known to those of ordinary skill in the art, and as described in WO 99/43711.

In a particular embodiment, the invention encompasses transmembrane fragments that modulate, and preferably inhibit the biological properties and activities of G-protein Chemokine Receptor (CCR5), by targeting the transmembrane domain of this receptor. In a further embodiment, the invention specifically comprises methods for disrupting G-protein Chemokine Receptor (CCR5) function by using these antagonists.

Chemical or recombinant DNA technology may be used to obtain G-protein Chemokine Receptor (CCR5) transmembrane fragments, which preferably are as small as possible while still retaining sufficiently high affinity for binding to, or association with, G-protein Chemokine Receptor. Non-limiting examples of G-protein Chemokine Receptor (CCR5) polypeptides include fragments of 10 to 50 amino acids corresponding to at least one transmembrane segment of segments 1–7.

In another embodiment, the invention encompasses an isolated G-protein Chemokine Receptor-modulating molecule comprising a fragment, a peptide, or peptidomimetic that is a structural analog of a portion of a transmembrane segment of G-protein Chemokine Receptor (CCR5), wherein said molecule has an extracellular end and an intracellular end and said molecule has at said extracellular end a negatively charged group and at said intracellular end a neutral charge under physiological conditions; said molecule spontaneously inserts into a membrane in the same orientation as the transmembrane domain from which it is derived; and said molecule modulates a biological property or activity of said G-protein Chemokine Receptor.

In a particular embodiment, the molecules contain a hydrophilic, negatively charged non-peptidic head group and an uncharged tail, which assures correct orientation of the molecule in the cell membrane. In another embodiment, the negatively charged head group is one or more acidic amino acids.

The G-protein Chemokine Receptor (CCR5) activity modulated by said fragment includes inhibition of G-protein Chemokine Receptor-mediated intracellular $Ca^{2+}$ release and inhibition of G-protein Chemokine Receptor-mediated HIV infection. The G-protein Chemokine Receptor (CCR5) activity modulated by said peptide also includes binding of a G-protein Chemokine Receptor (CCR5) ligand. Additional G-protein Chemokine Receptor (CCR5) activities modulated by said peptide include those in the Description and Examples herein.

In another embodiment, the invention comprises methods of modulating the biological activity of a G-protein Chemokine Receptor (CCR5) by contacting a cell that expresses G-protein Chemokine Receptor (CCR5) with a molecule of the invention. In one method, the modulated biological activity is inhibition of G-protein Chemokine Receptor-mediated HIV infection. In another method, the modulated biological activity is inhibition of G-protein Chemokine Receptor-mediated intracellular $Ca^{2+}$ release. Other activities modulated include those described elsewhere herein.

Another embodiment is a method of inhibiting HIV-1 infection, comprising contacting a cell that expresses G-protein Chemokine Receptor (CCR5) which binds HIV-1 with a molecule that comprises a polypeptide fragment, a peptide, or peptidomimetic that is a structural analog of a portion of the transmembrane domain of said G-protein Chemokine Receptor (CCR5), wherein contacting the cell with said molecule inhibits HIV-1 infection. The peptide or peptidomimetic may be a structural analog of a portion of a transmembrane domain of G-protein Chemokine Receptor.

In one embodiment, the molecules of the present invention mimic a transmembrane segment of G-protein Chemokine Receptor (CCR5) and block self-assembly of the receptor, possibly by competitive inhibition with the native TM segment. They thereby block or inhibit signal transduction in the affected cell.

The invention also includes peptide analogs and peptidomimetics which possess beneficial properties such as increased half-life, lack of immunogenicity, and the ability to cross the blood-brain barrier.

The peptide analogs of the invention mediate the chemical and/or biological effects of hormone agonists/antagonists or other peptides. They are useful for the development of pharmaceutical, therapeutic, and diagnostic techniques. Accordingly, the invention also provides methods for producing a prophylactic or therapeutic response in a mammal by administering to the mammal a pharmaceutically effective amount of one or more peptide analogs of the invention. In preferred embodiments, the present invention provides methods for producing such responses by modulating the activity of G-protein Chemokine Receptor (CCR5) by administering an effective amount of one or more peptide analogs of the invention.

In another embodiment, more than one peptide of the invention are administered as a cocktail to modulate the biological activity of G-protein Chemokine Receptor.

The term "G-protein Chemokine Receptor (CCR5) transmembrane peptide" can include a fragment of the transmembrane domain, a transmembrane segment, a fragment of a transmembrane segment, and/or a homologous peptide thereof. Preferred fragments include those of at least 4–50, and preferably at least 4–30, and preferably at least 10–30 amino acids in length, or any range therein. Further preferred fragments include those of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. Also included are any corresponding sequences having conservative amino acid substitutions.

Sample transmembrane fragments of the invention include, but are not limited to, any fragment described herein. A preferred transmembrane fragment of the present invention, when contacted with a cell or membrane structure (e.g., liposome) that contains biologically active G-protein Chemokine Receptor (CCR5), modulates the biological activity of said G-protein Chemokine Receptor (CCR5) in vitro, in vivo, or in situ. The concentration of the fragment in a solution that contacts the cell in vivo (e.g., blood plasma or interstitial fluid) or in vitro (e.g., culture medium) is between 1 nanomolar and 50 micromolar, preferably between 1 nanomolar and 1 micromolar, and most preferably less than 5 micromolar.

"Negatively charged" refers to those amino acids, amino acid derivatives, amino acid mimetics and chemical moieties that are negatively charged at physiological pH. Negatively charged amino acids include, for example Asp and Glu. An "acidic" residue is a residue that is negatively charged at physiological pH.

"Positively charged" refers to those amino acids, amino acid derivatives, amino acid mimetics and chemical moieties that are positively charged at physiological pH. Positively charged amino acids include, for example, Lys and Arg. A "basic residue" is a residue that is positively charged at physiological pH.

"Neutral" refers to those amino acids, amino acid derivatives, amino acid mimetics and chemical moieties that are neither positively nor negatively charged at physiological pH.

The term "modulates a biological property or activity" means that in the presence of a test transmembrane fragment a measurable biological parameter or event is increased or decreased relative to a control in the absence of said peptide. Examples of biological property or activity include: conformation of G-protein Chemokine Receptor (CCR5), association of the G-protein Chemokine Receptor (CCR5) with other molecules, signal transduction, extracellular secretion of cellular proteins, conformational changes in proteins, changes in enzymatic activity, changes in metabolic activity, changes in affinity for a ligand, changes in levels of viral infection, changes in vasodilation, modulation of heart rate, modulation of bronchodilation, modulation of endocrine secretions, and modulation of gut peristalsis. Note that the G-protein Chemokine Receptor (CCR5) biological activity need not be one that is limited to the precise in vivo role performed by the G-protein Chemokine Receptor. The term also covers G-protein Chemokine Receptor (CCR5) properties, such as viral protein binding, that are not part of the in vivo biological role of the G-protein Chemokine Receptor. It further covers intrinsic properties of G-protein Chemokine Receptor (CCR5) that are only disclosed by experimental manipulation in the laboratory, such as the ability of G-protein Chemokine Receptor (CCR5) in artificial bilayers (e.g., liposomes) to interact with G-protein Chemokine Receptor (CCR5) ligands.

"Signal transduction" is the process by which binding of a ligand to a receptor is translated into physiological change. In general, binding of a ligand to a receptor causes a change in a physical property of the receptor, for example a change in its conformation, or its orientation, or in its ability to bind other ligands. This change in a physical property can result, directly or indirectly, in increased or decreased ion fluxes, increased or decreased enzymatic activity, increased or decreased phosphorylation, increased or decreased translocation of the receptor or of any molecule (e.g., an inositol moiety or a G-protein subunit) from one cellular compartment to another.

"G-protein Chemokine Receptor (CCR5) ligands" refers to biological molecules that bind G-protein Chemokine Receptor (CCR5) in vitro, in situ, or in vivo, and may include hormones, neurotransmitters, viruses or receptor-binding domains thereof, G-proteins, opsins, rhodopsins, nucleosides, nucleotides, coagulation cascade factors, odorants or pheromones, toxins, colony stimulating factors, platelet activating factors, neuroactive peptides, neurohumor, or any biologically active compounds, such as drugs or synthetic or naturally occurring compounds.

The phrase "inhibits HIV infection" means that a peptide of the invention inhibits binding of a HIV to G-protein Chemokine Receptor (CCR5) or inhibits a G-protein Chemokine Receptor (CCR5) biological activity that mediates the entry and successful reproduction of a HIV virus into a G-protein Chemokine Receptor-expressing cell.

G-protein Chemokine Receptor (CCR5) polypeptides of the present invention, or nucleic acids encoding therefor, include a finite set of substantially corresponding sequences as substitution peptides or polynucleotide which can be routinely obtained by one of ordinary skill in the art, without undue experimentation, based on the teachings and guidance presented herein. For a detailed description of protein chemistry and structure, see Schulz et al., PRINCIPLES OF PROTEIN STRUCTURE, Springer-Verlag, New York, 1978, and Creighton, T. E., PROTEINS: STRUCTURE AND MOLECULAR PROPERTIES, W. H. Freeman & Co., San Francisco, 1983, which are hereby incorporated by reference. For a presentation of nucleotide sequence substitutions, such as codon preferences, see Ausubel et al, supra, at sections A.1.1–A.1.24, and Sambrook et al., supra, at Appendices C and D.

G-protein Chemokine Receptor (CCR5) polypeptides include homologous sequences and/or fragments of the transmembrane domain, in particular, at least one of transmembrane segment 1–7 of G-protein Chemokine Receptor (CCR5) or homologs thereof.

However, in the context of the present invention, G-protein Chemokine Receptor (CCR5) polypeptides of at least 15–20 amino acids are preferred such that the G-protein Chemokine Receptor (CCR5) polypeptides are able to span the lipid bilayer.

It is particularly preferred that peptides of the invention be selected or modified so that one end is charged and the other is neutral under physiological conditions. This is so that the peptide spontaneously inserts into a membrane. It is of particular importance that the peptide insert in the same orientation as the transmembrane G-protein Chemokine Receptor (CCR5) domain from which it is derived.

Peptides of the invention can be derived from any of the 7 TM segments. The amino acid positions of the TM segments can be determined using molecular modeling, optionally combined with hydrophobicity analysis (see Table 1), and/or fitting to model helices, as non-limiting examples. Such modeling can be accomplished according to known methods, for example, ECEPP, INSIGHT, DISCOVER, CHEM-DRAW, AMBER, FRODO, and CHEM-X. Such algorithms compare transmembrane domains and segments between related GPCRs, determine probable energy-minimized structures and define alternative transmembrane sequences.

Fragments of the G-protein Coupled Chemokine Receptor transmembrane domain which are useful as antagonists comprise, or alternatively consist of, the following portions of SEQ ID NO:2 or of the polypeptide encoded by the deposited clone:

Segment 1: amino acids 31–58, 32–58, 33–58, 34–58, 35–58, 36–58, 37–58, 38–58, 31–57, 32–57, 33–57, 34–57, 35–57, 36–57, 37–57, 31–56, 32–56, 33–56, 34–56, 35–56, 36–56, 31–55, 32–55, 33–55, 34–55, 35–55, 31–54, 32–54, 33–54, 34–54, 31–53, 32–53, 33–53, 31–52, 32–52, 31–51 of SEQ ID NO:2 or of the polypeptide encoded by the deposited clone, or any combination thereof, preferably at least 15 amino acids in length;

Segment 2: amino acids 68–97, 69–97, 70–97, 71–97, 72–97, 73–97, 74–97, 75–97, 76–97, 68–96, 69–96, 70–96, 71–96, 72–96, 73–96, 74–96, 75–96, 76–96, 68–95, 69–95, 70–95, 71–95, 72–95, 73–95, 74–95, 75–95, 68–94, 69–94, 70–94, 71–94, 72–94, 73–94, 74–94, 68–93, 69–93, 70–93, 71–93, 72–93, 73–93, 68–92, 69–92, 70–92, 71–92, 72–92, 68–91, 69–91, 70–91, 71–91, 68–90, 69–90, 70–90, 68–89, 69–89, 68–88 of SEQ ID NO:2 or of the polypeptide encoded by the deposited clone, or any combination thereof, preferably at least 15 amino acids in length;

Segment 3: amino acids 103–124, 104–124, 105–124, 106–124, 107–124, 108–124, 109–124, 103–123, 103–122, 103–121, 103–120, 103–119, 103–118 of SEQ ID NO:2 or of the polypeptide encoded by the deposited clone, or any combination thereof, preferably at least 15 amino acids in length;

Segment 4: amino acids 142–169, 143–169, 144–169, 145–169, 146–169, 147–169, 148–169, 149–169, 142–168, 143–168, 144–168, 145–168, 146–168, 147–168, 148–168, 142–167, 143–167, 144–167, 145–167, 146–167, 147–167, 142–166, 143–166, 144–166, 145–166, 146–166, 142–165, 143–165, 144–165, 145–165, 142–164, 143–164, 144–164, 142–163, 143–163, 142–163 of SEQ ID NO:2 or of the polypeptide encoded by the deposited clone, or any combination thereof, preferably at least 15 amino acids in length;

Segment 5: amino acids 196–223, 197–223, 198–223, 199–223, 200–223, 201–223, 202–223, 203–223, 196–222, 197–222, 198–222, 199–222, 200–222, 201–222, 202–222, 196–221, 197–221, 198–221, 199–221, 200–221, 201–221, 196–220, 197–220, 198–220, 199–220, 200–220, 196–219, 197–219, 198–219, 199–219, 196–218, 197–218, 198–218, 196–217, 197–217, 196–216 of SEQ ID NO:2 or of the polypeptide encoded by the deposited clone, or any combination thereof, preferably at least 15 amino acids in length, Segment 6: amino acids 236–260, 237–260, 238–260, 239–260, 240–260, 236–259, 237–259, 238–259, 239–259, 236–258, 237–258, 238–258, 236–257, 237–257, 236–256 of SEQ ID NO:2 or of the polypeptide encoded by the deposited clone, or any combination thereof, preferably at least 15 amino acids in length;

Segment 7: amino acids 275–305, 276–305, 277–305, 278–305, 279–305, 280–305, 281–305, 282–305, 283–305, 284–305, 285–305, 275–304, 276–304, 277–304, 278–304, 279–304, 280–304, 281–304, 282–304, 283–304, 284–304, 275–303, 276–303, 277–303, 278–303, 279–303, 280–303, 281–303, 282–303, 283–303, 275–302, 276–302, 277–302, 278–302, 279–302, 280–302, 281–302, 282–302, 275–301, 276–301, 277–301, 278–301, 279–301, 280–301, 281–301, 275–300, 276–300, 277–300, 278–300, 279–300, 280–300, 275–299, 276–299, 277–299, 278–299, 279–299, 275–298, 276–298, 277–298, 278–298, 275–297, 276–297, 277–297, 275–296, 276–296, 275–295 of SEQ ID NO:2 or of the polypeptide encoded by the deposited clone, or any combination thereof, preferably at least 15 amino acids in length;

The CCR5 fragments disclosed in WO 99/43711 are specifically excluded from the embodiments in this section.

Negatively charged amino acids, such as Asp or Glu, may be substituted or added at the extracellular end of the fragment. The number of negatively charged amino acids is typically 1, 2, or 3. Neutral amino acids may be substituted or added at the intracellular end of the fragment. See, also, Example 57.

Other Activities

A polypeptide, polynucleotide, agonist, or antagonist of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. The polypeptide, polynucleotide, agonist, or antagonist of the present invention may also be employed to stimulate angiogenesis and limb regeneration, as discussed above.

A polypeptide, polynucleotide, agonist, or antagonist of the present invention may also be employed for treating, preventing, and/or diagnosing wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

A polypeptide, polynucleotide, agonist, or antagonist of the present invention may also be employed stimulate neuronal growth and to treat and prevent neuronal damage which occurs in certain neuronal diseases, disorders, and/or conditions or neuro-degenerative conditions such as Alzheimer's disease, Parkinson's disease, and AIDS-related complex. A polypeptide, polynucleotide, agonist, or antagonist of the present invention may have the ability to stimulate chondrocyte growth, therefore, they may be employed to enhance bone and periodontal regeneration and aid in tissue transplants or bone grafts.

A polypeptide, polynucleotide, agonist, or antagonist of the present invention may be also be employed to prevent skin aging due to sunburn by stimulating keratinocyte growth.

A polypeptide, polynucleotide, agonist, or antagonist of the present invention may also be employed for preventing hair loss, since FGF family members activate hair-forming cells and promotes melanocyte growth. Along the same lines, a polypeptide, polynucleotide, agonist, or antagonist of the present invention may be employed to stimulate growth and differentiation of hematopoietic cells and bone marrow cells when used in combination with other cytokines.

A polypeptide, polynucleotide, agonist, or antagonist of the present invention may also be employed to maintain organs before transplantation or for supporting cell culture of primary tissues. A polypeptide, polynucleotide, agonist, or antagonist of the present invention may also be employed for inducing tissue of mesodermal origin to differentiate in early embryos.

A polypeptide, polynucleotide, agonist, or antagonist of the present invention may also increase or decrease the differentiation or proliferation of embryonic stem cells, besides, as discussed above, hematopoietic lineage.

A polypeptide, polynucleotide, agonist, or antagonist of the present invention may also be used to modulate mammalian characteristics, such as body height, weight, hair color, eye color, skin, percentage of adipose tissue, pigmentation, size, and shape (e.g., cosmetic surgery). Similarly, a polypeptide, polynucleotide, agonist, or antagonist of the present invention may be used to modulate mammalian metabolism affecting catabolism, anabolism, processing, utilization, and storage of energy.

A polypeptide, polynucleotide, agonist, or antagonist of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

A polypeptide, polynucleotide, agonist, or antagonist of the present invention may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Having generally described the invention, the same will be more readily understood by reference to the following examples, which are provided by way of illustration and are not intended as limiting.

EXAMPLES

Example 1

Bacterial Expression and Purification of HDGNR10

The DNA sequence encoding for HDGNR10, ATCC No. 97183 is initially amplified using PCR oligonucleotide primers corresponding to the 5' and sequences of the processed HDGNR10 protein (minus the signal peptide sequence) and the vector sequences 3' to the HDGNR10 gene. Additional nucleotides corresponding to HDGNR10 were added to the 5' and 3' sequences respectively. The 5' oligonucleotide primer has the sequence

```
5' CGGAATTCCTCCATGGATTATCAAGTGTCA 3' (SEQ ID NO:3)
```

and contains an EcoRI restriction enzyme site followed by 18 nucleotides of HDGNR10 coding sequence starting from the presumed terminal amino acid of the processed protein codon.

The 3' sequence 5'CGGAAGCTTCGTCACAAGCCCACAGATAT 3' (SEQ ID NO:4) contains complementary sequences to a HindIII site and is followed by 18 nucleotides of HDGNR10 coding sequence. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance ($Amp^r$), a bacterial origin of replication (ori), an IPTG-regulatable promoter operator (P/O), a ribosome binding site (RBS), a 6-His tag and restriction enzyme sites. pQE-9 was then digested with EcoRI and HindIII. The amplified sequences were ligated into pQE-9 and were inserted in frame with the sequence encoding for the histidine tag and the RBS. The ligation mixture was then used to transform *E. coli* strain M15/rep 4 (Qiagen, Inc.) by the procedure described in Sambrook, J. et al., *Molecular Cloning: A Laboratory Manual*, Cold Spring Laboratory Press, (1989). M15/rep4 contains multiple copies of the plasmid pREP4, which expresses the lacI repressor and also confers kanamycin resistance ($Kan^r$). Transformants are identified by their ability to grow on LB plates and ampicillin/kanamycin resistant colonies were selected. Plasmid DNA was isolated and confirmed by restriction analysis.

Clones containing the desired constructs were grown overnight (O/N) in liquid culture in LB media supplemented with both Amp (100 µg/ml) and Kan (25 µg/ml). The O/N culture is used to inoculate a large culture at a ratio of 1:100 to 1:250. The cells were grown to an optical density 600 ($O.D.^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized HDGNR10 was purified from this solution by chromatography on a Nickel-Chelate column under conditions that allow for tight binding by proteins containing the 6-His tag. Hochuli, E. et al., *J. Chromatography* 411:177–184 (1984). HDGNR10 was eluted from the column in 6 molar guanidine HC1 pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

Example 2

Expression of Recombinant HDGNR10 in COS Cells

The expression of plasmid HDGNR10 HA is derived from a vector pcDNAI/Amp (Invitrogen) containing: 1) SV40 origin of replication, 2) ampicillin resistance gene, 3) *E.coli* replication origin, 4) CMV promoter followed by a polylinker region, a SV40 intron and polyadenylation site. A DNA fragment encoding the entire HDGNR10 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, et al., *Cell* 37:767 (1984)). The infusion of HA tag to the target protein allows easy detection of the recombinant protein with an antibody that recognizes the HA epitope.

The plasmid construction strategy is described as follows:

The DNA sequence encoding for HDGNR10, ATCC No. 97183, was constructed by PCR using two primers: the 5' primer 5'GTCCAAGCTTGCCACCATGGATTATCA AGTGTCA 3' (SEQ ID NO:5) and contains a HindIII site followed by 18 nucleotides of HDGNR10 coding sequence starting from the initiation codon; the 3' sequence 5' CTAGCTCGAGTCAAGCGTAGTCTG-GACGTCGTATGGGTAGCACAA GCCCACA-GATATTTC 3' (SEQ ID NO:6) contains complementary sequences to an XhoI site, translation stop codon, HA tag and the last 18 nucleotides of the HDGNR10 coding sequence (not including the stop codon). Therefore, the PCR product contains a HindIII site HDGNR10 coding sequence followed by HA tag fused in frame, a translation termination stop codon next to the HA tag, and an XhoI site. The PCR amplified DNA fragment and the vector, pcDNAI/Amp, were digested with HindIII and XhoI restriction enzyme and ligated. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant HDGNR10, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the HDGNR10 HA protein was detected by radiolabelling and immunoprecipitation method. (E. Harlow, D. Lane, *Antibodies: A Laboratory Manual*, Cold Spring Harbor Laboratory Press, (1988)). Cells were labelled for 8 hours with $^{35}S$-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984) Both cell lysate and culture media were precipitated with a HA specific monoclonal antibody. Proteins precipitated were analyzed on 15% SDS-PAGE gels.

Example 3

Cloning and Expression of HDGNR10 Using the Baculovirus Expression System

The DNA sequence encoding the full length HDGNR10 protein, ATCC No. 97183, was amplified using PCR oligonucleotide primers corresponding to the 5' and 3' sequences of the gene:

The 5' primer has the sequence

```
5' CGGGATCCCTCCATGGATTATCAAGTGTCA 3' (SEQ ID NO:7)
```

and contains a BamHI restriction enzyme site followed by 4 nucleotides resembling an efficient signal for the initiation of translation in eukaryotic cells (Kozak, M., *J. Mol. Biol.* 196:947–950 (1987)) and just behind the first 18 nucleotides of the HDGNR10 gene (the initiation codon for translation is "ATG").

The 3' primer has the sequence

```
5' CGGGATCCCGCTCACAAGCCCACAGATAT 3'  (SEQ ID NO:8)
```

and contains the cleavage site for the restriction endonuclease BamHI and 18 nucleotides complementary to the 3' non-translated sequence of the HDGNR10 gene. The amplified sequences were isolated from a 1% agarose gel using a commercially available kit ("Geneclean," BIO 101 Inc., La Jolla, Calif.). The fragment was then digested with the endonuclease BamHi and purified as described above. This fragment is designated F2.

The vector pRGI (modification of pVL941 vector, discussed below) is used for the expression of the HDGNR10 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa califomica nuclear polyhedrosis virus (AcMNPV) followed by the recognition sites for the restriction endonuclease BamHI. The polyadenylation site of the simian virus (SV)40 is used for efficient polyadenylation. For an easy selection of recombinant viruses the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., *Virology* 170:31–39).

The plasmid was digested with the restriction enzyme BainHI and then dephosphorylated using calf intestinal phosphatase by procedures known in the art. The DNA was then isolated from a 1% agarose gel as described above. This vector DNA is designated V2.

Fragment F2 and the dephosphorylated plasmid V2 were ligated with T4 DNA ligase. *E. coli* HB101 cells were then transformed and bacteria identified that contained the plasmid (pBacHDGNR10) with the HDGNR10 gene using the enzyme BamHI. The sequence of the cloned fragment was confirmed by DNA sequencing.

5 μg of the plasmid pBacHDGNR10 were co-transfected with 1.0 μg of a commercially available linearized baculovirus ("BaculoGold™ baculovirus DNA", Pharmingen, San Diego, Calif.) using the lipofection method (Felgner, et al., *Proc. Natl. Acad. Sci.* USA 84:7413–7417 (1987)).

1 μg of BaculoGold™ virus DNA and 5 μg of the plasmid pBacHDGNR10 were mixed in a sterile well of a microtiter plate containing 50 μg of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added drop wise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, pages 9–10).

Four days after the serial dilution, the viruses were added to the cells, blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-HDGNR10 at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation and the labelled proteins visualized by SDS-PAGE and autoradiography.

Example 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added). This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, *DNA* 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar containing kanamycin for the purpose of confirming that the vector had the gene of interest properly inserted.

The amphotropic pA317 or GP+am12 packaging cells are grown in tissue culture to confluent density in Dulbecco's Modified Eagles medium (DMEM) with 10% calf serum (CS) penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Example 5

Isolation of the G-protein Chemokine Receptor (CCR5) DNA Clone From the Deposited Sample The DNA for G-protein Chemokine Receptor (CCR5) is inserted into the multiple cloning site of pQE-9. (Qiagen, Inc.) pQE-9 contains an Ampicillin resistance gene and may be transformed into *E. coli* strain DH10B, available from Life Technologies. (See, for instance, Gruber, C. E., et al., Focus 15:59-(1993).)

Two approaches can be used to isolate G-protein Chemokine Receptor (CCR5) from the deposited sample. First, the deposited clone is transformed into a suitable host (such as XL-1 Blue (Stratagene)) using techniques known to those of skill in the art, such as those provided by the vector supplier or in related publications or patents. The transformants are plated on 1.5% agar plates (containing the appropriate selection agent, e.g., ampicillin) to a density of about 150 transformants (colonies) per plate. A single colony is then used to generate DNA using nucleic acid isolation techniques well known to those skilled in the art. (e.g., Sambrook et al., Molecular Cloning: A Laboratory Manual, 2nd Edit., (1989), Cold Spring Harbor Laboratory Press.)

Alternatively, two primers of 17–20 nucleotides derived from both ends of the SEQ ID NO:1 or SEQ ID NO:21 (i.e., within the region of SEQ ID NO:1 or SEQ ID NO:21 bounded by the 5' NT and the 3' NT of the clone) are synthesized and used to amplify the G-protein Chemokine Receptor (CCR5) DNA using the deposited DNA plasmid as a template. The polymerase chain reaction is carried out under routine conditions, for instance, in 25 ul of reaction mixture with 0.5 ug of the above DNA template. A convenient reaction mixture is 1.5–5 mM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of the G-protein Chemokine Receptor (CCR5) gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the G-protein Chemokine Receptor (CCR5) gene of interest is used to PCR amplify the 5' portion of the G-protein Chemokine Receptor (CCR5) full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the G-protein Chemokine Receptor (CCR5) gene.

Example 6

Isolation of G-protein Chemokine Receptor (CCR5) Genomic Clones

A human genomic P1 library (Genomic Systems, Inc.) is screened by PCR using primers selected for the DNA sequence corresponding to SEQ ID NO:1 or SEQ ID NO:21, according to the method described in Example 5. (See also, Sambrook.)

Example 7

Tissue Distribution of G-protein Chemokine Receptor (CCR5) Polypeptides

Tissue distribution of mRNA expression of G-protein Chemokine Receptor (CCR5) is determined using protocols for Northern blot analysis, described by, among others, Sambrook et al. For example, a G-protein Chemokine Receptor (CCR5) probe produced by the method described in Example 5 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70 degree C. overnight, and the films developed according to standard procedures.

Example 8

Chromosomal Mapping of G-protein Chemokine Receptor

An oligonucleotide primer set is designed according to the sequence at the 5' end of SEQ ID NO:1 or SEQ ID NO:21.

This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 9

Bacterial Expression of G-protein Chemokine Receptor

G-protein Chemokine Receptor (CCR5) polynucleotide encoding a G-protein Chemokine Receptor (CCR5) polypeptide invention is amplified using PCR oligonucleotide primers corresponding to the 5' and 3' ends of the DNA sequence, as outlined in Example 5, to synthesize insertion fragments. The primers used to amplify the cDNA insert should preferably contain restriction sites, such as BamHI and XbaI, at the 5' end of the primers in order to clone the amplified product into the expression vector. For example, BamHi and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCI by stirring for 3–4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified G-protein Chemokine Receptor (CCR5) protein is then renatured by dialyzing it against phosphate-buffered saline (PBS) or 50 mM Na-acetate, pH 6 buffer plus 200 mM NaCl. Alternatively, the G-protein Chemokine Receptor (CCR5) protein can be successfully refolded while immobilized on the Ni-NTA column. The recommended conditions are as follows: renature using a linear 6M–1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Immidazole is removed by a final dialyzing step against PBS or 50 mM sodium acetate pH 6 buffer plus 200 mM NaCl. The purified G-protein Chemokine Receptor (CCR5) protein is stored at 4 degree C. or frozen at −80 degree C.

In addition to the above expression vector, the present invention further includes an expression vector comprising phage operator and promoter elements operatively linked to a G-protein Chemokine Receptor (CCR5) polynucleotide, called pHE4a. (ATCC Accession Number 209645, deposited Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 5, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 10

Purification of G-protein Chemokine Receptor (CCRS) Polypeptide from an Inclusion Body The following alternative method can be used to purify G-protein Chemokine Receptor (CCR5) polypeptide expressed in *E coli* when it is present in the form of inclusion bodies. Unless otherwise specified, all of the following steps are conducted at 4–10 degree C.

Upon completion of the production phase of the *E. coli* fermentation, the cell culture is cooled to 4–10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCI solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the G-protein Chemokine Receptor (CCR5) polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant G-protein Chemokine Receptor (CCR5) polypeptide should exhibit greater than 95% purity after the above refolding and purification steps. No major contaminant bands should be observed from Commassie blue stained 16% SDS-PAGE gel when 5 ug of purified protein is loaded. The purified G-protein Chemokine Receptor (CCR5) protein can also be tested for endotoxin/LPS contamination, and typically the LPS content is less than 0.1 ng/ml according to LAL assays.

Example 11

Cloning and Expression of G-protein Chemokine Receptor (CCR5) in a Baculovirus Expression System In this example, the plasmid shuttle vector pA2 is used to insert G-protein Chemokine Receptor (CCR5) polynucleotide into a baculovirus to express G-protein Chemokine Receptor. This expression vector contains the strong polyhedrin promoter of the Autographa californica nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned G-protein Chemokine Receptor (CCR5) polynucleotide.

Many other baculovirus vectors can be used in place of the vector above, such as pAc373, pVL941, and pAcIMi1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the G-protein Chemokine Receptor (CCR5) cDNA sequence contained in the deposited clone, including the AUG initiation codon and any naturally associated leader sequence, is amplified using the PCR protocol described in Example 5. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transfected with 1.0 ug of a commercially available linearized baculovirus DNA ("BaculoGold™ baculovirus DNA", Pharmingen, San Diego, Calif.), using the lipofection method described by Felgner et al., *Proc. Natl. Acad. Sci.* USA 84:7413–7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of $^{35}$S-methionine and 5 uCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced G-protein Chemokine Receptor (CCR5) protein.

Example 12

Expression of G-protein Chemokine Receptor (CCR5) in Mammalian Cells

G-protein Chemokine Receptor (CCR5) polypeptide can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2DHFR (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, G-protein Chemokine Receptor (CCR5) polypeptide can be expressed in stable cell lines containing the G-protein Chemokine Receptor (CCR5) polynucleotide integrated into a chromosome. The co-transfection with a selectable marker such as DHFR, gpt, neomycin, hygromycin allows the identification and isolation of the transfected cells.

The transfected G-protein Chemokine Receptor (CCR5) gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., *J. Biol. Chem.* 253: 1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-DHFR (ATCC Accession No. 37146), the expression vectors pC4 (ATCC Accession No. 209646) and pC6 (ATCC Accession No. 209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHi, XbaI and Asp718, facilitate the cloning of G-protein Chemokine Receptor. The vectors also contain the 3' intron, the polyadenylation and termination signal of the rat preproinsulin gene, and the mouse DHFR gene under control of the SV40 early promoter.

Specifically, the plasmid pC6 or pC4 is digested with restriction enzymes that cut within in the multiple cloning site and then dephosphorylated using calf intestinal phosphates by procedures known in the art. The vector is then isolated from a 1% agarose gel.

The vector can be modified to include a heterologous signal sequence in an effort to secrete the protein from the cell. (See, e.g., WO 96/34891.)

The amplified fragment is then digested with restriction enzymes that generate ends complementary to those of the digested vector and purified on a 1% agarose gel using a commercially available kit ("Geneclean," BIO 101 Inc., La Jolla, Calif.). The isolated fragment and the dephosphorylated vector are then ligated with T4 DNA ligase. *E. coli* HB101 or XL-1 Blue cells are then transformed and bacteria are identified that contain the fragment inserted into plasmid pC6 or pC4 using, for instance, restriction enzyme analysis.

Chinese hamster ovary cells lacking an active DHFR gene is used for transfection. Five μg of the expression plasmid pC6 or pC4 is cotransfected with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of G-protein Chemokine Receptor (CCR5) is analyzed, for instance, by SDS-PAGE and Western blot or by reversed phase HPLC analysis.

Example 13

Construction of N-Terminal and/or C-Terminal Deletion Mutants

The following general approach may be used to clone a N-terminal or C-terminal deletion G-protein Chemokine Receptor (CCR5) deletion mutant. Generally, two oligonucleotide primers of about 15–25 nucleotides are derived from the desired 5' and 3' positions of a polynucleotide of SEQ ID NO:1 or of the deposited clone (SEQ ID NO:21). The 5' and 3' positions of the primers are determined based on the desired G-protein Chemokine Receptor (CCR5) polynucleotide fragment. An initiation and stop codon are added to the 5' and 3' primers respectively, if necessary, to express the G-protein Chemokine Receptor (CCR5) polypeptide fragment encoded by the polynucleotide fragment. Preferred G-protein Chemokine Receptor (CCR5) polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the G-protein Chemokine Receptor (CCR5) polynucleotide fragment in a desired vector may also be added to the 5' and 3' primer sequences. The G-protein Chemokine Receptor (CCR5) polynucleotide fragment is amplified from genomic DNA or from the deposited cDNA clone using the appropriate PCR oligonucleotide primers and conditions discussed herein or known in the art. The G-protein Chemokine Receptor (CCR5) polypeptide fragments encoded by the G-protein Chemokine Receptor (CCR5) polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the G-protein Chemokine Receptor (CCR5) polypeptide fragment Y-37 to Q-280 is amplified and cloned as follows: A 5' primer is generated comprising a restriction enzyme site followed by an initiation codon in frame with the polynucleotide sequence encoding the N-terminal portion of the polypeptide fragment beginning with Y-37. A complementary 3' primer is generated comprising a restriction enzyme site followed by a stop codon in frame with the polynucleotide sequence encoding C-terminal portion of the G-protein Chemokine Receptor (CCR5) polypeptide fragment ending with Q-280.

The amplified polynucleotide fragment and the expression vector are digested with restriction enzymes which recognize the sites in the primers. The digested polynucleotides are then ligated together. The G-protein Chemokine Receptor (CCR5) polynucleotide fragment is inserted into the restricted expression vector, preferably in a manner which places the G-protein Chemokine Receptor (CCR5) polypeptide fragment coding region downstream from the promoter. The ligation mixture is transformed into competent *E. coli* cells using standard procedures and as described in the Examples herein. Plasmid DNA is isolated from resistant colonies and the identity of the cloned DNA confirmed by restriction analysis, PCR and DNA sequencing.

Example 14

Protein Fusions of G-protein Chemokine Receptor

G-protein Chemokine Receptor (CCR5) polypeptides are preferably fused to other proteins. These fusion proteins can be used for a variety of applications. For example, fusion of G-protein Chemokine Receptor (CCR5) polypeptides to His-tag, HA-tag, protein A, IgG domains, and maltose binding protein facilitates purification. (See Example 9; see also EP A 394,827; Traunecker, et al., Nature 331:84–86 (1988).) Similarly, fusion to IgG-1, IgG-3, and albumin increases the half-life time in vivo. Nuclear localization signals fused to G-protein Chemokine Receptor (CCR5) polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 9.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHli cloning site. Note that the 3' BamHI site should be destroyed. Next, the vector containing the human Fc portion is re-restricted with BamHI, linearizing the vector, and G-protein Chemokine Receptor (CCR5) polynucleotide, isolated by the PCR protocol described in Example 5, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

```
                                           (SEQ ID NO:10)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGACGTCACATGCGTGG

TGGTGGACGTAACCCACGAAGACCCTGAGGTCAAGTTCAACTGGTACGTG
```

-continued

```
GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

GGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACCCAGAAGAGCCTCTCCCTGTCTCCGGG

TAAATGAGTGCGACGGCCGCGACTCTAGAGGAT
```

Example 15

Production of an Antibody

Hybridoma Technology

The antibodies of the present invention can be prepared by a variety of methods. (See, Current Protocols, Chapter 2.) As one example of such methods, cells expressing G-protein Chemokine Receptor (CCR5) are administered to an animal to induce the production of sera containing polyclonal antibodies. In a preferred method, a preparation of G-protein Chemokine Receptor (CCR5) protein is prepared and purified to render it substantially free of natural contaminants. Such a preparation is then introduced into an animal in order to produce polyclonal antisera of greater specific activity.

Monoclonal antibodies specific for G-protein Chemokine Receptor (CCR5) protein are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with G-protein Chemokine Receptor (CCR5) polypeptide or, more preferably, with a secreted G-protein Chemokine Receptor (CCR5) polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the G-protein Chemokine Receptor (CCR5) polypeptide.

Alternatively, additional antibodies capable of binding to G-protein Chemokine Receptor (CCR5) polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the G-protein Chemokine Receptor (CCR5) protein-specific antibody can be blocked by G-protein Chemokine Receptor. Such antibodies comprise anti-idiotypic antibodies to the G-protein Chemokine Receptor (CCR5) protein-specific antibody and are used to immunize an animal to induce formation of further G-protein Chemokine Receptor (CCR5) protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Isolation of Antibody Fragments Directed Against G-Protein Chemokine Receptor (CCR5) from a Library of scFvs Naturally occurring V-genes isolated from human PBLs are constructed into a library of antibody fragments which contain reactivities against G-protein Chemokine Receptor (CCR5) to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 *E. coli* harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 μkg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 μg ampicillin/ml and 25 μg kanamycinlml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 16

Production of G-protein Chemokine Receptor (CCR5) Protein or Ligand For High-Throughput Screening Assays The following protocol produces a supernatant containing a soluble G-protein Chemokine Receptor (CCR5) polypeptide or a G-protein Chemokine Receptor (CCR5) ligand to be tested. Ligands of the G-protein Chemokine Receptor (CCR5) include MIP-1α, MIP-1β, MCP-1, MCP-2, MCP-3, MCP-4, Eotaxin, RANTES, and HIV. This supernatant can then be used in the Screening Assays described in Examples 18–25.

First, dilute Poly-D-Lysine (644 587 Boehringer-Mannheim) stock solution (1 mg/ml in PBS) 1:20 in PBS (w/o calcium or magnesium 17–516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM (Dulbecco's Modified Eagle Medium) (with 4.5 G/L glucose and L-glutamine (12-604F Biowhittaker))/10% heat inactivated FBS (14-503F Biowhittaker)/1× Penstrep (17-602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8–10, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either 1% BSA in DMEM with 1× penstrep, or HGS CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$—$H_2O$; 71.02 mg/L of $Na_2HPO4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-H20; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_2O$; and 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; 10 mg/L of Methyl-B-Cyclodextrin complexed with Retinal Acetate. Adjust osmolarity to 327 mOsm) with 2 mm glutamine and 1× penstrep. (BSA (81-068-3 Bayer) 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degree C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 18–25.

It is specifically understood that when activity is obtained in any of the assays described below using a supernatant, the activity originates from either the G-protein Chemokine Receptor (CCR5) polypeptide directly (e.g., as a secreted, soluble, or membrane associated protein) or the G-protein Chemokine Receptor (CCR5) ligand directly, or by the G-protein Chemokine Receptor (CCR5) ligand inducing expression of other proteins, which are then secreted into the supernatant. Thus, the invention further provides a method of identifying the protein in the supernatant characterized by an activity in a particular assay.

Example 17

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Statl and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table 3 below. (Adapted from review by Schidler and Darnell, *Ann. Rev. Biochem.* 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:11)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table 3 below.) Thus, by using GAS elements linked to reporter molecules, activators of the Jaks-STATs pathway can be identified.

TABLE 3

| | JAKs | | | | | |
|---|---|---|---|---|---|---|
| Ligand | tyk2 | Jak1 | Jak2 | Jak3 | STATS | GAS (elements) or ISRE |
| IFN family | | | | | | |
| IFN-a/B | + | + | − | − | 1,2,3 | ISRE |
| IFN-g | | + | + | − | 1 | GAS (IRF1 > Lys6 > IFP) |
| Il-10 | + | ? | ? | − | 1,3 | |
| gp130 family | | | | | | |
| IL-6 (Pleiotropic) | + | + | + | ? | 1,3 | GAS (IRF1 > Lys6 > IFP) |
| Il-11 (Pleiotropic) | ? | + | ? | ? | 1,3 | |
| OnM (Pleiotropic) | ? | + | + | ? | 1,3 | |
| LIF (Pleiotropic) | ? | + | + | ? | 1,3 | |
| CNTF (Pleiotropic) | −/+ | + | + | ? | 1,3 | |
| G-CSF (Pleiotropic) | ? | + | ? | ? | 1,3 | |
| IL-12 (Pleiotropic) | + | − | + | + | 1,3 | |
| g-C family | | | | | | |
| IL-2 (lymphocytes) | − | + | − | + | 1,3,5 | GAS |
| IL-4 (lymph/myeloid) | − | + | − | + | 6 | GAS (IRF1 = IFP >> Ly6)(IgH) |

TABLE 3-continued

| Ligand | JAKs tyk2 | Jak1 | Jak2 | Jak3 | STATS | GAS (elements) or ISRE |
|---|---|---|---|---|---|---|
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1,3,5 | |
| EPO | ? | − | + | − | 5 | GAS (B-CAS > IRF1 = IFP >> Ly6) |
| Receptor Tyrosine Kinases | | | | | | |
| EGF | ? | + | + | − | 1,3 | GAS (IRF1) |
| PDGF | ? | + | + | − | 1,3 | |
| CSF-1 | ? | + | + | − | 1,3 | GAS (not IRF1) |

To construct a synthetic GAS containing promoter element, which is used in the Biological Assays described in Examples 18–19, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is:

```
                                             (SEQ ID NO:12)
5':GCGCCTCGAGATTTCCCCGAAATCTAGATTTCCCCGAAATGATTT
CCCCGAAATGATTTCCCCGAAATATCTGCCATCTCAATTAG:3'
```

The downstream primer is complementary to the SV40 promoter and is flanked with a Hind III site:

```
5':GCGGCAAGCTTTTTGCAAAGCCTAGGC:3'  (SEQ ID NO:13)
```

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

```
                                             (SEQ ID NO:14)
5':CTCGAGATTTCCCCGAAATCTAGATTTCCCCGAAATGATTTCCCC

GAAATGATTTCCCCGAAATATCTGCCATCTCAATTAGTCAGCAACC

ATAGTCCCGCCCCTAACTCCGCCCATCCCGCCCCTAACTCCGCCCA

GTTCCGCCCATTCTCCGCCCCATGGCTGACTAATTTTTTTTATTTAT

GCAGAGGCCGAGGCCGCCTCGGCCTCTGAGCTATTCCAGAAGTAGT

GAGGAGGCTTTTTTGGAGGCCTAGGCTTTTGCAAAAAGCTT:3'
```

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 18–19.

Other constructs can be made using the above description and replacing GAS with a different promoter sequence. For example, construction of reporter molecules containing NFK-B and EGR promoter sequences are described in Examples 20 and 21. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, 11-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 18

High-Throughput Screening Assay for T-cell Activity

The following protocol is used to assess T-cell activity by identifying factors, and determining whether supernatant containing a polypeptide of the invention or a ligand thereof proliferates and/or differentiates T-cells. T-cell activity is assessed using the GAS/SEAP/Neo construct produced in Example 17. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies) (transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI +10% serum with 1%Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1\times10^7$ cells in OPTI-MEM to T25 flask and incubate at 37 degree C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing G-protein Chemokine Receptor (CCR5) polypeptides or G-protein Chemokine Receptor (CCR5) induced polypeptides as produced by the protocol described in Example 16.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20 degree C. until SEAP assays are performed according to Example 18. The plates containing the remaining treated cells are placed at 4 degree C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as stable transfected cells, which would be apparent to those of skill in the art.

Example 19

High-Throughput Screening Assay Identifying Myeloid Activity

The following protocol is used to assess myeloid activity of G-protein Chemokine Receptor (CCR5) by determining whether G-protein Chemokine Receptor (CCR5) or G-protein Chemokine Receptor (CCR5) ligand proliferates and/or differentiates myeloid cells. Myeloid cell activity is assessed using the GAS/SEAP/Neo construct produced in Example 17. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 17, a DEAE-Dextran method (Kharbanda et. al., 1994, Cell Growth & Differentiation, 5:259–265) is used. First, harvest $2\times10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.0.7H_2O$, 1 mM $MgCl_2$, and 675 uM $CaCl_2$. Incubate at 37 degrees C. for 45 min.

Wash the cells with RPMI 1640 medium containing 10% FBS and then resuspend in 10 ml complete medium and incubate at 37 degree C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1\times10^8$ cells (this is enough for ten 96-well plates assay) and wash with PBS. Suspend the cells in 200 ml above described growth medium, with a final density of $5\times10^5$ cells/ml. Plate 200 ul cells per well in the 96-well plate (or $1\times10^5$ cells/well).

Add 50 ul of the supernatant prepared by the protocol described in Example 16. Incubate at 37 degree C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 22.

Example 20

High-Throughput Screening Assay Identifying Neuronal Activity

When cells undergo differentiation and proliferation, a group of genes is activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells by G-protein Chemokine Receptor (CCR5) or a ligand thereof can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells by G-protein Chemokine Receptor (CCR5) or a ligand thereof can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

```
                    (SEQ ID NO:15)
5' GCGCTCGAGGGATGACAGCGATAGAACCCCGG-3'

                    (SEQ ID NO:16)
5' GCGAAGCTTCGCGACTCCCCGGATCCGCCTC-3'
```

Using the GAS:SEAP/Neo vector produced in Example 17, EGRI amplified product can then be inserted into this vector. Linearize the GAS:SEAP/Neo vector using restriction enzymes Xho/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat. No. 08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. No. 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 16. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5\times10^5$ cells/ml.

Add 200 ul of the cell suspension to each well of 96-well plate (equivalent to $1\times10^5$ cells/well). Add 50 ul supernatant produced by Example 12, 37 degree C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 22.

Example 21

High-Throughput Screening Assay for T-cell Activity

NF-KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KB regulates the expression of genes involved in immune cell activation, control of apoptosis (NF-KB appears to shield cells from apoptosis), B and T-cell development, anti-viral and antimicrobial responses, and multiple stress responses.

In non-stimulated conditions, NF-KB is retained in the cytoplasm with I-KB (Inhibitor KB). However, upon stimulation, I-KB is phosphorylated and degraded, causing NF-KB to shuttle to the nucleus, thereby activating transcription of target genes. Target genes activated by NF-KB include IL-2, IL-6, GM-CSF, ICAM-1 and class 1 MHC.

Due to its central role and ability to respond to a range of stimuli, reporter constructs utilizing the NF-KB promoter element are used to screen the supernatants produced in Example 16. Activators or inhibitors of NF-KB would be useful in treating, preventing, and/or diagnosing diseases. For example, inhibitors of NF-KB could be used to treat those diseases related to the acute or chronic activation of NF-KB, such as rheumatoid arthritis.

To construct a vector containing the NF-KB promoter element, a PCR based strategy is employed. The upstream primer contains four tandem copies of the NF-KB binding site (GGGGACTTTCCC) (SEQ ID NO:17), 18 bp of sequence complementary to the 5' end of the SV40 early promoter sequence, and is flanked with an XhoI site:

```
                                        (SEQ ID NO:18)
5':GCGGCCTCGAGGGGACTTTCCCGGGGACTTTCCGGGGACTTTCCGGG
ACTTTCCATCCTGCCATCTCAATTAG:3'
```

The downstream primer is complementary to the 3' end of the SV40 promoter and is flanked with a Hind III site:

```
5':GCGGCAAGCTTTTTGCAAAGCCTAGGC:3'  (SEQ ID NO:19)
```

PCR amplification is performed using the SV40 promoter template present in the pB-gal:promoter plasmid obtained from Clontech. The resulting PCR fragment is digested with XhoI and Hind III and subcloned into BLSK2-. (Stratagene)

Sequencing with the T7 and T3 primers confirms the insert contains the following sequence:

```
                                   (SEQ ID NO:20)
5':CTCGAGGGGACTTTCCCGGGGACTTTCCGGGGACTTTCCGGGACTTT

CCATCTGCCATCTCAATTAGTCAGCAACCATAGTCCCGCCCCTA

ACTCCGCCCATCCCGCCCCTAACTCCGCCCAGTTCCGCCCATTCTCC

GCCCCATGGCTGACTAATTTTTTTTATTTATGCAGAGGCCGAGGCC

GCCTCGGCCTCTGAGCTATTCCAGAAGTAGTGAGGAGGCTTTTTTG

GAGGCCTAGGCTTTTGCAAAAAGCTT:3'
```

Next, replace the SV40 minimal promoter element present in the pSEAP2-promoter plasmid (Clontech) with this NF-KB/SV40 fragment using XhoI and HindIII. However, this vector does not contain a neomycin resistance gene, and therefore, is not preferred for mammalian expression systems.

In order to generate stable mammalian cell lines, the NF-KB/SV40/SEAP cassette is removed from the above NF-KB/SEAP vector using restriction enzymes SalI and NotI, and inserted into a vector containing neomycin resistance. Particularly, the NF-KB/SV40/SEAP cassette was inserted into pGFP-1 (Clontech), replacing the GFP gene, after restricting pGFP-1 with SalI and NotI.

Once NF-KB/SV40/SEAP/Neo vector is created, stable Jurkat T-cells are created and maintained according to the protocol described in Example 18. Similarly, the method for assaying supernatants with these stable Jurkat T-cells is also described in Example 18. As a positive control, exogenous TNF alpha (0.1,1, 10 ng) is added to wells H9, H10, and H11, with a 5–10 fold activation typically observed.

Example 22

Assay for SEAP Activity

As a reporter molecule for the assays described in Examples 18–21, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 ul of 2.5× dilution buffer into Optiplates containing 35 ul of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

Reaction Buffer Formulation:

| # of plates | Rxn buffer diluent (ml) | CSPD (ml) |
|---|---|---|
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 23

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37 degrees C. in a $CO_2$ incubator for 60 min. The plate is washed four times in the Biotek washer with HBSS leaving 100 ul of buffer.

For non-adherent cells, the cells are spun down from culture media. Cells are re-suspended to 2–5×$10^6$ cells/ml with HBSS in a 50-ml conical tube. 4 ul of 1 mg/ml fluo-4 solution in 10% pluronic acid DMSO is added to each ml of cell suspension. The tube is then placed in a 37 degrees C. water bath for 30–60 min. The cells are washed twice with HBSS, resuspended to 1×$10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event caused by a molecule, such as G-protein Chemokine Receptor (CCR5) or a ligand thereof, or a molecule induced by G-protein Chemokine Receptor (CCR5), which has resulted in an increase in the intracellular $Ca^{++}$ concentration.

Example 24

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase (RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, identifying whether G-protein Chemokine Receptor (CCR5) or a ligand thereof, or a molecule induced by G-protein Chemokine Receptor (CCR5) is capable of activating tyrosine kinase signal transduction pathways is of interest. Therefore, the following protocol is designed to identify such molecules capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 16, the medium was removed and 100 ml of extraction buffer ((20 mM HEPES pH 7.5, 0.15 M NaCl, 1% Triton X-100, 0.1% SDS, 2 mM Na3VO4, 2 mM Na4P207 and a cocktail of protease inhibitors (# 1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degree C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add lOul of 5 uM Biotinylated Peptide, then 10 ul ATP/$Mg_2$+(5 mM ATP/50 mM $MgCl_2$), then 10 ul of 5× Assay Buffer (40 mM imidazole hydrochloride, pH 7.3, 40 mM beta-glycerophosphate, 1 mM EGTA, 100 mM $MgCl_2$, 5 mM $MnCl_2$, 0.5 mg/ml BSA), then Sul of Sodium Vanadate(1 mM), and then 5 ul of water. Mix the components gently and preincubate the reaction mix at 30 degree C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degree C. for 20 min. This allows the streptavadin coated 96 well plate to associate with the biotinylated peptide. Wash the MTP module with 300 ul/well of PBS four times. Next add 75 ul of anti-phosphotyrosine antibody conjugated to horse radish peroxidase (anti-P-Tyr-POD(0.5 u/ml)) to each well and incubate at 37 degree C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 25

High-Throughput Screening Assay Identifying Phosphorylation Activity

As a potential alternative and/or compliment to the assay of protein tyrosine kinase activity described in Example 24, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 degree C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 16 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation by G-protein Chemokine Receptor (CCR5) or a ligand thereof or a molecule induced by G-protein Chemokine Receptor.

Example 26

Method of Determining Alterations in the G-protein Chemokine Receptor (CCRS) Gene RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degree C. for 30 seconds; 60–120 seconds at 52–58 degree C.; and 60–120 seconds at 70 degree C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of G-protein Chemokine Receptor (CCR5) is also determined and genomic PCR products analyzed to confirm the results. PCR products harboring suspected mutations in G-protein Chemokine Receptor (CCR5) is then cloned and sequenced to validate the results of the direct sequencing.

PCR products of G-protein Chemokine Receptor (CCR5) are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in G-protein Chemokine Receptor (CCR5) not present in unaffected individuals.

Genomic rearrangements are also observed as a method of determining alterations in a gene corresponding to G-protein Chemokine Receptor. Genomic clones isolated according to Example 6 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the G-protein Chemokine Receptor (CCR5) genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of G-protein Chemokine Receptor (CCR5) (hybridized by the probe) are identified as insertions, deletions, and translocations. These G-protein Chemokine Receptor (CCR5) alterations are used as a diagnostic marker for an associated disease.

Example 27

Method of Detecting Abnormal Levels of G-Protein Chemokine Receptor (CCR5) in a Biological Sample G-protein Chemokine Receptor (CCR5) polypeptides can be detected in a biological sample, and if an increased or decreased level of G-protein Chemokine Receptor (CCR5) is detected, this polypeptide is a marker for a particular phenotype. Methods of detection are numerous, and thus, it is understood that one skilled in the art can modify the following assay to fit their particular needs.

For example, antibody-sandwich ELISAs are used to detect G-protein Chemokine Receptor (CCR5) in a sample, preferably a biological sample. Wells of a microtiter plate are coated with specific antibodies to G-protein Chemokine Receptor (CCR5), at a final concentration of 0.2 to 10 ug/ml. The antibodies are either monoclonal or polyclonal and are produced by the method described in Example 15. The wells are blocked so that non-specific binding of G-protein Chemokine Receptor (CCR5) to the well is reduced.

The coated wells are then incubated for >2 hours at RT with a sample containing G-protein Chemokine Receptor. Preferably, serial dilutions of the sample should be used to validate results. The plates are then washed three times with deionized or distilled water to remove unbounded G-protein Chemokine Receptor.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot G-protein Chemokine Receptor (CCR5) polypeptide concentration on the X-axis (log scale) and fluorescence or absorbance of the Y-axis (linear scale). Interpolate the concentration of the G-protein Chemokine Receptor (CCR5) in the sample using the standard curve.

Example 28

Formulation

The invention also provides methods of treatment and/or prevention of diseases, disorders, and/or conditions (such as, for example, any one or more of the diseases, disorders, and/or conditions disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Therapeutics of the invention are also suitably administered by sustained-release systems. Suitable examples of sustained-release Therapeutics include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci.(USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Therapeutic is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multidose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside/nucleotide reverse transcriptase inhibitors (NRTIs), non-nucleoside reverse transcriptase inhibitors (NNRTIs), and/or protease inhibitors (PIs). NRTIs that may be administered in combination with the Therapeutics of the invention, include, but are not limited to, RETROVIR™ (zidovudine/AZT), VIDEX™ (didanosine/ddl), HIVID™ (zalcitabine/ddC), ZERIT™ (stavudine/d4T), EPIVR™ (lamivudine/3TC), and COMBIVIR™ (zidovudine/lamivudine). NNRTIs that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

Additional NRTIs include LODENOSINE™ (F-ddA; an acid-stable adenosine NRTI; Triangle/Abbott; COVIRACIL™ (emtricitabine/FTC; structurally related to lamivudine (3TC) but with 3- to 10-fold greater activity in vitro; Triangle/Abbott); dOTC (BCH-10652, also structurally related to lamivudine but retains activity against a substantial proportion of lamivudine-resistant isolates; Biochem Pharma); Adefovir (refused approval for anti-HIV therapy by FDA; Gilead Sciences); PREVEON® (Adefovir Dipivoxil, the active prodrug of adefovir; its active form is PMEA-pp); TENOFOVIR™ (bis-POC PMPA, a PMPA prodrug; Gilead); DAPD/DXG (active metabolite of DAPD; Triangle/Abbott); D-D4FC (related to 3TC, with activity against AZT/3TC-resistant virus); GW420867X (Glaxo Wellcome); ZIAGEN™ (abacavir/159U89; Glaxo Wellcome Inc.); CS-87 (3'azido-2',3'-dideoxyuridine; WO 99/66936); and S-acyl-2-thioethyl (SATE)-bearing prodrug forms of β-L-FD4C and β-L-FddC (WO 98/17281).

Additional NNRTIs include COACTINON™ (Emivirine/MKC-442, potent NNRTI of the HEPT class; Triangle/Abbott); CAPRAVIRINE™ (AG-1549/S-1153, a next generation NNRTI with activity against viruses containing the K103N mutation; Agouron); PNU-142721 (has 20- to 50-fold greater activity than its predecessor delavirdine and is active against K103N mutants; Pharmacia & Upjohn); DPC-961 and DPC-963 (second-generation derivatives of efavirenz, designed to be active against viruses with the K103N mutation; DuPont); GW-420867X (has 25-fold greater activity than HBY097 and is active against K103N mutants; Glaxo Wellcome); CALANOLIDE A (naturally occurring agent from the latex tree; active against viruses containing either or both the Y181C and K103N mutations); and Propolis (WO 99/49830).

Additional protease inhibitors include LOPINAVIR™ (ABT378/r; Abbott Laboratories); BMS-232632 (an azapeptide; Bristol-Myres Squibb); TIPRANAVIR™ (PNU-140690, a non-peptic dihydropyrone; Pharmacia & Upjohn); PD-178390 (a nonpeptidic dihydropyrone; Parke-Davis); BMS 232632 (an azapeptide; Bristol-Myers Squibb); L-756, 423 (an indinavir analog; Merck); DMP-450 (a cyclic urea compound; Avid & DuPont); AG-1776 (a peptidomimetic with in vitro activity against protease inhibitor-resistant viruses; Agouron); VX-175/GW-433908 (phosphate prodrug of amprenavir; Vertex & Glaxo Welcome); CGP61755 (Ciba); and AGENERASE™ (amprenavir; Glaxo Wellcome Inc.).

Additional antiretroviral agents include fusion inhibitors/gp41 binders. Fusion inhibitors/gp41 binders include T-20 (a peptide from residues 643–678 of the HIV gp41 transmembrane protein ectodomain which binds to gp41 in its resting state and prevents transformation to the fusogenic state; Trimeris) and T-1249 (a second-generation fusion inhibitor; Trimeris).

Additional antiretroviral agents include fusion inhibitors/chemokine receptor antagonists. Fusion inhibitors/chemokine receptor antagonists include CXCR4 antagonists such as AMD 3100 (a bicyclam), SDF-1 and its analogs, and ALX40-4C (a cationic peptide), T22 (an 18 amino acid peptide; Trimeris) and the T22 analogs T134 and T140; CCR5 antagonists such as RANTES (9–68), AOP-RANTES, NNY-RANTES, and TAK-779; and CCR5/CXCR4 antagonists such as NSC 651016 (a distamycin analog). Also included are CCR2B, CCR3, and CCR6 antagonists. Chemokine recpetor agonists such as RANTES, SDF-1, MIP-1α, MIP-1β, etc., may also inhibit fusion.

Additional antiretroviral agents include integrase inhibitors. Integrase inhibitors include dicaffeoylquinic (DFQA) acids; L-chicoric acid (a dicaffeoyltartaric (DCTA) acid); quinalizarin (QLC) and related anthraquinones; ZINTEVIR™ (AR 177, an oligonucleotide that probably acts at cell surface rather than being a true integrase inhibitor; Arondex); and naphthols such as those disclosed in WO 98/50347.

Additional antiretroviral agents include hydroxyurea-like compunds such as BCX-34 (a purine nucleoside phosphorylase inhibitor; Biocryst); ribonucleotide reductase inhibitors such as DIDOX™ (Molecules for Health); inosine monophosphate dehydrogenase (IMPDH) inhibitors sucha as VX-497 (Vertex); and myvopholic acids such as CellCept (mycophenolate mofetil; Roche).

Additional antiretroviral agents include inhibitors of viral integrase, inhibitors of viral genome nuclear translocation such as arylene bis(methylketone) compounds; inhibitors of HIV entry such as AOP-RANTES, NNY-RANTES, RANTES-IgG fusion protein, soluble complexes of RANTES and glycosaminoglycans (GAG), and AMD-3100; nucleocapsid zinc finger inhibitors such as dithiane compounds; targets of HIV Tat and Rev; and pharmacoenhancers such as ABT-378.

Other antiretroviral therapies and adjunct therapies include cytokines and lymphokines such as MIP-1α, MIP-1β, SDF-1α, IL-2, PROLEUKIN™ (aldesleukin/L2-7001; Chiron), IL-4, IL-10, IL-12, and IL-13; interferons such as IFN-α2a; antagonists of TNFs, NFKB, GM-CSF, M-CSF, and IL-10; agents that modulate immune activation such as cyclosporin and prednisone; vaccines such as Remune™ (HIV Immunogen), APL 400-003 (Apollon), recombinant gp120 and fragments, bivalent (B/E) recombinant envelope glycoprotein, rgp120CM235, MN rgp120, SF-2 rgp120, gp120/soluble CD4 complex, Delta JR-FL protein, branched synthetic peptide derived from discontinuous gp120 C3/C4 domain, fusion-competent immunogens, and Gag, Pol, Nef, and Tat vaccines; gene-based therapies such as genetic suppressor elements (GSEs; WO 98/54366), and intrakines (genetically modified CC chemokines targetted to the ER to block surface expression of newly synthesized CCR5 (Yang et al., *PNAS* 94:11567–72 (1997); Chen et al., *Nat. Med.* 3:1110–16 (1997)); antibodies (for example, anti-CXCR4 antibodies such as the anti-CXCR4 antibody 12G5, anti-CCR5 antibodies such as the anti-CCR5 antibodies 2D7, 5C7, PA8, PA9, PA10, PA11, PA12, and PA14, anti-CD4 antibodies such as the anti-CD4 antibodies Q4120 and RPA-T4, anti-CCR3 antibodies such as the anti-CCR3 antibody 7B11, anti-gp120 antibodies such as the anti-gp120 antibodies 17b, 48d, 447–52D, 257-D, 268-D and 50.1, anti-Tat antibodies, anti-TNF-α antibodies, and monoclonal antibody 33A); aryl hydrocarbon (AH) receptor agonists and antagonists such as TCDD, 3,3',4,4',5-pentachlorobiphenyl, 3,3',4,4'-tetrachlorobiphenyl, and α-naphthoflavone (WO 98/30213); and antioxidants such as γ-L-glutamyl-L-cysteine ethyl ester (γ-GCE; WO 99/56764).

Additional agents that may be used with Therapeutics of the present invention with or without the agents above include anti-lymphoproliferative agents such as all-trans-retinoic acid (all-trans-RA), IFN-γ, EPOCH, and Cidofovir; inhibitors of angiogenesis such as thalidomide; cytostatic chemotherapeutic agents such as hydroxyurea; anti-infective agents such as Rifabutin, Isoniazid, and Rifampin; and antidementia agents such as LU 02-584 (CPI-1189; Centuar Pharmaceuticals Inc.).

Dosages of these various agents are known in the art, and can be found in, for example, The Physician's Desk Reference and the scientific literature.

The virus mutates very rapidly due to the error prone reverse transcriptase (RT), thus developing resistance to multiple therapeutic agents. By targeting multiple points in the viral pathway (RT, protease, viral entry and viral neutralization) using combination therapy, the high mutation rate should be effectively countered. Thus, Therapeutics of the invention may be used with combinations of antiretroviral agents, including two-drug, three-drug, four-drug, five drug, six-drug, seven-drug, eight-drug, nine-drug and greater combinations. Such combinations of antiretroviral agents may be referred to in the literature as active antiretroviral therapy (ART), highly active antiretroviral therapy (HAART), continuous HAART, intermittent HAART, "mega" HAART (more than 4, 5, 6, 7, or 8, and preferably more than 9 agents), intensive high-dose multi-drug therapy, early treatment intensification (ETI), maximally assisted therapy (MAT), self-administered therapy (SAT), subcutaneous recombinant human IL-2 in HIV-infected patients with low CD4+ counts under active antiretroviral therapy (SILCAAT), and maintenance therapy. Preferably, Therapeutics of the invention are used in combination with highly active antiretroviral therapy. Therapeutics of the invention may also be used in combination with adjunct agents, such as those above and otherwise disclosed herein and those well known in the art, either alone or together with antiretroviral agents.

When combining Therapeutics of the invention with any of the above agents or combinations of agents, the doses are adjusted as necessary. NRTIs generally do not require dose adjustments when combined, but NNRTIs and PIs may affect each other's levels and potency. Guidance for such dose adjustments and for initiating, continuing, managing, altering, and maintaining antiretroviral therapy in general are well known by practitioners and are readily available in, for example, *Guidelines for the Use of Antiretroviral Agents In HIV-Infected Adults and Adolescents*, Panel on Clinical Practices for Treatment of HIV Infection, Dept. Health and Human Services and Henry J. Kaiser Foundation, Jan. 28, 2000, and <<http://www.hivatis.org>> and other scientific literature.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOIE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, Therapeutics of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Therapeutics of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Therapeutics of the invention are used in any combination with RIFABUTIN™, CLARITHROMYCIN™, and/or AZITHROMYCIN™ to prophylactically treat or prevent an opportunistic *Mycobacterium* tuberculosis infection. In another specific embodiment, Therapeutics of the invention are used in any combination with GANCICLOVIR™, FOSCARNET™, and/or CIDOFOVIR™ to prophylactically treat or prevent an opportunistic cytomegalovirus infection. In another specific embodiment, Therapeutics of the invention are used in any combination with FLUCONAZOLE™, ITRACONAZOLE™, and/or KETOCONAZOLE™ to prophylactically treat or prevent an opportunistic fungal infection. In another specific embodiment, Therapeutics of the invention are used in any combination with ACYCLOVIR™ and/or FAMCICOLVIR™ to prophylactically treat or prevent an opportunistic herpes simplex virus type I and/or type II infection. In another specific embodiment, Therapeutics of the invention are used in any combination with PYRIMETHAMINE™ and/or LEUCOVORIN™ to prophylactically treat or prevent an opportunistic *Toxoplasma gondii* infection. In another specific embodiment, Therapeutics of the invention are used in any combination with LEUCOVORIM™ and/or NEUPOGEN™ to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMTNE™ (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR™, IVEEGAM™, SANDOGLOBULIN™, GAMMAGARD S/D™, and GAMIMUNE™. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, L-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE™ (SARGRAMOSTIM™) and NEUPOGEN™ (FILGRASTIM™).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In other embodiments, Therapeutics of the invention may be administered in combination with porcine or human insulin or mixtures thereof; insulin analogs; recombinant human insulin such as HUMULIN™ and NOVOLIN™; oral hypoglycemic agents such as ORAMIDE™ and ORINASE™ (tolbutamide), DIABINESE™ (chlorpropamide), TOLAMIDE™ and TOLINASE™ (tolazamide), DYMELOR™ (acetohexamide), glibenclamide, MICRONASE™, DIBETA™ and GLYNASE™ (glyburide), GLUCOTROL™ (glipizide), and DIAMICRON™ (gliclazide), GLUCOPHAGE™ (metformin), PRECOSE™ (acarbose), AMARYL™ (glimepiride), and ciglitazone; thiazolidinediones (TZDs) such as rosiglitazone, AVANDIA™ (rosiglitazone maleate) ACTOS™ (piogliatazone), and troglitazone; alpha-glucosidase inhibitors; bovine or porcine glucagon; somatostatins such as SANDOSTATIN™ (octreotide); and diazoxides such as PROGLYCEM™ (diazoxide). In still other embodiments, Therapeutics of the invention are administered in combination with one or more of the following: a biguanide antidiabetic agent, a glitazone antidiabetic agent, and a sulfonylurea antidiabetic agent.

In additional embodiments, the Therapeutics of the invention are administered in combination with other therapeutic or prophylactic regimens, such as, for example, radiation therapy.

Example 29

Method of Treating Decreased Levels of G-Protein Chemokine Receptor

The present invention relates to a method for treating an individual in need of an increased level of a polypeptide of the invention in the body comprising administering to such an individual a composition comprising a therapeutically effective amount of an agonist of the invention (including polynucleotides of the invention). Moreover, it will be appreciated that conditions caused by a decrease in the standard or normal expression level of G-protein Chemokine Receptor (CCR5) in an individual can be treated by administering a G-protein Chemokine Receptor (CCR5) agonist, preferably in the secreted form. Thus, the invention also provides a method of treatment of an individual in need of an increased level of G-protein Chemokine Receptor (CCR5) polypeptide comprising administering to such an individual a Therapeutic comprising an amount of G-protein Chemokine Receptor (CCR5) agonist to increase the activity level of G-protein Chemokine Receptor (CCR5) in such an individual.

For example, a patient with decreased levels of G-protein Chemokine Receptor (CCR5) polypeptide receives a daily dose 0.1–100 ug/kg of the agonist for six consecutive days. The exact details of the dosing scheme, based on administration and formulation, are provided in Example 28.

Example 30

Method of Treating Increased Levels of G-Protein Chemokine Receptor

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of G-protein Chemokine Receptor. This technology is one example of a method of decreasing levels of G-protein Chemokine Receptor (CCR5) polypeptide, preferably a soluble form, due to a variety of etiologies, such as cancer.

For example, a patient diagnosed with abnormally increased levels of G-protein Chemokine Receptor (CCR5) is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 28.

Other methods to decrease G-protein Chemokine Receptor (CCR5) or to inhibit its activity are described herein (such as in Example 57).

Example 31

Method of Treatment Using Gene Therapy—Ex Vivo

One method of gene therapy transplants fibroblasts, which are capable of expressing G-protein Chemokine Receptor (CCR5) polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The DNA encoding G-protein Chemokine Receptor (CCR5) can be amplified using PCR primers which correspond to the 5' and 3' end sequences respectively as set forth in Example 5. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted G-protein Chemokine Receptor.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the G-protein Chemokine Receptor (CCR5) gene is then added to the media and the packaging cells transduced with the vector. The packaging cells now produce infectious viral particles containing the G-protein Chemokine Receptor (CCR5) gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether G-protein Chemokine Receptor (CCR5) protein is produced.

The engineered fibroblasts are then transplanted onto the host, either alone or after having been grown to confluence on cytodex 3 microcarrier beads.

Example 32

Gene Therapy Using Endogenous G-Protein Chemokine Receptor (CCR5) Gene

Another method of gene therapy according to the present invention involves operably associating the endogenous G-protein Chemokine Receptor (CCR5) sequence with a promoter via homologous recombination as described, for example, in U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous G-protein Chemokine Receptor (CCR5), flanking the promoter. The targeting sequence will be sufficiently near the 5' end of G-protein Chemokine Receptor (CCR5) so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous G-protein Chemokine Receptor (CCR5) sequence. This results in the expression of G-protein Chemokine Receptor (CCR5) in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the G-protein Chemokine Receptor (CCR5) locus, plasmid pUC18 (MBI Fermentas, Amherst, N.Y.) is digested with HindIII. The CMV promoter is amplified by PCR with an XbaI site on the 5' end and a BamHI site on the 3'end. Two G-protein Chemokine Receptor (CCR5) non-coding sequences are amplified via PCR: one G-protein Chemokine Receptor (CCR5) non-coding sequence (G-protein Chemokine Receptor (CCR5) fragment 1) is amplified with a HindIII site at the 5' end and an Xba site at the 3'end; the other G-protein Chemokine Receptor (CCR5) non-coding sequence (G-protein Chemokine Receptor (CCR5) fragment 2) is amplified with a BamHI site at the 5'end and a HindIII site at the 3'end. The CMV promoter and G-protein Chemokine Receptor (CCR5) fragments (1 and 2) are digested with the appropriate enzymes (CMV promoter—XbaI and BamHI; G-protein Chemokine Receptor (CCR5) fragment 1—XbaI; G-protein Chemokine Receptor (CCR5) fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5.\times10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 33

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) G-protein Chemokine Receptor (CCR5) sequences into an animal to increase or decrease the expression of the G-protein Chemokine Receptor (CCR5) polypeptide. The G-protein Chemokine Receptor (CCR5) polynucleotide may be operatively linked to a promoter or any other genetic elements necessary for the expression of the G-protein Chemokine Receptor (CCR5) polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3): 470–479, Chao J et al. (1997) Pharmacol. Res. 35(6): 517–522, Wolff J. A. (1997) Neuromuscul. Disord. 7(5): 314–318, Schwartz B. et al. (1996) Gene Ther. 3(5):405–411, Tsurumi Y. et al. (1996) Circulation 94(12): 3281–3290 (incorporated herein by reference).

The G-protein Chemokine Receptor (CCR5) polynucleotide constructs may be delivered by any method that delivers injectable materials to the cells of an animal, such as, injection into the interstitial space of tissues (heart, muscle, skin, lung, liver, intestine and the like). The G-protein Chemokine Receptor (CCR5) polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the G-protein Chemokine Receptor (CCR5) polynucleotides may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The G-protein Chemokine Receptor (CCR5) polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The G-protein Chemokine Receptor (CCR5) polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked G-protein Chemokine Receptor (CCR5) polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked G-protein Chemokine Receptor (CCR5) polynucleotide constructs can be delivered to arteries during angioplasty by the catheter used in the procedure.

The dose response effects of injected G-protein Chemokine Receptor (CCR5) polynucleotide in muscle in vivo is determined as follows. Suitable G-protein Chemokine Receptor (CCR5) template DNA for production of mRNA coding for G-protein Chemokine Receptor (CCR5) polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The G-protein Chemokine Receptor (CCR5) template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for G-protein Chemokine Receptor (CCR5) protein expression. A time course for G-protein Chemokine Receptor (CCR5) protein expression may be done in a similar fashion except that quadriceps from different mice are harvested at different times. Persistence of G-protein Chemokine Receptor (CCR5) DNA in muscle following injection may be determined by Southern blot analysis after preparing total cellular DNA and HRT supernatants from injected and control mice. The results of the above experimentation in mice can be use to extrapolate proper dosages and other treatment parameters in humans and other animals using G-protein Chemokine Receptor (CCR5) naked DNA.

Example 34

G-Protein Chemokine Receptor (CCR5) Transgenic Animals

The G-protein Chemokine Receptor (CCR5) polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, “Transgenic Animals,” Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

In addition to expressing the polypeptide of the present invention in a ubiquitous or tissue specific manner in transgenic animals, it would also be routine for one skilled in the art to generate constructs which regulate expression of the polypeptide by a variety of other means (for example, developmentally or chemically regulated expression).

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of G-protein Chemokine Receptor (CCR5) polypeptides, studying diseases, disorders, and/or conditions associated with aberrant G-protein Chemokine Receptor (CCR5) expression, and in screening for compounds effective in ameliorating such diseases, disorders, and/or conditions.

Example 35

G-Protein Chemokine Receptor (CCR5) Knock-Out Animals

Endogenous G-protein Chemokine Receptor (CCR5) gene expression can also be reduced by inactivating or "knocking out" the G-protein Chemokine Receptor (CCR5) gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the G-protein Chemokine Receptor (CCR5) polypeptides. The engineered cells which express and, in one embodiment, preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of G-protein Chemokine Receptor (CCR5) polypeptides, studying diseases, disorders, and/or conditions associated with aberrant G-protein Chemokine Receptor (CCR5) expression, and in screening for compounds effective in ameliorating such diseases, disorders, and/or conditions.

Example 36

Assays Detecting Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay: Purified G-protein Chemokine Receptor (CCR5) protein, or truncated forms thereof, or purified G-protein Chemokine Receptor (CCR5) ligand is assessed for its ability to induce activation, proliferation, differentiation or inhibition and/or death in B-cell populations and their precursors. The activity of G-protein Chemokine Receptor (CCR5) protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5\times10^{-5}$M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay: BALB/c mice are injected (i.p.) twice per day with buffer only, or 2 mg/Kg of G-protein Chemokine Receptor (CCR5) protein, or truncated forms thereof or G-protein Chemokine Receptor (CCR5) ligand. Mice receive this treatment for 4 consecutive days, at which time they are sacrificed and various tissues and serum collected for analyses. Comparison of H&E sections from normal and G-protein Chemokine Receptor (CCR5) protein-treated spleens identify the results of the activity of G-protein Chemokine Receptor (CCR5) protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from G-protein Chemokine Receptor (CCR5) protein-treated mice is used to indicate whether G-protein Chemokine Receptor (CCR5) protein specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and G-protein Chemokine Receptor (CCR5) protein-treated mice.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 37

T Cell Proliferation Assay

A CD3-induced proliferation assay is performed on PBMCs and is measured by the uptake of $^3$H-thymidine. The assay is performed as follows. Ninety-six well plates are coated with 100 μl/well of mAb to CD3 (HIT3a, Pharmingen) or isotype-matched control mAb (B33.1) overnight at 4° C. (1 μg/ml in 0.05M bicarbonate buffer, pH 9.5), then washed three times with PBS. PBMC are isolated by F/H gradient centrifugation from human peripheral blood and added to quadruplicate wells ($5\times10^4$/well) of mAb coated plates in RPMI containing 10% FCS and P/S in the presence of varying concentrations of G-protein Chemokine Receptor (CCR5) protein (total volume 200 μl). Relevant protein buffer and medium alone are controls. After 48 hr. culture at 37° C., plates are spun for 2 min. at 1000 rpm and 100 μl of supernatant is removed and stored −20° C. for measurement of IL-2 (or other cytokines) if effect on proliferation is observed. Wells are supplemented with 100 μl of medium containing 0.5 μCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of G-protein Chemokine Receptor (CCR5) proteins.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 38

Effect of G-Protein Chemokine Receptor (CCR5) on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of G-protein Chemokine Receptor (CCR5) or a ligand thereof or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Thl helper T-cell immune response, and induces cytotoxic T and NK cell function. An ELISA is used to measure the IL-12 release as follows. Dendritic cells ($10^6$/ml) are treated with increasing concentrations of G-protein Chemokine Receptor (CCR5)

for 24 hours. LPS (100 ng/ml) is added to the cell culture as positive control. Supernatants from the cell cultures are then collected and analyzed for IL-12 content using commercial ELISA kit (e.g., R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of G-protein Chemokine Receptor (CCR5) or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. G-protein Chemokine Receptor (CCR5), agonists, or antagonists of G-protein Chemokine Receptor (CCR5) can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 μg/ml, and then incubated at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of $5\times10^5$ cells/ml with increasing concentrations of G-protein Chemokine Receptor (CCR5) and under the same conditions, but in the absence of G-protein Chemokine Receptor. For IL-12 production, the cells are primed overnight with IFN (100 U/ml) in presence of G-protein Chemokine Receptor. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g., R & D Systems (Minneapolis, Minn.)) and applying the standard protocols provided with the kit.

Oxidative Burst. Purified monocytes are plated in 96-w plate at $2–1\times10^5$ cell/well. Increasing concentrations of G-protein Chemokine Receptor (CCR5) are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 μl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 39

G-Protein Chemokine Receptor (CCR5) Biological Effects

Astrocyte and Neuronal Assays.

Recombinant G-protein Chemokine Receptor (CCR5), expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate G-protein Chemokine Receptor's activity on these cells.

Moreover, previous reports describing the biological effects of FGF-2 (basic FGF) on cortical or hippocampal neurons in vitro have demonstrated increases in both neuron survival and neurite outgrowth (Walicke, P. et al., "Fibroblast growth factor promotes survival of dissociated hippocampal neurons and enhances neurite extension." *Proc. Natl. Acad. Sci. USA* 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of G-protein Chemokine Receptor (CCR5) to induce neurite outgrowth can be compared to the response achieved with FGF-2 using, for example, a thymidine incorporation assay.

Fibroblast and Endothelial Cell Assays.

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or G-protein Chemokine Receptor (CCR5) with or without IL-1α for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or G-protein Chemokine Receptor (CCR5) with or without IL-1α for 24 hours. The supernatants are collected and assayed for IL-6 by ELISA kit (Endogen, Cambridge, Mass.).

Human lung fibroblasts are cultured with FGF-2 or G-protein Chemokine Receptor (CCR5) for 3 days in basal medium before the addition of Alamar Blue to assess effects on growth of the fibroblasts. FGF-2 should show a stimulation at 10–2500 ng/ml which can be used to compare stimulation with G-protein Chemokine Receptor.

Parkinson Models.

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, G-protein Chemokine Receptor (CCR5) can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of G-protein Chemokine Receptor (CCR5) is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/$cm^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if G-protein Chemokine Receptor (CCR5) acts to prolong the survival of dopaminergic neurons, it would suggest that G-protein Chemokine Receptor (CCR5) may be involved in Parkinson's Disease.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 40

The Effect of G-Protein Chemokine Receptor (CCR5) on the Growth of Vascular Endothelial Cells On day 1, human umbilical vein endothelial cells (HUVEC) are seeded at 2–5×$10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. G-protein Chemokine Receptor (CCR5) protein of SEQ ID NO. 2 or SEQ ID NO:22, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that G-protein Chemokine Receptor (CCR5) may proliferate vascular endothelial cells.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 41

Stimulatory Effect of G-Protein Chemokine Receptor (CCR5) on the Proliferation of Vascular Endothelial Cells For evaluation of mitogenic activity of growth factors, the calorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, $VEGF_{165}$ or G-protein Chemokine Receptor (CCR5) in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol.* 30A:512–518 (1994).

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 42

Stimulation of Endothelial Migration

This example will be used to explore the possibility that G-protein Chemokine Receptor (CCR5) may stimulate lymphatic endothelial cell migration.

Endothelial cell migration assays are performed using a 48 well microchemotaxis chamber (Neuroprobe Inc., Cabin John, Md.; Falk, W., et al., J. Immunological Methods 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, $2.5\times10^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 43

Effect of G-protein Chemokine Receptor (CCR5) on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or G-protein Chemokine Receptor (CCR5) (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 44

Angiogenic Effect on Chick Chorioallantoic Membrane

Chick chorioallantoic membrane (CAM) is a well-established system to examine angiogenesis. Blood vessel formation on CAM is easily visible and quantifiable. The ability of G-protein Chemokine Receptor (CCR5) or a ligand thereof to stimulate angiogenesis in CAM can be examined.

Fertilized eggs of the White Leghorn chick (Gallus gallus) and the Japanese quail (Cotumix coturnix) are incubated at 37.8° C. and 80% humidity. Differentiated CAM of 16-day-old chick and 13-day-old quail embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors are dissolved in distilled water and about 3.3 mgl 5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 45

Angiogenesis Assay Using a Matrigel Implant in Mouse

In vivo angiogenesis assay of G-protein Chemokine Receptor (CCR5) measures the ability of an existing capillary network to form new vessels in an implanted capsule of murine extracellular matrix material (Matrigel). The protein is mixed with the liquid Matrigel at 4 degree C. and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 degree C. the Matrigel material is a liquid. The Matrigel is mixed with G-protein Chemokine Receptor (CCR5) at 150 ng/ml at 4 degree C. and drawn into cold 3 ml syringes. Female C57B1/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 46

Rescue of Ischemia in Rabbit Lower Limb Model

To study the in vivo effects of G-protein Chemokine Receptor (CCR5) on ischemia, a rabbit hindlimb ischemia model is created by surgical removal of one femoral arteries as described previously (Takeshita, S. et al., *Am J. Pathol* 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al. *Am J. Pathol* 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked G-protein Chemokine Receptor (CCR5) expression plasmid by arterial gene transfer technology using a hydrogel-coated balloon catheter as described (Riessen, R. et al. *Hum Gene Ther.* 4:749–758 (1993); Leclerc, G. et al. *J. Clin. Invest.* 90: 936–944 (1992)). When G-protein Chemokine Receptor (CCR5) is used in the treatment, a single bolus of 500 mg G-protein Chemokine Receptor (CCR5) protein or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 47

Peripheral Arterial Disease Model

Angiogenic therapy using G-protein Chemokine Receptor (CCR5) is a novel therapeutic strategy to obtain restoration of blood flow around the ischemia in case of peripheral arterial diseases. The experimental protocol includes:

a) One side of the femoral artery is ligated to create ischemic muscle of the hindlimb, the other side of hindlimb serves as a control.

b) G-protein Chemokine Receptor (CCR5) protein, in a dosage range of 20 mg–500 mg, is delivered intravenously and/or intramuscularly 3 times (perhaps more) per week for 2–3 weeks.

c) The ischemic muscle tissue is collected after ligation of the femoral artery at 1, 2, and 3 weeks for the analysis of G-protein Chemokine Receptor (CCR5) expression and histology. Biopsy is also performed on the other side of normal muscle of the contralateral hindlimb.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 48

Ischemic Myocardial Disease Model

G-protein Chemokine Receptor (CCR5) is evaluated as a potent mitogen capable of stimulating the development of collateral vessels, and restructuring new vessels after coronary artery occlusion. Alteration of G-protein Chemokine Receptor (CCR5) expression is investigated in situ. The experimental protocol includes:

a) The heart is exposed through a left-side thoracotomy in the rat. Immediately, the left coronary artery is occluded with a thin suture (6–0) and the thorax is closed.

b) G-protein Chemokine Receptor (CCR5) protein, in a dosage range of 20 mg–500 mg, is delivered intravenously and/or intramuscularly 3 times (perhaps more) per week for 2–4 weeks.

c) Thirty days after the surgery, the heart is removed and cross-sectioned for morphometric and in situ analyzes.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 49

Suppression of TNF Alpha-Induced Adhesion Molecule Expression by G-protein Chemokine Receptor The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of G-protein Chemokine Receptor (CCR5) to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% $CO_2$. HUVECs are seeded in 96-well plates at concentrations of $1\times10^4$ cells/well in EGM medium at 37 degree C. for 18–24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 µl of 0.1% paraformaldehyde-PBS(with Ca++ and Mg++) is added to each well. Plates are held at 4° C. for 30 min.

Fixative is then removed from the wells and wells are washed 1× with PBS (+Ca, Mg) +0.5% BSA and drained. Do not allow the wells to dry. Add 10 µl of diluted primary antibody to the test and control wells. Anti-ICAM-1-Biotin, Anti-VCAM-1-Biotin and Anti-E-selectin-Biotin are used at a concentration of 10 µg/ml (1:10 dilution of 0.1 mg/ml stock antibody). Cells are incubated at 37° C. for 30 min. in a humidified environment. Wells are washed ×3 with PBS (+Ca, Mg)+0.5% BSA.

Then add 20 µl of diluted ExtrAvidin-Alkaline Phosphotase (1:5,000 dilution) to each well and incubated at 37° C. for 30 min. Wells are washed ×3 with PBS(+Ca,Mg)+0.5% BSA. 1 tablet of p-Nitrophenol Phosphate pNPP is dissolved in 5 ml of glycine buffer (pH 10.4). 100 µl of pNPP substrate in glycine buffer is added to each test well. Standard wells in triplicate are prepared from the working dilution of the ExtrAvidin-Alkaline Phosphotase in glycine buffer: 1:5,000 $(10^0)>10^{-0.5}>10^{-1}>10^{-1.5}$0.5 µl of each dilution is added to triplicate wells and the resulting AP content in each well is 5.50 ng, 1.74 ng, 0.55 ng, 0.18 ng. 100 µl of pNNP reagent must then be added to each of the standard wells. The plate must be incubated at 37° C. for 4 h. A volume of 50 µl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

The studies described in this example test activity in G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 50

Methods of Inhibiting G-protein Coupled Receptor Activity Using Transmembrane Fragments WO 94/05695 and U.S. Pat. No. 5,508,384 set forth sequences of transmembrane regions for 74 GPCRs. The WO 94/05695 patent publication describes and claims polypeptides corresponding to fragments or homologous sequences of GPCRs which can bind a GPCR ligand or which can modulate ligand binding. Both references disclose that a membrane spanning fragment of the third TM domain of the dopamine D2 receptor specifically bound a ligand of the intact receptor in a simple, small unilamellar vesicle model. The fragment used was terminated with a lysine (which is positively charged at physiological pH) at one end and with an aspartic acid (which is negatively charged at physiological pH) at the other. This peptide would not be expected to insert readily into a biological membrane.

In contrast, this example relates to modulating, especially inhibiting, biological activities of G-protein Chemokine Receptor (CCR5) by exposing it to molecules which interfere with correct receptor assembly. In particular, synthetic, isolated and/or recombinant peptides, fragments and/or consensus peptides of the transmembrane domain of G-protein Chemokine Receptor (CCR5) inhibit G-protein Chemokine Receptor (CCR5) mediated signal transduction. Charged residues may be added at one terminus to promote correct orientation of the peptide in the membrane. In particular, addition of two negatively charged residues, such as Asp, at the extracellular terminus of the fragment enhances antagonist activity.

Fragments of the transmembrane domain can be synthesized by flow-through solid phase peptide synthesis on 432A Applied Biosystems Peptide Synthesizer utilizing Fmoc amino acid derivatives. To overcome aggregation that may occur during synthesis of the peptides and that may lead to blockage of the growing peptide chain, FmocHmb derivatives of Ala, Val, and Leu are introduced. Charged residues are added to the peptide termini to assure a proper orientation of the peptides during penetration into the cellular membrane, and to improve solubility of hydrophobic peptides. Purity of the peptides is assessed by reverse phase HPLC and the structures are confirmed by matrix-assisted laser-desorption time-of-flight (MALDI-TOF) mass spectrometry (Tarasova et al., *Ad. Exp. Med. Biol.,* Plenum Press, NY, pp. 201–206 (1998).)

The antagonistic effect of the fragments is tested on human kidney carcinoma (HEK) cells stably expressing the G-protein Chemokine Receptor. RANTES is used as the agonist. Cells grown on Nunc cover glass chamber slides are incubated with 1 μM Fura-2/AM for 20 min. in a $CO_2$ incubator, rinsed with PBS, and mounted on the stage of a Zeiss Axiovert inverted microscope. $[Ca^{2+}]i$ measurements are performed using an Attofluor digital imaging system (Atto Instruments). Fluorescence is monitored by an intensified CCD camera using a 505 cut-off filter. Calibrations of $[Ca^{2+}]i$ is performed using $Ca^{2+}$ standards containing 1 μM Fura. The antagonist activity of the fragments is further optimized as described in Examples 1–4 of WO 99/43711.

The antagonist activity of the fragments is also tested by the ability to inhibit G-protein Chemokine Receptor-HIV cell fusion, and the ability to inhibit binding of a labeled ligand of G-protein Chemokine Receptor (CCR5), by methods well-known in the art and as described for CXCR4 in WO 99/43711.

Example 51

Herpes Virus Immortalized T cells which Express the G-protein Chemokine Receptor (CCR5)

The construction of a Herpes Virus immortalized T cell line which expresses the G-protein Chemokine Receptor (CCR5) is described in Vella, et al., *J. Virol. Methods* 79:51–63 (1999). This or a similar cell line is useful to assay agonists and antagonists in the methods disclosed herein.

Example 52

Isolation of CCR5 Ligands and Anti-CCR5 Antibodies

A general method for solubilizing CCR5 in its native state that may be used in ligand and antibody screening assays is disclosed in Mirzabekov et al., *J. Biol. Chem.* 274:28745–50 (1999). A method of selecting CCR5 antibody from a phage display library of human antibodies is disclosed in Osbourn et al., *Nat. Biotechnol.* 16:778–81 (1998). Lee et al. disclose that the epitope recognized by the CCR5-specific antibody 2D7 is a preferred target for antibodies to inhibit HIV entry. Lee et al. *J. Biol. Chem.* 274:9617–26 (1999). Other methods of screening for ligands and antibodies are well known in the art and are described herein.

Example 53

Assays for Antibody Neutralization

A cell-line based assay for measuring neutralization of HIV-1 by antibodies is disclosed in Trkola et al., *J. Virol.* 73:8966–74 (1999). An assay for HIV-neutralizing antibody and screen for a molecule that inhibits HIV binding or entry at any stage is disclosed in Boritz et al., *J. Virol.* 73:6937–45 (1999). A method for analyzing co-receptor inhibition is disclosed in Klasse et al., *J. Virol.* 73:7453–66 (1999). Additional methods of assaying neutralization of HIV entry, fusion, replication, etc., are well known in the art and disclosed herein.

Example 54

Generation of Anti-G-Protein Chemokine Receptor (CCR5) Antibodies Using Xenomouse™ Strains Xenomouse™ strains of mice engineered to express a repertoire of human IgM/Kappa or IgG2/kappa antibodies were obtained from Abgenix, Inc, (Fremont, Calif.). Groups of mice were immunized according to the following schedules:

Immunization Schedule 1 (XF3 Fusion):

Xenomouse™ mice (n=5) were initially injected in the base of the tail with 100 micrograms in PBS of a DNA plasmid expression vector encoding the full-length G-protein Chemokine Receptor (CCR5) gene (CCR5 pcDNA3T). This was followed by three sub-cutaneous injections given at two week intervals, each consisting of 10 million CHO cells transfected with a CCR5 expression vector (hereinafter "CCR5 CHO cells") in incomplete Freund's adjuvant. The animals were allowed to rest for 12 weeks and then given two more sub-cutaneous injections separated by two weeks, each consisting of 10 million NSO cells transfected with a CCR5 expression vector (hereinafter "CCR5 NSO cells") in incomplete Freund's adjuvant. Three days after the last injection. Mice were sacrificed and spleen and/or lymph node cells were collected for the purposes of generating hybridomas. Hybridomas generated from this fusion are referred to as "XF3. - - - " (Table 4).

Immunization Schedule 2 (XF6 Fusion):

Xenomouse™ mice (n=5) were initially injected intraperitoneally with 7 million CCR5 CHO cells in complete Freund's adjuvant. This was followed by six intraperitoneal injections given at two week intervals, each consisting of 10 million CCR5 CHO cells. The animals were allowed to rest for 5 weeks and then given two more intraperitoneal injections separated by two weeks, each consisting of 10 million CCR5 NSO cells in incomplete Freund's adjuvant. Three days after the last injection. Mice were sacrificed and spleen and/or lymph node cells were collected for the purposes of generating hybridomas. Hybridomas generated from this fusion are referred to as "XF6. - - - " (Table 4).

Immunization Schedule 3 (XF7 Fusion):

Xenomouse™ mice (n=5) were initially injected in the base of the tail with 7 million CCR5 CHO cells in complete Freund's adjuvant. This was followed by six additional injections in the base of the tail given at two week intervals, each consisting of 10 million CCR5 CHO cells. The animals were allowed to rest for 5 weeks and then given two more injections in the base of the tail separated by two weeks, each consisting of 10 million CCR5 NSO cells in incomplete Freund's adjuvant. Three days after the last injection, mice were sacrificed and spleen and/or lymph node cells were collected for the purposes of generating hybridomas. Hybridomas generated from this fusion are referred to as "XF7. - - - " (Table 4).

Immunization Schedule 4 (XF11 Fusion):

Xenomouse™ mice (n=5) were immunized via injection in the footpads given at two week intervals. Each immunization consisted of a total of 10 million CCR5 NSO cells in RIBI adjuvant. A total of eight such immunization were administered. Three days after the last injection, mice were sacrificed and spleen and/or lymph node cells were collected for the purposes of generating hybridomas. Hybridomas generated from this fusion are referred to as "XF11. - - - " (Table 4).

Immunization Schedule 5 (XF12 Fusion):

Xenomouse™ mice (n=5) were initially immunized with 10 million CCR5 NSO cells in complete Freund's adjuvant administered via a combination of intraperitoneal and subcutaneous routes. This was followed by six additional immunizations, given at two week intervals, each consisting of 10 million CCR5 CHO cells in incomplete Freund's adjuvant, also administered via a combination of intraperitoneal and subcutaneous routes. One animal was sacrificed for fusion three days after the third booster immunization in incomplete Freund's adjuvant. Three days after the last injection, the remaining mice were sacrificed and spleen and/or lymph node cells were collected for the purposes of generating hybridomas. Hybridomas generated from this fusion are referred to as "XF12. - - - " (Table 4).

Immunization Schedule 6 (XF27/28 Fusion):

Antibodies produced by these hybridomas were screened for the ability to bind CCR5 by both ELISA and FACS screening.

Membrane ELISA Screening for Anti-G-Protein Chemokine Receptor (CCR5) Specific Antibodies Plasma Membrane Preparation. Plasma membranes from CCR5 CHO cells and vector control transfected CHO cells were prepared. Briefly between $10^8$ to $10^9$ CCR5 CHO or CHO cells were suspended in 40–50 milliliters of cold 12 mM Tris, pH 7.5, 250 mM sucrose. Cells were lysed on ice, by homogenization using a variable speed electric homogenator. Cell lysis was confirmed by microscopy. The cell homogenate was centrifuged at 270×g, for 10 minutes at 4° C. The supernatant (containing the plasma membranes)was collected while the pellet (containing the nuclear fraction was discarded. Next, the supernatant was centrifuge at 8000×g, for 10 minutes at 4° C. Again, the supernatant (containing the plasma membranes) was collected while the pellet (containing the mitochondrial and lysosomal fractions) was discarded. The plasma membranes were then spun out of the supernatant by centrifugation in an ultracentrifuge at 100,000×g, for 60 minutes at 4° C. The supernatant was discarded. The pelleted plasma membranes were resuspended in approximately 1 ml of PBS. After resuspension the volume of plasma membranes was brought up to 5–10 ml with additional PBS. The membrane solution was kept on ice and sonicated (on ice) until a uniform solution was obtained. Care was taken not to overheat the solution during sonication. The plasma membrane protein concentration was determined using the BCA protein determination kit available from Pierce Chemical Company (Rockford Ill.). The plasma membranes were stored −70° C. until use.

Membrane ELISA. Immulon 4 plates (Dynex) were coated with 50 microliters of either CCR5 CHO or vector control transfected CHO plasma membranes (membrane solutions were at a concentration of 20 microgram/milliliter) overnight at 4° C. The next morning, the plates were washed three times with PBST (PBST=PBS containing 0.01% Tween20). The plates were then blocked for lhr at room temperature with 200 microliters/well of 3% BSA/PBS. The blocking solution was removed from the plates and 50 microliters/well of samples (hybridoma supernatant) and controls were added to the plates and incubated for 2 hours at room temperature or overnight at 4° C. Each sample/control was tested for binding to both CCR5 CHO membranes as well as vector control transfected CHO membranes. Next the plates were washed three times with PBST.

| | | CCR5/XF27&28 FP Immunization Schedule<br>Animals 20 mice | | | |
|---|---|---|---|---|---|
| Day No. | Action | Antigen | Amount | Volume | Adjuvant |
| Day 1 | Inject | CCR5 NSO cells | FP 5 × $10^6$ cells/ms | 50 µl | 1:1 PBS/RIBI |
| Day 14 | Inject | CCR5 NSO cells | FP 5 × $10^6$ cells/ms | 50 µl | 1:1 PBS/RIBI |
| Day 28 | Inject | CCR5 NSO cells | FP 5 × $10^6$ cells/ms | 50 µl | 1:1 PBS/RIBI |
| Day 38 | Inject | CCR5 NSO cells | FP 5 × $10^6$ cells/ms | 50 µl | PBS |
| Day 41 | Fusion | | | | |

Hybridomas were generated according to protocols which are commonly known in the art. The fusion partner used to generate these hybridomas was P3x63-AG8.653 purchased from the ATCC, Batch F11545.

Following washing, 50 microliters/well of secondary antibody (Vector Goat anti-Human IgG (H+L) at 0.25 ug/ml in 0.1% BSA/PBST+1% Goat Serum) was added to the wells and incubated for 1 hour at room temperature. While the plates were incubating, the ABC reagent (Vector Laboratories) was prepared. The plate was then three times with PBST. Next, 50 microliters/well of diluted ABC were added to the plates and incubated for 30 minutes at room temperature. The plates were then washed 6 times PBST. 100 microliters/well of TMB reagent (Sigma Chemical Company, St. Louis, Mo.) were added to the wells and incubated for 10 minutes at room temperature. The reaction was then stopped by adding 25 microliterslwell of 2M $H_2SO_4$. The plate was read at 405 nm.

Results. 238 hybridomas showed binding to membranes of CCR5 CHO cells, of which approximately one half showed increased binding to CCR5 CHO membranes compared to vector control transfected CHO membranes. 217 (Table 4) of these hybridomas were expanded and the membrane ELISA was repeated. Results from the second screening demonstrated that the results of this screening procedure were reproducible.

TABLE 4

Hybridomas that secrete antibodies that bind CCR5 CHO membranes

| XF3 Fusion | XF6 Fusion | XF7 Fusion | XF11 Fusion | XF12 Fusion |
|---|---|---|---|---|
| XF3.10B8 | XF6.LNG9 | XF7.1A10 | XF11.1E2 | XF12.10B2 |
| XF3.10C4 | XF6.4D11 | XF7.2E10 | XF11.1E6 | XF12.11F5 |
| XF3.10G4 | XF6.LNC6 | XF7.2A2 | XF11.1A11 | XF12.12B11 |
| XF3.10H12 | XF6.LNF6 | XF7.2C4 | XF11.1A2 | XF12.13H6 |
| XF3.11B5 | XF6.LNC11 | XF7.3A5 | XF11.1A8 | XF12.15B11 |
| XF3.13D3 | XF6.LND9 | XF7.3H1 | XF11.1B10 | XF12.1B8 |
| XF3.14E12 | XF6.LNF2 | XF7.3H2 | XF11.1B12 | XF12.2E1 |
| XF3.15C2 | | XF7.3H8 | XF11.1B4 | XF12.2E12 |
| XF3.15F6 | | XF7.4E8 | XF11.1B7 | XF12.2H5 |
| XF3.2A3 | | XF7.4E9 | XF11.1B9 | XF12.2H8 |
| XF3.2E5 | | XF7.4A6 | XF11.1C1 | XF12.3E2 |
| XF3.3H1 | | XF7.4B2 | XF11.1C7 | XF12.3A9 |
| XF3.4B6 | | XF7.4G3 | XF11.1D10 | XF12.3C2 |
| XF3.4C5 | | XF7.4G7 | XF11.1D8 | XF12.3G11 |
| XF3.5F1 | | XF7.4H4 | XF11.1F8 | XF12.4A8 |
| XF3.6A1 | | XF7.4H7 | XF11.1G11 | XF12.4G7 |
| XF3.6A2 | | XF7.5A1 | XF11.1G8 | XF12.5B10 |
| XF3.6H11 | | XF7.5B8 | XF11.1H7 | XF12.5B11 |
| XF3.7C11 | | XF7.5B9 | XF11.2E4 | XF12.5F1 |
| XF3.8D5 | | XF7.5H8 | XF11.2E5 | XF12.5H1 |
| XF3.8G10 | | XF7.6B11 | XF11.2B9 | XF12.6B12 |
| XF3.9G3 | | XF7.6B12 | XF11.2C9 | XF12.6H1 |
| XF3.LNA2 | | XF7.6B3 | XF11.2D1 | XF12.6H7 |
| XF3.LNB12 | | XF7.6D12 | XF11.2D10 | XF12.7F12 |
| XF3.LNC10 | | XF7.6D3 | XF11.2D11 | XF12.LN-D11 |
| XF3.LNC11 | | XF7.6D7 | XF11.2D5 | |
| XF3.LNC2 | | XF7.7A9 | XF11.2D8 | |
| XF3.LNC3 | | XF7.7B6 | XF11.2F3 | |
| XF3.LNC4 | | XF7.7C11 | XF11.2F5 | |
| XF3.LNC6 | | XF7.7C4 | XF11.2F6 | |
| XF3.LND9 | | XF7.7E8 | XF11.2F7 | |
| XF3.LNE7 | | XF7.7F8 | XF11.2F8 | |
| XF3.LNF1 | | XF7.7G4 | XF11.2F9 | |
| XF3.LNH5 | | XF7.LN1B1 | XF11.2G11 | |
| | | XF7.LN1B7 | XF11.2G4 | |
| | | XF7.LN1D10 | XF11.2G6 | |
| | | XF7.LN1D11 | XF11.2G8 | |
| | | XF7.LN1D9 | XF11.2G9 | |
| | | XF7.LN1E10 | XF11.2H10 | |
| | | XF7.LN1E11 | XF11.2H2 | |
| | | XF7.LN1E12 | XF11.2H4 | |
| | | XF7.LN2A11 | XF11.2H8 | |
| | | XF7.LN2A7 | XF11.3A3 | |
| | | | XF11.3B10 | |
| | | | XF11.3B9 | |
| | | | XF11.3C3 | |
| | | | XF11.3C6 | |
| | | | XF11.3C7 | |
| | | | XF11.3D1 | |
| | | | XF11.3D12 | |
| | | | XF11.3D2 | |

TABLE 4-continued

Hybridomas that secrete antibodies that bind CCR5 CHO membranes

| XF3 Fusion | XF6 Fusion | XF7 Fusion | XF11 Fusion | XF12 Fusion |
|---|---|---|---|---|
| | | | XF11.3D3 | |
| | | | XF11.3F4 | |
| | | | XF11.3G12 | |
| | | | XF11.3G2 | |
| | | | XF11.3G3 | |
| | | | XF11.3H7 | |
| | | | XF11.4E11 | |
| | | | XF11.4A1 | |
| | | | XF11.4A5 | |
| | | | XF11.4B10 | |
| | | | XF11.4B12 | |
| | | | XF11.4B3 | |
| | | | XF11.4B4 | |
| | | | XF11.4C10 | |
| | | | XF11.4C12 | |
| | | | XF11.4C4 | |
| | | | XF11.4D10 | |
| | | | XF11.4D12 | |
| | | | XF11.4D3 | |
| | | | XF11.4D4 | |
| | | | XF11.4D5 | |
| | | | XF11.4F11 | |
| | | | XF11.5E2 | |
| | | | XF11.5A2 | |
| | | | XF11.5C10 | |
| | | | XF11.5D12 | |
| | | | XF11.5F2 | |
| | | | XF11.5F3 | |
| | | | XF11.5G10 | |
| | | | XF11.5G11 | |
| | | | XF11.5G4 | |
| | | | XF11.5G5 | |
| | | | XF11.5G6 | |
| | | | XF11.5H1 | |
| | | | XF11.5H4 | |
| | | | XF11.5H5 | |
| | | | XF11.6E12 | |
| | | | XF11.6E4 | |
| | | | XF11.6E7 | |
| | | | XF11.6A3 | |
| | | | XF11.6A5 | |
| | | | XF11.6B3 | |
| | | | XF11.6B4 | |
| | | | XF11.6B9 | |
| | | | XF11.6C11 | |
| | | | XF11.6C5 | |
| | | | XF11.6D7 | |
| | | | XF11.6D8 | |
| | | | XF11.6D9 | |
| | | | XF11.6F2 | |
| | | | XF11.6F9 | |
| | | | XF11.6G1 | |
| | | | XF11.6G6 | |
| | | | XF11.6H11 | |
| | | | XF11.6H2 | |
| | | | XF11.6H4 | |
| | | | XF11.6H7 | |

FACS Screening for Anti-G-Protein Chemokine Receptor (CCR5) Specific Antibodies

G-Protein Chemokine Receptor (CCR5) transfected or vector control transfected CHO cells were harvested, washed with FACS buffer (PBS with 0.1% NaN3 and 0.1% BSA). One million cells in 100 ul were dispensed to FACS tubes (Falcon 2052). 10 microliters of hybridoma supernatant was added to each tube and incubated for 20 min at 4 C. Each supernatant was analyzed for binding to both CCR5 CHO and vector control transfected CHO cells. Cells were washed, and resuspended in 100 microliters of FACS buffer and 10 microliters of biotinylated Goat anti-Human IgG (H+L) (Vector) at 1 microgram/milliliter was added to the tubes and incubated 20 min at 4 C. Cells were washed, resuspended in 100 microliters of FACS buffer and 5 microliters of Streptavidin PE (DAKO) was added followed by a 10 minute incubation at 4 degrees C. Cells were washed, resuspended in 200 microliters of FACS buffer containing 0.5 micrograms/milliliter of propidium iodide and analyzed on FACScan (Becton Dickinson).

Results. Of the 217 hybridomas supernatants screened by FACS analysis, XF11.1D8, XF11.4D10, XF11.4C4, XF11.5H1, and XF11.1G8 were identified as showing significantly increased binding to CCR5 CHO compared to vector control transfected CHO cells.

Additional hybridomas were produced and their supernatents were screened for anti-G-protein Chemokine Receptor (CCR5) specific antibodies. A number of these were also found to have significantly increased binding to CCR5 compared to controls. They are described herein as preferred antibodies, and are listed in Table 2.

Example 55

Identification and Cloning of VH and VL Domains

One method to identify and clone VH and VL domains from cell lines expressing a particular antibody is to perform PCR with VH and VL specific primers on cDNA made from the antibody expressing cell lines. Briefly, RNA is isolated from the cell lines and used as a template for RT-PCR designed to amplify the VH and VL domains of the antibodies expressed by the EBV cell lines. Cells may lysed in the TRIzol® reagent (Life Technologies, Rockville. Md.) and extracted with one fifth volume of chloroform. After addition of chloroform, the solution is allowed to incubate at room temperature for 10 minutes, and the centrifuged at 14,000 rpm for 15 minutes at 4° C. in a tabletop centrifuge. The supernatant is collected and RNA is precipitated using an equal volume of isopropanol. Precipitated RNA is pelleted by centrifuging at 14,000 rpm for 15 minutes at 4° C. in a tabletop centrifuge. Following centrifugation, the supernatant is discarded and washed with 75% ethanol. Following washing, the RNA is centrifuged again at 800 rpm for 5 minutes at 4° C. The supernatant is discarded and the pellet allowed to air dry. RNA is the dissolved in DEPC water and heated to 60° C. for 10 minutes. Quantities of RNA can determined using optical density measurements.

cDNA may be synthesized, according to methods well-known in the art, from 1.5–2.5 micrograms of RNA using reverse transciptase and random hexamer primers. cDNA is then used as a template for PCR amplification of VH and VL domains. Primers used to amplify VH and VL genes are shown in Table 5. Typically a PCR reaction makes use of a single 5' primer and a single 3' primer. Sometimes, when the amount of available RNA template is limiting, or for greater efficiency, groups of 5' and/or 3' primers may be used. For example, sometimes all five VH-5' primers and all JH3' primers are used in a single PCR reaction. The PCR reaction is carried out in a 50 microliter volume containing 1×PCR buffer, 2 mM of each dNTP, 0.7 units of High Fidelity Taq polymerase, 5' primer mix, 3' primer mix and 7.5 microliters of cDNA. The 5' and 3' primer mix of both VH and VL can be made by pooling together 22 pmole and 28 pmole, respectively, of each of the individual primers. PCR conditions are: 96° C. for 5 minutes; followed by 25 cycles of 94° C. for 1 minute, 50° C. for 1 minute, and 72° C. for 1 minute; followed by an extension cycle of 72° C. for 10 minutes. After the reaction is completed, sample tubes were stored 4° C.

TABLE 5

Primer Sequences Used to Amplify VH and VL domains.

| Primer name | SEQ ID NO | Primer Sequence (5'–3') |
|---|---|---|
| VH Primers | | |
| Hu VH1-5' | 23 | CAGGTGCAGCTGGTGCAGTCTGC |
| Hu VH2-5' | 24 | CAGGTCAACTTAAGGGAGTCTGG |
| Hu VH3-5' | 25 | GAGGTGCAGCTGGTGGAGTCTGG |
| Hu VH4-5' | 26 | CAGGTGCAGCTGCAGGAGTCGGG |
| Hu VH5-5' | 27 | GAGGTGCAGCTGTTGCAGTCTGC |
| Hu VE6-5' | 28 | CAGGTACAGCTGCAGCAGTCAGG |
| Hu JH1,2-5' | 29 | TGAGGAGACGGTGACCAGGGTGCC |
| Hu JH3-5' | 30 | TGAAGAGACGGTGACCATTGTCCC |
| Hu JH4,5-5' | 31 | TGAGGAGACGGTGACCAGGGTTCC |
| Hu JH6-5' | 32 | TGAGGAGACGGTGACCGTGGTCCC |
| VL Primers | | |
| Hu Vkappa1-5' | 33 | GACATCCAGATGACCCAGTCTCC |
| Hu Vkappa2a-5' | 34 | GATGTTGTGATGACTCAGTCTCC |
| Hu Vkappa2b-5' | 35 | GATATTGTGATGACTCAGTCTCC |
| Hu Vkappa3-5' | 36 | GAAATTGTGTTGACGCAGTCTCC |
| Hu Vkappa4-5' | 37 | GACATCGTGATGACCCAGTCTCC |
| Hu Vkappa5-5' | 38 | GAAACGACACTCACGCAGTCTCC |
| Hu Vkappa6-5' | 39 | GAAATTGTGCTGACTCAGTCTCC |
| Hu Vlambda1-5' | 40 | CAGTCTGTGTTGACGCAGCCGCC |
| Hu Vlambda2-5' | 41 | CAGTCTGCCCTGACTCAGCCTGC |
| Hu Vlambda3-5' | 42 | TCCTATGTGCTGACTCAGCCACC |
| Hu Vlambda3b-5' | 43 | TCTTCTGAGCTGACTCAGGACCC |
| Hu Vlambda4-5' | 44 | CACGTTATACTGACTCAACCGCC |
| Hu Vlambda5-5' | 45 | CAGGCTGTGCTCACTCAGCCGTC |
| Hu Vlambda6-5' | 46 | AATTTTATGCTGACTCAGCCCCA |
| Hu Jkappa1-3' | 47 | ACGTTTGATTTCCACCTTGGTCCC |
| Hu Jkappa2-3' | 48 | ACGTTTGATCTCCAGCTTGGTCCC |
| Hu Jkappa3-3' | 49 | ACGTTTGATATCCACTTTGGTCCC |
| Hu Jkappa4-3' | 50 | ACGTTTGATCTCCACCTTGGTCCC |
| Hu Jkappa5-3' | 51 | ACGTTTAATCTCCAGTCGTGTCCC |
| Hu Jlambda1-3' | 52 | CAGTCTGTGTTGACGCAGCCGCC |
| Hu Jlambda2-3' | 53 | CAGTCTGCCCTGACTCAGCCTGC |
| Hu Jlambda3--3' | 54 | TCCTATGTGCTGACTCAGCCACC |
| Hu Jlambda3b-3' | 55 | TCTTCTGAGCTGACTCAGGACCC |
| Hu Jlambda4-3' | 56 | CACGTTATACTGACTCAACCGCC |

TABLE 5-continued

| Primer Sequences Used to Amplify VH and VL domains. | | |
|---|---|---|
| Primer name | SEQ ID NO | Primer Sequence (5'–3') |
| Hu Jlambda5-3' | 57 | CAGGCTGTGCTCACTCAGCGGTC |
| Hu Jlambda6-3' | 58 | AATTTTATGCTGACTCAGCCCCA |

TABLE 6

Anti-CCR5 Antibodies XF11.1D8, XF22.3C9 (e.g., XF22.3C9.6), and XF22.9E6

| Hybridoma Cell Line/ Antibody | VH DNA SEQ ID NO: | VH protein SEQ ID NO: | AAs of VH CDR1 | AAs of VH CDR2 | AAs of VH CDR3 | VL DNA SEQ ID NO: | VL protein SEQ ID NO: | AAs of VL CDR1 | AAs of VL CDR2 | AAs of VL CDR3 | ATCC Deposit Number | ATCC Deposit Date |
|---|---|---|---|---|---|---|---|---|---|---|---|---|
| XF11.1D8 | 59 | 60 | 31–35 | 50–65 | 98–110 | 61 | 62 | 24–35 | 51–57 | 90–98 | PTA-3030 | Feb. 7, 2001 |
| XF22.3C9 | 63 | 64 | 31–35 | 50–68 | 102–115 | 65 | 66 | 24–34 | 50–56 | 89–97 | PTA-3702 | Sep. 12, 2001 |
| XF22.9E6 | 67 | 68 | 31–35 | 50–65 | 98–115 | 69 | 70 | 24–35 | 51–57 | 90–98 | PTA-3859 | Nov. 14, 2001 |

PCR samples are then electrophoresed on a 1.3% agarose gel. DNA bands of the expected sizes (~506 base pairs for VH domains, and 344 base pairs for VL domains) can be cut out of the gel and purified using methods well known in the art. Purified PCR products can be ligated into a PCR cloning vector (TA vector from Invitrogen Inc., Carlsbad, Calif.). Individual cloned PCR products can be isolated after transfection of *E. coli* and blue/white color selection. Cloned PCR products may then be sequenced using methods commonly known in the art. The polynucleotide and amino acid sequences of the VH and VL domains of anti-CCR5 antibodies XF11.1D8, XF22.3C9.6, and XF22.9E6 are shown in FIGS. 4, 5, and 6 (see also, Table 6).

The PCR bands containing the VH domain and the VL domains can also be used to create full-length Ig expression vectors. VH and VL domains can be cloned into vectors containing the nucleotide sequences of a heavy (e.g., human IgG1 or human IgG4) or light chain (human kappa or human lambda) constant regions such that a complete heavy or light chain molecule could be expressed from these vectors when transfected into an appropriate host cell. Further, when cloned heavy and light chains are both expressed in one cell line (from either one or two vectors), they can assemble into a complete functional antibody molecule that is secreted into the cell culture medium. Methods using polynucleotides encoding VH and VL antibody domain to generate expression vectors that encode complete antibody molecules are well known within the art.

Example 56

Immunofluorescence Assay

The following immunofluorescence protocol may be used, for example, to verify G-protein Chemokine Receptor (CCR5) expression on cells, or to check for the presence of one or more antibodies that bind G-protein Chemokine Receptor (CCR5) expressed on the surface of cells. Briefly, Lab-Tek II chamber slides are coated at 4° C. overnight with 10 micrograms/milliliter of bovine collagen Type II in DPBS containing calcium and magnesium (DPBS++). The slides are then washed twice with cold DPBS++ and seeded with 8000 CHO-CCR5 or CHO pC4 transfected cells in a total volume of 125 microliters and incubated at 37° C. in the presence of 95% oxygen/5% carbon dioxide. The culture medium is gently aspirated out and the adhering cells are washed twice with DPBS++ at ambient temperature. The slides are blocked with DPBS++ containing 0.2% BSA (blocker) at 0–4° C. for one hour. The blocking solution is gently aspirated out and 125 microliters of antibody containing solution (an antibody containing solution may be, for example, a hybridoma culture supernatant which is usually used undiluted, or serum/plasma which is usually diluted—around a 1/100 dilution). The slides are incubated for 1 hour at 0–4° C. Antibody solutions are then gently aspirated off and the cells are washed 5 times with 400 microliters of ice cold blocking solution. Next. 125 microliters of a 1 microgram/milliliter of rhodamine labeled secondary antibody (e.g., anti-human IgG) in the blocker is added to the cells. Again, cells are incubated for 1 hour at 0–4° C. The secondary antibody solution is then aspirated off gently and the cells washed 3 times with 400 microliters of ice cold blocking solution and 5 times with cold DPBS++. The cells are then fixed with 125 microliters of 3.7% formaldehyde in DPBS++ for 15 minutes at ambient temperature. The cells are washed 5 times with 400 μl of DPBS++ at ambient temperature. Finally, the cells are mounted in 50% aqueous glycerol and viewed in a fluorescence microscope using rhodamine filters.

Example 57

Western Blotting to Detect Binding to G-protein Chemokine Receptor (CCR5)

G-protein Chemokine Receptor (CCR5) is a membrane embedded protein. In order to perform a western blot on G-protein Chemokine Receptor (CCR5) proteins, cell membranes must first be solubilized. The following protocol was worked out by Mirzabekov et al., J. Biol. Chem. 274:28745 (1999) which is hereby incorporated in its entirety by reference herein. A single cell suspension of G-protein Chemokine Receptor (CCR5)-CHO cells or pC4-CHO (vector transfected control CHO) cells, is pelleted and resuspended in solubilization buffer composed of 100 mM $(NH_4)_2SO_4$, 20 mM Tris-HCl (pH 7.5) and 1% (w/v) Cymal™-5 (Anatrace Inc., Maumee, Ohio), and protease inhibitor mixture (one tablet of Complete™ (Roche Molecular Biochemicals) per 25 ml. After a 30 minute incubation at 4 C on a rocking platform, the samples are centrifuged for 30 minutes at 14,000×g to remove cell debris. G-protein Chemokine Receptor (CCR5) is immunoprecipitated from the solubilized membrane using, for example, the monoclonal anti-G-protein Chemokine Receptor (CCR5) antibody 2D7 described in Wu et al., J. Exp. Med. 186:1373 (1997)

conjugated to sepharose beads. Following immunoprecipitation, the beads are washed extensively with solubilization buffer and resuspended in 2×SDS-sample buffer. Samples are incubated in SDS-sample buffer for 1 hour at 55 C prior to electrophoresis through an 11% SDS-polyacrylamide gel. Western blotting on the G-protein Chemokine Receptor (CCR5) samples can then be carried out according to standard protocols known in the art.

Example 58

Western Blotting, Immunoprecipitation, and Purification of G-protein Chemokine Receptor (CCR5)

The membrane solubilization protocol or Mirzabekov et al described in Example 57 above may also be used to prepare G-protein Chemokine Receptor (CCR5) containing samples for western blotting, immunoprecipitation or purification.

Example 59

BIAcore Analysis of the Affinity of G-Protein Chemokine Receptor (CCR5) Binding Polypeptides Binding of anti-G-protein Chemokine Receptor (CCR5) antibodies to G-protein Chemokine Receptor (CCR5), for example, can be analyzed by BIAcore analysis. Either G-protein Chemokine Receptor (CCR5) (or other antigen to which one wants to know the affinity of a anti-G-protein Chemokine Receptor (CCR5) antibody) or anti-G-protein Chemokine Receptor (CCR5) antibody can be covalently immobilized to a BIAcore sensor chip (CM5 chip) via amine groups using N-ethyl-N'-(dimethylaminopropyl)carboiimide/N-hydroxysuccinimide chemistry. Various dilutions of anti-G-protein Chemokine Receptor (CCR5) antibodies or G-protein Chemokine Receptor (CCR5) (or other antigen to which one wants to know the affinity of a anti-G-protein Chemokine Receptor (CCR5) antibody), respectively are flowed over the derivatized CM5 chip in flow cells at 15 microliters/min for a total volume of 50 microliters. The amount of bound protein is determined during washing of the flow cell with HBS buffer (10 mM HEPES, pH7.4, 150 mM NaCl, 3.4 mM EDTA, 0.005% surfactant p20). Binding specificity for the protein of interest is determined by competition with soluble competitor in the presence the protein of interest.

The flow cell surface can be regenerated by displacing bound protein by washing with 20 microliters of 10 mM glycine-HCl, pH 2.3. For kinetic analysis, the flow cells are tested at different flow rates and different polypeptide densities on the CM5 chip. The on-rates and off-rates can be determined using the kinetic evaluation program in a BIAevaluation 3 software.

Example 60

Virus Neutralization Assay

Antibodies of the invention may be assayed for their ability to inhibit or reduce ha ability of HIV-1 to infect (CCR5 expressing) cells using a virus neutralization assay such as the assay described in Zolla-Pazner and Sharpe, AIDS Res. Hum. Retrovir. 11:1449 (1995) which is incorporated in its entirety by reference herein. Briefly, $2\times10^5$ resting PBMC are added to appropriate dilution(s) of antibodies of the invention. After a one hour incubation, the cells are exposed to virus for 2 hours, washed and resuspended in culture medium containing PHA and IL-2. At various time points after infection, such as at days 7 and 9, the amount of HIV p24 antigen in culture supernatant is measured using ELISA. The percent neutralization was calculated relative to a control experiment in which HIV was allow to infect cells in the absence of antibodies of the invention, or alternatively (or in addition), in the presence of an (isotype matched, if necessary) control antibody with irrelevant specificity.

A variation of this assay is to perform it on activated, rather than resting, PBMC. This can be achieved by culturing the PBMC in the presence of PHA and IL-2 for two days before performing the virus neutralization assay.

Example 61

MIP-1beta Binding Assay

Antibodies of the invention may be assayed for their ability to prevent a natural ligand of CCR5, e.g., MIP1-beta, from binding to the CCR5 receptor.

The following $^{125}$I-MIP1-beta binding assay is an example of one assay that could be performed to determine the ability of an antibody of the invention to prevent a natural ligand of CCR5, MIP1-beta, from binding to the CCR5 receptor.

Twenty-five microCuries of $^{125}$I-MIP-1beta (Amersham Pharmacia Biotech, Cat# IM310, 25 microCuries, 2000 Ci/mmol) is dissolved in 1 milliliter of distilled water to make a 12.5 nM stock solution. If cultured cells, such as CCR5 CHO cells, are used in this experiment, they are trypsinized, washed and resuspended at $10\times10^6$ cells/milliliter in binding buffer (1 mM $CaCl_2$, 5 mM $MgCl_2$, 50 mM Hepes, 0.5% BSA, 0.1% $NaN_3$, pH 7.5). If Peripheral Blood mononuclear cells (PBMC) are to be used in this assay, they are isolated from healthy donors and resuspended at $2\times10^6$ cell/milliliter in binding buffer.

To determine what concentration or quantity of MIP-1beta would saturate the cells in this assay, a series of $^{125}$I-MIP-1beta dilutions at four times the desired final concentration is made. (For example, for final concentrations of 3 nM, a 12 nM solution should be prepared). Typically, the desired final concentration of $^{125}$I-MIP-1beta range from 3 nM down to 0.05 nM. Additionally, a solution of cold (non-radioactive) MIP-1beta at four times the desired final concentration is made. Typically, the desired final concentration of cold MIP-1beta is 200 nM, so an 800 nM solution is prepared.

To measure the total binding of $^{125}$I-MIP-1beta to cells, 25 microliters binding buffer, 25 microliters hot $^{125}$I-MIP-1beta, and 50 microliters cell suspension are added to a U-bottom 96 well microplate (Costa, Cat# 3799). The cells are always added last. If the binding of $^{125}$I-MIP-1beta is non-specific, it will not be effectively competed away by cold MIP-1beta. Therefore, to assess the specificity of binding, 25 microliters cold MIP-1beta (800 nM), 25 microliters hot $^{125}$I-MIP-1beta (various dilutions, and 50 microliters cell suspension are added to a U-bottom 96 well microplate. Again the cells are always added last. The mixtures are then incubated at room temperature in a shaker for one hour. After incubation, each sample is transferred to the top of tubes containing 200 microliters of an oil mixture (2:1 dibutyl phthalate:dioctyl phthalate). The tubes are spun at 12000 rpm for 20 seconds using a microcentrifuge. The bottom of the tube, containing the cell pellet, is cut off and counted in a gamma counter. If the binding of MIP-1beta is specific, less radioactivity will be measured in the gamma counter in the competition assay. As a control for ensuring that the MIP-1beta is binding, to G-protein Chemokine Receptor (CCR5), one may choose to perform the experiment on a suitable CCR5 non-expressing cells, e.g., vector transfected CHO cells.

To perform a competition assay to determine if a chemokine or antibody can compete with MIP-1 beta for binding to the same G-protein Coupled Receptor, a dilution series of cold chemokine or antibody at four times the desired final concentrations is prepared. Additionally, a solution of $^{125}$I-MIP-1beta at four times the desired final concentration is prepared. For this type of competition assay, a 2 nM solution of $^{125}$I-MIP-1beta, which will give a final concentration of 0.5 nM, is prepared.

To measure the total binding of $^{125}$I-MIP-1beta to cells, 25 microliters binding buffer, 25 microliters hot $^{125}$I-MIP-1eta (2 nM), and 50 microliters cell suspension are added to a U-bottom 96 well microplate. The cells are always added last. If another substance (e.g., anti-G-protein Chemokine Receptor (CCR5) antibody, or another chemokine) binds the receptor of MIP-1beta (i.e., G-protein Chemokine Receptor (CCR5)) the presence of increasing amounts of cold (non-radioactive) substance (e.g., anti-G-protein Chemokine Receptor (CCR5) antibody, or another chemokine) will compete for binding to the MIP-1beta receptor (i.e., G-protein Chemokine Receptor (CCR5). Therefore, to determine if a substance binds to the MIP-1beta receptor (i.e., G-protein Chemokine Receptor (CCR5), and inhibits (radioactively labelled) MIP-1beta from binding to its receptor (i.e., G-protein Chemokine Receptor (CCR5), 25 microliters of cold substance (e.g. anti-G-protein Chemokine Receptor (CCR5) antibody at various dilutions), 25 microliters hot $^{125}$-MIP-1beta (2 nM), and 50 microliters cell suspension are added to a U-bottom 96 well microplate. Again the cells are always added last. The mixtures are then incubated at room temperature in a shaker for one hour. After incubation, each sample is transferred to the top of tubes containing 200 microliters of an oil mixture (2:1 dibutyl phthalate:dioctyl phthalate). The tubes are spun at 12000 rpm for 20 seconds using a microcentrifuge. The bottom of the tube, containing the cell pellet, is cut off and counted in a gamma counter. If the binding of MIP-1beta is specific, less radioactivity will be measured in the gamma counter in the competition assay. As a control for ensuring that the MIP-1beta is binding, to G-protein Chemokine Receptor (CCR5), one may choose to perform the experiment on a suitable CCR5 non-expressing cells, e.g., vector transfected CHO cells.

An alternative assay, but similar, assay to determine the ability of an antibody of the invention to prevent a natural ligand of CCR5, MIP1-beta, from binding to the CCR5 receptor is described in Lopalco et al., J. Immunol., 164: 3426 (2000) and in Trkola et al., Nature, 384:184 (1996) which are incorporated in their entireties by reference herein. Briefly, $10^6$ CCR5 expressing cells (e.g., CD4+ T cells, CCR5 transfected-CHO cells) are incubated on ice with appropriate dilution(s) of antibody of the invention. After 45 minutes of incubation, 0.2 microCuries of radio-labelled MIP1-beta (e.g., 125I-MIP1-beta (DuPont-NEN, Boston, Mass.) is added to a final concentration of 0.1 nM. After a two hour incubation on ice, unbound radioactivity is removed using a two step gradient, as described in Grassi et al., J Exp Med. 174:53 (1991) which is incorporated in its entirety by reference herein, in which the lower layer consists of fetal calf serum containing 10% sucrose, and the upper layer consists of 80% silicone (Sigma Aldrich) and 20% mineral oil (Sigma Aldrich). Bound radioactivity in cell pellets is measured in a gamma counter.

Example 62

Chemotaxis Assay

Polypeptides, and agonists or antagonists thereof of the invention may be assayed for their ability to enhance, inhibit, or not significantly alter chemotaxis of G-protein Chemokine Receptor (CCR5) expressing cells in response to MIP1-beta. The G-protein Chemokine Receptor (CCR5) expressing cells may be a homogeneous population of purified G-protein Chemokine Receptor (CCR5) expressing cells or a heterogeneous population, (e.g., peripheral blood mononuclear cells, PBMC).

The following assay to measure MIP1-beta induced chemotaxis of CCR5 expressing cells involves labeling cells with a (fluorescent) tracer molecule, inducing chemotaxis in a well of a 96 well plate containing a filter through which cells can pass, and measuring the number of migrated cells via fluorescence emission. To perform this assay the following materials are needed:

HBSS, without calcium, without magnesium (Biofluids Cat#: p325-000)

Albumin, Bovine Powder, fraction V, IgG free (Sigma Cat#: A-2058)

ChemoTx# 105-2 (for T cell, PBMC, NK cell), 108-1(for eosinophil, PMN) (Neuro Probe, Inc)

Calcein, AM (1 milligram/milliliter in dry DMSO) (Molecular Probes Cat#: C-3099)

PBS, 1×, pH 7.4, without calcium and magnesium (Biofluids Cat#: p312-00

Briefly, cells (e.g. PBMC) are washed twice with HBSS (Biofluids Cat#: p325-000)/0.1% BSA and resuspended in the buffer at 10×$10^6$ cells/milliliter. 5 microliters of calcein AM (1 milligram/milliliter stock) is added to 1 milliliter of the cell suspension. Cells are incubated at 37° C. incubator with loose cap for 30 minutes. After incubation, cells are washed twice with HBSS/0.1% BSA and resuspended at 10×$10^6$/milliliter in HBSS/0.1% BSA buffer. Twenty-nine microliters of test chemokine or control buffer is added into bottom chamber of the chemotaxis microplate. The filter is snapped onto the 96-well plate position making sure no air bubbles get between the filter and the solution. Next, 20 microliters of the cells are loaded on top of the filter and the plate is covered to prevent evaporation. The plate is then incubated at 37° C. for 2 hours for T cells, PBMC, PMN and NK cells and 3 hours for eosinophils. After incubating, carefully flush the top surface of the filter with PBS buffer and then gently wipe the non-migrated cells off the top of the filter with a squeegee. Read the plate and filter at Excitation of 485 nm/Emission 530 nm using CytoFluor fluorescence reader. Results are expressed as chemotactic index, which represents the fold increase in the number of migrated cells in response to chemokine over the spontaneous cell migration in control medium.

This protocol can easily be modified to assay if an agonist or antagonist of G-protein Chemokine Receptor (e.g., anti-G-protein Chemokine Receptor (CCR5) antibodies can enhance, inhibit or not significantly alter the ability of MIP-1beta to induce chemotaxis in CCR5 expressing cells. To do this, one might preincubate the cells with anti-G-protein Chemokine Receptor (CCR5) antibodies (possibly at several concentrations in order to generate a dose-response curve) prior to loading the cells on top of the filter.

An alternative assay to measure the ability of polypeptides, and agonists or antagonists thereof of the invention to enhance, inhibit, or not significantly alter chemotaxis of G-protein Chemokine Receptor (CCR5) expressing cells in response to MIP-1beta can be performed in a transwell chamber, rather than in a 96 well microplate. To perform this assay the following materials are needed:

RPMI-1640 (GIBCO-BRL Cat#: 21870-084)

Albumin, Bovine Powder, fraction V, IgG free (Sigma Cat#: A-2058)

Transwell plate (Costar Cat#: 3421), 6.5 mm Diameter, 5.0 μm pore size

MIP-1β (R&D Systems Cat#: 271-BME)

Lymphocyte Separation Medium (ICN Biochemical Cat#: 50494)

Briefly, PBMC are isolated from fresh human peripheral blood by using Lymphocyte Separation Medium and cultured in RPMI-1640 with 10% FBS for 2 days. Cultured PBMC are resuspended in RPMI-1640/0.5% BSA at $20\times10^6$ cells/milliliter. MIP-1beta is diluted in RPMI-1640/0.5% BSA to final concentrations of 10, 100 and 1000 nanograms/milliliter. 600 microliters of MIP-1beta solution or RPMI-1640/0.5% BSA alone is added to the bottom chamber of the transwell and 100 microliters of the cell suspension is added to the top of the filter. Cells are incubated at 37° C. for 4 hours. After the incubation, collect the cells that are migrated to the bottom the chamber and then perform a FACS analysis, for example, to determine the number and type of the migrated cell population(s). Results are expressed as chemotactic index, which represents the fold increase in the number of migrated cells in response to chemokine over the spontaneous cell migration in control medium.

An additional assay to determine the ability of an antibody of the invention to prevent a natural ligand of CCR5, MIP1-beta, from inducing chemotaxis in MIP-1beta expressing cells is described in Lopalco et al., J. Immunol., 164:3426 (2000). Briefly PBMC are activated (e.g., with phytohemagglutinin and IL-2) for 3 days in the presence of antibodies of the invention. Then $3\times10^5$ activated PBMC in 50 microliters of 1640 RPMI containing 3% human serum albumin are placed in the upper chamber of a bare filter transwell with 5 micrometer pore size (CoStar). 1.5 micrograms of MIP1-beta is plated in the lower chambers. Chemotaxis was permitted to occur for one half hour while the transwell chamber was incubated at 37 degrees Celsius. Cells that migrated from the upper to the lower chamber were then quantified by FACS analysis. Results are expressed in terms of a migration index, (i.e. the number of cells migrating to a lower chamber containing MIP1-beta/ the number of cells migrating to a lower chamber containing only control medium.

Example 63

Calcium Mobilization Following Triggering of the G-Protein Chemokine Receptor (CCR5) Protein When the G-protein Chemokine Receptor (CCR5) is triggered, calcium from intracellular stores and from extracellular spaces is mobilized. This calcium mobilization can be monitored using Fluorescent $Ca^{++}$ indicators that can be excited with UV light, such as for example, Fura-2, AM available from Molecular Probes, Eugene, Oreg. (Cat# F-1221). An assay to monitor calcium mobilization using Fura-2 AM is described below.

Briefly, cells (e.g., purified PBMC or CCR5 transfected cells such as CCR5 CHO cells) are suspended at $5\times10^6$ cells/milliliter in calcium buffer (20 mM Hepes buffer, 125 mM NaCl, 5 mM KCl, 0.5 mM Glucose, 1 mM $CaCl_2$, 1 mM $MgCl_2$, 0.025% BSA, pH 7.4). Fura-2, AM (50 μg/vial) is dissolved in 25 μl of DMSO. Cells are labeled with dye by adding 1 μl of the Fura-2 AM to 2 ml of cell suspension. The cells are then incubated for 30 minutes at room temperature in the dark. After incubation, the cells are washed twice with calcium buffer and suspended at $1\times10^6$ cells/milliliter in calcium buffer. Two milliliters of the cell suspension is placed in a continuously stirring cuvette at 37° C. $[Ca^{++}]_i$ concentration is measured using dual excitation wavelengths 340 nm and 380 nm, and a single emission wavelength of 510 nm on an Hitachi spectrophotometer. A baseline is established for 60 seconds before adding the test chemokine, or anti-G-protein coupled Receptor (CCR5) antibody. Twenty microliters of the test chemokine (100 times the final concentration) is then added to the cuvette and changes in intracellular calcium concentration are monitored using the spectrophotometer. This assay can be used, for example, if an anti-G-protein coupled Receptor (CCR5) antibody is agonistic (induces calcium mobilization) or antagonistic (fails to induce calcium mobilization).

Example 64

Diabetic Mouse and Glucocorticoid-Impaired Wound Healing Models

Diabetic db+/db+ Mouse Model.

To demonstrate that G-protein Chemokine Receptor (CCR5) accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al., *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., *Diabetes* 29(1):60–67 (1980); Giacomelli et al., *Lab Invest.* 40(4):460–473 (1979); Coleman, D. L., *Diabetes* 31 (*Suppl*):1–6 (1982)). These homozygous diabetic mice develop hyperglycemia that is resistant to insulin analogous to human type II diabetes (Mandel et al., *J. Immunol.* 120:1375–1377 (1978)).

The characteristics observed in these animals suggests that healing in this model may be similar to the healing observed in human diabetes (Greenhalgh, et al., *Am. J. of Pathol.* 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

G-protein Chemokine Receptor (CCR5) is administered using at a range different doses of G-protein Chemokine Receptor (CCR5), from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated; and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 mm, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with G-protein Chemokine Receptor. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

Steroid Impaired Rat Model

The inhibition of wound healing by steroids has been well documented in various in vitro and in vivo systems (Wahl, S. M. Glucocorticoids and Wound healing. In: Anti-Inflammatory Steroid Action: Basic and Clinical Aspects. 280–302 (1989); Wahl, S. M. et al., *J. Immunol.* 115: 476–481 (1975); Werb, Z. et al., *J. Exp. Med.* 147:1684–1694 (1978)). Glucocorticoids retard wound healing by inhibiting angiogenesis, decreasing vascular permeability (Ebert, R. H., et al., *An. Intern. Med.* 37:701–705 (1952)), fibroblast proliferation, and collagen synthesis (Beck, L. S. et al., *Growth Factors.* 5: 295–304 (1991); Haynes, B. F. et al., *J. Clin. Invest.* 61: 703–797 (1978)) and producing a transient reduction of circulating monocytes (Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck, L. S. et al., *Growth Factors.* 5: 295–304 (1991); Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989); Pierce, G. F. et al., *Proc. Natl. Acad. Sci. USA* 86: 2229–2233 (1989)).

To demonstrate that G-protein Chemokine Receptor (CCR5 can accelerate the healing process, the effects of multiple topical applications of G-protein Chemokine Receptor (CCR5) on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

G-protein Chemokine Receptor (CCR5) is administered using at a range different doses of G-protein Chemokine Receptor (CCR5), from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered fonnalin in tissue cassettes between biopsy sponges for further processing.

Four groups of 10 animals each (5 with methylprednisolone and 5 without glucocorticoid) are evaluated: 1) Untreated group 2) Vehicle placebo control 3) G-protein Chemokine Receptor (CCR5) treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 mm , the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with G-protein Chemokine Receptor. A calibrated lens micrometer is used by a blinded observer to determine the distance of the wound gap.

Experimental data are analyzed using an unpaired t test. A p value of <0.05 is considered significant.

The studies described in this example test activity of G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 65

Evaluation of G-Protein Chemokine Receptor (CCR5) in a Diabetic Mouse Model

The diabetic mouse model used in Example 64 may also be used to determine whether G-protein Chemokine Receptor (CCR5) is efficacious in preventing, treating and/or ameliorating the diabetic condition per se. G-protein Chemokine Receptor (CCR5) is administered to db+/db+ mice parenterally for various periods of time either before or after the mice have developed diabetes, and blood glucose, and/or insulin levels, or other art-known methods for measuring disease severity, are measured to determine whether administration prevents, slows, or lessens the onset or severity of diabetes.

This example tests activity of G-protein Chemokine Receptor (CCR5) protein. However, one skilled in the art could easily modify the exemplified studies to test the activity of G-protein Chemokine Receptor (CCR5) polynucleotides (e.g., gene therapy), agonists (including ligands), and/or antagonists of G-protein Chemokine Receptor.

Example 66

Evaluation of G-Protein Chemokine Receptor (CCR5) in a Model of Inflammatory Bowel Disease & Colitis The purpose of this study is to determine whether G-protein Chemokine Receptor (CCR5) is efficacious in a model of murine colitis induced by ad libitum exposure to dextran sodium sulfate in the drinking water.

Six to eight week old female Swiss Webster mice (20–25 g, Charles River, Raleigh, N.C.)) are used in a model of inflammatory bowel disease induced with a 4% solution of sodium sulfate (DSS, 36,000–44,000 MW, American International Chemistry, Natick, Mass.)) administered ad libitum for one week. Agonists, antagonists, preferably antibodies of the present invention, of G-protein Chemokine Receptor (CCR5) is given by daily parenteral administration (n=10). Three parameters are used to determine efficacy: 1) clinical score, based on evaluation of the stool; 2) histological score, based on evaluation of the colon; and 3) weight change. The clinical score are comprised of two parts totaling a maximum of score of four. Stool consistency is graded as: 0=firm; 1=loose; 2 diarrhea. Blood in the stool is also evaluated on a 0 to 2 scale with 0=no blood; 1=occult blood; and 2=gross rectal bleeding. A mean group score above 3 indicates probable lethality, and disease which has progressed beyond its treatable stage. Clinical scores are taken on Day 0, 4, 5, 6, and 7. To arrive at a histological score, slides of the ascending, transverse and descending colon are evaluated in a blinded fashion based on inflammation score (0–3) and crypt score (0–4). Body weight is measured daily. Data is expressed as mean +SEM. An unpaired Student's t test is used to determine significant differences compared to the disease control (* p<0.05;  p<0.01; * p<0.001).

Results from this study may suggest G-protein Chemokine Receptor (CCR5) role in IBD and colitis, including ulcerative colitis. Thus, agonists, antagonists, including antibodies of the present invention, and fragments of G-protein Chemokine Receptor (CCR5) may be used to treat, prevent, or ameliorate patients having IBD, colitis, and/or ulcerative colitis, or any other inflammation of the intestine.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. The disclosure of U.S. application Ser. No. 09/195,662, filed Nov. 18, 1998, is herein incorporated by reference. The disclosure of U.S. Provisional Application Nos. 60/181,258 filed Feb. 9, 2000; No. 60/187,999 filed Mar. 9, 2000; and No. 60/234,336 filed Sep. 22, 2000 are herein incorporated by reference. The disclosure of International Publication WO 98/54317 is herein incorporated by reference. Additionally, the sequence listing of U.S. Pat. No. 5,707,815 is herein incorporated by reference.

What is claimed is:

1. An isolated antibody or fragment thereof comprising the amino acid sequence of SEQ ID NO:60 and the amino acid sequence of SEQ ID NO:62.

2. The antibody or the fragment thereof of claim 1 wherein the antibody or the fragment thereof is selected from the group consisting of a whole immunoglobulin molecule, an scFv, a Fab fragment, an Fab' fragment, an F(ab')2, an Fv, and a disulfide linked Fv.

3. The antibody or the fragment thereof of claim 1 wherein the antibody or the fragment thereof is monoclonal.

4. The antibody or the fragment thereof of claim 1 wherein the antibody or the fragment thereof is chimeric or humanized.

5. The antibody or the fragment thereof of claim 1 which comprises a heavy chain immunoglobulin constant domain.

6. The antibody or the fragment thereof of claim 5 wherein said heavy chain immunoglobulin constant domain is selected from the group consisting of an IgM constant domain, an IgG1 constant domain, an IgG2 constant domain, an IgG3 constant domain, an IgG4 constant domain and an IgA constant domain.

7. The antibody or the fragment thereof of claim 6 wherein said heavy chain immunoglobulin constant domain is human.

8. The antibody or the fragment thereof of claim 7 wherein said heavy chain immunoglobulin constant domain is a human IgG4 constant domain.

9. The antibody or the fragment thereof of claim 1 which comprises a light chain immunoglobulin constant domain.

10. The antibody or the fragment thereof of claim 9 which comprises a light chain immunoglobulin constant domain selected from the group consisting of a kappa constant domain and a lambda constant domain.

11. The antibody or the fragment thereof of claim 10 wherein said light chain immunoglobulin constant domain is human.

12. The antibody or the fragment thereof of claim 1 which comprises a human IgG4 heavy chain immunoglobulin constant domain and a human kappa chain immunoglobulin constant domain.

13. The antibody or the fragment thereof of claim 1 wherein the antibody or the fragment thereof is coupled or conjugated to a detectable label.

14. The antibody or the fragment thereof of claim 13, wherein the detectable label is a radiolabel.

15. The antibody or the fragment thereof of claim 14, wherein the radiolabel is $^{125}I$, $^{131}I$, $^{111}In$, $^{90}Y$, $^{99}Tc$, $^{177}Lu$, $^{166}Ho$, or $^{153}Sm$.

16. The antibody or the fragment thereof of claim 13, wherein the detectable label is an enzyme, a fluorescent label, a luminescent label, or a bioluminescent label.

17. The antibody or the fragment thereof of claim 1 wherein the antibody or fragment thereof is biotinylated.

18. The antibody or the fragment thereof of claim 1 wherein the antibody or the fragment thereof is attached to a solid support.

19. An isolated cell or cell line that produces the antibody or the fragment thereof of claim 1.

20. The antibody or the fragment thereof of claim 1 wherein the antibody or the fragment thereof inhibits the binding of HIV virus to CCR5 expressing cells.

21. The antibody or the fragment thereof of claim 1 wherein the antibody or the fragment thereof inhibits the ability of HIV virus to infect CCR5 expressing cells.

22. The XF11.1D8 hybridoma cell line deposited under ATCC Deposit Accession Number PTA-3030.

23. The antibody produced by the XF11.1D8 hybridoma cell line of claim 22.

24. A method of detecting expression of a G-protein Chemokine Receptor (CCR5) polypeptide in a biological sample from an individual comprising:

(a) contacting the biological sample with the antibody or the fragment thereof of claim 1 and (b) detecting the presence of the antibody or the fragment thereof that is specifically bound to CCR5 polypeptide from the biological sample;

wherein detection of the presence of the antibody or the fragment thereof specifically bound to CCR5 polypeptide indicates expression of CCR5 polypeptide.

* * * * *

UNITED STATES PATENT AND TRADEMARK OFFICE

CERTIFICATE OF CORRECTION

PATENT NO. : 7,175,988 B2 
APPLICATION NO. : 10/067800
DATED : February 13, 2007
INVENTOR(S) : Viktor Roschke It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (538) days Delete the phrase “by 538 days” and insert -- by 600 days--

Signed and Sealed this

Ninth Day of October, 2007

JON W. DUDAS

*Director of the United States Patent and Trademark Office*